(12) United States Patent

Schwarz et al.

(10) Patent No.: US 12,564,726 B1

(45) Date of Patent: Mar. 3, 2026

(54) DEVICES AND METHODS FOR APPLICATION OF A MAGNETIC FIELD TO THE NERVOUS SYSTEM

(71) Applicant: BTL Medical Solutions A.S., Prague (CZ)

(72) Inventors: Tomás Schwarz, Prague (CZ); Karel Nemecek, Prague (CZ); Radek Muzika, Plzen (CZ); Barbora Nezpeváková, Prague (CZ); Jan Mánek, Prague (CZ)

(73) Assignee: BTL Medical Solutions A.S., Prague (CZ)

( * ) Notice: Subject to any disclaimer, the term of this patent is extended or adjusted under 35 U.S.C. 154(b) by 0 days.

(21) Appl. No.: 19/030,808

(22) Filed: Jan. 17, 2025

Related U.S. Application Data

(63) Continuation of application No. 19/030,362, filed on Jan. 17, 2025.

(60) Provisional application No. 63/744,050, filed on Jan. 10, 2025, provisional application No. 63/738,196, filed on Dec. 23, 2024, provisional application No. 63/704,905, filed on Oct. 8, 2024.

(51) Int. Cl.
　　*A61N 2/00*　　　　(2006.01)
　　*A61N 2/02*　　　　(2006.01)

(52) U.S. Cl.
　　CPC ............... *A61N 2/006* (2013.01); *A61N 2/02* (2013.01)

(58) Field of Classification Search
　　None
　　See application file for complete search history.

(56) References Cited

U.S. PATENT DOCUMENTS

| | | | |
|---|---|---|---|
| 1,050,280 | A | 1/1913 | Krueger |
| 1,068,831 | A | 7/1913 | Worthington |
| 1,973,387 | A | 9/1934 | Neymann et al. |
| 2,021,676 | A | 11/1935 | Wood et al. |
| 3,163,161 | A | 12/1964 | Jacques et al. |
| 3,566,877 | A | 3/1971 | Smith et al. |
| 3,658,051 | A | 4/1972 | MacLean et al. |
| 3,709,228 | A | 1/1973 | Barker |
| 3,841,306 | A | 10/1974 | Hallgren et al. |
| 3,915,151 | A | 10/1975 | Kraus |
| 3,946,349 | A | 3/1976 | Haldeman, III |

(Continued)

FOREIGN PATENT DOCUMENTS

| | | |
|---|---|---|
| AU | 747678 B2 | 5/2002 |
| AU | 2011265424 B2 | 7/2014 |

(Continued)

OTHER PUBLICATIONS

US 10,398,895 B2, 09/2019, Schwarz (withdrawn)

(Continued)

*Primary Examiner* — Charles A Marmor, II
*Assistant Examiner* — Marc D. Honrath
(74) *Attorney, Agent, or Firm* — Sterne, Kessler, Goldstein & Fox P.L.L.C.

(57) ABSTRACT

The disclosure relates to devices and methods for applying a magnetic field on a body of a patient. The time-varying magnetic field may applied to a brain of the patient. The disclosure provides a method of finding the position suitable for application of the magnetic field to the brain. The devices and methods of the disclosure may be suitable for reducing of food craving.

30 Claims, 43 Drawing Sheets

(56) References Cited

U.S. PATENT DOCUMENTS

| | | | |
|---|---|---|---|
| 3,952,751 A | 4/1976 | Yarger |
| 3,971,387 A | 7/1976 | Mantell |
| 4,068,292 A | 1/1978 | Berry et al. |
| 4,143,661 A | 3/1979 | LaForge et al. |
| 4,197,851 A | 4/1980 | Fellus |
| 4,237,898 A | 12/1980 | Whalley |
| 4,261,364 A | 4/1981 | Haddad et al. |
| 4,305,115 A | 12/1981 | Armitage |
| 4,315,503 A | 2/1982 | Ryaby et al. |
| 4,392,040 A | 7/1983 | Rand et al. |
| 4,454,883 A | 6/1984 | Fellus |
| 4,456,001 A | 6/1984 | Pescatore |
| 4,550,714 A | 11/1985 | Talish et al. |
| 4,556,056 A | 12/1985 | Fischer et al. |
| 4,665,898 A | 5/1987 | Costa et al. |
| 4,674,482 A | 6/1987 | Waltonen et al. |
| 4,674,505 A | 6/1987 | Pauli et al. |
| 4,723,536 A | 2/1988 | Rauscher et al. |
| 4,736,752 A | 4/1988 | Munck et al. |
| 4,850,959 A | 7/1989 | Findl |
| 4,889,526 A | 12/1989 | Rauscher et al. |
| 4,907,602 A | 3/1990 | Sanders |
| 4,957,480 A | 9/1990 | Morenings |
| 4,989,604 A | 2/1991 | Fang |
| 4,993,413 A | 2/1991 | McLeod et al. |
| 5,061,234 A | 10/1991 | Chaney |
| 5,067,940 A | 11/1991 | Liboff et al. |
| 5,085,227 A | 2/1992 | Ramon |
| 5,085,626 A | 2/1992 | Frey |
| 5,143,063 A | 9/1992 | Fellner |
| 5,156,587 A | 10/1992 | Montone |
| 5,169,380 A | 12/1992 | Brennan |
| 5,181,902 A | 1/1993 | Erickson et al. |
| 5,199,951 A | 4/1993 | Spears |
| 5,246,438 A | 9/1993 | Langberg |
| 5,334,181 A | 8/1994 | Rubinsky et al. |
| 5,339,217 A | 8/1994 | Cohen et al. |
| 5,344,384 A | 9/1994 | Ostrow et al. |
| 5,401,233 A | 3/1995 | Erickson et al. |
| 5,415,617 A | 5/1995 | Kraus |
| 5,419,344 A | 5/1995 | DeWitt |
| 5,433,737 A | 7/1995 | Aimone |
| 5,433,740 A | 7/1995 | Yamaguchi |
| 5,562,706 A | 10/1996 | Lauterbach et al. |
| 5,584,863 A | 12/1996 | Rauch et al. |
| 5,620,463 A | 4/1997 | Drolet |
| 5,660,836 A | 8/1997 | Knowlton |
| 5,674,218 A | 10/1997 | Rubinsky et al. |
| 5,690,692 A | 11/1997 | Fleming |
| 5,691,873 A | 11/1997 | Masaki |
| 5,718,662 A | 2/1998 | Jalinous |
| 5,720,773 A | 2/1998 | Lopez-Claros |
| 5,725,471 A | 3/1998 | Davey et al. |
| 5,755,753 A | 5/1998 | Knowlton |
| 5,766,124 A | 6/1998 | Polson |
| 5,769,778 A | 6/1998 | Abrams et al. |
| 5,782,743 A | 7/1998 | Russell |
| 5,799,917 A * | 9/1998 | Li ..................... F16M 13/022 |
| | | 248/921 |
| 5,807,232 A | 9/1998 | Espinoza et al. |
| 5,857,957 A | 1/1999 | Lin |
| 5,904,712 A | 5/1999 | Axelgaard |
| 5,908,444 A | 6/1999 | Azure |
| 5,919,219 A | 7/1999 | Knowlton |
| 5,968,527 A | 10/1999 | Litovitz |
| 5,984,854 A | 11/1999 | Ishikawa et al. |
| RE36,495 E | 1/2000 | Blakeley et al. |
| 6,017,337 A | 1/2000 | Pira |
| 6,032,675 A | 3/2000 | Rubinsky |
| 6,038,485 A | 3/2000 | Axelgaard |
| 6,042,531 A | 3/2000 | Holcomb |
| 6,047,215 A | 4/2000 | McClure et al. |
| 6,050,994 A | 4/2000 | Sherman |
| 6,063,108 A | 5/2000 | Salansky et al. |
| 6,067,474 A | 5/2000 | Schulman et al. |

| | | | |
|---|---|---|---|
| 6,086,525 A | 7/2000 | Davey et al. |
| 6,094,599 A | 7/2000 | Bingham et al. |
| 6,099,459 A | 8/2000 | Jacobson |
| 6,099,523 A | 8/2000 | Kim et al. |
| 6,117,066 A | 9/2000 | Abrams et al. |
| 6,132,361 A | 10/2000 | Epstein et al. |
| 6,132,392 A | 10/2000 | Stone |
| 6,141,985 A | 11/2000 | Cluzeau et al. |
| 6,155,966 A | 12/2000 | Parker |
| 6,161,757 A | 12/2000 | Morris |
| 6,179,769 B1 | 1/2001 | Ishikawa et al. |
| 6,179,770 B1 | 1/2001 | Mould |
| 6,179,771 B1 | 1/2001 | Mueller |
| 6,200,259 B1 | 3/2001 | March |
| 6,213,933 B1 | 4/2001 | Lin |
| 6,223,750 B1 | 5/2001 | Ishikawa et al. |
| 6,246,905 B1 | 6/2001 | Mogul |
| 6,255,815 B1 | 7/2001 | Davey |
| 6,261,301 B1 | 7/2001 | Knesch et al. |
| 6,273,862 B1 | 8/2001 | Privitera et al. |
| 6,273,884 B1 | 8/2001 | Altshuler et al. |
| 6,280,376 B1 | 8/2001 | Holcomb |
| 6,282,448 B1 | 8/2001 | Katz et al. |
| D447,806 S | 9/2001 | Davey et al. |
| 6,311,090 B1 | 10/2001 | Knowlton |
| 6,324,430 B1 | 11/2001 | Zarinetchi et al. |
| 6,324,432 B1 | 11/2001 | Rigaux et al. |
| 6,334,069 B1 | 12/2001 | George et al. |
| 6,334,074 B1 | 12/2001 | Spertell |
| 6,350,276 B1 | 2/2002 | Knowlton |
| 6,366,814 B1 | 4/2002 | Boveja et al. |
| 6,402,678 B1 | 6/2002 | Fischell et al. |
| 6,413,255 B1 | 7/2002 | Stern |
| 6,418,345 B1 | 7/2002 | Tepper et al. |
| 6,424,864 B1 | 7/2002 | Matsuura |
| 6,425,852 B1 | 7/2002 | Epstein et al. |
| 6,443,883 B1 | 9/2002 | Ostrow et al. |
| 6,445,955 B1 | 9/2002 | Michelson et al. |
| 6,447,440 B1 | 9/2002 | Markoll |
| 6,453,202 B1 | 9/2002 | Knowlton |
| 6,461,375 B1 | 10/2002 | Baudry et al. |
| 6,491,620 B1 | 12/2002 | Davey |
| 6,500,110 B1 | 12/2002 | Davey et al. |
| 6,520,903 B1 | 2/2003 | Yamashiro |
| 6,527,694 B1 | 3/2003 | Ishikawa et al. |
| 6,527,695 B1 | 3/2003 | Davey et al. |
| 6,537,197 B1 | 3/2003 | Ruohonen et al. |
| 6,569,078 B2 | 5/2003 | Ishikawa et al. |
| 6,591,138 B1 | 7/2003 | Fischell et al. |
| 6,605,080 B1 | 8/2003 | Altshuler et al. |
| 6,629,941 B1 | 10/2003 | Ishibashi et al. |
| 6,635,053 B1 | 10/2003 | Lalonde et al. |
| 6,658,301 B2 | 12/2003 | Loeb et al. |
| 6,662,054 B2 | 12/2003 | Kreindel et al. |
| 6,663,556 B2 | 12/2003 | Barker |
| 6,663,659 B2 | 12/2003 | McDaniel |
| 6,701,185 B2 | 3/2004 | Burnett et al. |
| 6,702,808 B1 | 3/2004 | Kreindel |
| 6,713,733 B2 | 3/2004 | Kochman et al. |
| 6,735,481 B1 | 5/2004 | Bingham et al. |
| 6,738,667 B2 | 5/2004 | Deno et al. |
| 6,749,624 B2 | 6/2004 | Knowlton |
| 6,827,681 B2 | 12/2004 | Tanner et al. |
| 6,849,040 B2 | 2/2005 | Ruohonen et al. |
| 6,860,852 B2 | 3/2005 | Schönenberger et al. |
| 6,871,099 B1 | 3/2005 | Whitehurst et al. |
| 6,879,859 B1 | 4/2005 | Boveja |
| 6,889,090 B2 | 5/2005 | Kreindel |
| 6,920,883 B2 | 7/2005 | Bessette et al. |
| 6,926,660 B2 | 8/2005 | Miller |
| 6,939,287 B1 | 9/2005 | Ardizzone et al. |
| 6,939,344 B2 | 9/2005 | Kreindel |
| 6,960,202 B2 | 11/2005 | Cluzeau et al. |
| 6,990,427 B2 | 1/2006 | Kirsch et al. |
| 7,008,370 B2 | 3/2006 | Tanner et al. |
| 7,024,239 B2 | 4/2006 | George et al. |
| 7,030,764 B2 | 4/2006 | Smith et al. |
| 7,041,100 B2 | 5/2006 | Kreindel |
| 7,083,580 B2 | 8/2006 | Bernabei |

(56) References Cited

U.S. PATENT DOCUMENTS

| | | | |
|---|---|---|---|
| 7,104,947 B2 | 9/2006 | Riehl | |
| 7,153,256 B2 | 12/2006 | Riehl et al. | |
| 7,186,209 B2 | 3/2007 | Jacobson et al. | |
| 7,211,082 B2 | 5/2007 | Hall et al. | |
| 7,217,265 B2 | 5/2007 | Hennings et al. | |
| 7,238,183 B2 | 7/2007 | Kreindel | |
| 7,276,020 B2 | 10/2007 | Becker et al. | |
| 7,276,058 B2 | 10/2007 | Altshuler et al. | |
| 7,294,101 B2 | 11/2007 | Fischell et al. | |
| 7,309,309 B2 | 12/2007 | Wang et al. | |
| 7,318,821 B2 | 1/2008 | Lalonde et al. | |
| 7,320,664 B2 | 1/2008 | Riehl et al. | |
| 7,351,252 B2 | 4/2008 | Altshuler et al. | |
| 7,367,341 B2 | 5/2008 | Anderson et al. | |
| 7,367,936 B2 | 5/2008 | Myers et al. | |
| 7,367,988 B1 | 5/2008 | Litovitz | |
| 7,369,895 B2 | 5/2008 | Hurtado | |
| 7,372,271 B2 | 5/2008 | Roozen et al. | |
| 7,376,460 B2 | 5/2008 | Bernabei | |
| 7,396,326 B2 | 7/2008 | Ghiron et al. | |
| 7,407,478 B2 | 8/2008 | Zangen et al. | |
| 7,494,458 B2 | 2/2009 | Fischell et al. | |
| 7,496,401 B2 | 2/2009 | Bernabei | |
| 7,520,848 B2 | 4/2009 | Schneider et al. | |
| 7,520,849 B1 | 4/2009 | Simon | |
| 7,520,875 B2 | 4/2009 | Bernabei | |
| 7,524,276 B2 | 4/2009 | Muntermann | |
| 7,532,926 B2 | 5/2009 | Bernabei | |
| 7,560,058 B2 | 7/2009 | Riehl et al. | |
| 7,571,003 B2 | 8/2009 | Pozzato | |
| 7,591,776 B2 | 9/2009 | Phillips et al. | |
| 7,601,115 B2 | 10/2009 | Riehl | |
| 7,601,116 B2 | 10/2009 | Fischell et al. | |
| 7,608,035 B2 | 10/2009 | Farone | |
| 7,614,996 B2 | 11/2009 | Riehl et al. | |
| 7,618,429 B2 | 11/2009 | Mulholland | |
| 7,630,774 B2 | 12/2009 | Karni et al. | |
| 7,643,883 B2 | 1/2010 | Kreindel | |
| 7,651,459 B2 | 1/2010 | Cameron et al. | |
| 7,660,636 B2 | 2/2010 | Castel et al. | |
| 7,697,998 B2 | 4/2010 | Axelgaard | |
| 7,697,999 B2 | 4/2010 | Axelgaard | |
| 7,699,768 B2 | 4/2010 | Kishawi et al. | |
| 7,706,885 B2 | 4/2010 | Farone | |
| 7,711,431 B2 | 5/2010 | Tanner et al. | |
| 7,734,351 B2 | 6/2010 | Testerman et al. | |
| 7,740,574 B2 | 6/2010 | Pilla et al. | |
| 7,744,523 B2 | 6/2010 | Epstein | |
| 7,753,836 B2 | 7/2010 | Peterchev | |
| 7,783,348 B2 | 8/2010 | Gill et al. | |
| 7,785,358 B2 | 8/2010 | Lach | |
| 7,824,324 B2 | 11/2010 | Riehl et al. | |
| 7,854,232 B2 | 12/2010 | Aho et al. | |
| 7,854,754 B2 | 12/2010 | Ting et al. | |
| 7,857,746 B2 | 12/2010 | Riehl | |
| 7,857,775 B2 | 12/2010 | Rosenberg et al. | |
| 7,901,373 B2 | 3/2011 | Tavger | |
| 7,909,786 B2 | 3/2011 | Bonnefin et al. | |
| 7,914,469 B2 | 3/2011 | Torbati | |
| 7,925,066 B2 | 4/2011 | Ruohonen et al. | |
| 7,945,321 B2 | 5/2011 | Bernabei | |
| 7,946,973 B2 | 5/2011 | Peterchev | |
| 7,951,060 B2 | 5/2011 | Larsen et al. | |
| 7,953,500 B2 | 5/2011 | Bingham et al. | |
| 7,963,903 B2 | 6/2011 | Ghiron et al. | |
| 7,976,451 B2 | 7/2011 | Zangen et al. | |
| 7,981,146 B2 | 7/2011 | Korb et al. | |
| 7,998,053 B2 | 8/2011 | Aho | |
| 8,029,432 B2 | 10/2011 | Dennis et al. | |
| 8,035,385 B2 | 10/2011 | Tomiha et al. | |
| 8,052,591 B2 | 11/2011 | Mishelevich et al. | |
| RE43,007 E | 12/2011 | Lalonde et al. | |
| 8,088,058 B2 | 1/2012 | Juliana et al. | |
| 8,105,254 B2 | 1/2012 | Guantera et al. | |
| 8,118,722 B2 | 2/2012 | Riehl et al. | |
| 8,128,549 B2 | 3/2012 | Testani et al. | |
| 8,133,191 B2 | 3/2012 | Rosenberg et al. | |
| 8,137,258 B1 | 3/2012 | Dennis et al. | |
| 8,137,259 B1 | 3/2012 | Dennis et al. | |
| 8,170,643 B2 | 5/2012 | Turner et al. | |
| 8,172,835 B2 | 5/2012 | Leyh et al. | |
| 8,177,702 B2 | 5/2012 | Riehl et al. | |
| 8,192,474 B2 | 6/2012 | Levinson | |
| 8,204,446 B2 | 6/2012 | Scheer et al. | |
| 8,246,529 B2 | 8/2012 | Riehl et al. | |
| 8,251,986 B2 | 8/2012 | Chornenky et al. | |
| 8,262,556 B2 | 9/2012 | Fischell et al. | |
| 8,265,763 B2 | 9/2012 | Fahey | |
| 8,265,910 B2 | 9/2012 | Mishelevich et al. | |
| 8,267,850 B2 | 9/2012 | Schneider et al. | |
| 8,271,090 B1 | 9/2012 | Hartman et al. | |
| 8,275,442 B2 | 9/2012 | Allison | |
| 8,277,371 B2 | 10/2012 | Zangen et al. | |
| 8,285,390 B2 | 10/2012 | Levinson et al. | |
| 8,303,478 B2 | 11/2012 | Lebosse et al. | |
| 8,313,421 B2 | 11/2012 | Muntermann | |
| 8,335,566 B2 | 12/2012 | Müller et al. | |
| 8,337,539 B2 | 12/2012 | Ting et al. | |
| 8,366,756 B2 | 2/2013 | Tucek et al. | |
| 8,376,825 B2 | 2/2013 | Guinn et al. | |
| 8,376,925 B1 | 2/2013 | Dennis et al. | |
| 8,388,510 B2 | 3/2013 | Zangen et al. | |
| 8,428,735 B2 | 4/2013 | Littlewood et al. | |
| 8,435,166 B2 | 5/2013 | Burnett et al. | |
| 8,454,591 B2 | 6/2013 | Leyh et al. | |
| 8,457,751 B2 | 6/2013 | Pozzato | |
| 8,465,408 B2 | 6/2013 | Phillips et al. | |
| 8,475,354 B2 | 7/2013 | Phillips et al. | |
| 8,480,554 B2 | 7/2013 | Phillips et al. | |
| 8,493,286 B1 | 7/2013 | Agrama | |
| 8,506,468 B2 | 8/2013 | Ghiron et al. | |
| 8,517,908 B2 | 8/2013 | Riehl et al. | |
| 8,523,753 B2 | 9/2013 | Schneider et al. | |
| 8,523,927 B2 | 9/2013 | Levinson et al. | |
| 8,548,599 B2 | 10/2013 | Zarsky et al. | |
| 8,565,888 B2 | 10/2013 | Buhlmann et al. | |
| 8,579,953 B1 | 11/2013 | Dunbar et al. | |
| 8,585,568 B2 | 11/2013 | Phillips et al. | |
| 8,585,617 B2 | 11/2013 | Mashiach et al. | |
| 8,588,930 B2 | 11/2013 | DiUbaldi et al. | |
| 8,593,245 B2 | 11/2013 | Zeng et al. | |
| 8,603,073 B2 | 12/2013 | Allison | |
| 8,608,634 B2 | 12/2013 | Zangen et al. | |
| 8,641,710 B2 | 2/2014 | Doty et al. | |
| 8,646,239 B2 | 2/2014 | Rulon | |
| 8,657,731 B2 | 2/2014 | Riehl et al. | |
| 8,657,732 B2 | 2/2014 | Vasishta | |
| 8,666,492 B2 | 3/2014 | Muller et al. | |
| 8,676,338 B2 | 3/2014 | Levinson | |
| 8,684,901 B1 | 4/2014 | Zabara | |
| 8,700,176 B2 | 4/2014 | Azar et al. | |
| 8,702,774 B2 | 4/2014 | Baker et al. | |
| 8,721,572 B1 | 5/2014 | Linder et al. | |
| 8,723,628 B2 | 5/2014 | Mishelevich et al. | |
| 8,725,270 B2 | 5/2014 | Towe | |
| 8,731,657 B1 | 5/2014 | Shambayati et al. | |
| 8,740,765 B1 | 6/2014 | Fischell et al. | |
| 8,768,454 B2 | 7/2014 | Sham et al. | |
| 8,771,163 B2 | 7/2014 | Zangen et al. | |
| 8,771,326 B2 | 7/2014 | Myeong et al. | |
| 8,777,831 B2 | 7/2014 | Aho | |
| 8,788,040 B2 | 7/2014 | Haessler | |
| 8,788,044 B2 | 7/2014 | John | |
| 8,788,060 B2 | 7/2014 | Nebrigic et al. | |
| 8,795,148 B2 | 8/2014 | Schneider et al. | |
| 8,801,589 B2 | 8/2014 | Peterchev et al. | |
| 8,825,166 B2 | 9/2014 | John | |
| 8,834,547 B2 | 9/2014 | Anderson et al. | |
| 8,840,608 B2 | 9/2014 | Anderson et al. | |
| 8,845,508 B2 | 9/2014 | Schneider et al. | |
| 8,864,641 B2 | 10/2014 | Riehl et al. | |
| 8,868,177 B2 | 10/2014 | Simon et al. | |
| 8,870,737 B2 | 10/2014 | Phillips et al. | |
| 8,888,672 B2 | 11/2014 | Phillips et al. | |

(56) References Cited

U.S. PATENT DOCUMENTS

| | | | |
|---|---|---|---|
| 8,888,673 B2 | 11/2014 | Phillips et al. |
| 8,906,009 B2 | 12/2014 | Nebrigic et al. |
| 8,909,342 B2 | 12/2014 | Lozano |
| 8,915,948 B2 | 12/2014 | Altshuler et al. |
| 8,926,490 B2 | 1/2015 | Phillips et al. |
| 8,932,338 B2 | 1/2015 | Lim et al. |
| 8,956,273 B2 | 2/2015 | Mishelevich et al. |
| 8,956,274 B2 | 2/2015 | Schneider et al. |
| 8,961,386 B2 | 2/2015 | Phillips et al. |
| 8,979,727 B2 | 3/2015 | Ron et al. |
| 8,985,331 B2 | 3/2015 | Guenter et al. |
| 8,998,791 B2 | 4/2015 | Ron Edoute et al. |
| 9,002,477 B2 | 4/2015 | Burnett |
| 9,008,793 B1 | 4/2015 | Cosman, Sr. et al. |
| 9,015,057 B2 | 4/2015 | Phillips et al. |
| 9,020,590 B1 | 4/2015 | Honeycutt et al. |
| 9,028,469 B2 | 5/2015 | Jones et al. |
| 9,031,659 B2 | 5/2015 | Campbell et al. |
| 9,033,861 B2 | 5/2015 | Fischell et al. |
| 9,037,247 B2 | 5/2015 | Simon et al. |
| 9,044,595 B2 | 6/2015 | Araya et al. |
| 9,061,128 B2 | 6/2015 | Hall et al. |
| 9,067,052 B2 | 6/2015 | Moses et al. |
| 9,072,891 B1 | 7/2015 | Rao |
| 9,078,634 B2 | 7/2015 | Gonzales et al. |
| 9,089,719 B2 | 7/2015 | Simon et al. |
| 9,101,524 B2 | 8/2015 | Aghion |
| 9,114,256 B2 | 8/2015 | El Achhab et al. |
| 9,132,031 B2 | 9/2015 | Levinson et al. |
| 9,144,513 B2 | 9/2015 | Paulson |
| 9,149,650 B2 | 10/2015 | Shanks et al. |
| 9,168,096 B2 | 10/2015 | Kreindel |
| 9,216,287 B2 | 12/2015 | You et al. |
| 9,233,207 B2 | 1/2016 | Polyakov et al. |
| 9,233,257 B1 | 1/2016 | Zabara |
| 9,254,395 B1 | 2/2016 | Shambayati |
| 9,261,574 B2 | 2/2016 | Boskamp et al. |
| 9,265,690 B2 | 2/2016 | Kriksunov et al. |
| 9,295,840 B1 | 3/2016 | Thacker et al. |
| 9,308,120 B2 | 4/2016 | Anderson et al. |
| 9,314,368 B2 | 4/2016 | Allison et al. |
| 9,326,910 B2 | 5/2016 | Eckhouse et al. |
| 9,339,641 B2 | 5/2016 | Rajguru et al. |
| 9,358,068 B2 | 6/2016 | Schomacker et al. |
| 9,358,149 B2 | 6/2016 | Anderson et al. |
| 9,375,345 B2 | 6/2016 | Levinson et al. |
| 9,387,339 B2 | 7/2016 | Sham et al. |
| 9,398,975 B2 | 7/2016 | Müller et al. |
| 9,408,745 B2 | 8/2016 | Levinson et al. |
| 9,414,759 B2 | 8/2016 | Lang et al. |
| 9,433,797 B2 | 9/2016 | Pilla et al. |
| 9,439,805 B2 | 9/2016 | Gonzales et al. |
| 9,446,258 B1 | 9/2016 | Schwarz et al. |
| 9,468,774 B2 | 10/2016 | Zarsk et al. |
| 9,526,912 B1 | 12/2016 | Fischell et al. |
| 9,532,832 B2 | 1/2017 | Ron Edoute et al. |
| 9,545,523 B2 | 1/2017 | Nanda |
| 9,550,067 B1 | 1/2017 | Fischell et al. |
| 9,561,357 B2 | 2/2017 | Hall et al. |
| 9,561,384 B1 | 2/2017 | Fischell et al. |
| 9,586,048 B2 | 3/2017 | Ternes et al. |
| 9,586,057 B2 | 3/2017 | Ladman et al. |
| 9,596,920 B2 | 3/2017 | Shalev et al. |
| 9,597,225 B1 | 3/2017 | Guerrieri |
| 9,610,429 B2 | 4/2017 | Harris et al. |
| 9,610,459 B2 | 4/2017 | Burnett et al. |
| 9,615,854 B2 | 4/2017 | Matsushita |
| 9,616,217 B1 | 4/2017 | Pensler et al. |
| 9,636,516 B2 | 5/2017 | Schwarz |
| 9,636,519 B2 | 5/2017 | Ladman et al. |
| 9,649,220 B2 | 5/2017 | Anderson et al. |
| 9,655,770 B2 | 5/2017 | Levinson et al. |
| 9,675,800 B2 | 6/2017 | Li et al. |
| 9,675,815 B1 | 6/2017 | Fischell et al. |
| 9,694,194 B2 | 7/2017 | Ron Edoute et al. |
| 9,707,121 B2 | 7/2017 | Hyde et al. |
| 9,713,567 B2 | 7/2017 | Guantera et al. |
| 9,724,533 B1 | 8/2017 | Fischell et al. |
| 9,737,238 B2 | 8/2017 | Wright et al. |
| 9,737,434 B2 | 8/2017 | Allison |
| 9,757,584 B2 | 9/2017 | Burnett |
| 9,782,324 B2 | 10/2017 | Crunick et al. |
| 9,814,897 B2 | 11/2017 | Ron Edoute et al. |
| 9,844,460 B2 | 12/2017 | Weber et al. |
| 9,844,461 B2 | 12/2017 | Levinson et al. |
| 9,849,299 B2 | 12/2017 | Sham et al. |
| 9,849,302 B1 | 12/2017 | Fischell et al. |
| 9,855,166 B2 | 1/2018 | Anderson et al. |
| 9,861,421 B2 | 1/2018 | O'Neil et al. |
| 9,861,520 B2 | 1/2018 | Baker et al. |
| 9,867,996 B2 | 1/2018 | Zarsky et al. |
| 9,901,743 B2 | 2/2018 | Ron Edoute et al. |
| 9,919,161 B2 | 3/2018 | Schwarz et al. |
| 9,937,358 B2 | 4/2018 | Schwarz et al. |
| 9,962,553 B2 | 5/2018 | Schwarz et al. |
| 9,968,797 B2 | 5/2018 | Sham et al. |
| 9,974,519 B1 | 5/2018 | Schwarz et al. |
| 9,974,684 B2 | 5/2018 | Anderson et al. |
| 9,980,765 B2 | 5/2018 | Avram et al. |
| 9,981,143 B2 | 5/2018 | Ron Edoute et al. |
| 9,999,780 B2 | 6/2018 | Weyh et al. |
| 10,029,112 B1 | 7/2018 | Fischell et al. |
| 10,037,867 B2 | 7/2018 | Godyak |
| 10,039,929 B1 | 8/2018 | Schwarz et al. |
| 10,039,930 B2 | 8/2018 | Vallejo et al. |
| 10,046,160 B1 | 8/2018 | Kern |
| 10,080,906 B2 | 9/2018 | Schwarz |
| 10,092,346 B2 | 10/2018 | Levinson |
| 10,111,770 B2 | 10/2018 | Harris et al. |
| 10,111,774 B2 | 10/2018 | Gonzales et al. |
| 10,124,166 B2 | 11/2018 | Edgerton et al. |
| 10,124,187 B2 | 11/2018 | Schwarz et al. |
| 10,183,172 B2 | 1/2019 | Ghiron et al. |
| 10,195,010 B2 | 2/2019 | Sanders |
| 10,195,427 B2 | 2/2019 | Kent et al. |
| 10,195,453 B2 | 2/2019 | Schwarz et al. |
| 10,195,454 B2 | 2/2019 | Yamashiro |
| 10,195,456 B2 | 2/2019 | Cabrerizo et al. |
| 10,201,380 B2 | 2/2019 | Debenedictis et al. |
| 10,232,172 B1 | 3/2019 | O et al. |
| 10,245,439 B1 | 4/2019 | Schwarz et al. |
| 10,271,900 B2 | 4/2019 | Marchitto et al. |
| 10,279,185 B2 | 5/2019 | Meadows et al. |
| 10,342,988 B2 | 7/2019 | Midorikawa et al. |
| 10,363,419 B2 | 7/2019 | Simon et al. |
| 10,413,745 B2 | 9/2019 | Riehl |
| 10,463,869 B2 | 11/2019 | Ron Edoute et al. |
| 10,471,269 B1 | 11/2019 | Schwarz et al. |
| 10,471,271 B1 | 11/2019 | John |
| 10,478,588 B2 | 11/2019 | Walpole et al. |
| 10,478,633 B2 | 11/2019 | Schwarz et al. |
| 10,478,634 B2 | 11/2019 | Schwarz et al. |
| 10,493,293 B2 | 12/2019 | Schwarz et al. |
| 10,518,087 B2 | 12/2019 | Oku et al. |
| 10,518,098 B2 | 12/2019 | Hong et al. |
| 10,525,277 B1 | 1/2020 | Chau |
| 10,549,109 B2 | 2/2020 | Schwarz et al. |
| 10,549,110 B1 | 2/2020 | Schwarz et al. |
| 10,556,121 B2 | 2/2020 | Gurfein |
| 10,556,122 B1 | 2/2020 | Schwarz et al. |
| 10,569,094 B2 | 2/2020 | Schwarz et al. |
| 10,569,095 B1 | 2/2020 | Schwarz et al. |
| 10,583,287 B2 | 3/2020 | Schwarz |
| 10,589,117 B1 | 3/2020 | Fischell et al. |
| 10,596,366 B2 | 3/2020 | Sama |
| 10,596,386 B2 | 3/2020 | Schwarz et al. |
| 10,610,696 B2 | 4/2020 | Peled |
| 10,632,321 B2 | 4/2020 | Schwarz et al. |
| 10,639,490 B2 | 5/2020 | Simon et al. |
| 10,661,093 B2 | 5/2020 | Ron Edoute et al. |
| 10,675,819 B2 | 6/2020 | Li et al. |
| 10,688,310 B2 | 6/2020 | Schwarz et al. |
| 10,695,575 B1 | 6/2020 | Schwarz et al. |
| 10,695,576 B2 | 6/2020 | Schwarz et al. |

(56) References Cited

U.S. PATENT DOCUMENTS

| | | |
|---|---|---|
| 10,709,894 B2 | 7/2020 | Schwarz et al. |
| 10,709,895 B2 | 7/2020 | Schwarz et al. |
| 10,773,094 B1 | 9/2020 | Rzasa et al. |
| 10,806,943 B2 | 10/2020 | Sokolowski |
| 10,821,295 B1 | 11/2020 | Schwarz et al. |
| 10,835,418 B1 | 11/2020 | Darbandi et al. |
| 10,849,784 B2 | 12/2020 | Jurna et al. |
| 10,864,368 B2 | 12/2020 | Stanslaski et al. |
| 10,898,710 B1 | 1/2021 | Sanderford |
| 10,946,195 B2 | 3/2021 | Strohl |
| 11,052,251 B2 | 7/2021 | Muller et al. |
| 11,141,219 B1 | 10/2021 | Schwarz |
| 11,185,690 B2 | 11/2021 | Schwarz |
| 11,207,540 B2 | 12/2021 | Zangen et al. |
| 11,247,039 B2 | 2/2022 | Schwarz et al. |
| 11,247,063 B2 | 2/2022 | Schwarz et al. |
| 11,253,717 B2 | 2/2022 | Schwarz et al. |
| 11,253,718 B2 | 2/2022 | Prouza et al. |
| 11,266,850 B2 | 3/2022 | Prouza et al. |
| 11,266,852 B2 | 3/2022 | Schwarz et al. |
| 11,278,732 B2 | 3/2022 | Casalino et al. |
| 11,400,289 B2 | 8/2022 | Alyagon et al. |
| 11,413,471 B2 | 8/2022 | Zheng et al. |
| 11,420,061 B2 | 8/2022 | Caparso et al. |
| 11,464,994 B2 | 10/2022 | Schwarz et al. |
| 11,478,638 B2 | 10/2022 | Toong et al. |
| 11,484,263 B2 | 11/2022 | Leaper |
| 11,484,725 B2 | 11/2022 | Schwarz et al. |
| 11,484,727 B2 | 11/2022 | Schwarz et al. |
| 11,529,514 B2 | 12/2022 | Bolea et al. |
| 11,534,619 B2 | 12/2022 | Schwarz et al. |
| 11,564,861 B1 | 1/2023 | Gaines |
| 11,590,356 B2 | 2/2023 | Schwarz et al. |
| 11,607,556 B2 | 3/2023 | Schwarz et al. |
| 11,672,999 B1 | 6/2023 | John |
| 11,679,255 B2 | 6/2023 | Schwarz et al. |
| 11,679,270 B2 | 6/2023 | Btl |
| 11,691,024 B2 | 7/2023 | Schwarz et al. |
| 11,730,969 B1 | 8/2023 | Vaughn et al. |
| 11,730,972 B2 | 8/2023 | Semin et al. |
| 11,779,767 B1 | 10/2023 | John |
| 11,794,029 B2 | 10/2023 | Schwarz et al. |
| 11,806,528 B2 | 11/2023 | Schwarz et al. |
| 11,819,689 B1 | 11/2023 | Gaines et al. |
| 11,850,441 B2 | 12/2023 | Hong et al. |
| 11,964,155 B1 | 4/2024 | Soin et al. |
| 12,343,182 B2 | 7/2025 | Hu |
| 2001/0011152 A1 | 8/2001 | Ishikawa et al. |
| 2001/0018547 A1 | 8/2001 | Mechlenburg et al. |
| 2001/0031906 A1 | 10/2001 | Ishikawa et al. |
| 2001/0031999 A1 | 10/2001 | Carter et al. |
| 2002/0010414 A1 | 1/2002 | Coston et al. |
| 2002/0049483 A1 | 4/2002 | Knowlton |
| 2002/0058972 A1 | 5/2002 | Minogue et al. |
| 2002/0077688 A1 | 6/2002 | Kirkland |
| 2002/0082466 A1 | 6/2002 | Han |
| 2002/0103411 A1 | 8/2002 | Bailey et al. |
| 2002/0128686 A1 | 9/2002 | Minogue et al. |
| 2002/0143365 A1 | 10/2002 | Herbst |
| 2002/0143373 A1 | 10/2002 | Courtnage et al. |
| 2002/0151887 A1 | 10/2002 | Stern et al. |
| 2002/0160436 A1 | 10/2002 | Markov et al. |
| 2002/0165590 A1 | 11/2002 | Crowe et al. |
| 2002/0193709 A1 | 12/2002 | Bolze et al. |
| 2003/0028072 A1 | 2/2003 | Fischell et al. |
| 2003/0032900 A1 | 2/2003 | Ella |
| 2003/0032950 A1 | 2/2003 | Altshuler et al. |
| 2003/0050527 A1 | 3/2003 | Fox et al. |
| 2003/0056281 A1 | 3/2003 | Hasegawa |
| 2003/0069464 A1 | 4/2003 | Muntermann |
| 2003/0074037 A1 | 4/2003 | Moore et al. |
| 2003/0078646 A1 | 4/2003 | Axelgaard |
| 2003/0093133 A1 | 5/2003 | Crowe et al. |
| 2003/0097162 A1 | 5/2003 | Kreindel |
| 2003/0130711 A1 | 7/2003 | Pearson et al. |
| 2003/0134545 A1 | 7/2003 | McAdams et al. |
| 2003/0139740 A1 | 7/2003 | Kreindel |
| 2003/0139789 A1 | 7/2003 | Tvinnereim et al. |
| 2003/0149451 A1 | 8/2003 | Chomenky et al. |
| 2003/0153958 A1 | 8/2003 | Yamazaki et al. |
| 2003/0158585 A1 | 8/2003 | Burnett |
| 2003/0199866 A1 | 10/2003 | Stern et al. |
| 2003/0216729 A1 | 11/2003 | Marchitto et al. |
| 2003/0220635 A1 | 11/2003 | Knowlton et al. |
| 2003/0220674 A1 | 11/2003 | Anderson et al. |
| 2003/0236487 A1 | 12/2003 | Knowlton |
| 2004/0015163 A1 | 1/2004 | Buysse et al. |
| 2004/0034346 A1 | 2/2004 | Stern et al. |
| 2004/0039279 A1 | 2/2004 | Ruohonen |
| 2004/0044385 A1 | 3/2004 | Fenn et al. |
| 2004/0073079 A1 | 4/2004 | Altshuler et al. |
| 2004/0077977 A1 | 4/2004 | Ella et al. |
| 2004/0093042 A1 | 5/2004 | Altshuler et al. |
| 2004/0102768 A1 | 5/2004 | Cluzeau et al. |
| 2004/0111087 A1 | 6/2004 | Stern et al. |
| 2004/0152943 A1 | 8/2004 | Zimmerman et al. |
| 2004/0162583 A1 | 8/2004 | Bingham et al. |
| 2004/0171970 A1 | 9/2004 | Schleuniger et al. |
| 2004/0193000 A1 | 9/2004 | Riehl |
| 2004/0193003 A1 | 9/2004 | Mechlenburg et al. |
| 2004/0206365 A1 | 10/2004 | Knowlton |
| 2004/0210214 A1 | 10/2004 | Knowlton |
| 2004/0210282 A1 | 10/2004 | Flock et al. |
| 2004/0210287 A1 | 10/2004 | Greene |
| 2004/0230226 A1 | 11/2004 | Bingham et al. |
| 2004/0260210 A1 | 12/2004 | Ella et al. |
| 2004/0267169 A1 | 12/2004 | Sun et al. |
| 2005/0004632 A1 | 1/2005 | Benedict |
| 2005/0038313 A1 | 2/2005 | Ardizzone |
| 2005/0049543 A1 | 3/2005 | Anderson et al. |
| 2005/0075701 A1 | 4/2005 | Shafer |
| 2005/0075702 A1 | 4/2005 | Shafer |
| 2005/0080466 A1 | 4/2005 | Homer |
| 2005/0085865 A1 | 4/2005 | Tehrani |
| 2005/0085866 A1 | 4/2005 | Tehrani |
| 2005/0085874 A1 | 4/2005 | Davis et al. |
| 2005/0090814 A1 | 4/2005 | Lalonde et al. |
| 2005/0096711 A1 | 5/2005 | Adib |
| 2005/0107656 A1 | 5/2005 | Jang et al. |
| 2005/0113630 A1 | 5/2005 | Fox et al. |
| 2005/0134193 A1 | 6/2005 | Myers et al. |
| 2005/0148808 A1 | 7/2005 | Cameron et al. |
| 2005/0159737 A1 | 7/2005 | Kreindel |
| 2005/0177203 A1 | 8/2005 | Brighton et al. |
| 2005/0182457 A1 | 8/2005 | Thrope et al. |
| 2005/0187599 A1 | 8/2005 | Sharkey et al. |
| 2005/0203504 A1 | 9/2005 | Wham et al. |
| 2005/0215987 A1 | 9/2005 | Slatkine |
| 2005/0216062 A1 | 9/2005 | Herbst |
| 2005/0228210 A1 | 10/2005 | Muntermann |
| 2005/0251120 A1 | 11/2005 | Anderson et al. |
| 2005/0251229 A1 | 11/2005 | Pilla et al. |
| 2006/0004244 A1 | 1/2006 | Phillips et al. |
| 2006/0020236 A1 | 1/2006 | Ben-Nun |
| 2006/0036194 A1 | 2/2006 | Schultheiss et al. |
| 2006/0036300 A1 | 2/2006 | Kreindel |
| 2006/0047281 A1 | 3/2006 | Kreindel |
| 2006/0064082 A1 | 3/2006 | Bonutti |
| 2006/0064140 A1 | 3/2006 | Whitehurst et al. |
| 2006/0069420 A1 | 3/2006 | Rademacher et al. |
| 2006/0094924 A1 | 5/2006 | Riehl |
| 2006/0100550 A1 | 5/2006 | Schultheiss et al. |
| 2006/0100552 A1 | 5/2006 | Schultheiss et al. |
| 2006/0106375 A1 | 5/2006 | Werneth et al. |
| 2006/0149337 A1 | 7/2006 | John |
| 2006/0152301 A1 | 7/2006 | Rohwedder |
| 2006/0161039 A1 | 7/2006 | Juliana et al. |
| 2006/0170486 A1 | 8/2006 | Tranchina et al. |
| 2006/0173518 A1 | 8/2006 | Kreindel |
| 2006/0183252 A1 | 8/2006 | Lee |
| 2006/0184214 A1 | 8/2006 | McDaniel |
| 2006/0187607 A1 | 8/2006 | Mo |
| 2006/0195168 A1 | 8/2006 | Dunbar et al. |
| 2006/0199992 A1 | 9/2006 | Eisenberg et al. |

(56) References Cited

U.S. PATENT DOCUMENTS

| | | |
|---|---|---|
| 2006/0206103 A1 | 9/2006 | Altshuler et al. |
| 2006/0206163 A1 | 9/2006 | Wahlstrand et al. |
| 2006/0206180 A1 | 9/2006 | Alcidi |
| 2006/0229487 A1 | 10/2006 | Goodwin et al. |
| 2006/0253176 A1 | 11/2006 | Caruso et al. |
| 2006/0259102 A1 | 11/2006 | Slatkine |
| 2006/0271028 A1 | 11/2006 | Altshuler et al. |
| 2006/0271110 A1 | 11/2006 | Vernon et al. |
| 2006/0287566 A1 | 12/2006 | Zangen et al. |
| 2006/0293719 A1 | 12/2006 | Naghavi |
| 2007/0010766 A1 | 1/2007 | Gil et al. |
| 2007/0010861 A1 | 1/2007 | Anderson et al. |
| 2007/0015951 A1 | 1/2007 | Culhane |
| 2007/0016274 A1 | 1/2007 | Boveja et al. |
| 2007/0027411 A1 | 2/2007 | Ella et al. |
| 2007/0060862 A1 | 3/2007 | Sun et al. |
| 2007/0078373 A1 | 4/2007 | Sharma et al. |
| 2007/0083237 A1 | 4/2007 | Teruel |
| 2007/0088413 A1 | 4/2007 | Weber et al. |
| 2007/0088419 A1 | 4/2007 | Fiorina |
| 2007/0093806 A1 | 4/2007 | Desai et al. |
| 2007/0100195 A1 | 5/2007 | Goodwin et al. |
| 2007/0135811 A1 | 6/2007 | Hooven |
| 2007/0142753 A1 | 6/2007 | Warlick et al. |
| 2007/0142886 A1 | 6/2007 | Fischell et al. |
| 2007/0173749 A1 | 7/2007 | Williams et al. |
| 2007/0173805 A1 | 7/2007 | Weinberg et al. |
| 2007/0173908 A1 | 7/2007 | Begnaud |
| 2007/0173916 A1 | 7/2007 | Axelgaard |
| 2007/0179534 A1 | 8/2007 | Firlik et al. |
| 2007/0198071 A1 | 8/2007 | Ting et al. |
| 2007/0208340 A1 | 9/2007 | Ganz et al. |
| 2007/0232966 A1 | 10/2007 | Applebaum et al. |
| 2007/0238944 A1 | 10/2007 | Axelgaard |
| 2007/0239073 A1 | 10/2007 | Schaden et al. |
| 2007/0239080 A1 | 10/2007 | Schaden et al. |
| 2007/0244530 A1 | 10/2007 | Ren |
| 2007/0255085 A1 | 11/2007 | Kishawi et al. |
| 2007/0255355 A1 | 11/2007 | Altshuler et al. |
| 2007/0255362 A1 | 11/2007 | Levinson et al. |
| 2007/0260107 A1 | 11/2007 | Mishelevich et al. |
| 2007/0270795 A1 | 11/2007 | Francischelli et al. |
| 2007/0270924 A1 | 11/2007 | McCann et al. |
| 2007/0270925 A1 | 11/2007 | Levinson |
| 2007/0276451 A1 | 11/2007 | Rigaux |
| 2007/0282156 A1 | 12/2007 | Konings |
| 2007/0293911 A1 | 12/2007 | Crowe et al. |
| 2007/0293918 A1 | 12/2007 | Thompson et al. |
| 2007/0299482 A1 | 12/2007 | Littlewood et al. |
| 2008/0009885 A1 | 1/2008 | Del Giglio |
| 2008/0021506 A1 | 1/2008 | Grocela |
| 2008/0046053 A1 | 2/2008 | Wagner et al. |
| 2008/0058699 A1 | 3/2008 | Hause et al. |
| 2008/0077201 A1 | 3/2008 | Levinson et al. |
| 2008/0077202 A1 | 3/2008 | Levinson |
| 2008/0077211 A1 | 3/2008 | Levinson et al. |
| 2008/0082094 A1 | 4/2008 | McPherson et al. |
| 2008/0082153 A1 | 4/2008 | Gadsby et al. |
| 2008/0103407 A1 | 5/2008 | Bolea et al. |
| 2008/0103559 A1 | 5/2008 | Thacker et al. |
| 2008/0103565 A1 | 5/2008 | Altshuler et al. |
| 2008/0109048 A1 | 5/2008 | Moffitt |
| 2008/0114199 A1 | 5/2008 | Riehl et al. |
| 2008/0114423 A1 | 5/2008 | Grenon et al. |
| 2008/0132971 A1 | 6/2008 | Pille et al. |
| 2008/0139871 A1 | 6/2008 | Muntermann |
| 2008/0146865 A1 | 6/2008 | Muntermann |
| 2008/0161636 A1 | 7/2008 | Hurme et al. |
| 2008/0161883 A1 | 7/2008 | Conor |
| 2008/0167585 A1 | 7/2008 | Khen et al. |
| 2008/0177128 A1 | 7/2008 | Riehl et al. |
| 2008/0183167 A1 | 7/2008 | Britva et al. |
| 2008/0183251 A1 | 7/2008 | Azar et al. |
| 2008/0183252 A1 | 7/2008 | Khen |
| 2008/0188915 A1 | 8/2008 | Mills et al. |
| 2008/0188947 A1 | 8/2008 | Sanders |
| 2008/0195181 A1 | 8/2008 | Cole |
| 2008/0200749 A1 | 8/2008 | Zheng et al. |
| 2008/0200778 A1 | 8/2008 | Taskinen et al. |
| 2008/0208287 A1 | 8/2008 | Palermo et al. |
| 2008/0221504 A1 | 9/2008 | Aghion |
| 2008/0228520 A1 | 9/2008 | Day et al. |
| 2008/0234534 A1 | 9/2008 | Mikas et al. |
| 2008/0234609 A1 | 9/2008 | Kreindel et al. |
| 2008/0246573 A1 | 10/2008 | Souder et al. |
| 2008/0249350 A1 | 10/2008 | Marchitto et al. |
| 2008/0255572 A1 | 10/2008 | Zeller et al. |
| 2008/0255637 A1 | 10/2008 | Oishi |
| 2008/0262287 A1 | 10/2008 | Dussau |
| 2008/0262574 A1 | 10/2008 | Briefs et al. |
| 2008/0269593 A1 | 10/2008 | Weinstock |
| 2008/0269851 A1 | 10/2008 | Deem et al. |
| 2008/0275289 A1 | 11/2008 | Olree et al. |
| 2008/0287839 A1 | 11/2008 | Rosen et al. |
| 2008/0287948 A1 | 11/2008 | Newton et al. |
| 2008/0288035 A1 | 11/2008 | Gill et al. |
| 2008/0294211 A1 | 11/2008 | Moffitt |
| 2008/0306325 A1 | 12/2008 | Burnett et al. |
| 2008/0306326 A1 | 12/2008 | Epstein |
| 2008/0312647 A1 | 12/2008 | Knopp et al. |
| 2008/0312651 A1 | 12/2008 | Pope et al. |
| 2009/0005631 A1 | 1/2009 | Simenhaus et al. |
| 2009/0012508 A1 | 1/2009 | Dougal |
| 2009/0018384 A1 | 1/2009 | Boyden et al. |
| 2009/0018611 A1 | 1/2009 | Campbell et al. |
| 2009/0018623 A1 | 1/2009 | Levinson et al. |
| 2009/0018624 A1 | 1/2009 | Levinson et al. |
| 2009/0018625 A1 | 1/2009 | Levinson et al. |
| 2009/0018626 A1 | 1/2009 | Levinson et al. |
| 2009/0018627 A1 | 1/2009 | Levinson et al. |
| 2009/0018628 A1 | 1/2009 | Burns et al. |
| 2009/0024192 A1 | 1/2009 | Mulholland |
| 2009/0024193 A1 | 1/2009 | Altshuler et al. |
| 2009/0030352 A1 | 1/2009 | Schultheiss et al. |
| 2009/0036803 A1 | 2/2009 | Warlick et al. |
| 2009/0036938 A1 | 2/2009 | Shipley et al. |
| 2009/0036958 A1 | 2/2009 | Mehta |
| 2009/0043185 A1 | 2/2009 | McAdams et al. |
| 2009/0043188 A1 | 2/2009 | Rauscher |
| 2009/0043293 A1 | 2/2009 | Pankratov et al. |
| 2009/0062885 A1 | 3/2009 | Brighton et al. |
| 2009/0062897 A1 | 3/2009 | Axelgaard |
| 2009/0082690 A1 | 3/2009 | Phillips et al. |
| 2009/0083071 A1 | 3/2009 | Phillips et al. |
| 2009/0093740 A1 | 4/2009 | Helgeson et al. |
| 2009/0099405 A1 | 4/2009 | Schneider et al. |
| 2009/0105706 A1 | 4/2009 | Livneh |
| 2009/0108969 A1 | 4/2009 | Sims et al. |
| 2009/0118722 A1 | 5/2009 | Ebbers et al. |
| 2009/0118789 A1 | 5/2009 | Buhlmann et al. |
| 2009/0118790 A1 | 5/2009 | Van Herk |
| 2009/0149300 A1 | 6/2009 | Chen |
| 2009/0149925 A1 | 6/2009 | Macdonald et al. |
| 2009/0149929 A1 | 6/2009 | Levinson et al. |
| 2009/0149930 A1 | 6/2009 | Schenck |
| 2009/0156958 A1 | 6/2009 | Mehta et al. |
| 2009/0163761 A1 | 6/2009 | Culhane |
| 2009/0198144 A1 | 8/2009 | Phillips et al. |
| 2009/0204015 A1 | 8/2009 | Phillips et al. |
| 2009/0209840 A1 | 8/2009 | Axelgaard |
| 2009/0210028 A1 | 8/2009 | Rigaux et al. |
| 2009/0216293 A1 | 8/2009 | Sasaki et al. |
| 2009/0221938 A1 | 9/2009 | Rosenberg et al. |
| 2009/0227830 A1 | 9/2009 | Pillutla et al. |
| 2009/0227831 A1 | 9/2009 | Burnett et al. |
| 2009/0234423 A1 | 9/2009 | Vetanze |
| 2009/0240096 A1 | 9/2009 | Riehl et al. |
| 2009/0248004 A1 | 10/2009 | Altshuler et al. |
| 2009/0254007 A1 | 10/2009 | Schultheiss et al. |
| 2009/0254144 A1 | 10/2009 | Bhadra et al. |
| 2009/0254154 A1 | 10/2009 | De Taboada et al. |
| 2009/0270945 A1 | 10/2009 | Markoll et al. |
| 2009/0270947 A1 | 10/2009 | Stone et al. |
| 2009/0281464 A1 | 11/2009 | Cioanta et al. |

(56)　　References Cited

U.S. PATENT DOCUMENTS

| | | |
|---|---|---|
| 2009/0284339 A1 | 11/2009 | Choi et al. |
| 2009/0306648 A1 | 12/2009 | Podhajsky et al. |
| 2009/0312679 A1 | 12/2009 | Elliott et al. |
| 2009/0319002 A1 | 12/2009 | Simon |
| 2009/0326528 A1 | 12/2009 | Karni et al. |
| 2009/0326571 A1 | 12/2009 | Mulholland |
| 2010/0004536 A1 | 1/2010 | Rosenberg |
| 2010/0004715 A1 | 1/2010 | Fahey |
| 2010/0016761 A1 | 1/2010 | Rosenberg |
| 2010/0016850 A1 | 1/2010 | Ron Edoute et al. |
| 2010/0023097 A1 | 1/2010 | Peterson et al. |
| 2010/0030298 A1 | 2/2010 | Martens et al. |
| 2010/0036191 A1 | 2/2010 | Walter et al. |
| 2010/0036368 A1 | 2/2010 | England et al. |
| 2010/0042180 A1 | 2/2010 | Mueller et al. |
| 2010/0049188 A1 | 2/2010 | Nelson et al. |
| 2010/0062633 A1 | 3/2010 | Puttinger et al. |
| 2010/0069704 A1 | 3/2010 | Peterchev |
| 2010/0081971 A1 | 4/2010 | Allison |
| 2010/0087699 A1 | 4/2010 | Peterchev |
| 2010/0087816 A1 | 4/2010 | Roy |
| 2010/0094379 A1 | 4/2010 | Meadows et al. |
| 2010/0106064 A1 | 4/2010 | Kreindel et al. |
| 2010/0114191 A1 | 5/2010 | Newman |
| 2010/0121131 A1 | 5/2010 | Mathes |
| 2010/0125314 A1 | 5/2010 | Bradley et al. |
| 2010/0130945 A1 | 5/2010 | Laniado et al. |
| 2010/0137760 A1 | 6/2010 | Schulz et al. |
| 2010/0145399 A1 | 6/2010 | Johari et al. |
| 2010/0152522 A1 | 6/2010 | Roth et al. |
| 2010/0152824 A1 | 6/2010 | Allison |
| 2010/0160712 A1 | 6/2010 | Burnett et al. |
| 2010/0168501 A1 | 7/2010 | Burnett et al. |
| 2010/0174225 A1 | 7/2010 | Pesach et al. |
| 2010/0179372 A1 | 7/2010 | Glassman |
| 2010/0179373 A1 | 7/2010 | Pille et al. |
| 2010/0185042 A1 | 7/2010 | Schneider et al. |
| 2010/0197993 A1 | 8/2010 | Vasishta |
| 2010/0198102 A1 | 8/2010 | Moore |
| 2010/0210894 A1 | 8/2010 | Pascual-Leone et al. |
| 2010/0217253 A1 | 8/2010 | Mehta |
| 2010/0217349 A1 | 8/2010 | Fahey |
| 2010/0222629 A1 | 9/2010 | Burnett et al. |
| 2010/0228075 A1 | 9/2010 | Lu |
| 2010/0228250 A1 | 9/2010 | Brogna |
| 2010/0228304 A1 | 9/2010 | Kriksunov et al. |
| 2010/0256438 A1 | 10/2010 | Mishelevich et al. |
| 2010/0256439 A1 | 10/2010 | Schneider et al. |
| 2010/0261992 A1 | 10/2010 | Axelgaard |
| 2010/0274327 A1 | 10/2010 | Carroll et al. |
| 2010/0274329 A1 | 10/2010 | Bradley et al. |
| 2010/0280582 A1 | 11/2010 | Baker et al. |
| 2010/0286470 A1 | 11/2010 | Schneider et al. |
| 2010/0286691 A1 | 11/2010 | Kerr et al. |
| 2010/0298623 A1 | 11/2010 | Mishelevich et al. |
| 2010/0298895 A1 | 11/2010 | Ghaffari et al. |
| 2010/0309689 A1 | 12/2010 | Coulson |
| 2010/0312166 A1 | 12/2010 | Castel |
| 2010/0315225 A1 | 12/2010 | Teague |
| 2010/0324611 A1 | 12/2010 | Deming et al. |
| 2010/0331602 A1 | 12/2010 | Mishelevich et al. |
| 2010/0331603 A1 | 12/2010 | Szecsi |
| 2010/0331604 A1 | 12/2010 | Okamoto et al. |
| 2011/0004261 A1 | 1/2011 | Sham et al. |
| 2011/0007745 A1 | 1/2011 | Schultz et al. |
| 2011/0009737 A1 | 1/2011 | Manstein |
| 2011/0009923 A1 | 1/2011 | Lee |
| 2011/0015464 A1 | 1/2011 | Riehl et al. |
| 2011/0015625 A1 | 1/2011 | Adanny et al. |
| 2011/0015687 A1 | 1/2011 | Nebrigic et al. |
| 2011/0021863 A1 | 1/2011 | Burnett et al. |
| 2011/0046432 A1 | 2/2011 | Simon et al. |
| 2011/0046523 A1 | 2/2011 | Altshuler et al. |
| 2011/0054564 A1 | 3/2011 | Valencia |
| 2011/0054566 A1 | 3/2011 | Nathanson |
| 2011/0060179 A1 | 3/2011 | Aho et al. |
| 2011/0065976 A1 | 3/2011 | Chornenky et al. |
| 2011/0066216 A1 | 3/2011 | Ting et al. |
| 2011/0077451 A1 | 3/2011 | Marchitto et al. |
| 2011/0081333 A1 | 4/2011 | Shantha et al. |
| 2011/0082383 A1 | 4/2011 | Cory et al. |
| 2011/0087312 A1 | 4/2011 | Shanks et al. |
| 2011/0105826 A1 | 5/2011 | Mishelevich et al. |
| 2011/0106220 A1 | 5/2011 | DeGiorgio et al. |
| 2011/0112520 A1 | 5/2011 | Michael |
| 2011/0118722 A1 | 5/2011 | Lischinsky et al. |
| 2011/0125203 A1 | 5/2011 | Simon et al. |
| 2011/0125213 A1 | 5/2011 | Simon et al. |
| 2011/0130617 A1 | 6/2011 | Dennis et al. |
| 2011/0130618 A1 | 6/2011 | Ron Edoute et al. |
| 2011/0130713 A1 | 6/2011 | Dufay |
| 2011/0130796 A1 | 6/2011 | Louise |
| 2011/0133872 A1 | 6/2011 | Souder |
| 2011/0137381 A1 | 6/2011 | Lee et al. |
| 2011/0152965 A1 | 6/2011 | Mashiach et al. |
| 2011/0152967 A1 | 6/2011 | Simon et al. |
| 2011/0160810 A1 | 6/2011 | Griffith |
| 2011/0172735 A1 | 7/2011 | Johari |
| 2011/0172752 A1 | 7/2011 | Bingham et al. |
| 2011/0172756 A1 | 7/2011 | Doerr et al. |
| 2011/0190569 A1 | 8/2011 | Simon et al. |
| 2011/0196438 A1 | 8/2011 | Mnozil et al. |
| 2011/0202058 A1 | 8/2011 | Eder et al. |
| 2011/0207988 A1 | 8/2011 | Ruohonen et al. |
| 2011/0208182 A1 | 8/2011 | Szasz et al. |
| 2011/0218464 A1 | 9/2011 | Iger |
| 2011/0224761 A1 | 9/2011 | Manstein |
| 2011/0230701 A1 | 9/2011 | Simon et al. |
| 2011/0237921 A1 | 9/2011 | Askin, III et al. |
| 2011/0238050 A1 | 9/2011 | Allison et al. |
| 2011/0238051 A1 | 9/2011 | Levinson et al. |
| 2011/0245735 A1 | 10/2011 | Eckhouse et al. |
| 2011/0245900 A1 | 10/2011 | Turner et al. |
| 2011/0263925 A1 | 10/2011 | Bratton |
| 2011/0270360 A1 | 11/2011 | Harris et al. |
| 2011/0273251 A1 | 11/2011 | Mishelevich et al. |
| 2011/0275881 A1 | 11/2011 | Aho |
| 2011/0275927 A1 | 11/2011 | Wagner et al. |
| 2011/0275963 A1 | 11/2011 | Wagner et al. |
| 2011/0276107 A1 | 11/2011 | Simon et al. |
| 2011/0276108 A1 | 11/2011 | Crowe et al. |
| 2011/0295160 A1 | 12/2011 | Hart |
| 2011/0300079 A1 | 12/2011 | Martens et al. |
| 2011/0306905 A1 | 12/2011 | Novak et al. |
| 2011/0306943 A1 | 12/2011 | Dunbar et al. |
| 2011/0319700 A1 | 12/2011 | Schneider |
| 2012/0016177 A1 | 1/2012 | Mishelevich et al. |
| 2012/0016359 A1 | 1/2012 | Podhajsky |
| 2012/0022518 A1 | 1/2012 | Levinson |
| 2012/0029264 A1 | 2/2012 | Roth et al. |
| 2012/0029394 A1 | 2/2012 | Babaev |
| 2012/0029596 A1 | 2/2012 | Barker |
| 2012/0035608 A1 | 2/2012 | Marchitto et al. |
| 2012/0041296 A1 | 2/2012 | Garstka et al. |
| 2012/0046598 A1 | 2/2012 | Kardos et al. |
| 2012/0046653 A1 | 2/2012 | Welches et al. |
| 2012/0053396 A1 | 3/2012 | Deegan et al. |
| 2012/0053449 A1 | 3/2012 | Moses et al. |
| 2012/0053645 A1 | 3/2012 | Ayanoor-Vitikkate et al. |
| 2012/0083709 A1 | 4/2012 | Parker et al. |
| 2012/0083858 A1 | 4/2012 | Yarnitsky |
| 2012/0101326 A1 | 4/2012 | Simon et al. |
| 2012/0101366 A1 | 4/2012 | Ruohonen et al. |
| 2012/0108883 A1 | 5/2012 | Peterchev |
| 2012/0108884 A1 | 5/2012 | Bechler et al. |
| 2012/0109241 A1 | 5/2012 | Rauscher |
| 2012/0116271 A1 | 5/2012 | Caruso et al. |
| 2012/0116477 A1 | 5/2012 | Crowe et al. |
| 2012/0143281 A1 | 6/2012 | Birkill et al. |
| 2012/0150079 A1 | 6/2012 | Rosenberg |
| 2012/0150266 A1 | 6/2012 | Shalev et al. |
| 2012/0157747 A1 | 6/2012 | Rybski et al. |
| 2012/0157804 A1 | 6/2012 | Rogers et al. |
| 2012/0158100 A1 | 6/2012 | Schomacker |

(56) References Cited

U.S. PATENT DOCUMENTS

| | | |
|---|---|---|
| 2012/0172653 A1 | 7/2012 | Chornenky et al. |
| 2012/0191018 A1 | 7/2012 | Willeford |
| 2012/0191169 A1 | 7/2012 | Rothstein et al. |
| 2012/0195100 A1 | 8/2012 | Saitoh et al. |
| 2012/0197361 A1 | 8/2012 | Gonzales et al. |
| 2012/0203054 A1 | 8/2012 | Riehl et al. |
| 2012/0203146 A1 | 8/2012 | Uebelacker et al. |
| 2012/0203320 A1 | 8/2012 | Digiore et al. |
| 2012/0215210 A1 | 8/2012 | Brown et al. |
| 2012/0226139 A1 | 9/2012 | Peyman |
| 2012/0226272 A1 | 9/2012 | Chernov et al. |
| 2012/0226330 A1 | 9/2012 | Kolen et al. |
| 2012/0239120 A1 | 9/2012 | Karni et al. |
| 2012/0239123 A1 | 9/2012 | Weber et al. |
| 2012/0240940 A1 | 9/2012 | Paraschac et al. |
| 2012/0245483 A1 | 9/2012 | Lundqvist |
| 2012/0253098 A1 | 10/2012 | George et al. |
| 2012/0259382 A1 | 10/2012 | Trier et al. |
| 2012/0265111 A1 | 10/2012 | Glenzer et al. |
| 2012/0265193 A1 | 10/2012 | Lischinsky et al. |
| 2012/0271206 A1 | 10/2012 | Shalev et al. |
| 2012/0271294 A1 | 10/2012 | Barthe et al. |
| 2012/0277587 A1 | 11/2012 | Adanny et al. |
| 2012/0302821 A1 | 11/2012 | Burnett |
| 2012/0303076 A1 | 11/2012 | Fahey |
| 2012/0310033 A1 | 12/2012 | Muntermann |
| 2012/0310035 A1 | 12/2012 | Schneider et al. |
| 2012/0310311 A1 | 12/2012 | Elkah |
| 2012/0323232 A1 | 12/2012 | Wolf et al. |
| 2012/0330090 A1 | 12/2012 | Sham et al. |
| 2012/0330394 A1 | 12/2012 | Dar et al. |
| 2013/0006039 A1 | 1/2013 | Sadler |
| 2013/0006324 A1 | 1/2013 | Bradley |
| 2013/0012755 A1 | 1/2013 | Slayton |
| 2013/0023748 A1 | 1/2013 | Afanasewicz et al. |
| 2013/0030239 A1 | 1/2013 | Weyh et al. |
| 2013/0035680 A1 | 2/2013 | Ben-Haim et al. |
| 2013/0035745 A1 | 2/2013 | Ahmed et al. |
| 2013/0042876 A1 | 2/2013 | Hermanson et al. |
| 2013/0053620 A1 | 2/2013 | Susedik et al. |
| 2013/0066309 A1 | 3/2013 | Levinson |
| 2013/0071805 A1 | 3/2013 | Doll et al. |
| 2013/0072925 A1 | 3/2013 | Ben-Haim et al. |
| 2013/0072930 A1 | 3/2013 | Ben-Haim et al. |
| 2013/0073001 A1 | 3/2013 | Campbell |
| 2013/0079684 A1 | 3/2013 | Rosen et al. |
| 2013/0085317 A1 | 4/2013 | Feinstein |
| 2013/0085551 A1 | 4/2013 | Bachinski et al. |
| 2013/0096363 A1 | 4/2013 | Schneider et al. |
| 2013/0103127 A1 | 4/2013 | Mueller et al. |
| 2013/0116758 A1 | 5/2013 | Levinson et al. |
| 2013/0116759 A1 | 5/2013 | Levinson et al. |
| 2013/0123568 A1 | 5/2013 | Hamilton et al. |
| 2013/0123629 A1 | 5/2013 | Rosenberg et al. |
| 2013/0123764 A1 | 5/2013 | Zarsky et al. |
| 2013/0123765 A1 | 5/2013 | Zarsky et al. |
| 2013/0131764 A1 | 5/2013 | Grove |
| 2013/0137918 A1 | 5/2013 | Phillips et al. |
| 2013/0138193 A1 | 5/2013 | Durand et al. |
| 2013/0144106 A1 | 6/2013 | Phillips et al. |
| 2013/0144107 A1 | 6/2013 | Phillips et al. |
| 2013/0144108 A1 | 6/2013 | Phillips et al. |
| 2013/0144280 A1 | 6/2013 | Eckhouse et al. |
| 2013/0150650 A1 | 6/2013 | Phillips et al. |
| 2013/0150651 A1 | 6/2013 | Phillips et al. |
| 2013/0150653 A1 | 6/2013 | Borsody |
| 2013/0158440 A1 | 6/2013 | Allison |
| 2013/0158634 A1 | 6/2013 | Ron et al. |
| 2013/0158636 A1 | 6/2013 | Ting et al. |
| 2013/0172959 A1 | 7/2013 | Azoulay |
| 2013/0178693 A1 | 7/2013 | Neuvonen et al. |
| 2013/0178764 A1 | 7/2013 | Eckhouse et al. |
| 2013/0184693 A1 | 7/2013 | Neev |
| 2013/0190744 A1 | 7/2013 | Avram et al. |
| 2013/0190838 A1 | 7/2013 | Caparso |
| 2013/0218242 A1 | 8/2013 | Schomacker |
| 2013/0226275 A1 | 8/2013 | Duncan |
| 2013/0238043 A1 | 9/2013 | Beardall et al. |
| 2013/0238061 A1 | 9/2013 | Ron et al. |
| 2013/0238062 A1 | 9/2013 | Ron Edoute et al. |
| 2013/0238066 A1 | 9/2013 | Boggs, II et al. |
| 2013/0245731 A1 | 9/2013 | Allison |
| 2013/0253384 A1 | 9/2013 | Anderson et al. |
| 2013/0253493 A1 | 9/2013 | Anderson et al. |
| 2013/0253494 A1 | 9/2013 | Anderson et al. |
| 2013/0253495 A1 | 9/2013 | Anderson et al. |
| 2013/0253496 A1 | 9/2013 | Anderson et al. |
| 2013/0261374 A1 | 10/2013 | Elder |
| 2013/0261683 A1 | 10/2013 | Soikum et al. |
| 2013/0267759 A1 | 10/2013 | Jin |
| 2013/0267760 A1 | 10/2013 | Jin |
| 2013/0267943 A1 | 10/2013 | Hancock |
| 2013/0274841 A1 | 10/2013 | Eckhous et al. |
| 2013/0282085 A1 | 10/2013 | Lischinsky et al. |
| 2013/0282095 A1 | 10/2013 | Mignolet et al. |
| 2013/0289433 A1 | 10/2013 | Jin et al. |
| 2013/0303904 A1 | 11/2013 | Barthe et al. |
| 2013/0304159 A1 | 11/2013 | Simon et al. |
| 2013/0317281 A1 | 11/2013 | Schneider et al. |
| 2013/0317282 A1 | 11/2013 | Ron Edoute et al. |
| 2013/0317580 A1 | 11/2013 | Simon et al. |
| 2013/0331637 A1 | 12/2013 | Greff |
| 2013/0331913 A1 | 12/2013 | Levi et al. |
| 2013/0338424 A1 | 12/2013 | Pascual-Leone et al. |
| 2013/0338483 A1 | 12/2013 | Neuvonen et al. |
| 2014/0005645 A1 | 1/2014 | Ben-Haim et al. |
| 2014/0005758 A1 | 1/2014 | Ben-Yehuda et al. |
| 2014/0005759 A1 | 1/2014 | Fahey et al. |
| 2014/0005760 A1 | 1/2014 | Levinson et al. |
| 2014/0012064 A1 | 1/2014 | Riehl et al. |
| 2014/0018767 A1 | 1/2014 | Harris et al. |
| 2014/0024882 A1 | 1/2014 | Chornenky et al. |
| 2014/0025033 A1 | 1/2014 | Mirkov et al. |
| 2014/0025142 A1 | 1/2014 | Zarksy et al. |
| 2014/0046114 A1 | 2/2014 | Nishikawa et al. |
| 2014/0046232 A1 | 2/2014 | Sham et al. |
| 2014/0046339 A1 | 2/2014 | Bonuttti |
| 2014/0046423 A1 | 2/2014 | Rajguru et al. |
| 2014/0049377 A1 | 2/2014 | Krusor et al. |
| 2014/0051962 A1 | 2/2014 | Krusor et al. |
| 2014/0052029 A1 | 2/2014 | Khen et al. |
| 2014/0066786 A1 | 3/2014 | Naghavi et al. |
| 2014/0067010 A1 | 3/2014 | Sumners et al. |
| 2014/0067025 A1 | 3/2014 | Levinson et al. |
| 2014/0074203 A1 | 3/2014 | Na et al. |
| 2014/0081069 A1 | 3/2014 | Tai et al. |
| 2014/0081348 A1 | 3/2014 | Fischell |
| 2014/0081353 A1 | 3/2014 | Cook et al. |
| 2014/0081359 A1 | 3/2014 | Sand |
| 2014/0088674 A1 | 3/2014 | Bradley |
| 2014/0121446 A1 | 5/2014 | Phillips et al. |
| 2014/0135565 A9 | 5/2014 | Schneider |
| 2014/0141938 A1 | 5/2014 | Dristle |
| 2014/0142669 A1 | 5/2014 | Cook et al. |
| 2014/0148870 A1 | 5/2014 | Burnett |
| 2014/0163305 A1 | 6/2014 | Watterson |
| 2014/0179980 A1 | 6/2014 | Phillips et al. |
| 2014/0194790 A1 | 7/2014 | Crunick et al. |
| 2014/0194946 A1 | 7/2014 | Thomas et al. |
| 2014/0194958 A1 | 7/2014 | Chabal et al. |
| 2014/0200388 A1 | 7/2014 | Schneider et al. |
| 2014/0207217 A1 | 7/2014 | Lischinsky et al. |
| 2014/0213844 A1 | 7/2014 | Pilla et al. |
| 2014/0221725 A1 | 8/2014 | Mishelevich et al. |
| 2014/0221990 A1 | 8/2014 | Kreindel |
| 2014/0228620 A1 | 8/2014 | Vasishta |
| 2014/0235926 A1 | 8/2014 | Zangen et al. |
| 2014/0235927 A1 | 8/2014 | Zangen et al. |
| 2014/0235928 A1 | 8/2014 | Zangen et al. |
| 2014/0235929 A1 | 8/2014 | Rohan |
| 2014/0236139 A1 | 8/2014 | Payman |
| 2014/0236262 A1 | 8/2014 | You et al. |
| 2014/0243933 A1 | 8/2014 | Ginggen |
| 2014/0249352 A1 | 9/2014 | Zangen et al. |

(56) References Cited

U.S. PATENT DOCUMENTS

| | | |
|---|---|---|
| 2014/0249353 A1 | 9/2014 | Pesola et al. |
| 2014/0249355 A1 | 9/2014 | Martinez |
| 2014/0249601 A1 | 9/2014 | Bachinski et al. |
| 2014/0249609 A1 | 9/2014 | Zarsky et al. |
| 2014/0249613 A1 | 9/2014 | Kaib |
| 2014/0257071 A1 | 9/2014 | Curran et al. |
| 2014/0257145 A1 | 9/2014 | Emery |
| 2014/0257443 A1 | 9/2014 | Baker et al. |
| 2014/0276248 A1 | 9/2014 | Hall et al. |
| 2014/0276252 A1 | 9/2014 | Hyde et al. |
| 2014/0276357 A1 | 9/2014 | Sheftel et al. |
| 2014/0276693 A1 | 9/2014 | Altshuler et al. |
| 2014/0277219 A1 | 9/2014 | Nanda |
| 2014/0277302 A1 | 9/2014 | Weber et al. |
| 2014/0296933 A1 | 10/2014 | Haessler |
| 2014/0296934 A1 | 10/2014 | Gozani et al. |
| 2014/0303425 A1 | 10/2014 | Pilla et al. |
| 2014/0303525 A1 | 10/2014 | Sitharaman |
| 2014/0303682 A1 | 10/2014 | Siff |
| 2014/0303696 A1 | 10/2014 | Anderson et al. |
| 2014/0303697 A1 | 10/2014 | Anderson et al. |
| 2014/0309628 A1 | 10/2014 | Vaynberg et al. |
| 2014/0316188 A1 | 10/2014 | Peterchev et al. |
| 2014/0316310 A1 | 10/2014 | Ackermann et al. |
| 2014/0316393 A1 | 10/2014 | Levinson |
| 2014/0316485 A1 | 10/2014 | Ackermann et al. |
| 2014/0324118 A1 | 10/2014 | Simon et al. |
| 2014/0324120 A1 | 10/2014 | Bogie et al. |
| 2014/0330067 A1 | 11/2014 | Jordan |
| 2014/0330336 A1 | 11/2014 | Errico et al. |
| 2014/0336545 A1 | 11/2014 | Bonuttti |
| 2014/0336721 A1 | 11/2014 | Simon et al. |
| 2014/0336730 A1 | 11/2014 | Simon et al. |
| 2014/0336733 A1 | 11/2014 | Nebrigic et al. |
| 2014/0342428 A1 | 11/2014 | Goodwin et al. |
| 2014/0343351 A1 | 11/2014 | Tojo et al. |
| 2014/0350438 A1 | 11/2014 | Papirov et al. |
| 2014/0357935 A1 | 12/2014 | Ilmoniemi et al. |
| 2014/0364841 A1 | 12/2014 | Kornstein |
| 2014/0364920 A1 | 12/2014 | Doan et al. |
| 2014/0371515 A1 | 12/2014 | John |
| 2014/0371802 A1 | 12/2014 | Mashiach et al. |
| 2014/0371812 A1 | 12/2014 | Ackermann et al. |
| 2014/0378875 A1 | 12/2014 | Ron Edoute et al. |
| 2015/0005569 A1 | 1/2015 | Missoli |
| 2015/0005759 A1 | 1/2015 | Welches et al. |
| 2015/0005852 A1 | 1/2015 | Hershey et al. |
| 2015/0018667 A1 | 1/2015 | Radman et al. |
| 2015/0018692 A1 | 1/2015 | Neuvonen et al. |
| 2015/0018895 A1 | 1/2015 | El Achhab et al. |
| 2015/0018910 A1 | 1/2015 | Chen |
| 2015/0025299 A1 | 1/2015 | Ron et al. |
| 2015/0025545 A1 | 1/2015 | Grenon et al. |
| 2015/0038768 A1 | 2/2015 | Saitoh et al. |
| 2015/0073401 A1 | 3/2015 | Kreindel |
| 2015/0080769 A1 | 3/2015 | Lotsch |
| 2015/0087888 A1 | 3/2015 | Hurme et al. |
| 2015/0088105 A1 | 3/2015 | Fatemi |
| 2015/0088212 A1 | 3/2015 | De Ridder |
| 2015/0094788 A1 | 4/2015 | Pierenkemper |
| 2015/0100112 A1 | 4/2015 | Chang et al. |
| 2015/0112118 A1 | 4/2015 | Mishelevich et al. |
| 2015/0112412 A1 | 4/2015 | Anderson et al. |
| 2015/0119849 A1 | 4/2015 | Aronhalt et al. |
| 2015/0119949 A1 | 4/2015 | Tscherch et al. |
| 2015/0123661 A1 | 5/2015 | Yui et al. |
| 2015/0126914 A1 | 5/2015 | Crunick et al. |
| 2015/0127075 A1 | 5/2015 | Ward et al. |
| 2015/0133717 A1 | 5/2015 | Ghiron et al. |
| 2015/0133718 A1 | 5/2015 | Schneider et al. |
| 2015/0140633 A1 | 5/2015 | Vladila |
| 2015/0141877 A1 | 5/2015 | Feldman |
| 2015/0148858 A1 | 5/2015 | Kaib |
| 2015/0148877 A1 | 5/2015 | Thakkar et al. |
| 2015/0151137 A1 | 6/2015 | Hynninen et al. |
| 2015/0157873 A1 | 6/2015 | Sokolowski |
| 2015/0157874 A1 | 6/2015 | Aho et al. |
| 2015/0165186 A1 | 6/2015 | Dar et al. |
| 2015/0165226 A1 | 6/2015 | Simon et al. |
| 2015/0165232 A1 | 6/2015 | Altshuler et al. |
| 2015/0165238 A1 | 6/2015 | Slayton et al. |
| 2015/0174002 A1 | 6/2015 | Burbank et al. |
| 2015/0174399 A1 | 6/2015 | Moore |
| 2015/0190630 A1 | 7/2015 | Kent et al. |
| 2015/0190648 A1 | 7/2015 | Fischell et al. |
| 2015/0196772 A1 | 7/2015 | Ghiron et al. |
| 2015/0202428 A1 | 7/2015 | Miller |
| 2015/0202454 A1 | 7/2015 | Burnett |
| 2015/0209574 A1 | 7/2015 | Farhat et al. |
| 2015/0213724 A1 | 7/2015 | Shoshani |
| 2015/0216719 A1 | 8/2015 | DeBenedictis et al. |
| 2015/0216720 A1 | 8/2015 | DeBenedictis et al. |
| 2015/0216816 A1 | 8/2015 | O'Neil et al. |
| 2015/0217125 A1 | 8/2015 | Chornenky et al. |
| 2015/0217127 A1 | 8/2015 | Fischell et al. |
| 2015/0223975 A1 | 8/2015 | Anderson et al. |
| 2015/0224321 A1 | 8/2015 | Staeuber et al. |
| 2015/0227680 A1 | 8/2015 | Mainkar et al. |
| 2015/0238248 A1 | 8/2015 | Thompson et al. |
| 2015/0238771 A1 | 8/2015 | Zarsk et al. |
| 2015/0246238 A1 | 9/2015 | Moses et al. |
| 2015/0265830 A1 | 9/2015 | Simon et al. |
| 2015/0265836 A1 | 9/2015 | Simon et al. |
| 2015/0272776 A1 | 10/2015 | Gonzales et al. |
| 2015/0273220 A1 | 10/2015 | Osypka et al. |
| 2015/0283022 A1 | 10/2015 | Lee et al. |
| 2015/0283025 A1 | 10/2015 | Ledany |
| 2015/0283026 A1 | 10/2015 | Rosenberg |
| 2015/0283383 A1 | 10/2015 | Ternes et al. |
| 2015/0290028 A1 | 10/2015 | Isserow et al. |
| 2015/0297909 A1 | 10/2015 | Peashock |
| 2015/0306403 A1 | 10/2015 | Langer et al. |
| 2015/0306419 A1 | 10/2015 | Domankevitz |
| 2015/0314133 A1 | 11/2015 | Yamashiro |
| 2015/0328077 A1 | 11/2015 | Levinson |
| 2015/0328475 A1 | 11/2015 | Kim et al. |
| 2015/0335875 A1 | 11/2015 | Goldwasser et al. |
| 2015/0335877 A1 | 11/2015 | Jeffery et al. |
| 2015/0342661 A1 | 12/2015 | Ron Edoute |
| 2015/0342780 A1 | 12/2015 | Levinson et al. |
| 2015/0351690 A1 | 12/2015 | Toth et al. |
| 2015/0360045 A1 | 12/2015 | Fischell et al. |
| 2015/0367141 A1 | 12/2015 | Goetz et al. |
| 2015/0375005 A1 | 12/2015 | Segal |
| 2016/0001092 A1 | 1/2016 | Solehmainen |
| 2016/0008273 A1 | 1/2016 | Sheftel et al. |
| 2016/0008619 A1 | 1/2016 | Pell et al. |
| 2016/0015588 A1 | 1/2016 | Tamiya et al. |
| 2016/0015995 A1 | 1/2016 | Leung et al. |
| 2016/0016013 A1 | 1/2016 | Capelli et al. |
| 2016/0020070 A1 | 1/2016 | Kim et al. |
| 2016/0022349 A1 | 1/2016 | Woloszko et al. |
| 2016/0030763 A1 | 2/2016 | Midorikawa et al. |
| 2016/0038183 A1 | 2/2016 | Ignon et al. |
| 2016/0045728 A1 | 2/2016 | Lockwood et al. |
| 2016/0045755 A1 | 2/2016 | Chun et al. |
| 2016/0051401 A1 | 2/2016 | Yee et al. |
| 2016/0051827 A1 | 2/2016 | Ron et al. |
| 2016/0059027 A1 | 3/2016 | Zangen et al. |
| 2016/0066977 A1 | 3/2016 | Neal, II et al. |
| 2016/0066994 A1 | 3/2016 | Shanks |
| 2016/0067474 A1 | 3/2016 | Muessig et al. |
| 2016/0067516 A1 | 3/2016 | Schneider et al. |
| 2016/0067517 A1 | 3/2016 | Burnett |
| 2016/0067518 A1 | 3/2016 | Mishelevich et al. |
| 2016/0082253 A1 | 3/2016 | Moffitt et al. |
| 2016/0082290 A1 | 3/2016 | Hart |
| 2016/0086458 A1 | 3/2016 | Biggs |
| 2016/0089550 A1 | 3/2016 | Debenedictis et al. |
| 2016/0096025 A1 | 4/2016 | Moffitt et al. |
| 2016/0096032 A9 | 4/2016 | Schneider |
| 2016/0100977 A1 | 4/2016 | Lee et al. |
| 2016/0106982 A1 | 4/2016 | Cakmak et al. |
| 2016/0106994 A1 | 4/2016 | Crosby et al. |

(56)                 References Cited

U.S. PATENT DOCUMENTS

| | | |
|---|---|---|
| 2016/0106995 A1 | 4/2016 | Järnefelt et al. |
| 2016/0114181 A1 | 4/2016 | Vaynberg et al. |
| 2016/0121112 A1 | 5/2016 | Azar |
| 2016/0121118 A1 | 5/2016 | Franke et al. |
| 2016/0129273 A1 | 5/2016 | Park |
| 2016/0129274 A1 | 5/2016 | Park |
| 2016/0136415 A1 | 5/2016 | Bunch |
| 2016/0136462 A1 | 5/2016 | Lewis, Jr. et al. |
| 2016/0144175 A1 | 5/2016 | Simon et al. |
| 2016/0150494 A1 | 5/2016 | Tabet et al. |
| 2016/0151637 A1 | 6/2016 | Abe et al. |
| 2016/0158528 A1 | 6/2016 | Gonterman |
| 2016/0158548 A1 | 6/2016 | Ackermann et al. |
| 2016/0158571 A1 | 6/2016 | Goadsby et al. |
| 2016/0158574 A1 | 6/2016 | Eckhouse et al. |
| 2016/0175193 A1 | 6/2016 | Jung |
| 2016/0175605 A1 | 6/2016 | Borsody |
| 2016/0184585 A1 | 6/2016 | Kealey et al. |
| 2016/0184601 A1 | 6/2016 | Gleich et al. |
| 2016/0193006 A1 | 7/2016 | Azoulay |
| 2016/0193466 A1 | 7/2016 | Burnett |
| 2016/0206895 A1 | 7/2016 | Zangen et al. |
| 2016/0206896 A1 | 7/2016 | Zangen et al. |
| 2016/0213426 A1 | 7/2016 | Ben-Haim et al. |
| 2016/0213924 A1 | 7/2016 | Coleman et al. |
| 2016/0213943 A1 | 7/2016 | Mauger et al. |
| 2016/0213944 A1 | 7/2016 | Talebinejad et al. |
| 2016/0220834 A1 | 8/2016 | Schwarz |
| 2016/0220837 A1 | 8/2016 | Jin |
| 2016/0228178 A1 | 8/2016 | Lei |
| 2016/0228698 A1 | 8/2016 | Horton et al. |
| 2016/0236004 A1 | 8/2016 | Fischell et al. |
| 2016/0243375 A1 | 8/2016 | Simon et al. |
| 2016/0243376 A1 | 8/2016 | Phillips |
| 2016/0250494 A1 | 9/2016 | Sakaki et al. |
| 2016/0256685 A1 | 9/2016 | Haessler |
| 2016/0256689 A1 | 9/2016 | Vallejo et al. |
| 2016/0256702 A1 | 9/2016 | Schwarz et al. |
| 2016/0256703 A1 | 9/2016 | Schwarz et al. |
| 2016/0270951 A1 | 9/2016 | Martins et al. |
| 2016/0271392 A1 | 9/2016 | Vallejo et al. |
| 2016/0303393 A1 | 10/2016 | Riehl et al. |
| 2016/0310315 A1 | 10/2016 | Smith |
| 2016/0310756 A1 | 10/2016 | Boll et al. |
| 2016/0317346 A1 | 11/2016 | Kovach |
| 2016/0317803 A1 | 11/2016 | Sama |
| 2016/0317827 A1 | 11/2016 | Schwarz et al. |
| 2016/0324684 A1 | 11/2016 | Levinson et al. |
| 2016/0338900 A1 | 11/2016 | Khen et al. |
| 2016/0339239 A1 | 11/2016 | Yoo et al. |
| 2016/0346561 A1 | 12/2016 | Ron Edoute et al. |
| 2016/0346562 A1 | 12/2016 | Saitoh et al. |
| 2016/0354035 A1 | 12/2016 | Reihl et al. |
| 2016/0354237 A1 | 12/2016 | Gonzales et al. |
| 2016/0361560 A1 | 12/2016 | Bean |
| 2016/0367795 A1 | 12/2016 | Ackermann et al. |
| 2017/0001024 A1 | 1/2017 | Prouza |
| 2017/0001025 A1 | 1/2017 | Schwarz et al. |
| 2017/0001026 A1 | 1/2017 | Schwarz et al. |
| 2017/0001027 A1 | 1/2017 | Ladman et al. |
| 2017/0001028 A1 | 1/2017 | Ladman et al. |
| 2017/0001029 A1 | 1/2017 | Pribula et al. |
| 2017/0001030 A1 | 1/2017 | Pribula et al. |
| 2017/0007309 A1 | 1/2017 | Debenedictis et al. |
| 2017/0021188 A1 | 1/2017 | Lu |
| 2017/0027595 A1 | 2/2017 | Bonutti |
| 2017/0027596 A1 | 2/2017 | Bonutti |
| 2017/0028166 A1 | 2/2017 | Walpole et al. |
| 2017/0028212 A1 | 2/2017 | Roth et al. |
| 2017/0036019 A1 | 2/2017 | Matsushita |
| 2017/0043177 A1 | 2/2017 | Ron Edoute et al. |
| 2017/0049612 A1 | 2/2017 | Hussain et al. |
| 2017/0050019 A1 | 2/2017 | Ron Edoute et al. |
| 2017/0050038 A1 | 2/2017 | Cosman |
| 2017/0056651 A1 | 3/2017 | Li et al. |
| 2017/0071790 A1 | 3/2017 | Grenon et al. |
| 2017/0072212 A1 | 3/2017 | Ladman et al. |
| 2017/0087009 A1 | 3/2017 | Badawi et al. |
| 2017/0087373 A1 | 3/2017 | Schwarz |
| 2017/0095207 A1 | 4/2017 | Thomas et al. |
| 2017/0100585 A1 | 4/2017 | Hall et al. |
| 2017/0105869 A1 | 4/2017 | Frangineas, Jr. |
| 2017/0106201 A1 | 4/2017 | Schwarz et al. |
| 2017/0106203 A1 | 4/2017 | Schneider et al. |
| 2017/0112568 A1 | 4/2017 | Epstein |
| 2017/0113058 A1 | 4/2017 | Schneider |
| 2017/0120065 A1 | 5/2017 | Jiles et al. |
| 2017/0120066 A1 | 5/2017 | Phillips et al. |
| 2017/0120067 A1 | 5/2017 | Prouza |
| 2017/0136254 A1 | 5/2017 | Simon et al. |
| 2017/0143958 A1 | 5/2017 | Shalev et al. |
| 2017/0151436 A1 | 6/2017 | Flaherty et al. |
| 2017/0151443 A1 | 6/2017 | Mishelevich et al. |
| 2017/0156907 A1 | 6/2017 | Harris et al. |
| 2017/0156973 A1 | 6/2017 | Hart |
| 2017/0157397 A1 | 6/2017 | Lockwood et al. |
| 2017/0157398 A1 | 6/2017 | Wong et al. |
| 2017/0157430 A1 | 6/2017 | Cheatham, III et al. |
| 2017/0165470 A1 | 6/2017 | Jeffery |
| 2017/0165473 A1 | 6/2017 | Bihler et al. |
| 2017/0165497 A1 | 6/2017 | Lu |
| 2017/0171666 A1 | 6/2017 | Biggs |
| 2017/0173347 A1 | 6/2017 | Schwarz et al. |
| 2017/0182334 A1 | 6/2017 | Altshuler et al. |
| 2017/0182335 A1 | 6/2017 | Altshuler et al. |
| 2017/0189227 A1 | 7/2017 | Brunson et al. |
| 2017/0189703 A1 | 7/2017 | Lei |
| 2017/0189704 A1 | 7/2017 | Palero et al. |
| 2017/0189707 A1 | 7/2017 | Zabara |
| 2017/0196731 A1 | 7/2017 | Debenedictis et al. |
| 2017/0197077 A1 | 7/2017 | Harpak et al. |
| 2017/0203117 A1 | 7/2017 | Biginton |
| 2017/0209708 A1 | 7/2017 | Schwarz |
| 2017/0216593 A1 | 8/2017 | Lee |
| 2017/0232267 A1 | 8/2017 | Riehl et al. |
| 2017/0239079 A1 | 8/2017 | Root et al. |
| 2017/0239467 A1 | 8/2017 | Shalev et al. |
| 2017/0252574 A1 | 9/2017 | Cabrerizo et al. |
| 2017/0259065 A1 | 9/2017 | Baru et al. |
| 2017/0259077 A1 | 9/2017 | Jin |
| 2017/0266443 A1 | 9/2017 | Rajguru et al. |
| 2017/0266460 A1 | 9/2017 | Upton et al. |
| 2017/0266461 A1 | 9/2017 | Boll et al. |
| 2017/0274210 A1 | 9/2017 | Papay |
| 2017/0280889 A1 | 10/2017 | Koch |
| 2017/0281935 A1 | 10/2017 | De Oliveira et al. |
| 2017/0290708 A1 | 10/2017 | Rapp |
| 2017/0291036 A1 | 10/2017 | Pell et al. |
| 2017/0296837 A1 | 10/2017 | Jin |
| 2017/0296838 A1 | 10/2017 | Asahina et al. |
| 2017/0304614 A1 | 10/2017 | Yoo et al. |
| 2017/0304641 A1 | 10/2017 | Eisenmann et al. |
| 2017/0304642 A1 | 10/2017 | Ron Edoute et al. |
| 2017/0304645 A1 | 10/2017 | Schomacker et al. |
| 2017/0312536 A1 | 11/2017 | Phillips et al. |
| 2017/0319378 A1 | 11/2017 | Anderson et al. |
| 2017/0325992 A1 | 11/2017 | Debenedictis et al. |
| 2017/0325993 A1 | 11/2017 | Jimenez et al. |
| 2017/0326042 A1 | 11/2017 | Zeng et al. |
| 2017/0326346 A1 | 11/2017 | Jimenez et al. |
| 2017/0326357 A1 | 11/2017 | Sacristan et al. |
| 2017/0326377 A1 | 11/2017 | Neuvonen et al. |
| 2017/0333705 A1 | 11/2017 | Schwarz |
| 2017/0333725 A1 | 11/2017 | Hotani |
| 2017/0340385 A1 | 11/2017 | Reinhard et al. |
| 2017/0340884 A1 | 11/2017 | Franke et al. |
| 2017/0340894 A1 | 11/2017 | Rohan |
| 2017/0348143 A1 | 12/2017 | Rosen et al. |
| 2017/0348539 A1 | 12/2017 | Schwarz et al. |
| 2017/0354530 A1 | 12/2017 | Shagdar et al. |
| 2017/0354818 A1 | 12/2017 | De Toni et al. |
| 2017/0361095 A1 | 12/2017 | Mueller et al. |
| 2017/0368332 A1 | 12/2017 | Ackermann et al. |
| 2017/0368366 A1 | 12/2017 | Lowin |

(56) References Cited

U.S. PATENT DOCUMENTS

| | | |
|---|---|---|
| 2017/0372006 A1 | 12/2017 | Mainkar et al. |
| 2018/0000347 A1 | 1/2018 | Perez et al. |
| 2018/0000533 A1 | 1/2018 | Boll et al. |
| 2018/0001101 A1 | 1/2018 | Hulings et al. |
| 2018/0001106 A1 | 1/2018 | Schwarz |
| 2018/0001107 A1 | 1/2018 | Schwarz et al. |
| 2018/0021565 A1 | 1/2018 | Dar et al. |
| 2018/0028831 A1 | 2/2018 | Ron Edoute et al. |
| 2018/0036548 A1 | 2/2018 | Nusse |
| 2018/0043151 A1 | 2/2018 | Ejiri et al. |
| 2018/0043175 A1 | 2/2018 | Karpf |
| 2018/0056083 A1 | 3/2018 | Jin |
| 2018/0064575 A1 | 3/2018 | Vaynberg et al. |
| 2018/0064950 A1 | 3/2018 | Segal |
| 2018/0064952 A1 | 3/2018 | Zangen et al. |
| 2018/0071544 A1 | 3/2018 | Ghiron et al. |
| 2018/0071545 A1 | 3/2018 | Saitoh et al. |
| 2018/0085580 A1 | 3/2018 | Perez et al. |
| 2018/0099141 A1 | 4/2018 | Chang |
| 2018/0103991 A1 | 4/2018 | Linhart et al. |
| 2018/0104484 A1 | 4/2018 | Ryaby et al. |
| 2018/0104504 A1 | 4/2018 | Jin et al. |
| 2018/0116905 A1 | 5/2018 | Capelli et al. |
| 2018/0116906 A1 | 5/2018 | Hirashiki et al. |
| 2018/0117322 A1 | 5/2018 | Chang et al. |
| 2018/0117352 A1 | 5/2018 | Rastogi et al. |
| 2018/0125416 A1 | 5/2018 | Schwarz et al. |
| 2018/0126184 A1 | 5/2018 | Phillips et al. |
| 2018/0133473 A1 | 5/2018 | Yoo et al. |
| 2018/0133478 A1 | 5/2018 | Caparso et al. |
| 2018/0133490 A1 | 5/2018 | Taff et al. |
| 2018/0133498 A1 | 5/2018 | Chornenky et al. |
| 2018/0140860 A1 | 5/2018 | Ledany |
| 2018/0153736 A1 | 6/2018 | Mills et al. |
| 2018/0153760 A1 | 6/2018 | Rosen et al. |
| 2018/0154137 A1 | 6/2018 | Ackermann et al. |
| 2018/0154165 A1 | 6/2018 | Schneider |
| 2018/0154188 A1 | 6/2018 | Altshuler et al. |
| 2018/0161197 A1 | 6/2018 | Baker et al. |
| 2018/0171327 A1 | 6/2018 | Goodwin et al. |
| 2018/0177996 A1 | 6/2018 | Gozani et al. |
| 2018/0178026 A1 | 6/2018 | Riehl et al. |
| 2018/0185081 A1 | 7/2018 | O'Neil et al. |
| 2018/0185189 A1 | 7/2018 | Weber et al. |
| 2018/0192942 A1 | 7/2018 | Clark et al. |
| 2018/0193640 A1 | 7/2018 | Murphy et al. |
| 2018/0200503 A1 | 7/2018 | Ryaby et al. |
| 2018/0214300 A1 | 8/2018 | Anderson et al. |
| 2018/0221660 A1 | 8/2018 | Suri et al. |
| 2018/0228646 A1 | 8/2018 | Gonzales et al. |
| 2018/0229048 A1 | 8/2018 | Sikora et al. |
| 2018/0229049 A1 | 8/2018 | Phillips et al. |
| 2018/0236254 A1 | 8/2018 | Schwarz et al. |
| 2018/0250056 A1 | 9/2018 | Avram et al. |
| 2018/0250521 A1 | 9/2018 | Wölfel et al. |
| 2018/0256887 A1 | 9/2018 | Wingeier et al. |
| 2018/0256906 A1 | 9/2018 | Pivonka et al. |
| 2018/0263677 A1 | 9/2018 | Hilton et al. |
| 2018/0264245 A1 | 9/2018 | Edwards et al. |
| 2018/0271767 A1 | 9/2018 | Jimenez et al. |
| 2018/0272118 A1 | 9/2018 | Goldwasser et al. |
| 2018/0280711 A1 | 10/2018 | Sekino et al. |
| 2018/0280714 A1 | 10/2018 | Souder |
| 2018/0289533 A1 | 10/2018 | Johnson et al. |
| 2018/0296831 A1 | 10/2018 | Matsushita |
| 2018/0304079 A1 | 10/2018 | Kim et al. |
| 2018/0310950 A1 | 11/2018 | Yee et al. |
| 2018/0318597 A1 | 11/2018 | Simon et al. |
| 2018/0325729 A1 | 11/2018 | Rynerson |
| 2018/0333576 A1 | 11/2018 | Rigaux |
| 2018/0339151 A1 | 11/2018 | De Toni et al. |
| 2018/0339168 A1 | 11/2018 | Cobley et al. |
| 2018/0345012 A1 | 12/2018 | Schwarz et al. |
| 2018/0345014 A1 | 12/2018 | Gozani et al. |
| 2018/0345032 A1 | 12/2018 | Lu |
| 2018/0345833 A1 | 12/2018 | Gallagher et al. |
| 2018/0353767 A1 | 12/2018 | Biginton |
| 2018/0361154 A1 | 12/2018 | Levin |
| 2018/0368593 A1 | 12/2018 | Bourgeois |
| 2018/0369062 A1 | 12/2018 | Khen et al. |
| 2018/0369601 A1 | 12/2018 | Saitoh et al. |
| 2019/0000524 A1 | 1/2019 | Rosen et al. |
| 2019/0000529 A1 | 1/2019 | Kothare et al. |
| 2019/0000663 A1 | 1/2019 | Anderson et al. |
| 2019/0001139 A1 | 1/2019 | Mishra et al. |
| 2019/0009101 A1 | 1/2019 | Neuwirth |
| 2019/0015661 A1 | 1/2019 | Leonhardt et al. |
| 2019/0022392 A1 | 1/2019 | Franke et al. |
| 2019/0029876 A1 | 1/2019 | Anderson et al. |
| 2019/0030356 A1 | 1/2019 | Schwarz |
| 2019/0046791 A1 | 2/2019 | Ebbers et al. |
| 2019/0046810 A1 | 2/2019 | Carmeli et al. |
| 2019/0053870 A1 | 2/2019 | Azoulay |
| 2019/0053871 A1 | 2/2019 | Moosmann et al. |
| 2019/0053940 A1 | 2/2019 | Biser et al. |
| 2019/0053941 A1 | 2/2019 | Samson |
| 2019/0053967 A1 | 2/2019 | Moosmann et al. |
| 2019/0054306 A1 | 2/2019 | Steinke et al. |
| 2019/0060646 A1 | 2/2019 | Ng et al. |
| 2019/0060659 A1 | 2/2019 | Ginhoux et al. |
| 2019/0070428 A1 | 3/2019 | Phillips et al. |
| 2019/0099599 A1 | 4/2019 | Kreindel |
| 2019/0111255 A1 | 4/2019 | Errico et al. |
| 2019/0111273 A1 | 4/2019 | Ghiron et al. |
| 2019/0117965 A1 | 4/2019 | Iger et al. |
| 2019/0117966 A1 | 4/2019 | Kent |
| 2019/0117967 A1 | 4/2019 | Scheiner |
| 2019/0125442 A1 | 5/2019 | Hancock et al. |
| 2019/0125477 A1 | 5/2019 | Azoulay |
| 2019/0126036 A1 | 5/2019 | Franco-Obregon et al. |
| 2019/0126041 A1 | 5/2019 | Kerselaers |
| 2019/0126055 A1 | 5/2019 | Etkin et al. |
| 2019/0133673 A1 | 5/2019 | Boll et al. |
| 2019/0134390 A1 | 5/2019 | Shimada et al. |
| 2019/0134414 A1 | 5/2019 | Prouza et al. |
| 2019/0143116 A1 | 5/2019 | Mowery et al. |
| 2019/0151604 A1 | 5/2019 | Harper et al. |
| 2019/0151655 A1 | 5/2019 | Hall et al. |
| 2019/0151657 A1 | 5/2019 | Tyulmankov et al. |
| 2019/0160286 A1 | 5/2019 | Yang et al. |
| 2019/0167978 A1 | 6/2019 | Ackermann et al. |
| 2019/0168012 A1 | 6/2019 | Biginton |
| 2019/0183562 A1 | 6/2019 | Widgerow |
| 2019/0184171 A1 | 6/2019 | Mustakos et al. |
| 2019/0192219 A1 | 6/2019 | Kreindel |
| 2019/0192853 A1 | 6/2019 | Kim et al. |
| 2019/0192872 A1 | 6/2019 | Schwarz et al. |
| 2019/0192873 A1 | 6/2019 | Schwarz et al. |
| 2019/0192874 A1 | 6/2019 | Shukla |
| 2019/0192875 A1 | 6/2019 | Schwarz et al. |
| 2019/0201280 A1 | 7/2019 | Bak et al. |
| 2019/0201705 A1 | 7/2019 | Schwarz et al. |
| 2019/0201706 A1 | 7/2019 | Schwarz et al. |
| 2019/0206545 A1 | 7/2019 | Mainkar et al. |
| 2019/0209836 A1 | 7/2019 | Yakoub et al. |
| 2019/0209856 A1 | 7/2019 | Segal |
| 2019/0217090 A1 | 7/2019 | Ryaby et al. |
| 2019/0217114 A1* | 7/2019 | Luzi ........................ A61N 2/02 |
| 2019/0224490 A1 | 7/2019 | Goadsby et al. |
| 2019/0240486 A1 | 8/2019 | Simon et al. |
| 2019/0247654 A1 | 8/2019 | Alyagon et al. |
| 2019/0254911 A1 | 8/2019 | Brask |
| 2019/0255346 A1 | 8/2019 | Ghiron |
| 2019/0255347 A1 | 8/2019 | Masotti et al. |
| 2019/0269909 A1 | 9/2019 | Gozani et al. |
| 2019/0269931 A1 | 9/2019 | Riehl et al. |
| 2019/0275320 A1 | 9/2019 | Kim et al. |
| 2019/0282804 A1 | 9/2019 | Ackermann et al. |
| 2019/0290533 A1 | 9/2019 | Le et al. |
| 2019/0290537 A1 | 9/2019 | Engles et al. |
| 2019/0290925 A1 | 9/2019 | Gellman et al. |
| 2019/0290928 A1 | 9/2019 | Biginton |
| 2019/0298998 A1 | 10/2019 | Coleman et al. |
| 2019/0299016 A1 | 10/2019 | Altman |

(56) References Cited

U.S. PATENT DOCUMENTS

| | | |
|---|---|---|
| 2019/0299018 A1 | 10/2019 | Chornenky et al. |
| 2019/0308029 A1 | 10/2019 | Ho |
| 2019/0314629 A1 | 10/2019 | Kreindel |
| 2019/0314638 A1 | 10/2019 | Kreindel |
| 2019/0328478 A1 | 10/2019 | Schuele |
| 2019/0329065 A1 | 10/2019 | Gandel |
| 2019/0336196 A1 | 11/2019 | Wolf et al. |
| 2019/0336765 A1 | 11/2019 | Charlesworth et al. |
| 2019/0336782 A1 | 11/2019 | Shealy et al. |
| 2019/0336783 A1 | 11/2019 | Sokolowski |
| 2019/0336787 A1 | 11/2019 | Kweon et al. |
| 2019/0343714 A1 | 11/2019 | Gordon |
| 2019/0344089 A1 | 11/2019 | Jadwizak et al. |
| 2019/0344091 A1 | 11/2019 | Fischer |
| 2019/0350646 A1 | 11/2019 | Kreindel |
| 2019/0358465 A1 | 11/2019 | Segal |
| 2019/0358466 A1 | 11/2019 | Leung et al. |
| 2019/0365462 A1 | 12/2019 | Casalino et al. |
| 2019/0366076 A1 | 12/2019 | Simon et al. |
| 2019/0374773 A1 | 12/2019 | Simon et al. |
| 2019/0381314 A1 | 12/2019 | Howard |
| 2019/0388697 A1 | 12/2019 | Pell et al. |
| 2019/0388698 A1 | 12/2019 | Schwarz et al. |
| 2020/0000428 A1* | 1/2020 | Kim ..................... A61B 8/4209 |
| 2020/0001103 A1 | 1/2020 | Schwarz et al. |
| 2020/0016401 A1 | 1/2020 | Papay et al. |
| 2020/0016422 A1 | 1/2020 | Ron Edoute et al. |
| 2020/0016423 A1 | 1/2020 | Ron Edoute et al. |
| 2020/0022866 A1 | 1/2020 | Cohen et al. |
| 2020/0030622 A1 | 1/2020 | Weyh et al. |
| 2020/0030655 A1 | 1/2020 | Wu et al. |
| 2020/0037079 A1 | 1/2020 | Biggs |
| 2020/0037080 A1 | 1/2020 | Biggs |
| 2020/0038674 A1 | 2/2020 | John |
| 2020/0038675 A1 | 2/2020 | Neuvonen et al. |
| 2020/0054395 A1 | 2/2020 | Marchitto et al. |
| 2020/0054519 A1 | 2/2020 | Engles et al. |
| 2020/0054890 A1 | 2/2020 | Schwarz et al. |
| 2020/0061385 A1 | 2/2020 | Schwarz et al. |
| 2020/0061386 A1 | 2/2020 | Schwarz et al. |
| 2020/0078212 A1 | 3/2020 | Seo et al. |
| 2020/0078599 A1 | 3/2020 | Chen et al. |
| 2020/0086123 A1 | 3/2020 | Kibler et al. |
| 2020/0086134 A1 | 3/2020 | Johnson et al. |
| 2020/0086314 A1 | 3/2020 | Wang et al. |
| 2020/0093297 A1 | 3/2020 | Dennewald |
| 2020/0094066 A1 | 3/2020 | Heath |
| 2020/0100837 A1 | 4/2020 | Ben-Haim et al. |
| 2020/0100932 A1 | 4/2020 | Hermanson et al. |
| 2020/0101291 A1 | 4/2020 | Yakovlev et al. |
| 2020/0101308 A1 | 4/2020 | Ilmoniemi et al. |
| 2020/0108266 A1 | 4/2020 | Chou |
| 2020/0114160 A1 | 4/2020 | Blendermann |
| 2020/0114161 A1 | 4/2020 | Fox et al. |
| 2020/0121924 A1 | 4/2020 | Sama |
| 2020/0121984 A1 | 4/2020 | Sama |
| 2020/0129759 A1 | 4/2020 | Schwarz |
| 2020/0138540 A1 | 5/2020 | Azoulay |
| 2020/0139148 A1 | 5/2020 | Schwarz et al. |
| 2020/0146881 A1 | 5/2020 | Linder et al. |
| 2020/0147392 A1 | 5/2020 | Doan et al. |
| 2020/0155221 A1 | 5/2020 | Marchitto et al. |
| 2020/0155841 A1 | 5/2020 | Bhagat et al. |
| 2020/0155866 A1 | 5/2020 | Lu |
| 2020/0163827 A1 | 5/2020 | Hart |
| 2020/0171297 A1 | 6/2020 | Kirson et al. |
| 2020/0179690 A1 | 6/2020 | Schepis et al. |
| 2020/0197696 A1 | 6/2020 | Nagel et al. |
| 2020/0197717 A1 | 6/2020 | Ishikawa et al. |
| 2020/0206522 A1 | 7/2020 | Riehl et al. |
| 2020/0206524 A1 | 7/2020 | Katznelson et al. |
| 2020/0214569 A1 | 7/2020 | Kim |
| 2020/0222069 A1 | 7/2020 | Bonutti |
| 2020/0222708 A1 | 7/2020 | Simon et al. |
| 2020/0230400 A1 | 7/2020 | Shepherd et al. |
| 2020/0230431 A1 | 7/2020 | Saitoh et al. |
| 2020/0237424 A1 | 7/2020 | Hunziker et al. |
| 2020/0237612 A1 | 7/2020 | Liu et al. |
| 2020/0238076 A1 | 7/2020 | Ackermann et al. |
| 2020/0238098 A1 | 7/2020 | Chornenky et al. |
| 2020/0246617 A1 | 8/2020 | Errico et al. |
| 2020/0251203 A1 | 8/2020 | Mainkar et al. |
| 2020/0254256 A1 | 8/2020 | Moffitt et al. |
| 2020/0268597 A1 | 8/2020 | Gordon |
| 2020/0269062 A1 | 8/2020 | Chou |
| 2020/0276435 A1 | 9/2020 | Ryaby et al. |
| 2020/0281642 A1 | 9/2020 | Kreindel |
| 2020/0281813 A1 | 9/2020 | Chao |
| 2020/0289826 A1 | 9/2020 | Leonhardt |
| 2020/0289837 A1 | 9/2020 | Lowin et al. |
| 2020/0289838 A1 | 9/2020 | Schwarz et al. |
| 2020/0297995 A1 | 9/2020 | Toong et al. |
| 2020/0306554 A1 | 10/2020 | Ron Edoute et al. |
| 2020/0316379 A1 | 10/2020 | Yoo et al. |
| 2020/0316396 A1 | 10/2020 | Jin |
| 2020/0323680 A1 | 10/2020 | Hussain et al. |
| 2020/0324133 A1 | 10/2020 | Schwarz et al. |
| 2020/0330782 A1 | 10/2020 | Zabara |
| 2020/0346010 A1 | 11/2020 | Papay et al. |
| 2020/0346024 A1 | 11/2020 | Caparso et al. |
| 2020/0352633 A1 | 11/2020 | Treen et al. |
| 2020/0353244 A1 | 11/2020 | Yamazaki |
| 2020/0353256 A1 | 11/2020 | Vallejo et al. |
| 2020/0353273 A1 | 11/2020 | Zucco |
| 2020/0353274 A1 | 11/2020 | Ansari et al. |
| 2020/0360681 A1 | 11/2020 | Lay |
| 2020/0376263 A1 | 12/2020 | Zhu |
| 2020/0384281 A1 | 12/2020 | Jin et al. |
| 2020/0390997 A1 | 12/2020 | Jovanov |
| 2020/0398055 A1 | 12/2020 | Flaherty et al. |
| 2020/0398057 A1 | 12/2020 | Esteller et al. |
| 2020/0398070 A1 | 12/2020 | Phillips et al. |
| 2020/0406050 A1 | 12/2020 | Casanova et al. |
| 2021/0001139 A1 | 1/2021 | Shukla |
| 2021/0007668 A1 | 1/2021 | Leaper |
| 2021/0008369 A1 | 1/2021 | Crosson |
| 2021/0008382 A1 | 1/2021 | Vaidya |
| 2021/0015552 A1 | 1/2021 | Curran et al. |
| 2021/0022914 A1 | 1/2021 | Badawi et al. |
| 2021/0023364 A1 | 1/2021 | Shalev et al. |
| 2021/0023365 A1 | 1/2021 | Lo et al. |
| 2021/0023380 A1 | 1/2021 | Zheng et al. |
| 2021/0023382 A1 | 1/2021 | Kirk et al. |
| 2021/0031040 A1 | 2/2021 | Franke et al. |
| 2021/0038891 A1 | 2/2021 | Goldfarb |
| 2021/0038894 A1 | 2/2021 | Mowery et al. |
| 2021/0038907 A1 | 2/2021 | Riehl |
| 2021/0052216 A1 | 2/2021 | Badawi |
| 2021/0052893 A1 | 2/2021 | Suri et al. |
| 2021/0052894 A1 | 2/2021 | Sanderford |
| 2021/0052910 A1 | 2/2021 | Carter et al. |
| 2021/0052911 A1 | 2/2021 | Fischer |
| 2021/0065590 A1 | 3/2021 | Huang et al. |
| 2021/0093858 A1 | 4/2021 | Thakkar et al. |
| 2021/0093880 A1 | 4/2021 | Zhong et al. |
| 2021/0106429 A1 | 4/2021 | Pacca |
| 2021/0106824 A1 | 4/2021 | Caparso et al. |
| 2021/0106842 A1 | 4/2021 | Zangen et al. |
| 2021/0138232 A1 | 5/2021 | Paz et al. |
| 2021/0146119 A1 | 5/2021 | Prouza et al. |
| 2021/0146150 A1 | 5/2021 | Frangineas, Jr. et al. |
| 2021/0146151 A1 | 5/2021 | Phillips et al. |
| 2021/0161590 A1 | 6/2021 | Kreindel |
| 2021/0162211 A1 | 6/2021 | Chase et al. |
| 2021/0169325 A1 | 6/2021 | Thomas et al. |
| 2021/0169682 A1 | 6/2021 | Alvarez et al. |
| 2021/0170188 A1 | 6/2021 | Paulus |
| 2021/0170189 A1 | 6/2021 | Souder |
| 2021/0178174 A1 | 6/2021 | Lowin et al. |
| 2021/0186330 A1 | 6/2021 | Hall et al. |
| 2021/0187278 A1 | 6/2021 | Lu |
| 2021/0196197 A1 | 7/2021 | Leaper |
| 2021/0196957 A1 | 7/2021 | Yakovlev et al. |
| 2021/0205131 A1 | 7/2021 | Grenon et al. |

(56) References Cited

U.S. PATENT DOCUMENTS

| | | |
|---|---|---|
| 2021/0205631 A1 | 7/2021 | Ghiron et al. |
| 2021/0212634 A1 | 7/2021 | Leaper |
| 2021/0213283 A1 | 7/2021 | Yoo et al. |
| 2021/0219062 A1 | 7/2021 | Biggs |
| 2021/0228898 A1 | 7/2021 | Ghiron |
| 2021/0235901 A1 | 8/2021 | Dennewald |
| 2021/0236809 A1 | 8/2021 | Ackermann et al. |
| 2021/0260369 A1 | 8/2021 | Steier |
| 2021/0260398 A1 | 8/2021 | Bilston et al. |
| 2021/0268299 A1 | 9/2021 | Casalino et al. |
| 2021/0268300 A1 | 9/2021 | Peled |
| 2021/0275747 A1 | 9/2021 | Sobel et al. |
| 2021/0275825 A1 | 9/2021 | Kreindel |
| 2021/0283395 A1 | 9/2021 | Kreindel |
| 2021/0283411 A1 | 9/2021 | Dietz |
| 2021/0283412 A1 | 9/2021 | Neuvonen et al. |
| 2021/0290969 A1 | 9/2021 | Shukla |
| 2021/0298817 A1 | 9/2021 | Schwarz et al. |
| 2021/0299420 A1 | 9/2021 | Sobel et al. |
| 2021/0299446 A1 | 9/2021 | Errico et al. |
| 2021/0330102 A1 | 10/2021 | Monico |
| 2021/0330987 A1 | 10/2021 | Sun et al. |
| 2021/0353940 A1 | 11/2021 | Lim et al. |
| 2021/0361343 A1 | 11/2021 | Gershonowitz |
| 2021/0361938 A1 | 11/2021 | Gershonowitz |
| 2021/0361939 A1 | 11/2021 | Müller-Bruhn |
| 2021/0361964 A1 | 11/2021 | Pargger et al. |
| 2021/0361965 A1 | 11/2021 | Yakobson et al. |
| 2021/0361967 A1 | 11/2021 | Cohen et al. |
| 2021/0369381 A1 | 12/2021 | Azoulay |
| 2021/0386992 A1 | 12/2021 | Simon et al. |
| 2022/0001168 A1 | 1/2022 | Ko et al. |
| 2022/0001175 A1 | 1/2022 | Ko et al. |
| 2022/0003112 A1 | 1/2022 | Leach et al. |
| 2022/0008244 A1 | 1/2022 | Hart et al. |
| 2022/0008741 A1 | 1/2022 | Chornenky et al. |
| 2022/0015942 A1 | 1/2022 | Biser |
| 2022/0016413 A1 | 1/2022 | John et al. |
| 2022/0023654 A1 | 1/2022 | Carmeli et al. |
| 2022/0031408 A1 | 2/2022 | Cai et al. |
| 2022/0032052 A1 | 2/2022 | Kent |
| 2022/0032079 A1 | 2/2022 | Riehl et al. |
| 2022/0036584 A1 | 2/2022 | Sun et al. |
| 2022/0037071 A1 | 2/2022 | Kim et al. |
| 2022/0040491 A1 | 2/2022 | Sun et al. |
| 2022/0062622 A1 | 3/2022 | Errico et al. |
| 2022/0062634 A1 | 3/2022 | Masko et al. |
| 2022/0079502 A1 | 3/2022 | Simon et al. |
| 2022/0079811 A1 | 3/2022 | Kleinman Ben Tsvi et al. |
| 2022/0080217 A1 | 3/2022 | Peterchev et al. |
| 2022/0096146 A1 | 3/2022 | Vaynberg et al. |
| 2022/0111223 A1 | 4/2022 | Taylor et al. |
| 2022/0125546 A1 | 4/2022 | Azoulay |
| 2022/0126095 A1 | 4/2022 | Rajguru et al. |
| 2022/0126109 A1 | 4/2022 | Katznelson et al. |
| 2022/0152379 A1 | 5/2022 | Frangineas, Jr. et al. |
| 2022/0152394 A1 | 5/2022 | Levin |
| 2022/0152409 A1 | 5/2022 | Frangineas, Jr. et al. |
| 2022/0161042 A1 | 5/2022 | Lu |
| 2022/0161043 A1 | 5/2022 | Phillips et al. |
| 2022/0161044 A1 | 5/2022 | Phillips et al. |
| 2022/0168136 A1 | 6/2022 | Badawi et al. |
| 2022/0168584 A1 | 6/2022 | Schwarz et al. |
| 2022/0176101 A1 | 6/2022 | Ryaby et al. |
| 2022/0176114 A1 | 6/2022 | Shalev et al. |
| 2022/0176142 A1 | 6/2022 | Ghiron et al. |
| 2022/0176144 A1 | 6/2022 | Velasco Valcke |
| 2022/0184379 A1 | 6/2022 | Lindenthaler et al. |
| 2022/0184389 A1 | 6/2022 | Shalev et al. |
| 2022/0184390 A1 | 6/2022 | Johari et al. |
| 2022/0184409 A1 | 6/2022 | Schwarz et al. |
| 2022/0192580 A1 | 6/2022 | Toth et al. |
| 2022/0193437 A1 | 6/2022 | Leung et al. |
| 2022/0203112 A1 | 6/2022 | Iger et al. |
| 2022/0211325 A1 | 7/2022 | Malish |
| 2022/0211573 A1 | 7/2022 | Capelli et al. |
| 2022/0212006 A1 | 7/2022 | Rondoni et al. |
| 2022/0226645 A1 | 7/2022 | Shalev et al. |
| 2022/0226646 A1 | 7/2022 | Shalev et al. |
| 2022/0226647 A1 | 7/2022 | Shalev et al. |
| 2022/0226648 A1 | 7/2022 | Shalev et al. |
| 2022/0226649 A1 | 7/2022 | Shalev et al. |
| 2022/0226662 A1 | 7/2022 | Casalino et al. |
| 2022/0233851 A1 | 7/2022 | Shalev et al. |
| 2022/0241107 A1 | 8/2022 | Kim et al. |
| 2022/0241604 A1 | 8/2022 | Lee |
| 2022/0241605 A1 | 8/2022 | Tortolero et al. |
| 2022/0249836 A1 | 8/2022 | Schwarz et al. |
| 2022/0266008 A1 | 8/2022 | Saltis |
| 2022/0273962 A1 | 9/2022 | Prouza et al. |
| 2022/0280785 A1 | 9/2022 | Rynerson |
| 2022/0280799 A1 | 9/2022 | Altman |
| 2022/0288409 A1 | 9/2022 | Järnefelt |
| 2022/0362570 A1 | 11/2022 | Pemberton |
| 2022/0370006 A1 | 11/2022 | Zieger |
| 2022/0370814 A1 | 11/2022 | Epshtein et al. |
| 2022/0370818 A1 | 11/2022 | Taylor et al. |
| 2022/0378359 A1 | 12/2022 | Simon et al. |
| 2022/0379114 A1 | 12/2022 | Kent |
| 2022/0379132 A1 | 12/2022 | Ring et al. |
| 2022/0395681 A1 | 12/2022 | Martinot |
| 2022/0401256 A1 | 12/2022 | Durand |
| 2023/0001181 A1 | 1/2023 | Paz et al. |
| 2023/0001224 A1 | 1/2023 | Shukla |
| 2023/0013787 A1 | 1/2023 | Sitt et al. |
| 2023/0043685 A1 | 2/2023 | Helekar et al. |
| 2023/0050715 A1 | 2/2023 | Murphy et al. |
| 2023/0059748 A1 | 2/2023 | Simon et al. |
| 2023/0065587 A1 | 3/2023 | Shnaiderman et al. |
| 2023/0079691 A1 | 3/2023 | Schwarz et al. |
| 2023/0092226 A1 | 3/2023 | Ko et al. |
| 2023/0108122 A1 | 4/2023 | Click et al. |
| 2023/0111038 A1 | 4/2023 | Talebinejad et al. |
| 2023/0114732 A1 | 4/2023 | Talebinejad et al. |
| 2023/0123145 A1 | 4/2023 | Ko |
| 2023/0124830 A1 | 4/2023 | Doan et al. |
| 2023/0125236 A1 | 4/2023 | Sandell et al. |
| 2023/0128482 A1 | 4/2023 | Gayes et al. |
| 2023/0130856 A1 | 4/2023 | Sandell et al. |
| 2023/0148962 A1 | 5/2023 | Leaper |
| 2023/0165721 A1 | 6/2023 | Kleinman Ben Tsvi et al. |
| 2023/0173294 A1 | 6/2023 | Lu et al. |
| 2023/0191076 A1 | 6/2023 | Lee et al. |
| 2023/0191144 A1 | 6/2023 | Ko |
| 2023/0200904 A1 | 6/2023 | Brockett et al. |
| 2023/0201589 A1 | 6/2023 | Schwarz et al. |
| 2023/0201621 A1 | 6/2023 | Gries |
| 2023/0211169 A1 | 7/2023 | Châtillon |
| 2023/0211170 A1 | 7/2023 | Gin |
| 2023/0211171 A1 | 7/2023 | Gries |
| 2023/0211172 A1 | 7/2023 | Oliveros Maita |
| 2023/0218915 A1 | 7/2023 | Casalino et al. |
| 2023/0226368 A1 | 7/2023 | Schwarz et al. |
| 2023/0240784 A1 | 8/2023 | Azoulay |
| 2023/0241384 A1 | 8/2023 | Schwarz et al. |
| 2023/0241405 A1* | 8/2023 | Schwarz .................. A61N 1/40 600/15 |
| 2023/0241407 A1 | 8/2023 | Cassano et al. |
| 2023/0248989 A1 | 8/2023 | Gries |
| 2023/0277862 A1* | 9/2023 | Schwarz ................ A61N 2/004 600/14 |
| 2023/0285767 A1 | 9/2023 | Kim et al. |
| 2023/0285768 A1 | 9/2023 | Murphy et al. |
| 2023/0293354 A1 | 9/2023 | Rao et al. |
| 2023/0293901 A1 | 9/2023 | Yun |
| 2023/0293903 A1 | 9/2023 | Järnefelt |
| 2023/0310878 A1 | 10/2023 | Yoon et al. |
| 2023/0355967 A1 | 11/2023 | Kishi et al. |
| 2023/0355998 A1 | 11/2023 | Müller-Bruhn et al. |
| 2023/0364413 A1 | 11/2023 | Romaniw et al. |
| 2023/0364439 A1 | 11/2023 | Müller-Bruhn et al. |
| 2023/0368599 A1 | 11/2023 | Ruggiero et al. |
| 2023/0372724 A1 | 11/2023 | Casalino et al. |
| 2023/0381499 A1 | 11/2023 | Simon et al. |

(56) References Cited

U.S. PATENT DOCUMENTS

| | | |
|---|---|---|
| 2023/0381504 A1 | 11/2023 | Yoo et al. |
| 2023/0381507 A1 | 11/2023 | Errico et al. |
| 2023/0381530 A1 | 11/2023 | Kim |
| 2023/0397893 A1 | 12/2023 | Hu |
| 2023/0398352 A1 | 12/2023 | Errico et al. |
| 2023/0405306 A1 | 12/2023 | Simon et al. |
| 2023/0405319 A1 | 12/2023 | Simon et al. |
| 2023/0414931 A1 | 12/2023 | Shapiro et al. |
| 2023/0414960 A1 | 12/2023 | Ghiron et al. |
| 2023/0414961 A1 | 12/2023 | Gries |
| 2024/0001110 A1 | 1/2024 | Ko et al. |
| 2024/0001114 A1 | 1/2024 | Shalev et al. |
| 2024/0001136 A1 | 1/2024 | Choa et al. |
| 2024/0009450 A1 | 1/2024 | Ko et al. |
| 2024/0009476 A1 | 1/2024 | Krinke et al. |
| 2024/0017083 A1 | 1/2024 | Soekadar et al. |
| 2024/0017084 A1 | 1/2024 | Kozel et al. |
| 2024/0024692 A1 | 1/2024 | Khan et al. |
| 2024/0024693 A1 | 1/2024 | Gonzalez |
| 2024/0042227 A1 | 2/2024 | Lee et al. |
| 2024/0042228 A1 | 2/2024 | Ghiron et al. |
| 2024/0050762 A1 | 2/2024 | Phillips et al. |
| 2024/0075309 A1 | 3/2024 | Paulus |
| 2024/0090970 A1 | 3/2024 | Andersen et al. |
| 2024/0100321 A1 | 3/2024 | Wasserman et al. |
| 2024/0108909 A1 | 4/2024 | Ring et al. |
| 2024/0122537 A1 | 4/2024 | Vaughn et al. |
| 2024/0123248 A1 | 4/2024 | Vaughn et al. |
| 2024/0123251 A1 | 4/2024 | Vaughn et al. |
| 2024/0130817 A1 | 4/2024 | Lee et al. |
| 2024/0139537 A1 | 5/2024 | Isakovic |
| 2024/0148300 A1 | 5/2024 | Schepis et al. |
| 2024/0156403 A1 | 5/2024 | Whitfield-Gabrieli et al. |
| 2024/0173559 A1 | 5/2024 | Cohen et al. |
| 2024/0207633 A1 | 6/2024 | Moreau-Gobard et al. |
| 2024/0216692 A1 | 7/2024 | Tesfayesus et al. |
| 2024/0216707 A1 | 7/2024 | Liang et al. |
| 2024/0251974 A1 | 8/2024 | Tsunoda |
| 2024/0252824 A1 | 8/2024 | Verzal et al. |
| 2024/0285964 A1 | 8/2024 | Keller et al. |
| 2024/0293663 A1 | 9/2024 | McNutt |
| 2024/0299763 A1 | 9/2024 | Ho et al. |
| 2024/0316357 A1 | 9/2024 | Kishi et al. |
| 2024/0316358 A1 | 9/2024 | Kishi et al. |
| 2024/0325773 A1 | 10/2024 | Postrel |
| 2024/0341510 A1 | 10/2024 | Dennewald |
| 2024/0342497 A1 | 10/2024 | Phillips et al. |
| 2024/0342499 A1 | 10/2024 | Kataja et al. |
| 2024/0350820 A1 | 10/2024 | Kuehne et al. |
| 2025/0010089 A1 | 1/2025 | Hosseini-Fahraji et al. |
| 2025/0025715 A1 | 1/2025 | Florou et al. |
| 2025/0050124 A1 | 2/2025 | Vaidya |
| 2025/0065110 A1 | 2/2025 | Huang et al. |
| 2025/0065144 A1 | 2/2025 | Ansari et al. |
| 2025/0073451 A1 | 3/2025 | Huang et al. |
| 2025/0090855 A1 | 3/2025 | Roth et al. |
| 2025/0108228 A1 | 4/2025 | Song et al. |
| 2025/0127653 A1 | 4/2025 | Sandstrom |
| 2025/0152939 A1 | 5/2025 | Simon et al. |
| 2025/0152957 A1 | 5/2025 | Liu et al. |
| 2025/0177769 A1 | 6/2025 | Wang |
| 2025/0177770 A1 | 6/2025 | Châtillon et al. |
| 2025/0186798 A1 | 6/2025 | Ghiron et al. |
| 2025/0195906 A1 | 6/2025 | Vaughn et al. |
| 2025/0201371 A1 | 6/2025 | Vaughn et al. |
| 2025/0229097 A1 | 7/2025 | Bied et al. |
| 2025/0249271 A1 | 8/2025 | Bied et al. |
| 2025/0269195 A1 | 8/2025 | Jiles et al. |

FOREIGN PATENT DOCUMENTS

| | | | |
|---|---|---|---|
| AU | 2012200610 B2 | 7/2014 | |
| AU | 2012244313 B2 | 11/2014 | |
| AU | 2014203094 B2 | 7/2015 | |
| AU | 2015227382 A1 | 10/2015 | |
| AU | 2013207657 B2 | 11/2015 | |
| BR | PI0701434 A2 | 11/2008 | |
| BR | PI0812502 A2 | 6/2015 | |
| CA | 2484880 A1 | 4/2006 | |
| CA | 2915928 A1 | 12/2014 | |
| CA | 2845438 C | 2/2015 | |
| CA | 2604112 C | 7/2016 | |
| CA | 3019140 A1 | 10/2017 | |
| CA | 3019410 A1 | 10/2017 | |
| CA | 3023821 A1 | 11/2017 | |
| CH | 714113 A2 | 3/2019 | |
| CN | 86204070 U | 9/1987 | |
| CN | 87203746 U | 12/1987 | |
| CN | 87215926 U | 7/1988 | |
| CN | 1026953 C | 12/1994 | |
| CN | 1027958 C | 3/1995 | |
| CN | 2192348 Y | 3/1995 | |
| CN | 1206975 C | 6/2005 | |
| CN | 101234231 A | 8/2008 | |
| CN | 101327358 A | 12/2008 | |
| CN | 201906360 U | 7/2011 | |
| CN | 102319141 A | 1/2012 | |
| CN | 102711706 A | 10/2012 | |
| CN | 102847231 A | 1/2013 | |
| CN | 202637725 U | 1/2013 | |
| CN | 202822496 U | 3/2013 | |
| CN | 103079640 A | 5/2013 | |
| CN | 203123345 U | 8/2013 | |
| CN | 203169831 U | 9/2013 | |
| CN | 203647557 U | 6/2014 | |
| CN | 102319141 B | 8/2014 | |
| CN | 204767045 U | 11/2015 | |
| CN | 205698901 U | 11/2016 | |
| CN | 106540375 A | 3/2017 | |
| CN | 106606819 A | 5/2017 | |
| CN | 206613045 U | 11/2017 | |
| CN | 107569773 A | 1/2018 | |
| CN | 107613914 A | 1/2018 | |
| CN | 107802956 A | 3/2018 | |
| CN | 207462462 U | 6/2018 | |
| CN | 108355240 A | 8/2018 | |
| CN | 108853728 A | 11/2018 | |
| CN | 108882992 A | 11/2018 | |
| CN | 109260595 A | 1/2019 | |
| CN | 109310516 A | 2/2019 | |
| CN | 208511024 U | 2/2019 | |
| CN | 208710812 U | 4/2019 | |
| CN | 109745620 A | 5/2019 | |
| CN | 208809311 U | 5/2019 | |
| CN | 109865196 A | 6/2019 | |
| CN | 110180083 A | 8/2019 | |
| CN | 209221337 U | 8/2019 | |
| CN | 209221338 U | 8/2019 | |
| CN | 110339480 A | 10/2019 | |
| CN | 210770219 U | 6/2020 | |
| CN | 111408041 A | 7/2020 | |
| CN | 211097114 U | 7/2020 | |
| CN | 211357457 U | 8/2020 | |
| CN | 111728712 A | 10/2020 | |
| CN | 111840804 A | 10/2020 | |
| CN | 111939460 A | 11/2020 | |
| CN | 112023260 A | 12/2020 | |
| CN | 112023270 A | 12/2020 | |
| CN | 112221015 A | 1/2021 | |
| CN | 212416683 U | 1/2021 | |
| CN | 212516751 U | 2/2021 | |
| CN | 112472506 A | 3/2021 | |
| CN | 112494815 A | 3/2021 | |
| CN | 112582159 A | 3/2021 | |
| CN | 212700107 U | 3/2021 | |
| CN | 212730732 U | 3/2021 | |
| CN | 213031672 U | 4/2021 | |
| CN | 112891749 A | 6/2021 | |
| CN | 112915390 A | 6/2021 | |
| CN | 112932933 A | 6/2021 | |
| CN | 113041500 A | 6/2021 | |
| CN | 113041502 A | 6/2021 | |
| CN | 213432603 U | 6/2021 | |
| CN | 213554920 U | 6/2021 | |

(56) References Cited

FOREIGN PATENT DOCUMENTS

| | | | |
|---|---|---|---|
| CN | 113082529 | A | 7/2021 |
| CN | 113274646 | A | 8/2021 |
| CN | 113317962 | A | 8/2021 |
| CN | 213911989 | U | 8/2021 |
| CN | 213994598 | U | 8/2021 |
| CN | 214099374 | U | 8/2021 |
| CN | 214105531 | U | 9/2021 |
| CN | 113499542 | A | 10/2021 |
| CN | 113647936 | A | 11/2021 |
| CN | 214971184 | U | 12/2021 |
| CN | 215025228 | U | 12/2021 |
| CN | 215081635 | U | 12/2021 |
| CN | 215084285 | U | 12/2021 |
| CN | 215309722 | U | 12/2021 |
| CN | 114209957 | A | 3/2022 |
| CN | 216091295 | U | 3/2022 |
| CN | 216091887 | U | 3/2022 |
| CN | 114344725 | A | 4/2022 |
| CN | 216169399 | U | 4/2022 |
| CN | 216365670 | U | 4/2022 |
| CN | 114504729 | A | 5/2022 |
| CN | 114588546 | A | 6/2022 |
| CN | 114712160 | A | 7/2022 |
| CN | 216986082 | U | 7/2022 |
| CN | 115083724 | A | 9/2022 |
| CN | 115212462 | A | 10/2022 |
| CN | 217526108 | U | 10/2022 |
| CN | 217548800 | U | 10/2022 |
| CN | 115282486 | A | 11/2022 |
| CN | 115364376 | A | 11/2022 |
| CN | 217908619 | U | 11/2022 |
| CN | 217908621 | U | 11/2022 |
| CN | 115454185 | A | 12/2022 |
| CN | 217960287 | U | 12/2022 |
| CN | 218129587 | U | 12/2022 |
| CN | 115591124 | A | 1/2023 |
| CN | 115639868 | A | 1/2023 |
| CN | 115645737 | A | 1/2023 |
| CN | 115645748 | A | 1/2023 |
| CN | 218220824 | U | 1/2023 |
| CN | 218220826 | U | 1/2023 |
| CN | 218356631 | U | 1/2023 |
| CN | 219049396 | U | 5/2023 |
| CN | 116271528 | A | 6/2023 |
| CN | 116328189 | A | 6/2023 |
| CN | 116350949 | A | 6/2023 |
| CN | 219110650 | U | 6/2023 |
| CN | 116370834 | A | 7/2023 |
| CN | 116650831 | A | 8/2023 |
| CN | 219462335 | U | 8/2023 |
| CN | 219614745 | U | 9/2023 |
| CN | 117116592 | A | 11/2023 |
| CN | 117180084 | A | 12/2023 |
| CN | 117198676 | A | 12/2023 |
| CN | 117205444 | A | 12/2023 |
| CN | 220778839 | U | 4/2024 |
| CN | 220778841 | U | 4/2024 |
| CN | 118267627 | A | 7/2024 |
| CN | 119488672 | A | 2/2025 |
| CN | 119607423 | A | 3/2025 |
| CZ | 33663 | U1 | 1/2020 |
| CZ | 2022299 | A3 | 1/2024 |
| DE | 718637 | C | 3/1942 |
| DE | 1118902 | B | 12/1961 |
| DE | 2533244 | A1 | 2/1977 |
| DE | 2748780 | A1 | 5/1978 |
| DE | 3128263 | A1 | 2/1983 |
| DE | 3205048 | A1 | 8/1983 |
| DE | 3340974 | A1 | 5/1985 |
| DE | 3610474 | A1 | 10/1986 |
| DE | 3825165 | A1 | 1/1990 |
| DE | 4020522 | A1 | 1/1992 |
| DE | 3340974 | C2 | 7/1994 |
| DE | 69318706 | T2 | 1/1999 |
| DE | 10062050 | A1 | 4/2002 |
| DE | 102004006192 | A1 | 9/2005 |
| DE | 60033756 | T2 | 6/2007 |
| DE | 202006009799 | U1 | 10/2007 |
| DE | 102007044445 | A1 | 3/2009 |
| DE | 202010005501 | U1 | 8/2010 |
| DE | 102009023855 | A1 | 12/2010 |
| DE | 102009049145 | A1 | 4/2011 |
| DE | 102009050010 | A1 | 5/2011 |
| DE | 102010004307 | A1 | 7/2011 |
| DE | 102006024467 | B4 | 4/2012 |
| DE | 102011014291 | A1 | 9/2012 |
| DE | 102012220121 | B3 | 9/2013 |
| DE | 102014106797 | B3 | 1/2015 |
| DE | 102013211859 | B4 | 7/2015 |
| DE | 102014001185 | A1 | 7/2015 |
| DE | 202017107602 | U1 | 2/2018 |
| DE | 102016116399 | A1 | 3/2018 |
| DE | 202019100373 | U1 | 3/2019 |
| DE | 102017122942 | A1 | 4/2019 |
| DE | 102017123854 | A1 | 4/2019 |
| DE | 102017125678 | A1 | 5/2019 |
| DE | 202018106565 | U1 | 10/2019 |
| DE | 202019105412 | U1 | 1/2020 |
| DE | 202020100975 | U1 | 3/2020 |
| DE | 202016008884 | U1 | 7/2020 |
| DE | 102010014157 | B4 | 2/2021 |
| DE | 102021111627 | A1 | 11/2022 |
| DK | 0633008 | T3 | 3/1999 |
| EA | 000494 | B1 | 8/1999 |
| EA | 002087 | B1 | 12/2001 |
| EA | 002179 | B1 | 2/2002 |
| EA | 003851 | B1 | 10/2003 |
| EA | 007347 | B1 | 8/2006 |
| EA | 007975 | B1 | 2/2007 |
| EP | 0048451 | A1 | 3/1982 |
| EP | 0039206 | B1 | 10/1984 |
| EP | 0209246 | A1 | 1/1987 |
| EP | 0459101 | A1 | 12/1991 |
| EP | 0459401 | A1 | 12/1991 |
| EP | 0633008 | A1 | 1/1995 |
| EP | 0788813 | A1 | 8/1997 |
| EP | 0633008 | B1 | 5/1998 |
| EP | 0692993 | B1 | 9/1999 |
| EP | 1022034 | A1 | 7/2000 |
| EP | 1916013 | A1 | 4/2008 |
| EP | 2069014 | A2 | 6/2009 |
| EP | 1883447 | B1 | 9/2009 |
| EP | 2139560 | A1 | 1/2010 |
| EP | 2124800 | B1 | 11/2010 |
| EP | 1917935 | B1 | 1/2011 |
| EP | 2308559 | A2 | 4/2011 |
| EP | 2139560 | B1 | 5/2012 |
| EP | 2461765 | A1 | 6/2012 |
| EP | 2564895 | A1 | 3/2013 |
| EP | 1863569 | B1 | 5/2013 |
| EP | 2069014 | B1 | 6/2013 |
| EP | 1850781 | B1 | 7/2013 |
| EP | 2614807 | A1 | 7/2013 |
| EP | 2676700 | A2 | 12/2013 |
| EP | 2694159 | A2 | 2/2014 |
| EP | 2749259 | A1 | 7/2014 |
| EP | 2814445 | A1 | 12/2014 |
| EP | 2856986 | A1 | 4/2015 |
| EP | 2878336 | A1 | 6/2015 |
| EP | 2564894 | B1 | 11/2015 |
| EP | 3009167 | A1 | 4/2016 |
| EP | 2501352 | B1 | 7/2016 |
| EP | 3209246 | A1 | 8/2017 |
| EP | 3342379 | A1 | 7/2018 |
| EP | 3389532 | A1 | 10/2018 |
| EP | 3415199 | A1 | 12/2018 |
| EP | 3434323 | A1 | 1/2019 |
| EP | 3476433 | A1 | 5/2019 |
| EP | 3479872 | A1 | 5/2019 |
| EP | 3656442 | A1 | 5/2020 |
| EP | 3666325 | A1 | 6/2020 |
| EP | 3721939 | A1 | 10/2020 |
| EP | 1890762 | B1 | 12/2020 |
| EP | 3744392 | A1 | 12/2020 |

(56) References Cited

FOREIGN PATENT DOCUMENTS

| | | | |
|---|---|---|---|
| EP | 3772362 | A1 | 2/2021 |
| EP | 3797825 | A1 | 3/2021 |
| EP | 3988164 | A1 | 4/2022 |
| EP | 3988165 | A1 | 4/2022 |
| EP | 4046660 | A1 | 8/2022 |
| EP | 4406469 | A1 | 7/2024 |
| EP | 3644797 | B1 | 3/2025 |
| EP | 4523730 | A1 | 3/2025 |
| EP | 4069353 | B1 | 4/2025 |
| ES | 2118925 | T3 | 10/1998 |
| ES | 2300569 | T3 | 6/2008 |
| ES | 2305698 | T3 | 11/2008 |
| ES | 2359581 | T3 | 5/2011 |
| ES | 2533145 | A2 | 4/2015 |
| ES | 2533145 | B1 | 7/2016 |
| ES | 2533145 | R1 | 10/2018 |
| ES | 1314427 | U | 3/2025 |
| FR | 2987275 | A1 | 8/2013 |
| FR | 2970656 | B1 | 6/2014 |
| FR | 3039072 | A1 | 1/2017 |
| FR | 3041881 | A1 | 4/2017 |
| FR | 3061012 | A1 | 6/2018 |
| FR | 3071395 | A1 | 3/2019 |
| GB | 260116 | A | 10/1926 |
| GB | 304587 | A | 3/1930 |
| GB | 390500 | A | 4/1933 |
| GB | 871672 | A | 6/1961 |
| GB | 2176009 | A | 12/1986 |
| GB | 2188238 | A | 9/1987 |
| GB | 2176009 | B | 12/1989 |
| GB | 2261820 | A | 6/1993 |
| GB | 2286660 | A | 8/1995 |
| GB | 2298370 | A | 9/1996 |
| GB | 2395907 | B | 12/2004 |
| GB | 2459157 | A | 10/2009 |
| GB | 2504984 | A | 2/2014 |
| GB | 2521240 | A | 6/2015 |
| GB | 2521609 | A | 7/2015 |
| GB | 2549466 | A | 10/2017 |
| GB | 2552004 | A | 1/2018 |
| GB | 2552810 | A | 2/2018 |
| GB | 2554043 | A | 3/2018 |
| GB | 2555809 | A | 5/2018 |
| GB | 2567872 | A | 5/2019 |
| GB | 2568051 | A | 5/2019 |
| GB | 2587392 | A | 3/2021 |
| GB | 2591692 | A | 8/2021 |
| GB | 2602603 | A | 7/2022 |
| GB | 2631305 | A | 1/2025 |
| GB | 2634713 | A | 4/2025 |
| GR | 3027678 | T3 | 11/1998 |
| IT | 1217550 | B | 3/1990 |
| IT | RE20120010 | A1 | 8/2013 |
| IT | UB20159823 | A1 | 7/2017 |
| IT | 201800002490 | U1 | 11/2019 |
| IT | 201800005119 | A1 | 11/2019 |
| IT | 202100020471 | A1 | 1/2023 |
| JP | S5541836 | U | 3/1980 |
| JP | H07135376 | A | 5/1995 |
| JP | H09276418 | A | 10/1997 |
| JP | H105270 | A | 1/1998 |
| JP | H10216242 | A | 8/1998 |
| JP | 2002513621 | A | 5/2002 |
| JP | 2002299026 | A | 10/2002 |
| JP | 2003085523 | A | 3/2003 |
| JP | 2003305131 | A | 10/2003 |
| JP | 2005245585 | A | 9/2005 |
| JP | 2006130055 | A | 5/2006 |
| JP | 2008245836 | A | 10/2008 |
| JP | 4178762 | B2 | 11/2008 |
| JP | 4324673 | B2 | 9/2009 |
| JP | 2009297350 | A | 12/2009 |
| JP | 2010504792 | A | 2/2010 |
| JP | 2010063007 | A | 3/2010 |
| JP | 2010207268 | A | 9/2010 |

| | | | |
|---|---|---|---|
| JP | 2010533054 | A | 10/2010 |
| JP | 2011194176 | A | 10/2011 |
| JP | 4837723 | B2 | 12/2011 |
| JP | 4934805 | B2 | 5/2012 |
| JP | 2012125546 | A | 7/2012 |
| JP | 2013012285 | A | 1/2013 |
| JP | 2013063285 | A | 4/2013 |
| JP | 2013066597 | A | 4/2013 |
| JP | 2013116271 | A | 6/2013 |
| JP | 3192971 | U | 9/2014 |
| JP | 2014158973 | A | 9/2014 |
| JP | 2015208504 | A | 11/2015 |
| JP | 2017023286 | A | 2/2017 |
| JP | 2017070427 | A | 4/2017 |
| JP | 2017518857 | A | 7/2017 |
| JP | 2018501927 | A | 1/2018 |
| JP | 2018018650 | A | 2/2018 |
| JP | 6393460 | B2 | 9/2018 |
| JP | 2018187510 | A | 11/2018 |
| JP | 2018534028 | A | 11/2018 |
| JP | 2022044180 | A | 3/2022 |
| JP | 2023174724 | A | 12/2023 |
| JP | 2024082438 | A | 6/2024 |
| KR | 20010095888 | A | 11/2001 |
| KR | 200261417 | Y1 | 3/2002 |
| KR | 20030004976 | A | 1/2003 |
| KR | 20030065126 | A | 8/2003 |
| KR | 100484618 | B1 | 4/2005 |
| KR | 100491988 | B1 | 5/2005 |
| KR | 200407524 | Y1 | 1/2006 |
| KR | 100556230 | B1 | 3/2006 |
| KR | 200410065 | Y1 | 3/2006 |
| KR | 100841596 | B1 | 6/2008 |
| KR | 20090063618 | A | 6/2009 |
| KR | 20090095143 | A | 9/2009 |
| KR | 100936914 | B1 | 1/2010 |
| KR | 20100026107 | A | 3/2010 |
| KR | 101022244 | B1 | 3/2011 |
| KR | 101050069 | B1 | 7/2011 |
| KR | 20110123474 | A | 11/2011 |
| KR | 20110123831 | A | 11/2011 |
| KR | 20120037011 | A | 4/2012 |
| KR | 101233286 | B1 | 2/2013 |
| KR | 101233287 | B1 | 2/2013 |
| KR | 20130046469 | A | 5/2013 |
| KR | 101275228 | B1 | 6/2013 |
| KR | 20130072244 | A | 7/2013 |
| KR | 101292289 | B1 | 8/2013 |
| KR | 20130106977 | A | 10/2013 |
| KR | 20130128391 | A | 11/2013 |
| KR | 101413022 | B1 | 7/2014 |
| KR | 101415141 | B1 | 7/2014 |
| KR | 101445687 | B1 | 10/2014 |
| KR | 101447532 | B1 | 10/2014 |
| KR | 101511444 | B1 | 4/2015 |
| KR | 20150049386 | A | 5/2015 |
| KR | 20150058102 | A | 5/2015 |
| KR | 20150063839 | A | 6/2015 |
| KR | 101539633 | B1 | 7/2015 |
| KR | 20150079619 | A | 7/2015 |
| KR | 20150106379 | A | 9/2015 |
| KR | 101610762 | B1 | 4/2016 |
| KR | 101650155 | B1 | 8/2016 |
| KR | 101673182 | B1 | 11/2016 |
| KR | 101687583 | B1 | 12/2016 |
| KR | 101702400 | B1 | 2/2017 |
| KR | 101754395 | B1 | 7/2017 |
| KR | 20170084848 | A | 7/2017 |
| KR | 101770364 | B1 | 8/2017 |
| KR | 20170090654 | A | 8/2017 |
| KR | 20170107603 | A | 9/2017 |
| KR | 101794269 | B1 | 11/2017 |
| KR | 20180059114 | A | 6/2018 |
| KR | 20180092020 | A | 8/2018 |
| KR | 101900491 | B1 * | 9/2018 |
| KR | 101901215 | B1 | 9/2018 |
| KR | 101921033 | B1 | 11/2018 |
| KR | 101941863 | B1 | 1/2019 |
| KR | 20190005981 | A | 1/2019 |

(56) References Cited

FOREIGN PATENT DOCUMENTS

| | | | |
|---|---|---|---|
| KR | 20190027491 | A | 3/2019 |
| KR | 101955542 | B1 | 5/2019 |
| KR | 20190061187 | A | 6/2019 |
| KR | 20190073169 | A | 6/2019 |
| KR | 102000971 | B1 | 7/2019 |
| KR | 20190001779 | U | 7/2019 |
| KR | 20190103532 | A | 9/2019 |
| KR | 20190112530 | A | 10/2019 |
| KR | 102046924 | B1 | 11/2019 |
| KR | 102063730 | B1 | 1/2020 |
| KR | 20200001717 | A | 1/2020 |
| KR | 20200001978 | A | 1/2020 |
| KR | 200491572 | Y1 | 5/2020 |
| KR | 20200000889 | U | 5/2020 |
| KR | 20200050488 | A | 5/2020 |
| KR | 20200052602 | A | 5/2020 |
| KR | 20200056692 | A | 5/2020 |
| KR | 20200056693 | A | 5/2020 |
| KR | 20200056801 | A | 5/2020 |
| KR | 20200056802 | A | 5/2020 |
| KR | 20200057154 | A | 5/2020 |
| KR | 20200061765 | A | 6/2020 |
| KR | 20200133652 | A | 11/2020 |
| KR | 102185926 | B1 | 12/2020 |
| KR | 20210002973 | A | 1/2021 |
| KR | 20210002974 | A | 1/2021 |
| KR | 20210006624 | A | 1/2021 |
| KR | 20210009510 | A | 1/2021 |
| KR | 102234264 | B1 | 3/2021 |
| KR | 20210041171 | A | 4/2021 |
| KR | 20210052126 | A | 5/2021 |
| KR | 20210096894 | A | 8/2021 |
| KR | 20210105758 | A | 8/2021 |
| KR | 20210111197 | A | 9/2021 |
| KR | 20210117049 | A | 9/2021 |
| KR | 102315486 | B1 | 10/2021 |
| KR | 20210149359 | A | 12/2021 |
| KR | 20210153862 | A | 12/2021 |
| KR | 20220004537 | A | 1/2022 |
| KR | 20220007771 | A | 1/2022 |
| KR | 20220009045 | A | 1/2022 |
| KR | 20220009066 | A | 1/2022 |
| KR | 20220011851 | A | 2/2022 |
| KR | 20220012823 | A | 2/2022 |
| KR | 20220012825 | A | 2/2022 |
| KR | 20220029838 | A | 3/2022 |
| KR | 20220052896 | A | 4/2022 |
| KR | 20220055028 | A | 5/2022 |
| KR | 20220055065 | A | 5/2022 |
| KR | 20220072075 | A | 6/2022 |
| KR | 20220108282 | A | 8/2022 |
| KR | 20220122960 | A | 9/2022 |
| KR | 20220123612 | A | 9/2022 |
| KR | 102453614 | B1 | 10/2022 |
| KR | 20220140452 | A | 10/2022 |
| KR | 102462186 | B1 | 11/2022 |
| KR | 20220166212 | A | 12/2022 |
| KR | 20230045777 | A | 4/2023 |
| KR | 20230045778 | A | 4/2023 |
| KR | 20230045779 | A | 4/2023 |
| KR | 20230046655 | A | 4/2023 |
| KR | 20230050717 | A | 4/2023 |
| KR | 20230064250 | A | 5/2023 |
| KR | 20230094311 | A | 6/2023 |
| KR | 20230094312 | A | 6/2023 |
| KR | 20230094313 | A | 6/2023 |
| KR | 102576847 | B1 | 9/2023 |
| KR | 20230134278 | A | 9/2023 |
| KR | 20230168735 | A | 12/2023 |
| KR | 20230168737 | A | 12/2023 |
| KR | 20230169024 | A | 12/2023 |
| KR | 20240012685 | A | 1/2024 |
| KR | 20240013316 | A | 1/2024 |
| KR | 20240023930 | A | 2/2024 |
| KR | 20240043736 | A | 4/2024 |
| KR | 20240050633 | A | 4/2024 |
| KR | 20240074691 | A | 5/2024 |
| KR | 20240083844 | A | 6/2024 |
| KR | 20240083849 | A | 6/2024 |
| KR | 20240083850 | A | 6/2024 |
| KR | 20240096032 | A | 6/2024 |
| KR | 20240128462 | A | 8/2024 |
| KR | 20240132686 | A | 9/2024 |
| KR | 20240133060 | A | 9/2024 |
| KR | 20240133061 | A | 9/2024 |
| KR | 20240160880 | A | 11/2024 |
| KR | 20240174636 | A | 12/2024 |
| KR | 20250007897 | A | 1/2025 |
| KR | 102801459 | B1 | 4/2025 |
| KR | 102801469 | B1 | 4/2025 |
| KR | 102814899 | B1 | 5/2025 |
| MX | 2012012158 | A | 4/2014 |
| NL | 7510644 | A | 3/1977 |
| NL | 1037451 | C2 | 5/2011 |
| RU | 2212909 | C2 | 9/2003 |
| RU | 2226115 | C2 | 3/2004 |
| RU | 2281128 | C2 | 8/2006 |
| RU | 2373971 | C2 | 11/2009 |
| RU | 2392979 | C2 | 6/2010 |
| RU | 2395267 | C2 | 7/2010 |
| RU | 2496532 | C2 | 10/2013 |
| RU | 2529471 | C2 | 9/2014 |
| RU | 2596053 | C2 | 8/2016 |
| RU | 2637104 | C2 | 11/2017 |
| RU | 2645923 | C2 | 2/2018 |
| SI | 23086 | A | 12/2010 |
| SI | 23195 | A | 4/2011 |
| SI | 24921 | A | 8/2016 |
| SI | 25942 | A | 6/2021 |
| SI | 26251 | A | 3/2023 |
| TW | 510797 | B | 11/2002 |
| TW | 200423986 | A | 11/2004 |
| TW | 201825045 | A | 7/2018 |
| TW | 202523372 | A | 6/2025 |
| WO | WO 9115263 | A1 | 10/1991 |
| WO | WO-9312835 | A1 | 7/1993 |
| WO | WO-9521655 | A1 | 8/1995 |
| WO | WO-9527533 | A1 | 10/1995 |
| WO | WO-9932191 | A1 | 7/1999 |
| WO | WO-0006251 | A2 | 2/2000 |
| WO | WO-0013749 | A1 | 3/2000 |
| WO | WO-0044346 | A1 | 8/2000 |
| WO | WO-0107111 | A2 | 2/2001 |
| WO | WO-0112089 | A1 | 2/2001 |
| WO | WO-0193797 | A2 | 12/2001 |
| WO | WO-0225675 | A1 | 3/2002 |
| WO | WO-0226147 | A1 | 4/2002 |
| WO | WO-0230511 | A2 | 4/2002 |
| WO | WO-0232504 | A2 | 4/2002 |
| WO | WO-02096514 | A1 | 12/2002 |
| WO | WO-03013334 | A2 | 2/2003 |
| WO | WO-03075820 | A1 | 9/2003 |
| WO | WO-03078596 | A2 | 9/2003 |
| WO | WO-03079916 | A1 | 10/2003 |
| WO | WO-03090863 | A1 | 11/2003 |
| WO | WO-03103769 | A1 | 12/2003 |
| WO | WO-2004078255 | A1 | 9/2004 |
| WO | WO-2004080526 | A2 | 9/2004 |
| WO | WO-2004080527 | A2 | 9/2004 |
| WO | WO-2004087255 | A1 | 10/2004 |
| WO | WO-2004095385 | A2 | 11/2004 |
| WO | WO-2004095835 | A1 | 11/2004 |
| WO | WO-2004096343 | A2 | 11/2004 |
| WO | WO-2004108211 | A1 | 12/2004 |
| WO | WO-2005032660 | A1 | 4/2005 |
| WO | WO-2005044375 | A1 | 5/2005 |
| WO | WO-2005049132 | A1 | 6/2005 |
| WO | WO-2005061051 | A2 | 7/2005 |
| WO | WO-2005065032 | A2 | 7/2005 |
| WO | WO-2005102188 | A1 | 11/2005 |
| WO | WO-2005105013 | A2 | 11/2005 |
| WO | WO-2005107866 | A1 | 11/2005 |
| WO | WO-2006034306 | A2 | 3/2006 |
| WO | WO-2006050279 | A2 | 5/2006 |

(56)        References Cited

FOREIGN PATENT DOCUMENTS

| | | |
|---|---|---|
| WO | WO-2006061867 A1 | 6/2006 |
| WO | WO-2006077567 A1 | 7/2006 |
| WO | WO-2006077582 A2 | 7/2006 |
| WO | WO-2006115120 A1 | 11/2006 |
| WO | WO-2006116728 A2 | 11/2006 |
| WO | WO-2006133636 A1 | 12/2006 |
| WO | WO-2007005373 A1 | 1/2007 |
| WO | WO-2007011583 A1 | 1/2007 |
| WO | WO-2007051896 A1 | 5/2007 |
| WO | WO-2007096206 A1 | 8/2007 |
| WO | WO-2007130308 A2 | 11/2007 |
| WO | WO-2007131248 A1 | 11/2007 |
| WO | WO-2007140584 A1 | 12/2007 |
| WO | WO-2008012827 A2 | 1/2008 |
| WO | WO-2008049775 A1 | 5/2008 |
| WO | WO-2008060494 A2 | 5/2008 |
| WO | WO-2008063478 A1 | 5/2008 |
| WO | WO-2008085162 A1 | 7/2008 |
| WO | WO-2008109058 A1 | 9/2008 |
| WO | WO-2008124112 A1 | 10/2008 |
| WO | WO-2008127011 A2 | 10/2008 |
| WO | WO-2008145260 A2 | 12/2008 |
| WO | WO-2009011708 A1 | 1/2009 |
| WO | WO-2009013729 A2 | 1/2009 |
| WO | WO-2009036040 A1 | 3/2009 |
| WO | WO-2009042863 A1 | 4/2009 |
| WO | WO-2009044400 A2 | 4/2009 |
| WO | WO-2009045358 A1 | 4/2009 |
| WO | WO-2009047628 A2 | 4/2009 |
| WO | WO-2009083915 A2 | 7/2009 |
| WO | WO-2009095013 A2 | 8/2009 |
| WO | WO-2009127840 A1 | 10/2009 |
| WO | WO-2010007614 A2 | 1/2010 |
| WO | WO-2010022278 A1 | 2/2010 |
| WO | WO-2010007614 A3 | 5/2010 |
| WO | WO-2010095147 A2 | 8/2010 |
| WO | WO-2010100643 A2 | 9/2010 |
| WO | WO-2010129997 A1 | 11/2010 |
| WO | WO-2010135425 A1 | 11/2010 |
| WO | WO-2010139376 A1 | 12/2010 |
| WO | WO-2010151619 A2 | 12/2010 |
| WO | WO-2011011749 A1 | 1/2011 |
| WO | WO-2011016019 A1 | 2/2011 |
| WO | WO-2011021184 A1 | 2/2011 |
| WO | WO-2011044173 A1 | 4/2011 |
| WO | WO-2011044176 A1 | 4/2011 |
| WO | WO-2011044178 A1 | 4/2011 |
| WO | WO-2011044179 A1 | 4/2011 |
| WO | WO-2011045002 A1 | 4/2011 |
| WO | WO-2011053607 A1 | 5/2011 |
| WO | WO-2011058556 A2 | 5/2011 |
| WO | WO-2011058565 A2 | 5/2011 |
| WO | WO-2011068727 A1 | 6/2011 |
| WO | WO-2011085020 A1 | 7/2011 |
| WO | WO-2011137262 A1 | 11/2011 |
| WO | WO-2011156495 A2 | 12/2011 |
| WO | WO-2012003451 A2 | 1/2012 |
| WO | WO-2012005766 A1 | 1/2012 |
| WO | WO-2012024169 A2 | 2/2012 |
| WO | WO-2012029065 A2 | 3/2012 |
| WO | WO-2012033932 A2 | 3/2012 |
| WO | WO-2012040243 A1 | 3/2012 |
| WO | WO-2012052986 A2 | 4/2012 |
| WO | WO-2012033932 A3 | 6/2012 |
| WO | WO-2012072978 A1 | 6/2012 |
| WO | WO-2012073232 A1 | 6/2012 |
| WO | WO-2012082960 A2 | 6/2012 |
| WO | WO-2012102837 A1 | 8/2012 |
| WO | WO-2012103632 A1 | 8/2012 |
| WO | WO-2012106735 A2 | 8/2012 |
| WO | WO-2012119293 A1 | 9/2012 |
| WO | WO-2012126044 A1 | 9/2012 |
| WO | WO-2012138169 A2 | 10/2012 |
| WO | WO-2013019796 A1 | 2/2013 |
| WO | WO-2013021380 A1 | 2/2013 |
| WO | WO-2013026393 A1 | 2/2013 |
| WO | WO-2013035088 A1 | 3/2013 |
| WO | WO-2013036761 A1 | 3/2013 |
| WO | WO-2013037618 A1 | 3/2013 |
| WO | WO-2013074576 A2 | 5/2013 |
| WO | WO-2013098815 A1 | 7/2013 |
| WO | WO-2013121265 A1 | 8/2013 |
| WO | WO-2013131639 A1 | 9/2013 |
| WO | WO-2013191699 A1 | 12/2013 |
| WO | WO-2014004051 A2 | 1/2014 |
| WO | WO-2014009875 A2 | 1/2014 |
| WO | WO-2014016820 A2 | 1/2014 |
| WO | WO-2014031857 A2 | 2/2014 |
| WO | WO-2014049501 A1 | 4/2014 |
| WO | WO-2014105964 A1 | 7/2014 |
| WO | WO-2014109653 A1 | 7/2014 |
| WO | WO-2014137344 A1 | 9/2014 |
| WO | WO-2014141213 A1 | 9/2014 |
| WO | WO-2014141229 A1 | 9/2014 |
| WO | WO-2014147624 A1 | 9/2014 |
| WO | WO-2014149021 A2 | 9/2014 |
| WO | WO-2014151431 A2 | 9/2014 |
| WO | WO-2014163020 A1 | 10/2014 |
| WO | WO-2014164926 A1 | 10/2014 |
| WO | WO-2014170887 A2 | 10/2014 |
| WO | WO-2014176420 A1 | 10/2014 |
| WO | WO-2015004540 A2 | 1/2015 |
| WO | WO-2015012639 A1 | 1/2015 |
| WO | WO-2015012672 A1 | 1/2015 |
| WO | WO-2015040049 A1 | 3/2015 |
| WO | WO-2015049495 A1 | 4/2015 |
| WO | WO-2015052705 A1 | 4/2015 |
| WO | WO-2015066670 A2 | 5/2015 |
| WO | WO-2015083305 A1 | 6/2015 |
| WO | WO-2015104454 A1 | 7/2015 |
| WO | WO-2015114629 A1 | 8/2015 |
| WO | WO-2015129887 A1 | 9/2015 |
| WO | WO-2015137733 A1 | 9/2015 |
| WO | WO-2015150625 A1 | 10/2015 |
| WO | WO-2015155545 A1 | 10/2015 |
| WO | WO-2015157725 A1 | 10/2015 |
| WO | WO-2015170184 A1 | 11/2015 |
| WO | WO-2015171869 A1 | 11/2015 |
| WO | WO-2015177670 A1 | 11/2015 |
| WO | WO-2015177682 A1 | 11/2015 |
| WO | WO-2015179571 A1 | 11/2015 |
| WO | WO-2015185352 A1 | 12/2015 |
| WO | WO-2015185583 A1 | 12/2015 |
| WO | WO-2015187858 A1 | 12/2015 |
| WO | WO-2015196164 A2 | 12/2015 |
| WO | WO-2016005719 A1 | 1/2016 |
| WO | WO-2016042499 A1 | 3/2016 |
| WO | WO-2016049284 A1 | 3/2016 |
| WO | WO-2016059556 A1 | 4/2016 |
| WO | WO-2016069689 A1 | 5/2016 |
| WO | WO-2016081767 A1 | 5/2016 |
| WO | WO-2016104411 A1 * | 6/2016 |
| WO | WO-2016104578 A1 | 6/2016 |
| WO | WO-2016113661 A1 | 7/2016 |
| WO | WO-2016116747 A1 | 7/2016 |
| WO | WO-2016124739 A1 | 8/2016 |
| WO | WO-2016135996 A1 | 9/2016 |
| WO | WO-2016137319 A1 | 9/2016 |
| WO | WO-2016140871 A1 | 9/2016 |
| WO | WO-2016143145 A1 | 9/2016 |
| WO | WO-2016149176 A1 | 9/2016 |
| WO | WO-2016155773 A1 | 10/2016 |
| WO | WO-2016177780 A1 | 11/2016 |
| WO | WO-2016183307 A1 | 11/2016 |
| WO | WO-2016183689 A1 | 11/2016 |
| WO | WO-2016185464 A1 | 11/2016 |
| WO | WO-2017002065 A1 | 1/2017 |
| WO | WO-2017004156 A1 | 1/2017 |
| WO | WO-2017012895 A1 | 1/2017 |
| WO | WO-2017040739 A2 | 3/2017 |
| WO | WO-2017048731 A1 | 3/2017 |
| WO | WO-2017051412 A1 | 3/2017 |
| WO | WO-2017055465 A1 | 4/2017 |
| WO | WO-2017055471 A1 | 4/2017 |

(56) References Cited

FOREIGN PATENT DOCUMENTS

| | | | |
|---|---|---|---|
| WO | WO-2017065239 A1 | 4/2017 |
| WO | WO-2017066620 A1 | 4/2017 |
| WO | WO-2017087681 A1 | 5/2017 |
| WO | WO-2017103923 A1 | 6/2017 |
| WO | WO-2017106878 A1 | 6/2017 |
| WO | WO 2017125909 A1 | 7/2017 |
| WO | WO-2017130133 A1 | 8/2017 |
| WO | WO-2017153840 A1 | 9/2017 |
| WO | WO-2017158498 A1 | 9/2017 |
| WO | WO-2017159959 A1 | 9/2017 |
| WO | WO-2017160097 A2 | 9/2017 |
| WO | WO-2017175907 A1 | 10/2017 |
| WO | WO-2017176621 A1 | 10/2017 |
| WO | WO-2017178946 A1 | 10/2017 |
| WO | WO-2017187184 A1 | 11/2017 |
| WO | WO-2017189757 A1 | 11/2017 |
| WO | WO-2017189890 A1 | 11/2017 |
| WO | WO-2017191624 A1 | 11/2017 |
| WO | WO-2017196548 A1 | 11/2017 |
| WO | WO-2017197150 A1 | 11/2017 |
| WO | WO-2017212253 A1 | 12/2017 |
| WO | WO-2017212258 A1 | 12/2017 |
| WO | WO-2017212343 A1 | 12/2017 |
| WO | WO-2018006086 A1 | 1/2018 |
| WO | WO-2018008023 A1 | 1/2018 |
| WO | WO-2018044054 A1 | 3/2018 |
| WO | WO-2018044825 A1 | 3/2018 |
| WO | WO-2018045056 A1 | 3/2018 |
| WO | WO-2018047164 A1 | 3/2018 |
| WO | WO-2018052958 A1 | 3/2018 |
| WO | WO-2018057637 A1 | 3/2018 |
| WO | WO-2018075394 A1 | 4/2018 |
| WO | WO-2018075514 A1 | 4/2018 |
| WO | WO-2018078973 A1 | 5/2018 |
| WO | WO-2018089450 A1 | 5/2018 |
| WO | WO-2018098417 A1 | 5/2018 |
| WO | WO-2018116161 A1 | 6/2018 |
| WO | WO-2018121998 A2 | 7/2018 |
| WO | WO-2018122535 A1 | 7/2018 |
| WO | WO-2018125538 A1 | 7/2018 |
| WO | WO-2018132678 A1 | 7/2018 |
| WO | WO-2017160097 A3 | 9/2018 |
| WO | WO-2018160670 A1 | 9/2018 |
| WO | WO-2018182188 A1 | 10/2018 |
| WO | WO-2018185369 A1 | 10/2018 |
| WO | WO-2018189387 A1 | 10/2018 |
| WO | WO-2018189393 A1 | 10/2018 |
| WO | WO-2018199661 A1 | 11/2018 |
| WO | WO-2018206067 A1 | 11/2018 |
| WO | WO-2018208992 A1 | 11/2018 |
| WO | WO-2018215879 A1 | 11/2018 |
| WO | WO-2018221903 A2 | 12/2018 |
| WO | WO-2018234571 A1 | 12/2018 |
| WO | WO-2018235629 A1 | 12/2018 |
| WO | WO-2019021288 A1 | 1/2019 |
| WO | WO-2019043628 A2 | 3/2019 |
| WO | WO-2019057511 A2 | 3/2019 |
| WO | WO-2019083863 A1 | 5/2019 |
| WO | WO-2019093023 A1 | 5/2019 |
| WO | WO-2019097488 A1 | 5/2019 |
| WO | WO-2019099068 A1 | 5/2019 |
| WO | WO-2019110595 A1 | 6/2019 |
| WO | WO-2019111053 A2 | 6/2019 |
| WO | WO-2019112935 A1 | 6/2019 |
| WO | WO-2019117740 A2 | 6/2019 |
| WO | WO-2019118709 A1 | 6/2019 |
| WO | WO-2019120420 A1 | 6/2019 |
| WO | WO-2019126080 A1 | 6/2019 |
| WO | WO-2019126792 A1 | 6/2019 |
| WO | WO-2019138407 A1 | 7/2019 |
| WO | WO-2019142196 A1 | 7/2019 |
| WO | WO-2019144316 A1 | 8/2019 |
| WO | WO-2019145762 A1 | 8/2019 |
| WO | WO-2019150378 A1 | 8/2019 |
| WO | WO-2019154834 A1 | 8/2019 |
| WO | WO-2019154837 A1 | 8/2019 |
| WO | WO-2019154839 A1 | 8/2019 |
| WO | WO-2019164173 A1 | 8/2019 |
| WO | WO-2019164471 A1 | 8/2019 |
| WO | WO-2019166965 A1 | 9/2019 |
| WO | WO-2019173866 A1 | 9/2019 |
| WO | WO-2019183306 A1 | 9/2019 |
| WO | WO-2019183622 A1 | 9/2019 |
| WO | WO-2019184904 A1 | 10/2019 |
| WO | WO-2019193000 A1 | 10/2019 |
| WO | WO-2019212972 A1 | 11/2019 |
| WO | WO-2019227150 A1 | 12/2019 |
| WO | WO-2019227203 A1 | 12/2019 |
| WO | WO-2019239275 A1 | 12/2019 |
| WO | WO-2020002801 A1 | 1/2020 |
| WO | WO-2020011290 A1 | 1/2020 |
| WO | WO-2020035852 A2 | 2/2020 |
| WO | WO-2020041502 A1 | 2/2020 |
| WO | WO-2020041633 A1 | 2/2020 |
| WO | WO-2020044331 A1 | 3/2020 |
| WO | WO-2020053848 A1 | 3/2020 |
| WO | WO-2020065651 A1 | 4/2020 |
| WO | WO-2020072243 A1 | 4/2020 |
| WO | WO-2020079218 A1 | 4/2020 |
| WO | WO-2020086552 A1 | 4/2020 |
| WO | WO-2020092653 A1 | 5/2020 |
| WO | WO-2020122374 A1 | 6/2020 |
| WO | WO 2020123154 A1 | 6/2020 |
| WO | WO 2020126392 A1 | 6/2020 |
| WO | WO-2020142470 A1 | 7/2020 |
| WO | WO-2020144486 A1 | 7/2020 |
| WO | WO-2020145185 A1 | 7/2020 |
| WO | WO-2020163042 A1 | 8/2020 |
| WO | WO-2020174444 A1 | 9/2020 |
| WO | WO-2020183508 A1 | 9/2020 |
| WO | WO-2020185549 A1 | 9/2020 |
| WO | WO-2020190401 A1 | 9/2020 |
| WO | WO-2020190514 A1 | 9/2020 |
| WO | WO-2020194278 A1 | 10/2020 |
| WO | WO-2020208590 A1 | 10/2020 |
| WO | WO-2020213819 A1 | 10/2020 |
| WO | WO-2020213820 A1 | 10/2020 |
| WO | WO-2020227288 A1 | 11/2020 |
| WO | WO-2020251177 A1 | 12/2020 |
| WO | WO-2020252406 A1 | 12/2020 |
| WO | WO-2020264263 A1 | 12/2020 |
| WO | WO-2021003473 A1 | 1/2021 |
| WO | WO-2021011255 A1 | 1/2021 |
| WO | WO-2021013654 A1 | 1/2021 |
| WO | WO-2021023749 A1 | 2/2021 |
| WO | WO-2021033139 A1 | 2/2021 |
| WO | WO-2021048854 A1 | 3/2021 |
| WO | WO-2021050829 A1 | 3/2021 |
| WO | WO 2021074453 A1 | 4/2021 |
| WO | WO-2021074455 A1 | 4/2021 |
| WO | WO-2021080392 A1 | 4/2021 |
| WO | WO-2021095889 A1 | 5/2021 |
| WO | WO-2021102365 A1 | 5/2021 |
| WO | WO 2021204981 A1 | 10/2021 |
| WO | WO 2021204982 A1 | 10/2021 |
| WO | WO 2021222185 A1 | 11/2021 |
| WO | WO-2021232096 A1 | 11/2021 |
| WO | WO 2021239523 A1 | 12/2021 |
| WO | WO 2021251571 A1 | 12/2021 |
| WO | WO 2021258068 A1 | 12/2021 |
| WO | WO-2022016086 A1 | 1/2022 |
| WO | WO 2022016106 A1 | 1/2022 |
| WO | WO-2022018532 A1 | 1/2022 |
| WO | WO-2022019695 A1 | 1/2022 |
| WO | WO-2022019696 A1 | 1/2022 |
| WO | WO-2022041657 A1 | 3/2022 |
| WO | WO-2022049360 A1 | 3/2022 |
| WO | WO 2022063931 A1 | 3/2022 |
| WO | WO-2022063934 A1 | 3/2022 |
| WO | WO-2022065800 A1 | 3/2022 |
| WO | WO-2022076455 A1 | 4/2022 |
| WO | WO-2022076913 A1 | 4/2022 |
| WO | WO-2022085989 A1 | 4/2022 |
| WO | WO-2022099067 A1 | 5/2022 |

(56) References Cited

FOREIGN PATENT DOCUMENTS

| WO | WO-2022118028 A1 | 6/2022 |
|---|---|---|
| WO | WO-2022118347 A1 | 6/2022 |
| WO | WO-2022119577 A1 | 6/2022 |
| WO | WO-2022122923 A1 | 6/2022 |
| WO | WO-2022128991 A1 | 6/2022 |
| WO | WO-2022133054 A1 | 6/2022 |
| WO | WO-2022144555 A1 | 7/2022 |
| WO | WO-2022171218 A1 | 8/2022 |
| WO | WO-2022182756 A1 | 9/2022 |
| WO | WO 2022196914 A1 | 9/2022 |
| WO | WO-2022197674 A2 | 9/2022 |
| WO | WO-2022204725 A1 | 9/2022 |
| WO | WO-2022204726 A1 | 9/2022 |
| WO | WO-2022204727 A1 | 9/2022 |
| WO | WO-2022214197 A1 | 10/2022 |
| WO | WO-2022221644 A2 | 10/2022 |
| WO | WO-2022240226 A1 | 11/2022 |
| WO | WO 2022244310 A1 | 11/2022 |
| WO | WO 2022244559 A1 | 11/2022 |
| WO | WO-2022246320 A1 | 11/2022 |
| WO | WO-2022256388 A1 | 12/2022 |
| WO | WO-2023003501 A1 | 1/2023 |
| WO | WO-2023280332 A1 | 1/2023 |
| WO | WO-2023281448 A1 | 1/2023 |
| WO | WO 2023286065 A1 | 1/2023 |
| WO | WO-2023010656 A1 | 2/2023 |
| WO | WO-2023011503 A1 | 2/2023 |
| WO | WO-2023023367 A1 | 2/2023 |
| WO | WO 2023028262 A1 | 3/2023 |
| WO | WO-2023047662 A1 | 3/2023 |
| WO | WO-2023066020 A1 | 4/2023 |
| WO | WO-2023080310 A1 | 5/2023 |
| WO | WO-2023080329 A1 | 5/2023 |
| WO | WO 2023092072 A1 | 5/2023 |
| WO | WO 2023094415 A1 | 6/2023 |
| WO | WO-2023100130 A1 | 6/2023 |
| WO | WO-2023108881 A1 | 6/2023 |
| WO | WO-2023118023 A2 | 6/2023 |
| WO | WO-2023130108 A1 | 7/2023 |
| WO | WO-2023133573 A1 | 7/2023 |
| WO | WO-2023135597 A1 | 7/2023 |
| WO | WO 2023146191 A1 | 8/2023 |
| WO | WO-2023146875 A1 | 8/2023 |
| WO | WO-2023169614 A1 | 9/2023 |
| WO | WO-2023175610 A1 | 9/2023 |
| WO | WO-2023222910 A1 | 11/2023 |
| WO | WO 2023234274 A1 | 12/2023 |
| WO | WO-2023238038 A1 | 12/2023 |
| WO | WO-2023238039 A1 | 12/2023 |
| WO | WO-2023238040 A1 | 12/2023 |
| WO | WO-2023238041 A1 | 12/2023 |
| WO | WO 2024006939 A2 | 1/2024 |
| WO | WO 2024013472 A1 | 1/2024 |
| WO | WO-2024015444 A1 | 1/2024 |
| WO | WO 2024031086 A1 | 2/2024 |
| WO | WO 2024033563 A1 | 2/2024 |
| WO | WO 2024081171 A1 | 4/2024 |
| WO | WO 2024091837 A1 | 5/2024 |
| WO | WO 2024134614 A1 | 6/2024 |
| WO | WO 2024182674 A1 | 9/2024 |
| WO | WO-2024234537 A1 | 11/2024 |
| WO | WO 2025003647 A1 | 1/2025 |
| WO | WO 2025023457 A1 | 1/2025 |
| WO | WO 2025037714 A1 | 2/2025 |
| WO | WO 2025038540 A2 | 2/2025 |
| WO | WO 2025076527 A1 | 4/2025 |

OTHER PUBLICATIONS

Stokes, M. G., Chambers, C. D., & Gould, I. C. (2005). Simple metric for scaling motor threshold based on scalp-cortex distance: Application to studies using transcranial magnetic stimulation. Journal of Neurophysiology, 94(6), 4520-4527. https://doi.org/10.1152/jn.00067.2005 (Year: 2005).*

Double 6" Rudy Arm—Universal Jan. 4, 2020 & Mar. 8, 2016. Upgrade Innovations. (Jun. 22, 2024). https://upgradeinnovations.com/product/double-6-rudy-arm/ (Year: 2024).*

2018 Cutera University, Clinical Forum, Cutera 20, 26 pages.

501(k) K030708 Slendertone FLEX Letter from Department of Health and Humane Serivces, Public Health Service, Jun. 25, 2003, 6 pages.

501(k) K163165 AM-100 Letter from Department of Health and Human Services, Public Health Service, Feb. 16, 2017, 9 pages.

Abulhasan, J.F., et al., "Peripheral Electrical and Magnetic Stimulation to Augment Resistance Training," Journal of Functional Morphology and Kinesiology, 1(3):328-342, (Sep. 2016).

Accent Radiofrequency System, Operator's Manual, Alma Lasers, Wellbeing Through Technology, 2008, 82 Pages.

Agilent Technologies, Inc., "Agilent 33500 Series 30 MHz Function / Arbitrary Waveform Generator User's Guide," Publication No. 33520-90001 (Dec. 2010), 278 pages.

Agilent Technologies, Inc., "Agilent Announces 30 MHz Function/Arbitrary Waveform Generators," Microwave J., Url: (Aug. 3, 2010), 8 pages.

Allais, G., et al., "Non-pharmacological Approaches to Chronic Headaches: Transcutaneous Electrical Nerve Stimulation, Lasertherapy and Acupuncture in Transformed Migraine Treatment," Neurological Sciences 24 Suppl 2:S138-S142, Springer-Verlag Italia, Italy (May 2003).

*Allergan, Inc. et al* v. *BTL Healthcare Technologies A.S.*, PTAB-PGR2021-00015, Paper 16 (Decision Denying Institution of Post-Grant Review), Jun. 17, 2021, 20 pages.

*Allergan, Inc. et al* v. *BTL Healthcare Technologies A.S.*, PTAB-PGR2021-00016, Paper 16 (Decision Denying Institution of Post-Grant Review), Jun. 17, 2021, 20 pages.

*Allergan, Inc. et al* v. *BTL Healthcare Technologies A.S.*, PTAB-PGR2021-00017, Paper 16 (Decision Denying Institution of Post-Grant Review), Jun. 16, 2021, 33 pages.

*Allergan, Inc. et al* v. *BTL Healthcare Technologies A.S.*, PTAB-PGR2021-00018, Paper 16 (Decision Denying Institution of Post-Grant Review), Jun. 16, 2021, 42 pages.

*Allergan, Inc. et al* v. *BTL Healthcare Technologies A.S.*, PTAB-PGR2021-00020, Paper 16 (Decision Denying Institution of Post-Grant Review), Jun. 16, 2021, 35 pages.

*Allergan, Inc. et al* v. *BTL Healthcare Technologies A.S.*, PTAB-PGR2021-00021, Paper 17 (Decision Denying Institution of Post-Grant Review), Jun. 16, 2021, 33 pages.

*Allergan, Inc. et al* v. *BTL Healthcare Technologies A.S.*, PTAB-PGR2021-00022; PTAB-PGR2021-00023; PTAB-PGR2021-00024; PTAB-PGR2021-00025; PTAB-IPR2021-00296; PTAB-IPR2021-00312, Paper 11 (Decision Settlement Prior to Institution of Trial), Jul. 6, 2021, 4 pages.

Alma Lasers., "Accent Radiofrequency System, Operator's Manual," Wellbeing Through Technology, 2008, Chapters 1-8, Appendix A.

Arjunan, P.A., et al., "Computation and Evaluation of Features of Surface Electromyogram to Identify the Force of Muscle Contraction and Muscle Fatigue," BioMed research international 2014:197960, Hindawi Pub. Co, United States (2014).

Avram, M.M and Harry, R.S., "Cryolipolysis for Subcutaneous Fat Layer Reduction," Lasers in Surgery and Medicine, 41(10):703-708, Wiley-Liss, United States (Dec. 2009).

Bachasson, D., et al., "Quadriceps Function Assessment Using an Incremental Test and Magnetic Neurostimulation: a Reliability Study," Journal of Electromyography and Kinesiology, 23(3):649-658, Elsevier, England, (Jun. 2013).

Baranov, A., Krion, Whole Body Cryotherapy, Russia, 19 Pages.

Barker, A.T, "An Introduction to the Basic Principles of Magnetic Nerve Stimulation," Journal of Clinical Neurophysiology, 8(1):26-37, Lippincott Williams and Wilkins, United States, (Jan. 1991).

Barker, A.T., et al., "Non-Invasive Magnetic Stimulation of Human Motor Cortex," Lancet 1(8437):1106-1107, Elsevier, England (May 1985).

Barker, A.T., "The History and Basic Principles of Magnetic Nerve Stimulation," Electroencephalography and Clinical Neurophysiology 51:3-21, Elsevier, Netherlands (1999).

Barrett, J., et al., "Mechanisms of Action Underlying the Effect of Repetitive Transcranial Magnetic Stimulation on Mood: Behavioral

(56)          References Cited

OTHER PUBLICATIONS and Brain Imaging Studies," Neuropsychopharmacology 29(6):1172-1189, Nature Publishing Group, England (Jan. 14, 2004).

Basic Protocol of Salus, Talent with Incontinence Chair, REMED, 1 page.

Behrens, M., et al., "Repetitive Peripheral Magnetic Stimulation (15 Hz RPMS) of the Human Soleus Muscle did not Affect Spinal Excitability," Journal of Sports Science and Medicine, 10(1):39-44, Dept. of Sports Medicine, Medical Faculty of Uludag University, Turkey (Mar. 2011).

Beijing ADSS Development Co., Ltd., K231318 510(k) Summary, Electromagnetic Stimulator Device (Models: EM Contouring and Tesla Duet), 11 pages (Jul. 2023).

Beijing Sano Laser S&T Development Co., Ltd, K230024 510(k) Summary, HI-EMT Magshape, (Sep. 2023), 15 pages.

Beilin, G., et al., "Electromagnetic Fields Applied to the Reduction of Abdominal Obesity," Journal of Cosmetic and Laser Therapy, 14(1):24-42, Informa Healthcare, England, (Feb. 2012).

Belanger, A-Y., "Chapter 13: Neuromuscular Electrical Stimulation," in Therapeutic Electrophysical Agents: Evidence Behind Practice, 3rd Edition, Lupash, E., ed., pp. 220-255, Lippincott Williams and Wilkins, United States (2015).

Benton, et al., "Functional Electrical Stimulation—A Practical Clinical Guide," Second Edition, The Professional Staff Association of the Rancho Los Amigos Hospital, Inc., 42 pages (1981).

Benton, L.A., et al., "Chapter 2: Physiological Basis of Nerve and Muscle Excitation" and "Chapter 4: General Uses of Electrical Stimulation," in Functional Electrical Stimulation: A Practical Guide, 2nd Edition, pp. 11-30 and 53-71, Rancho Los Amigos Rehabilitation Engineering Center, Downey, CA (1981), 42 pages.

Bergh, U., and Ekblom, B., "Influence of Muscle Temperature on Maximal Muscle Strength and Power Output in Human Skeletal Muscles," Acta Physiologica Scandinavica 107(1):33-37, Blackwell Scientific Publications, England (Aug. 1979).

Binder-Macleod, S.A., et al., "Force Output of Cat Motor Units Stimulated with Trains of Linearly Varying Frequency," Journal of Neurophysiology 61(1):208-217, American Physiological Society, United States (Jan. 1989).

Binder-Macleod, S.A., et al., "Use of a Catchlike Property of Human Skeletal Muscle to Reduce Fatigue," Muscle and Nerve 14(9):850-857, John Wiley and Sons, United States (Sep. 1991).

Bio Medical Research Limited., "Slendertone Flex Abdominal Training System, Instructions for Use," All pages (Aug. 2006).

Bio Medical Research Limited., "Slendertone Flex Max Instruction Manual," All pages (Apr. 2006).

Bio-Medical Research Ltd., K010335, 510(k) Summary, Slendertone Flex, All pages (Sep. 2001).

Bio-Medical Research Ltd., K022855 510(k) Summary, Slendertone, 1-6 (Mar. 2003).

Bios s.r.l., K201239 510(k) Summary, NuEra Tight Family, EMS Model, 9 pages (Dec. 2020).

Bischoff, C., et al., "Repetitive Magnetic Nerve Stimulation: Technical Considerations and Clinical Use in the Assessment of Neuromuscular Transmission," Electroencephalography and Clinical Neurophysiology 93(1):15-20, Elsevier, Ireland (Feb. 1994).

Bourland, J.D., et al., "Transchest Magnetic (Eddy-Current) Stimulation of the Dog Heart," Medical and Biological Engineering and Computing 28(2):196-198, Springer, United States (Mar. 1990).

BTL Industries, Inc., K163165 510(k) Summary, AM- 100, All pages (Feb. 2017).

BTL Industries, Inc., K180813 510(k) Summary, Emsculpt, All pages (Mar. 2018).

*BTL Industries, Inc. v. Allergan Ltd. et al* DDE-1-20-cv-01046, Complaint for Patent Infringement and Exhibits 1-38, 821 pages (Aug. 2020).

*BTL Industries, Inc. v. Allergan Ltd et al.,* DDE-1-20-cv-01046, Order Administratively Closing Case, Jul. 26, 2021, 1 page.

*BTL Industries, Inc. v. Allergan Ltd et al* DDE-1-20-cv-01046, Order Granting Motion to Stay Pending Resolution of Proceedings at the International Trade Commission (Unopposed), 2 pages (Oct. 2020).

*BTL Industries, Inc. v. Allergan PLC et al* DDE-1-19-cv-02356, Complaint for Patent Infringement and Exhibits 1-34, 375 pages (Dec. 2019).

*BTL Industries, Inc. v. Allergan PLC et al* DDE-1-19-cv-02356, Order Granting Stipulation to Stay, Oct. 1, 2020, 1 page.

*BTL Industries, Inc. v. Allergan USA, Inc. et al.,* DDE-1-19-cv-02356, Order Administratively Closing Case, Jul. 26, 2021, 1 page.

Buenos Aires, Oct. 14, 2014, Venus Concept, Provision No. 7246, 56 pages (With Machine Translation).

Burge, S.M and Dawber, R.P., "Hair Follicle Destruction and Regeneration in Guinea Pig Skin After Cutaneous Freeze Injury," Cryobiology, 27(2):153-163, Elsevier, Netherlands (Apr. 1990).

Busso, M. and Denkova, R., "Efficacy of High Intensity Focused Electro-Magnetic (HIFEM) Field Therapy When Used for Non-Invasive Buttocks Augmentation and Lifting: A Clinical Study" American Society for Laser Medicine and Surgery Abstracts, 382 (2018).

Bustamante, V., et al., "Muscle Training With Repetitive Magnetic Stimulation of the Quadriceps in Severe COPD Patients," Respiratory Medicine, 104(2):237-245, Elsevier, England, (Feb. 2010).

Bustamante, V., et al., "Redox Balance Following Magnetic Stimulation Training in the Quadriceps of Patients With Severe COPD," Free Radical Research, 42(11-12):939-948, Informa Healthcare, England, (Nov. 2008).

Callaghan, M.J., et al., "Electric Muscle Stimulation of the Quadriceps in the Treatment of Patellofemoral Pain," Archives of Physical Medicine and Rehabilitation 85(6):956-962, W.B. Saunders, United Staes (Jun. 2004).

Carbonaro, M., et al., "Architectural Changes in Superficial and Deep Compartments of the Tibialis Anterior during Electrical Stimulation over Different Sites," IEEE transactions on Neural Systems and Rehabilitation Engineering 28(11):2557-2565, IEEE, United States (Nov. 2020).

Caress, J.B., et al., "A Novel Method of Inducing Muscle Cramps Using Repetitive Magnetic Stimulation," Muscle Nerve, 23(1):126-128, John Wiley and Sons, United States, (Jan. 2000).

CEFALY Enhanced User Manual, (2023), 116 pages.

CEFALY Technology, K201895 510(k) Summary, Cefaly Dual, (Sep. 2020), 8 pages.

Certain Non-Invasive Aesthetic Body Contouring Devices, Components Thereof, and Methods of Using the Same, Inv. No. 337-TA-1219, BTL's Statement of Suggested Claim Terms to Be Construed Pursuant to Ground Rule 6b, Nov. 4, 2020, 2 pages.

Certain Non-Invasive Aesthetic Body Contouring Devices, Components Thereof, and Methods of Using the Same, Inv. No. 337-TA-1219, Complainant BTL's Proposed Construction of Disputed Claim Terms, Dec. 8, 2020, 19 pages.

Certain Non-Invasive Aesthetic Body Contouring Devices, Components Thereof, and Methods of Using the Same, Inv. No. 337-TA-1219, Complaint, Aug. 5, 2020, 93 pages.

Certain Non-Invasive Aesthetic Body Contouring Devices, Components Thereof, and Methods of Using the Same, Inv. No. 337-TA-1219, Joint Claim Construction Chart, Dec. 14, 2020, 15 pages.

Certain Non-Invasive Aesthetic Body Contouring Devices, Components Thereof, and Methods of Using the Same; Inv. No. 337-TA-1219, Joint Claim Construction Chart, Dec. 18, 2020, 15 pages.

Certain Non-Invasive Aesthetic Body Contouring Devices, Components Thereof, and Methods of Using the Same, Inv. No. 337-TA-1219, Respondents' Allergan Limited, Allergan USA, Inc., Allergan, Inc., Zeltiq Aesthetics, Inc., Zeltiq Ireland Unlimited Company, and Zimmer MedizinSysteme GmbH's Notice of Prior Art, Nov. 20, 2020, 5 pages.

Certain Non-Invasive Aesthetic Body Contouring Devices, Components Thereof, and Methods of Using the Same, Inv. No. 337-TA-1219, Respondents' List of Claim Terms for Construction, Nov. 4, 2020, 8 pages.

Certain Non-Invasive Aesthetic Body Contouring Devices, Components Thereof, and Methods of Using the Same; Inv. No. 337-

(56)                    References Cited

OTHER PUBLICATIONS

TA-1219, Respondents' List of Proposed Claim Constructions and Their Intrinsic and Extrinsic Support, filed Dec. 15, 2020, 23 pages.

Certain Non-Invasive Aesthetic Body Contouring Devices, Components Thereof, and Methods of Using the Same, Inv. No. 337-TA-1219, Response of Respondent Zimmer MedizinSysteme GmbH to the Complaint and Notice of Investigation, Oct. 22, 2020, 68 pages.

Certain Non-Invasive Aesthetic Body Contouring Devices, Components Thereof, and Methods of Using the Same, Inv. No. 337-TA-1219, Response of Respondents Allergan Limited, Allergan USA, Inc., Allergan, Inc., Zeltiq Aesthetics, Inc., and Zeltiq IrelandUnlimited Company to the Complaint and Notice of Investigation, Oct. 22, 2020, 69 pages.

Certain Non-Invasive Aesthetic Body-Contouring Devices, Components Thereof, and Methods of Using Same, Notice of Institution of Investigation, Inv. No. 337-TA-1219, Notice of Institution of Investigation, Sep. 2, 2020, 21 pages.

Certain Non-Invasive Aesthetic Body-Contouring Devices, Components Thereof, and Methods of Using the Same, Inv. No. 337-TA-1219, Order No. 17: Amending Procedural Schedule, Apr. 9, 2021, 4 pages.

Certain Non-Invasive Aesthetic Body-Contouring Devices, Components Thereof, and Methods of Using the Same, Inv. No. 337-TA-1219, Order No. 30 (Order Concerning the Procedural Schedule), Aug. 4, 2021, 3 pages.

Certain Non-Invasive Aesthetic Body-Contouring Devices, Components Thereof, and Methods of Using the Same, Inv. No. 337-TA-1219, Order No. 30 (Order Concerning the Procedural Schedule), August 4, 2021, 3 pages.

Certified English Translation of Belyaev, A.G., "Effect of Magnetic Stimulation on the Strength Capacity of Skeletal Muscles," Ph.D. Thesis ABSTRACT, Smolensk State Academy of Physical Culture, Sport, and Tourism, Dec. 11, 2020, 23 pages.

Certified English Translation of Belyaev, A.G., "Effect of Magnetic Stimulation on the Strength Capacity of Skeletal Muscles," Ph.D. Thesis, Smolensk State Academy of Physical Culture, Sport, and Tourism, Dec. 11, 2020, 117 pages.

Chattanooga Group of Encore Medical, L.P., "Intelect SWD 100 User Manual, Operation and Installation Instructions for Intelect SWD 00- Model 1600," All pages (2009).

Chesterton, L.S., et al., "Skin Temperature Response to Cryotherapy," Archives of Physical Medicine and Rehabilitation, 83(4):543-549, W.B. Saunders, United States (Apr. 2002).

Clinical Application of Electro Magnetic Stimulation, SALUS-TALENT, Korea Society of interventional Muscle and Soft Tissue Stimulation Therapy, CR Technology, 141 pages.

Collins, D.F., et al., "Large Involuntary Forces Consistent With Plateau-Like Behavior of Human Motoneurons," Journal of Neuroscience 21(11):4059-4065, Society for Neuroscience, United States (Jun. 2001).

Colson, S., et al., "Re-Examination of Training Effects by Electrostimulation in the Human Elbow Musculoskeletal System," International Journal of Sports Medicine 21(4):281-288, Stuttgart, Thieme (May 2000).

Comorbid Anxiety, Clinical benefits of TMS for patients with Major Depressive disorders, Rev. 1.0; 2 pages.

Course in Physical Therapy, Presentation, Jan. 4, 2013, 156 pages.

CR Technologies, "Salus Talent Pop Manual KFDA First Approval Document" (English Translation), Nov. 25, 2011, 47 pages.

CR Technologies, "Notification of medical device manufacturing item permission, Salus Talent Pop KFDA Approval Document" (English Translation), 3 pages (Sep. 2011).

CR Technology Co, Ltd., "Salus-Talent DOUBLE Sales Brochure" 2 pages, (Oct. 2020).

CR Technology Co. Ltd., "Medical Laser Irradiator Salus-Talent-Pop User Manual Version 1.00" (Nov. 2020).

CR Technology Co. Ltd., Salus Talent Pop User Manual, Ver. 1.00, All pages, Approx. 2012.

CR Technology, SALUS-TALENT, Technical File of Electromagnetic Stimulator, Document No. TF-C05, 2008, 241 pages.

CR Technology, Technology for Health and Business for Human Being, investor relations, 2008, 21 pages.

CryoGenTech GmbH, Company Profile, Creating CRYO, Medica, 9 pages.

Currier, D. P., "Effects of Electrical and Electromagnetic Stimulation after Anterior Cruciate Ligament Reconstruction," The Journal of Orthopaedic and Sports Physical Therapy 17(4): 177-84, Williams And Wilkins, United States (1993).

Cutera, truSculptflex, Brochure, dated 2019, 2 pages.

Cynosure, SculpSure TM, The New Shape of Energy-Based bodyContouring, 2015, Cynosure INC, 2 pages.

Cynosure, Smooth Shapes XV, Now with Smoothshape petite, Transforming non-invasive Body Shaping, Retrieved from the Internet: (www.cynosure.com), 2011, Cynosure Inc, 8 pages.

Davies, C.T., et al., "Contractile Properties of the Human Triceps Surae With Some Observations on the Effects of Temperature and Exercise," European Journal of Applied Physiology and Occupational Physiology 49(2):255-269, Springer Verlag, Germany (Aug. 1982).

Deng, Z.D., et al., "Electric Field Depth-Focality Tradeoff in Transcranial Magnetic Stimulation: Simulation Comparison of 50 Coil Designs," Brain stimulation 6(1):1-13, Elsevier, New York (Jan. 2013).

Depatment of Health and Human Services, 501(k) Letter and Summary for K092476 Body Control System 4M Powered Muscle Stimulator, dated May 7, 2010, 5 pages.

Depatment of Health and Human Services, 501(k) Letter and Summary for K160992 HPM-6000 Powered Muscle Stimulator, dated Oct. 21, 2016, 9 pages.

Depatment of Health and Human Services, 501(k) Letter and Summary for K163415 SlimShape System Powered Muscle Stimulator, dated Apr. 20, 2017, 8 pages.

Depatment of Health and Human Services, 501(k) Letter and Summary for K182106 BTL 799-2T Powered Muscle Stimulator, dated Oct. 23, 2018, 9 pages.

Depatment of Health and Human Services, 501 (k) Letter and Summary for K190456 BTL 799-2L Powered Muscle Stimulator, dated Jul. 5, 2019, 9 pages.

Depatment of Health and Human Services, 501(k) Letter and Summary for K192224 BTL 899 Powered Muscle Stimulator, dated Dec. 5, 2019, 11 pages.

Doucet, B., et al., "Neuromuscular Electrical Stimulation for Skeletal Muscle Function," Yale Journal of Biology and Medicine 85:201-215, Yale Journal of Biology and Medicine, United States (Jun. 2012).

Dudley, G. and Stevenson, S., "Use of Electrical Stimulation in Strength and Power Training," Special Problems in Strength and Power Training :426-435 (2003).

Duncan, D., et al., "Noninvasive Induction of Muscle Fiber Hypertrophy and Hyperplasia: Effects of High-Intensity Focused Electromagnetic Field Evaluated in an In-Vivo Porcine Model: A Pilot Study," Aesthetic Surgery Journal 40(5):568-574, Oxford University Press, United States (Apr. 2020).

DuoMAG Magnetic Stimulator, Alien Technik User Manuel, Jun. 26, 2012,48 pages, Version 2.1.

Dybek, T., et al., "Impact of 10 Sessions of Whole Body Cryostimulation on Aerobic and Anaerobic Capacity and on Selected Blood Count Parameters," Biology of Sport, 29(1):39-43 (Jan. 2012).

Dynatronics., "Better Rehab Solutions for Better Outcomes," Rehabilitation Products Guide 2.3, 2017, 52 pages.

Effective PEMF Magnetic Fat Reduction Slimming Body Beauty Salon Machine (PEMF Star), Wolfbeauty 1980, PEMF STAR, China, Retrieved from the Internet: (URL: https://www.ec21.com/product-details/Effective-PEMF-Magnetic-Fat-Reduction--8928746.html), 2019, 5 pages.

Elamed, Magnetic Therapeutic Apparatus for Running Pulse Magfield small-sized ALMAG-01 Manual, allegedly accessed on Nov. 18, 2020, All pages.

Electrocore, Inc., K211856 510(k) Summary, GammaCore Sapphire, (Sep. 2021), 12 pages.

(56) References Cited

OTHER PUBLICATIONS

Eliminate Stubborn Fat without Surgery or Downtime and Feel Great From Every Angle, Fear No Mirror®, Consultation Guide, Coolsculpting, 2014, 20 pages.
EndyMed PRO, 3 Deep, 3 Dimensional Control of the Target Zone, a Brilliant RadioFrequency Innovation, Eclipse Aesthetics, 7 Pages.
Energist Ltd—Acquired Chromogenez—Old Account, iLipo—Laser Liposuction (i-Lipo), Video Screenshots, Aug. 10, 2009, 5 pages.
eNeura Inc, K162797 510(k) Summary, Spring TMS, (Jun. 2017), 9 pages.
Enoka, R.M., "Muscle Strength and Its Development," Sports Medicine 6:146-168, Springer (Oct. 1988).
Epstein, C., et al., "The Oxford Handbook of Transcranial Stimulation," 773 pages (2008).
European Commission, Neuodegenerative Disorders, 10 pages printed Dec. 27, 2016.
European Commission, "Neurogenerative Disorders," 10 pages printed Dec. 27, 2016.
European Patent Office, International Search Report and Written Opinion for International Application No. PCT/IB2016/053930, dated Dec. 12, 2016, 19 pages.
Exilis, Operator's Manual, BTL, 2012, 44 Pages.
Faghri, P.D., et al., "The Effects of Functional Electrical Stimulation on Shoulder Subluxation, Arm Function Recovery, and Shoulder Pain in Hemiplegic Stroke Patients," Archives of Physical Medicine and Rehabilitation 75(1):73-79, W.B. Saunders, United States (Jan. 1994).
FDA letter to Venus Legacy, Dec. 19, 2014, 7 pages.
File History for U.S. Appl. No. 62/812,123, to Caselino et al., filed Feb. 28, 2019.
File History for U.S. Appl. No. 62/884,099, to Caselino et al., filed Aug. 7, 2019.
File History for U.S. Appl. No. 62/908,741, to Caselino et al., filed Oct. 1, 2019.
Final Office Action mailed Sep. 12, 2016, in U.S. Appl. No. 14/873,110, Ladman, J., et al., filed Oct. 1, 2015.
Final Office Action mailed Apr. 18, 2016, in U.S. Appl. No. 14/700,349, Schwarz T., et al., filed Apr. 30, 2015.
Final Office Action mailed Dec. 1, 2016, in U.S. Appl. No. 14/789,658, Ladman, J., et al., filed Jul. 1, 2015.
Final Office Action mailed Jan. 27, 2017 in U.S. Appl. No. 15/060,375, Schwarz, T., et al., filed Mar. 3, 2016.
Final Office Action mailed Jan. 4, 2017, in U.S. Appl. No. 15/073,318, Schwarz, T., et al., filed Mar. 17, 2016.
Final Office Action mailed Jul. 1, 2016, in U.S. Appl. No. 14/870,713, Schwarz, T., et al., filed Sep. 30, 2015.
Final Office Action mailed Jul. 14, 2017, in U.S. Appl. No. 15/344,811, Schwarz, T., et al., filed Nov. 7, 2016.
Final Office Action mailed Jun. 22, 2017, in U.S. Appl. No. 15/151,012, Schwarz, T., et al., filed May 10, 2016.
Final Office Action mailed Jun. 26, 2017, in U.S. Appl. No. 15/099,274, Pribula, O., et al., filed Apr. 14, 2016.
Final Office Action mailed May 20, 2016, in U.S. Appl. No. 14/697,934, Zarsky, J., et al., filed Apr. 28, 2015.
Final Office Action mailed Nov. 4, 2016, in U.S. Appl. No. 14/951,093, Schwarz, T., et al., filed Nov. 24, 2015.
Final Office Action mailed Aug. 12, 2016, in U.S. Appl. No. 14/926,365, Prouza, O., et al., filed Oct. 29, 2015.
Fischer, J., et al., "Precise Subpixel Position Measurement with Linear Interpolation of CMOS Sensor Image Data," The 6th IEEE International Conference on Intelligent Data Acquisition and Advanced Computing Systems, 500-504 (Sep. 2011).
Fisher, R., et al., "ILAE Official Report: a Practical Clinical Definition of Epilepsy, " Epilepsia, 55(4):475-482, Blackwell Science, United States (Apr. 2014).
FMS Tesla Stym—AKCE, Medila Cenova nabidika, Price offerc. 191, 24 pages.
Fotona d.o.o., K221274 510(k) Summary, StarFormer, (Sep. 2023), 10 pages.

Fotona d.o.o., K234061 510(k) Summary, StarFormer, (Jul. 2024), 7 pages.
Fujimura, K., et al., "Effects of Repetitive Peripheral Magnetic Stimulation on Shoulder Subluxations Caused by Stroke: A Preliminary Study," Neuromodulation : Journal of the International Neuromodulation Society 23(6):847-851, Wiley-Blackwell, United States (Nov. 2020).
Gaines, M., "Slendertone Abdominal Training System, the First FDA-Cleared Abdominal Belt, Introduced in United States by Compex Technologies on Time for Holiday Gift-Giving," Business Wire 44199 (Oct. 2003).
Geddes, L.A., "History of Magnetic Stimulation of the Nervous System," Journal of Clinical Neurophysiology 8(1):3-9, Lippincott Williams and Wilkins, United States (Jan. 1991).
Goetz, S.M., et al., "Coil Design for Neuromuscular Magnetic Stimulation Based on a Detailed 3-D Thigh Model," IEEE Transactions on Magnetics, 50(6):10, IEEE, (Jun. 2014).
Goodman, B.E., "Channels Active in the Excitability of Nerves and Skeletal Muscles Across the Neuromuscular Junction: Basic Function and Pathophysiology," Advances in Physiology Education 32(2):127-135, American Physiological Society, United States (Jun. 2008).
Gorgey, A., et al., "Effects of Electrical Stimulation Parameters on Fatigue in Skeletal Muscle," The Journal of Orthopaedic and Sports Physical Therapy 39(9): 684-692, Williams And Wilkins, United States (Sep. 2009).
Gorodnichev, R.M., et al., "The Effect of Electromagnetic Stimulation on the Parameters of Muscular Strength," Human Physiology 40:65-69 (2014).
Gorodnichev, R.M., "Magnetic Stimulation of Muscles as New Method to Enhance Their Strength, " Velikie Luki State Academy of Physical Culture and Sport, Velikie Luki, 2016, 5 pages.
Guangzhou HEMS Tech, PEMF Star, May 31, 2019, 5 pages.
Guidance for Insdustry and Food and Drug Administration Staff, (Jul. 2011), 26 pages.
Halaas, Y. and Bernardy, J., "Biochemical Perspective of Fat Physiology after Application of HIFEM Field Technology: Additional Investigation of Fat Disruption Effects in a Porcine Study," American Society for Laser Medicine and Surgery Abstracts, S4 (2019).
Hamnegard, C.H., et al., "Quadriceps Strength Assessed by Magnetic Stimulation of the Femoral Nerve in Normal Subjects," Clinical Physiology and Functional Imaging, 24(5):276-280, Blackwell, England, (Sep. 2004).
Han, B.H., et al., "Development of four-channel magnetic nerve stimulator," 2001 Proceedings of the 23rd Annual EMBS International Conference, pp. 1325-1327, Turkey (2001).
Han, T.R., et al., "Magnetic Stimulation of the Quadriceps Femoris Muscle: Comparison of Pain With Electrical Stimulation," American Journal of Physical Medicine and Rehabilitation, 85(7):593-599, Lippincott Williams and Wilkins, United States, (Jul. 2006).
Harkey, M.S., "Disinhibitory Interventions and Voluntary Quadriceps Activation: A Systematic Review," Journal of Athletic Training 49(3):411-421, National Athletic Trainers' Association, United States (2014).
Hasala, O., et al., Case Study of Treating Acute Ankle Distortion Using TMS, Charles University, Faculty of Physical Education and Sports, Prague, Czech Republic, 4 Pages.
Hebei JT Medical Co., Ltd., K232181 510(k) Summary, Body Contouring Machine, (Apr. 2024), 10 pages.
Heidland, A., et al., "Neuromuscular Electrostimulation Techniques: Historical Aspects and Current Possibilities in Treatment of Pain and Muscle Waisting," Clinical Nephrology 79 Suppl 1:S12-S23, Dustri-Verlag Dr. Karl Feistle, Germany (Jan. 2012).
Heisel, Jurgen, Physikalische Medizin, Stuttgart: Georg Thieme Verlag KG, 2005. ISBN 3-13-139881-7. p. 159.
Hera Estetik Medikal, "LIPOSTAR" dated Jul. 7, 2014, accessed at https://www.youtube.com/watch?v =- R7OnFIK9go, accessed on Dec. 15, 2021.
Hera Estetik Medikal, "Lipostar Manyetik Incelme", accessed at https://www.heraestetik.com/en/urundetay/lipostar-manyetik-incelme, accessed on Dec. 15, 2021.

(56)　　　　　References Cited

OTHER PUBLICATIONS

Hill, A., "The Influence of Temperature on the Tension Developed in an Isometric Twitch," Proceeding of the Royal Society B 138:349-354, (Sep. 1951).

Hirvonen, H.E., et al., "Effectiveness of Different Cryotherapies on Pain and Disease Activity in Active Rheumatoid Arthritis. A Randomised Single Blinded Controlled Trial, "Clinical and Experimental Rheumatology, 24(3):295-301, Clinical and Experimental Rheumatology S.A.S, Italy (May-Jun. 2006).

Hovey, C. and Jalinous, R., "The Guide to Magnetic Stimulation" Magstim, Pioneers in Nerve Stimulation and Monitoring, pp. 1-44 (2016).

Hovey, C., et al., "The Guide to Magnetic Stimulation," The Magstim Company Limited, 48 pages (Jul. 2006).

Huang, Y.Z., et al., "Theta Burst Stimulation of the Human Motor Cortex," Neuron 45(2):201-206, Cell Press, United States (Jan. 2005).

I-Lipo by Chromo genex, i-Lipo Ultra is the Intelligent, Non-Surgical Alternative to Liposuction, 2011, 2 pages.

Increasing Physiotherapy Presence in Cosmetology, Spa Inspirations, Jan. 2012, pp. 34-35.

InMode Ltd., K191855 K10(k) Summary, Em Face Device, 10 pages (Oct. 2019).

InMode Ltd., K210877 K10(k) Summary, Evolve System with the T3 Applicator, 18 pages (Oct. 2023).

InMode Ltd., K231495 K10(k) Summary, The Evolve System with the Transform Applicator, 9 pages (Oct. 2023).

Irazoqui P., Post Grant Review of U.S. Pat. No. 10,695,576, PTAB-PGR2021-00024, filed as EX1085, Dec. 14, 2020, 25 pages.

Iskra Medical, Magneto System, 2012, 2 pages.

Iskra Medical, "TESLA Stym—Functional Magnetic Stimulation FMS," Nov. 2013, http://ww.iskramedical.eu/magneto-therapy-medical/tesla-stym, 5 pages.

Iskra Medical, "TESLA Stym Website," URL: https://web.archive.org/web/20131106123126/http:/www.iskramedical.eu:80/magneto-therapy-medical/tesla-stym (Nov. 6, 2013).

Izumiya, Y., et al., "Fast/Glycolytic Muscle Fiber Growth Reduces Fat Mass and Improves Metabolic Parameters in Obese Mice", Cell Metabolism 7(2):159-172, Cell Press, United States (Feb. 2008).

Jacob, C., et al., "High Intensity Focused Electro-Magnetic Technology (HIFEM) for Non-Invasive Buttock Lifting and Toning of Gluteal Muscles: A Multi-Center Efficacy And Safety Study," Journal of Drugs in Dermatology 17(11):1229-1232, Physicians Continuing Education Corporation, United States (Nov. 2018).

Jacob, C.I., et al., "Safety And Efficacy of a Novel High-Intensity Focused Electromagnetic Technology Device for Noninvasive Abdominal Body Shaping," Journal of Cosmetic Dermatology, 17(5):783-787, Blackwell Science, United States (Oct. 2018).

Jacobm C., and Paskova, "A Novel Non-Invasive Technology Based on Simultaneous Induction of Changes in Adipose and Muscle Tissues: Safety and Efficacy of a High Intensity Focused Electro-Magnetic (HIFEM) Field Device Used For Abdominal Body Shaping," American Society for Laser Medicine and Surgery, 2018 Electronic Posters (ePosters) Town Hall and ePosters, 369, p. 1, Wiley Periodicals, Inc. (2018).

Jalinous, R., "Technical and Practical Aspects of Magnetic Nerve Stimulation," Journal of Clinical Neurophysiology 8(1):10-25, Lippincott Williams and amp; Wilkins, United States (Jan. 1991).

Jeanrenaud, B., "Lipid components of adipose tissue," Handbook of Physiology, Adipose Tissue, Chapter 15, 8 Pages.

Johari Digital Healthcare Ltd., 510(k)—K062439 Powertone Letter from Department of Health and Humane Services Summary, Public Health Service, Jan. 8, 2007, 6 pages.

Johari Digital Healthcare Ltd., "510(k)—K131291 Torc Body Letter from Department of Health and Humane Services", Public Health Service, Jun. 14, 2013, 10 pages.

Johari Digital Healthcare Ltd., K131291 510(k) Summary, TorcBody, All pages (Jun. 2013).

Jutte, L.S., et al., "The Relationship Between Intramuscular Temperature, Skin Temperature, and Adipose Thickness During Cryotherapy and Rewarming," Archives of Physical Medicine and Rehabilitation, 82(6):845-850, W.B. Saunders, United States (Jun. 2001).

Katuscakova, Z.L., et al., High Induction Magnet Therapy in Rehabilitation, Department of Physiactric Rehabilitation, 2012, 72 pages.

Katz, B., et al., "Changes in Subcutaneous Abdominal Fat Thickness Following High-Intensity Focused Electro-Magnetic (HIFEM) Field Treatments: A Multi Center Ultrasound Study," American Society for Laser Medicine and Surgery Abstracts, 360-361 (2018).

Katz, B., et al., "Ultrasound Assessment of Subcutaneous Abdominal Fat Thickness after Treatments with a High-Intensity Focused Electromagnetic Field Device: A Multicenter Study," Dermatologic Surgery 45(12):1542-1548, Williams and Wilkins, United States (Dec. 2019).

Kavanagh, S., et al., "Use of a Neuromuscular Electrical Stimulation Device for Facial Muscle Toning: A Randomized, Controlled Trial," Journal of Cosmetic Dermatology 11(4):261-266, Blackwell Science, United States (Dec. 2012).

Kent, D., and Jacob C., "Computed Tomography (CT) Based Evidence of Simultaneous Changes in Human Adipose and Muscle Tissues Following a High Intensity Focused Electro- Magnetic Field (HIFEM) Application: A New Method for Non-Invasive Body Sculpting," American Society for Laser Medicine and Surgery Abstracts, p. 370 (2018).

Kent, D,E. and Jacob, C.I., Simultaneous Changes in Abdominal Adipose and Muscle Tissues Following Treatments by High-Intensity Focused Electromagnetic HIFEM Technology-Based Device: Computed Tomography Evaluation, Journal of Drugs in Dermatology 18(11):1098-1102, Physicians Continuing Education Corporation, United States (Nov. 2019).

Kim, Y.H., et al., "The Effect of Cold Air Application on Intra-Articular and Skin Temperatures in the Knee," Yonsei Medical Journal, 43(5):621-626, Yonsei University, Korea (South) (Oct. 2002).

Kinney, B.M. and Lozanova P., "High Intensity Focused Electromagnetic Therapy Evaluated by Magnetic Resonance Imaging: Safety and Efficacy Study of a Dual Tissue Effect Based Non-Invasive Abdominal Body Shaping," Lasers in Surgery and Medicine 51(1):40-46, Wiley-Liss, United States (Jan. 2019).

Kocbach et al., "A Simulation Approach to Optimizing Perfermance of Equipment for Thermostimulation of Muscle Tissue using COMSOL Multiphysics" Article in Biophysics and Bioeng. dated 2011, 26 pages.

Kolin, A., et al., "Stimulation of Irritable Tissues by means of an Alternating Magnetic Field," Proceedings of the Society for Experimental Biology and Medicine 102:251-253, Blackwell Science, United States (Oct. 1959).

Korman, P., et al., "Temperature Changes In Rheumatoid Hand Treated With Nitrogen Vapors and Cold Air," Rheumatology International, 32(10):2987-2992, Springer International, Germany (Oct. 2012).

Kotz, Y., "Theory and Practice of Physical Culture," Training of Skeletal Muscle With Method of Electrostimulation, 64-67 (Mar. 1971).

Kotz, Y., "Theory and Practice of Physical Culture," Training of Skeletal Muscle With Method of Electrostimulation, 66-72 (Apr. 1971).

Krueger, N et al., "Safety and Efficacy of a New Device Combining Radiofrequency and Low-Frequency Pulsed Electromagnetic Fields for the Treatment of Facial Rhytides," Journal of Drugs in Dermatology 11(11):1306-1309, Physicians Continuing Education Corporation, United States (Nov. 2012).

Kumar, N. and Agnihotri, R.C., "Effect of Frequency and Amplitude of Fes Pulses on Muscle Fatigue During Toning of Muscles," Journal of Scientific and Industrial Research 67(4):288-290, (Apr. 2008).

Lampropoulou, S.I., et al., "Magnetic Versus Electrical Stimulation in the Interpolation Twitch Technique of Elbow Flexors," Journal of Sports Science and Medicine, 11(4):709-718, Dept. of Sports Medicine, Medical Faculty of Uludag University, Turkey (Dec. 2012).

Langford, J. and McCarthy, P.W., "Randomised controlled clinical trial of magnet use in chronic low back pain; a pilot study," Clinical Chiropractic 8(1):13-19, Elsevier (Mar. 2005).

(56)         References Cited

OTHER PUBLICATIONS

Lanzamiento de BTL Vanquish ME en Argentina, BTL Aesthetics Int., 2018 at 0:33, 0:34; available at:https://www.youtube.com/watch?v=5yb51%20MmN76Q&ab_channel=BTLAestheticsInt, downloaded Jul. 12, 2023; 2 pages.
Lee, P.B., et al., "Efficacy of Pulsed Electromagnetic Therapy for Chronic Lower Back Pain: a Randomized, Double-blind, Placebcontrolled Study," The Journal of International Medical Research 34(2):160-167, Cambridge Medical Publications, England (Mar-Apr. 2006).
Leitch, M., et al., "Intramuscular Stimulation of Tibialis Anterior in Human Subjects: The Effects of Discharge Variability on Force Production and Fatigue," Physiological Reports 5(15):e13326, Wiley Periodicals, Inc., United States (Aug. 2017).
Leon-Salas, W.D., et al., "A Dual Mode Pulsed Electro-Magnetic Cell Stimulator Produces Acceleration of Myogenic Differentiation," Recent Patents on Biotechnology 7(1):71-81, Bentham Science Publishers, United Arab Emirates (Apr. 2013).
Letter from Department of Health and Human Services, Public Health Service, Dec. 19, 2014, 7 pages.
Letter from US Food & Drug Administration to Johari Digital Healthcare Ltd. regarding K212866, attaching 510(K) summary; Dec. 3, 2022; 17 pages.
Lin, V.W., et al., "Functional Magnetic Stimulation: A New Modality for Enhancing Systemic Fibrinolysis," Archives of Physical Medicine and Rehabilitation 80(5):545-550, W.B. Saunders, United States (May 1999).
Lin, V.W., et al., "Functional Magnetic Stimulation for Conditioning of Expiratory Muscles in Patients with Spinal Cord Injury.," Archives of Physical medicine and Rehabilitation 82(2):162-166, W.B. Saunders, United States (Feb. 2001).
Lin, V.W., et al., "Functional Magnetic Stimulation for Restoring Cough in Patients With Tetraplegia," Archives of Physical Medicine and Rehabilitation, 79(5):517-522, W.B. Saunders, United States, (May 1998).
Lin, V.W., et al., "Functional Magnetic Stimulation of Expiratory Muscles: a Noninvasive and New Method for Restoring Cough," Journal of Applied Physiology (1985), 84(4):1144-1150, American Physiological Society, United States, (Apr. 1998).
Lin, V.W., et al., "Functional Magnetic Stimulation of the Respiratory Muscles in Dogs," Muscle and Nerve 21(8):1048-1057, John Wiley and Sons, United States (Aug. 1998).
Linehan, C., et al., "Brainwave the Irish EpilepsyAssoication, The Prevalence of Epilepsy in Ireland" Summary Report,pp. 1-8 (May 2009).
Lotz, B.P., et al., "Preferential Activation of Muscle Fibers with Peripheral Magnetic Stimulation of the Limb," Muscle and Nerve, 12(8):636-639, John Wiley and Sons, United States (Aug. 1989).
Lumenis Be Ltd. v. BTL Healthcare Technologies A.S., PTAB-IPR2021-01402, Declaration of Dr. Marom Bikson (EX1002), Sep. 13, 2021, 244 pages.
Lumenis Be Ltd. v. BTL Healthcare Technologies A.S., PTAB-IPR2021-01402, U.S. Pat. No. 10,821,295 Petition for Inter Partes Review, Sep. 13, 2021, 81 pages.
Lumenis Be Ltd. v. BTL Healthcare Technologies A.S., PTAB-IPR2021-01403, Declaration of Dr. Marom Bikson (EX1002), Sep. 13, 2021, 243 pages.
Lumenis Be Ltd. v. BTL Healthcare Technologies A.S., PTAB-IPR2021-01403, U.S. Pat. No. 10,821,295 Petition for Inter Partes Review, Sep. 13, 2021, 84 pages.
Lumenis Be Ltd. v. BTL Healthcare Technologies A.S., PTAB-IPR2021-01404, Declaration of Dr. Marom Bikson (EX1002), Sep. 13, 2021, 245 pages.
Lumenis Be Ltd. v. BTL Healthcare Technologies A.S., PTAB-IPR2021-01404, U.S. Pat. No. 10,124,187 Petition for Inter Partes Review, Sep. 13, 2021, 82 pages.
Lumenis Be Ltd. v. BTL Healthcare Technologies A.S., PTAB-IPR2021-01405, Declaration of Dr. Marom Bikson (EX1002), Sep. 13, 2021, 247 pages.

Lumenis Be Ltd. v. BTL Healthcare Technologies A.S., PTAB-IPR2021-01405, U.S. Pat. No. 10,124,187 Petition for Inter Partes Review, Sep. 13, 2021, 86 pages.
Lumenis Be Ltd. v. BTL Healthcare Technologies A.S., PTAB-IPR2022-00126, Declaration of Dr. Marom Bikson (EX1002), Nov. 10, 2021, 263 pages.
Lumenis Be Ltd. v. BTL Healthcare Technologies A.S., PTAB-IPR2022-00126, U.S. Pat. No. 10,695,576 Petition for Inter Partes Review, Nov. 10, 2021, 83 pages.
Lumenis Be Ltd. v. BTL Healthcare Technologies A.S., PTAB-IPR2022-00127, Declaration of Dr. Marom Bikson (EX1002), Nov. 10, 2021, 269 pages.
Lumenis Be Ltd. v. BTL Healthcare Technologies A.S., PTAB-IPR2022-00127, U.S. Pat. No. 10,695,576 Petition for Inter Partes Review, Nov. 10, 2021, 84 pages.
Lumenis Be Ltd. v. BTL Healthcare Technologies A.S., PTAB-IPR2022-00451, Declaration of Dr. Marom Bikson (EX1002), Jan. 24, 2022, 236 pages.
Lumenis Be Ltd. v. BTL Healthcare Technologies A.S., PTAB-IPR2022-00451, U.S. Pat. No. 10,806,943 Petition for Inter Partes Review, Jan. 24, 2022, 87 pages.
Lumenis Be Ltd. v. BTL Healthcare Technologies A.S., PTAB-IPR2022-00452, Declaration of Dr. Marom Bikson (EX1002), Jan. 24, 2022, 229 pages.
Lumenis Be Ltd. v. BTL Healthcare Technologies A.S., PTAB-IPR2022-00452, U.S. Pat. No. 10,806,943 Petition for Inter Partes Review, Jan. 24, 2022, 81 pages.
Lumenis Ltd. v. BTL Healthcare Technologies A.S., PTAB-IPR2021-01273, Declaration of Dr. Marom Bikson (EX1002), Aug. 13, 2021, 225 pages.
Lumenis Ltd. v. BTL Healthcare Technologies A.S., PTAB-IPR2021-01273, U.S. Pat. No. 10,478,634, Petition for Inter Partes Review, Aug. 13, 2021, 70 pages.
Lumenis Ltd. v. BTL Healthcare Technologies A.S., PTAB-IPR2021-01275, Declaration of Dr. Marom Bikson (EX1002), Aug. 5, 2021, 282 pages.
Lumenis Ltd. v. BTL Healthcare Technologies A.S., PTAB-IPR2021-01275, U.S. Pat. No. 10,632,321, Petition for Inter Partes Review, Aug. 5, 2021, 92 pages.
Lumenis Ltd. v. BTL Healthcare Technologies A.S., PTAB-IPR2021-01276, Declaration of Dr. Marom Bikson (EX1002), Aug. 5, 2021, 241 pages.
Lumenis Ltd. v. BTL Healthcare Technologies A.S., PTAB-IPR2021-01276, U.S. Pat. No. 10,965,575, Petition for Inter Partes Review, Aug. 5, 2021, 79 pages.
Lumenis Ltd. v. BTL Healthcare Technologies A.S., PTAB-IPR2021-01278, Declaration of Dr. Marom Bikson (EX1002), Aug. 13, 2021, 255 pages.
Lumenis Ltd. v. BTL Healthcare Technologies A.S., PTAB-IPR2021-01278, U.S. Pat. No. 10,709,894, Petition for Inter Partes Review, Aug. 13, 2021, 85 pages.
Lumenis Ltd. v. BTL Healthcare Technologies A.S., PTAB-IPR2021-01279, Declaration of Dr. Marom Bikson (EX1002), Aug. 5, 2021, 258 pages.
Lumenis Ltd. v. BTL Healthcare Technologies A.S., PTAB-IPR2021-01279, U.S. Pat. No. 10,709,895, Petition for Inter Partes Review, Aug. 5, 2021, 88 pages.
Lumenis Ltd. v. BTL Healthcare Technologies A.S., PTAB-IPR2021-01280, Declaration of Dr. Marom Bikson (EX1002), Aug. 13, 2021, 235 pages.
Lumenis Ltd. v. BTL Healthcare Technologies A.S., PTAB-IPR2021-01280, U.S. Pat. No. 10,478,634, Petition for Inter Partes Review, Aug. 13, 2021, 69 pages.
Lumenis Ltd. v. BTL Healthcare Technologies A.S., PTAB-IPR2021-01282, Declaration of Dr. Marom Bikson (EX1002), Aug. 5, 2021, 267 pages.
Lumenis Ltd. v. BTL Healthcare Technologies A.S., PTAB-IPR2021-01282, U.S. Pat. No. 10,632,321, Petition for Inter Partes Review, Aug. 5, 2021, 89 pages.
Lumenis Ltd. v. BTL Healthcare Technologies A.S., PTAB-IPR2021-01283, Declaration of Dr. Marom Bikson (EX1002), Aug. 5, 2021, 241 pages.

(56) References Cited

OTHER PUBLICATIONS

*Lumenis Ltd.* v. *BTL Healthcare Technologies A.S.*, PTAB-IPR2021-01283, U.S. Pat. No. 10,695,575, Petition for Inter Partes Review, Aug. 5, 2021, 84 pages.
*Lumenis Ltd.* v. *BTL Healthcare Technologies A.S.*, PTAB-IPR2021-01284, Declaration of Dr. Marom Bikson (EX1002), Aug. 5, 2021, 279 pages.
*Lumenis Ltd.* v. *BTL Healthcare Technologies A.S.*, PTAB-IPR2021-01284, U.S. Pat. No. 10,709,895, Petition for Inter Partes Review, Aug. 5, 2021, 93 pages.
*Lumenis Ltd.* v. *BTL Healthcare Technologies A.S.*, PTAB-IPR2021-01285, Declaration of Dr. Marom Bikson (EX1002), Aug. 13, 2021, 249 pages.
*Lumenis Ltd.* v. *BTL Healthcare Technologies A.S.*, PTAB-IPR2021-01285, Pat. No. 10,709,894, Petition for Inter Partes Review, Aug. 13, 2021, 79 pages.
Lutronic Corporation, K213748 510(k) Summary, CoreLevee, 8 pages (Oct. 2022).
Madariaga, V.B., et al., "[Magnetic Stimulation of the Quadriceps: Analysis of 2 Stimulators Used for Diagnostic and Therapeutic Applications]," Archivos De Bronconeumología, 43(7):411-417, Elsevier Espana, Spain, (Jul. 2007).
Maffiuletti, N.A., et al., "Activation of Human Plantar Flexor Muscles Increases After Electromyostimulation Training," Journal of Applied Physiology 92(4):1383-1392, American Physiological Society, United States (Nov. 2001).
Maffiuletti, N.A., et al., "The Effects of Electromyostimulation Training and Basketball Practice on Muscle Strength and Jumping Ability," International journal of sports medicine 21(6):437-443, Thieme, Germany (Aug. 2000).
MAG and MORE Gmbh, Magnetic and Life Science System, Power Mag, 12 Pages.
MAG Expert, 2 pages.
Mag Venture, Magnetic Stimulation, Accessories Catalogue, Accessories Catalogue, 2011, 54 pages.
Magneris—ASTAR—Magnetotherapy Unit, 2010 at 1:16, 1:35, 1:40 and 1:50 available at: https://www.youtube.com/watch?v=1001LYnaq4g&ab_channel=Astar-aparatydlafizjotera, downloaded Jul. 12, 2023; 2 pages.
Magnetic neural stimulation system, (2014), 2 pages.
Magnetic stimulatio equipment, YY/T 0994-2015; 2016, with attached English-language translation, 11 pages.
Magstim Company Limited, K051864 510(k) Summary, Magstim Rapid and Magstim Super Rapid, All pages (Dec. 2005).
Magstim Company US, Llc, K060847 510(k) Summary, Magstim Model 200-2 with Double 70mm Remote Coil, All pages (Sep. 2006).
Magstim Corporation US, K992911 510(k) Summary, Magstim Rapid, All pages (Jan. 2000).
MAGVENTURE—Magpro Family, (Aug. 2021), 30 pages.
Magventure, MagPro® by MagVenture®, Versatility in Magnetic Stimulation, World Leading Transcranial Magnetic Stimulation Systems, 2011, 6 Pages.
Magventure Product Catalog, (2022), 37 pages.
Man, W.D-C., et al., "Magnetic Stimulation for the Measurement of Respiratory and Skeletal Muscle Function," The European Respiratory Journal 24(5):846-60, European Respiratory Society, England (2004).
Manstein, D., et al., "Selective Cryolysis: A Novel Method of Non-Invasive Fat Removal," Lasers in Surgery and Medicine, 40(9):595-604, Wiley-Liss, United States (Nov. 2008).
Mantis, The non-invasive solution that restores natural beauty, improves health, and offers a renewed psychophysical sense of balance, MR991 theramagnetic, 2020, 8 pages.
Mantis Theramagnetic Compact: the compact that guarantees utmost efficiency and maximum performance, theramagnetic, 2020, 8 pages.
Mantovani, A., et al., "Applications of Transcranial Magnetic Stimulation to Therapy in Pyschiatry," Psychiatric Times 21(9), Intellisphere, 29 pages (Aug. 2004).

Marek Heinfarth, "Lipostar" dated Jan. 9, 2013, accessed at https://www.youtube.com/watch?v=hZurkn8iU_U , accessed on Dec. 15, 2021.
Markov, M.S., "Pulsed Electromagnetic Field Therapy History, State of the Art and Future," Environment Systems and Decisions 27(4):465-475, Springer (Dec. 2007).
MecoTec Freezing Technology, Presentation Cryoair Whole Body Cryotherapy Chambers, Germany, Jul. 2017, 52 Pages.
Medline, Body Temperature Norms, 2 pages (Year: 2019).
Mekawy et al., "Influence of Electro-lipolysis on Lipid Profile and Central Obesity in Obese Premenopausal Women" Bull. Fac. Ph. Th. Cairo Univ., vol. 17, No. (1), dated Jan. 2012, pp. 59-68.
Mettler J.A., et al., "Low-Frequency Electrical Stimulation With Variable Intensity Preserves Torque," Journal of Electromyography and Kinesiology : Official Journal of the International Society of Electrophysiological Kinesiology 42:49-56, Oxford:Elsevier, England (Oct. 2018).
Mogyoros, I., et al., "Strength-Duration Properties of Human Peripheral Nerve," Brain 119(Pt 2):439-447, Oxford University Press, England (Apr. 1996).
Moon, Chi-Woong"Study on the Pulsed Electromagnetic Fields Effect of Adipocyte Decomposition" Final Report of a Middle-grade Researcher Support Project, Inje University, 2017.
Morrissey. M., "Electromyostimulation from a Clinical Perspective," Sports Medicine 6(1):29-41, Springer International, New Zealand (Aug. 1988).
Mulholland, R.S., "Synergistic Multi-polar Radiofrequency and Pulsed Magnetic Fields in the Non-Invasive Treatment of Skin Laxity and Body Contouring," 4 pages.
Mustafa, B., "Design and Construction of a Low Cost dsPIC Controller Based Repetitive Transcranial Magnetic Stimulator TMS," Journal of medical systems 34(1): 15-24, Kluwer Academic/Plenum Publishers, United States (2010).
Nadler, S.F., et al., "The Physiologic Basis and Clinical Applications of Cryotherapy and Thermotherapy for the Pain Practitioner," Pain Physician, 7(3):395-399, American Society of Interventional Pain Physicians, United States (Jul. 2004).
Nanjing Vishee Medical Technology Co., Ltd., K222875 510(k) Summary, MagGraver F200, 12 pages (Mar. 2023).
Nanjing Vishee Medical Technology Co., Ltd., K230767 510(k) Summary, Pelvic Floor Muscle Stimulator, 7 pages (Sep. 2023).
Nassab, R.,"The Evidence Behind Noninvasive Body Contouring Devices," Aesthetic Surgery Journal, 35(3):279-293, Oxford University Press, England (Mar. 2015).
National Institute of Neurological Disorders and Stroke, Epilepsy Information p. www.ninds.nih.gov/disorders/epilepsy/epilepsy.htm, pp. 1-6 (Feb. 1, 2016).
Neotonus, Inc., K973096 510(k) Summary, Neotonus Model 1000 Muscle Stimulator System, All pages (Jun. 1998).
Neotonus, Inc., K973929 510(k) Summary and FDA Correspondence, Neotonus, All pages (May 1998).
Neuro Star , TMS Therapy, Bringing Hope to Patients with Depression, 2013, 6 Pages.
Neurolief Ltd., K212106 510(k) Summary, Relivion, (Aug. 2021), 11 pages.
Neurosoft, Ivanovo, Since 1992, Magnetic Stimulator, NEURO-MS, Technical Manual, Neurosoft Ltd, Ivanovo, Russia, 2006, 67 Pages.
Neurostar system—instructions for use, (Dec. 2020), 258 pages.
Nexstim NBS System, Navigated Brain Stimulation, Noninvasive, direct cortical mapping, 2012, 5 Pages.
Neyroud, D., et al., "Comparison of Electrical Nerve Stimulation, Electrical Muscle Stimulation and Magnetic Nerve Stimulation to Assess the Neuromuscular Function of the Plantar Flexor Muscles," European journal of applied physiology 115(7):1429-1439, Springer-Verlag, Germany (2015).
Nielsen, J.F., et al., "A New High-frequency Magnetic Stimulator With an Oil-cooled Coil," Journal of Clinical Neurophysiology 12(5):460-467, Lippincott Williams and Wilkins, United States (Sep. 1995).
Non Final Office Action mailed Dec. 1, 2016, in U.S. Appl. No. 15/151,012, Schwarz, T., et al., filed May 10, 2016.

(56) References Cited

OTHER PUBLICATIONS

Non Final Office Action mailed Dec. 12, 2016, in U.S. Appl. No. 15/099,274, Pribula, O., et al., filed Apr. 14, 2016.
Non Final Office Action mailed Dec. 17, 2015, in U.S. Appl. No. 14/697,934, Zarsky, J., et al., filed Apr. 28, 2015.
Non Final Office Action mailed Feb. 10, 2016, in U.S. Appl. No. 14/873,110, Ladman, J., et al., filed Oct. 1, 2015.
Non Final Office Action mailed Feb. 11, 2016, in U.S. Appl. No. 14/926,365, Prouza, P., et al., filed Oct. 29, 2015.
Non Final Office Action mailed Feb. 25, 2016, in U.S. Appl. No. 14/870,713, Schwarz, T., et al., filed Sep. 30, 2015.
Non Final Office Action mailed Jun. 16, 2016, in U.S. Appl. No. 15/073,318, Schwarz, T., et al., filed Mar. 17, 2016.
Non Final Office Action mailed Jun. 23, 2017, in U.S. Appl. No. 15/473,390, Schwarz, T., et al., filed Mar. 29, 2017.
Non Final Office Action mailed Jun. 27, 2017 in U.S. Appl. No. 15/601,719, Schwarz, T., et al., filed May 22, 2017.
Non Final Office Action mailed Jun. 28, 2017, in U.S. Appl. No. 15/073,318, Schwarz, T., et al., filed Mar. 17, 2016.
Non Final Office Action mailed Jun. 29, 2017, in U.S. Appl. No. 14/789,156 , Ladman, J., et al., filed Jul. 1, 2015.
Non Final Office Action mailed Jun. 30, 2017, in U.S. Appl. No. 15/471,946, Schwarz, T., et al., filed Mar. 28, 2017.
Non Final Office Action mailed Mar. 24, 2017, in U.S. Appl. No. 15/396,073, Schwarz, T., et al., filed Dec. 30, 2016.
Non final Office Action mailed Mar. 28, 2017, in U.S. Appl. No. 15/344,811, Schwarz, T., et al., filed Nov. 7, 2016.
Non Final Office Action mailed May 9, 2016, in U.S. Appl. No. 14/789,658, Ladman, J., et al., filed Jul. 1, 2015.
Non Final Office Action mailed May 9, 2016, in U.S. Appl. No. 14/951,093, Schwarz, T., et al., filed Nov. 24, 2015.
Non Final Office Action mailed Nov. 4, 2015, in U.S. Appl. No. 14/700,349, Schwarz T., et al., filed Apr. 30, 2015.
Non Final Office Action mailed May 4, 2016, in U.S. Appl. No. 14/873,110, Ladman, J., et al., filed Oct. 1, 2015.
Notice of Allowance dated Jul. 21, 2021 for U.S. Appl. No. 17/087,850 (pp. 1-8).
Notice of Allowance dated May 6, 2020 for U.S. Appl. No. 16/194,800 (pp. 1-8).
Notice of Allowance dated Oct. 8, 2019 for US App. No. 15/603,162 (pp. 1-8).
Notice of Allowance dated Mar. 24, 2021 for U.S. Appl. No. 17/087,850 (pp. 1-8).
Novickij, V., et al., "Compact Microsecond Pulsed Magnetic Field Generator for Application in Bioelectronics," Elektronika ir Elektrotechnika 19(8):25-28 (Oct. 2013).
Novickij, V., et al., "Design and Optimization of Pulsed Magnetic Field Generator for Cell Magneto-Permeabilization," Elektronika ir Elektrotechnika(Electronics and Electrical Engineering) 23(2):21-25 (Apr. 2017).
Novickij, V., et al., "Magneto-Permeabilization of Viable Cell Membrane Using High Pulsed Magnetic Field," IEEE Transactions on Magnetics 51(9), All pages (Sep. 2015).
Novickij, V., et al., "Programmable Pulsed Magnetic Field System for Biological Applications," IEEE Transactions on Magnetics 50(11):5 (Nov. 2014).
NPF Electroapparat, Amplipulse-5Br Manual, allegedly accessed on Nov. 18, 2020, All pages.
Nu Eyne Co. Ltd., K192773 510(k) Summary, Allive, (Dec. 2019), 14 pages.
Nu Eyne Co., Ltd, K211380 510(k) Summary, Elexir, (Jul. 2021), 15 pages.
Nuerosoft Ltd., "Neurosoft—Neuro-MS Transcranial Magnetic Simulator Technical Manual," All pages (Nov. 2014).
Obsluze, "Apparatus for High Induction Magnetic Stimulation," 2016, 42 pages.
Obsluze, N.K., Usage Instructions, User's Manual, Device for high-induction magnetic stimulation of type designation: Saluter Moti, 2016,88 Pages.

Office Action dated Aug. 15, 2019 for U.S. Appl. No. 16/194,800 (pp. 1-12).
Office Action dated Jul. 10, 2020 for U.S. Appl. No. 15/678,915 (pp. 1-9).
Office Action dated Jun. 14, 2021 for U.S. Appl. No. 15/786,303 (pp. 1-13).
Office Action dated Jun. 28, 2021 for U.S. Appl. No. 16/727,458 (pp. 1-11).
Office Action dated Oct. 7, 2019 for U.S. Appl. No. 15/678,915 (pp. 1-8).
Oliveira, P.De., et al., "Neuromuscular Fatigue After Low-and Medium-frequency Electrical Stimulation in Healthy Adults," Muscle and Nerve 58(2):293-299, John Wiley and Sons, United States (Aug. 2018).
Operating Manual: Magstim $D70^2$ Coil, MOP06-EN, Revision 01, The Magstim Company Limited, Feb. 2012, 14 Pages.
Operating Manual: Magstim Magstim $200^2$, MOP01-EN, Revision 01, The Magstim Company Limited, Sep. 2011, 25 Pages.
Operating Manual: Magstim, Magstim Alpha Coil Range, MOP11-EN, Revision 01, Oct. 2012, 18 Pages.
Operating Manual: Magstim, Magstim $Bistim^2$, MOP02-EN, Revision, The Magstim Company Limited, 01, Sep. 2011, 27 Pages.
Operating Manual, MAGSTIM, Model 200, P/N 3001-01, Double 70mm, Remote Coil, P/N 3190-00, The Magstim Company Limited, 2006, 32 pages.
Operating Manual: Magstim R, 2nd, Generation Coil Family, 3100-23-02, Magstim Coils, The Magstim Company Limited, Nov. 2002, 14 Pages.
Operating Manual, Magstim R Air-Cooled Double 70mm Coil System, 1600-23-04, The Magstim Company Limited, 1999, 18 Pages.
Operating Manual: Magstim R, Bistim System, P/N 3234-23-01, The Magstim Company Limited, Nov. 2004, 30 Pages.
Operating Manual: Magstim R, Coils and Accessories, 1623-23-07, Magstim Coils and Accessories, May 2010, 24 Pages.
Operating Manual: Magstim, RAPID2, P/N 3576-23-09, The MAGSTIM Company LTD, Nov. 2009, 61 Pages.
Operating Manual: Magstim ® 2002, P/N 3001-23-04, The Magstim Company Limited, Mar. 18, 2005, 34 pages.
Operator's Manual: BTL EMSCULPT, BTL Industries Ltd, United Kingdom, 2018, 35 pages.
Operator's Manual: BTL, HPM-6000U, Btl Industries Ltd, United Kingdom, Dec. 2016, 36 pages.
Otte, U.S., et al., "Subcutaneous Adipose Tissue Thickness Alters Cooling Time During Cryotherapy, "Archives of Physical Medicine and Rehabilitation, 83(11):1501-1505, W.B. Saunders, United States (Nov. 2002).
Pain Management Technologies, "Pain Management Technologies Product Catalog," (2012).
Papimi, For Scientific Research, Pap lon Magnetic Inductor, Presentation, Magnetotherapeutic Device, Nov. 2009, 61 Pages.
Pascual-Leone, A., et al., "Handbook of Transcranial Magnetic Stimulation," Chapters 1-4, 58 pages, Arnold Publishers, England (2002).
PELVIPOWER—Power from the core, (Oct. 2020), 32 pages.
Periso Sa, Ctu mega Diamagnetic Pump 20: Device For Diamagnetic Therapy, CTU Mega 20 Manual, dated Aug. 28, 2019, 44 pages, Pazzallo Switzerland.
Photograph, Alleged Photograph of Components of a Salus Talent Pop Double Device with an Alleged Manufacture date of Nov. 14, 2012, 1 page.
Physiomed, MAG-Expert, Physiomed Manual, Dec. 19, 2012.
Physiomed, Physiomed Mag-Expert, Physiomed Catalog, pp. 81-83.
Platil, A., "Magnetopneumography Using Optical Position Reference," Sensor Letters 11(1):69-73, ResearchGate (2013).
Podebradsky.K., et al., Clinical study of high-inductive electromagnetic stimulator SALUS talent, 2010, 8 pages.
Pohanka, J., et al., "An Embedded Stereovision System: Aspects of Measurement Precision," 12th Biennial Baltic Electronics Conference, pp. 157-160 (Oct. 2010).

(56) References Cited

OTHER PUBLICATIONS

Polk, C., "Therapeutic Applications of Low-Frequency Sinusoidal and Pulsed Electric and Magnetic Fields," The Biomedical Engineering Handbook, vol. 1, 2000, Second edition, CRC Press LLC, pp. 1625-1636.

Polkey M.I., et al., "Functional Magnetic Stimulation of the Abdominal Muscles in Humans, " American Journal of Respiratory and Critical Care Medicine 160(2):513-522, American Thoracic Society, United States (Aug. 1999).

Polkey, M.I., et al., "Quadriceps Strength and Fatigue Assessed by Magnetic Stimulation of the Femoral Nerve in Man," Muscle Nerve 19(5):549-555, John Wiley and Sons, United States, (May 1996).

Pollegen, K200545, Legend Pro DMA, Indications for use, dated Oct. 20, 2021,11 pages.

Pollogen, Trilipo MED Procedure, Brochure, dated Apr. 7, 2021, 76 pages.

Pollogen, Maximus Non-invasive body shaping System, User Manual, dated May 1, 2012, 44 pages, http://download.lifvation.com/Maximus_UserManual.pdf .

Porcari, J.P., et al., "Effects of Electrical Muscle Stimulation on Body Composition, Muscle Strength, and Physical Appearance," Journal of Strength and Conditioning Reasearch 16(2):165-172, Human Kinetics Pub., United States (May 2002).

Porcari, J.P., et al., "The Effects of Neuromuscular Electrical Stimulation Training on Abdominal Strength, Endurance, and Selected Anthropometric Measures," Journal of Sports Science and Medicine 4(1):66-75, Dept. of Sports Medicine, Turkey (Mar. 2005).

Pribula, O. and Fischer, J., "Real Time Precise Position Measurement Based on Low-Cost CMOS Image Sensor," IEEE, 5 pages (2011).

Pribula, O., et al., "cost-effective Image Acquisition System for Precise Pc-based Measurements," Przeglad Elektrotechniczny (Electrical Review), 259-263, 2011,.

Pribula, O., et al., "Optical Position Sensor Based on Digital Image Processing: Magnetic Field Mapping Improvement," Radioengineering 20 (1):55-60, (Apr. 2011).

Pribula, O., et al., "Real-Time Video Sequences Matching Spatio-Temporal Fingerprint," IEEE, 911-916 (Jun. 2010).

Prouza, O., et al., "High-Intensity Electromagnetic Stimulation Can Reduce Spasticity in Post-Stroke Patients," International Journal of Physiotherapy 5(3):87-91 (2018).

Prouza, O., "Ex-Post Analyza Spot Rebnich Dani," All pages, (2008).

Prouza, O., "Targeted Radiofrequency Therapy for Training Induced Muscle Fatigue—Effective or Not?," International Journal of Physiotherapy 3(6):707-710 (Dec. 2016).

PTAB-IPR2021-00296, U.S. Pat. No. 10,493,293, Petition for Inter Partes Review, Dec. 14, 2020, 117 pages.

PTAB-IPR2021-00312, U.S. Pat. No. 10,478,634, Petition for Inter Partes Review, Dec. 14, 2020, 108 pages.

PTAB-PGR2021-00015, U.S. Pat. No. 10,709,895, Petition for Post-Grant Review, Dec. 14, 2020, 140 pages.

PTAB-PGR2021-00016, U.S. Pat. No. 10,709,895, Petition for Post-Grant Review, Dec. 14, 2020, 144 pages.

PTAB-PGR2021-00017, U.S. Pat. No. 10,632,321, Petition for Post-Grant Review, Dec. 14, 2020, 121 pages.

PTAB-PGR2021-00018, U.S. Pat. No. 10,632,321, Petition for Post-Grant Review, Dec. 14, 2020, 140 pages.

PTAB-PGR2021-00020, U.S. Pat. No. 10,695,575, Petition for Post-Grant Review, Dec. 14, 2020, 112 pages.

PTAB-PGR2021-00021, U.S. Pat. No. 10,695,575, Petition for Post-Grant Review, Dec. 14, 2020, 117 pages.

PTAB-PGR2021-00022, U.S. Pat. No. 10,709,894, Petition for Post-Grant Review, Dec. 14, 2020, 119 pages.

PTAB-PGR2021-00023, U.S. Pat. No. 10,709,894, Petition for Post-Grant Review, Dec. 14, 2020, 136 pages.

PTAB-PGR2021-00024, U.S. Pat. No. 10,695,576, Petition for Post-Grant Review, Dec. 14, 2020, 136 pages.

PTAB-PGR2021-00025, U.S. Pat. No. 10,695,576, Petition for Post-Grant Review, Dec. 14, 2020, 135 pages.

Publication of Medical Device Manufacturing Approval of Salus-TALENT-Pro, approval date Mar. 11, 2014, 39 pages.

Quick Start Manuals, Magstim Super Rapid Plus Quick Start, Aalto TMS Laboratory, Aalto School of Science, 2013, 7 Pages.

Radakovic T. and Radakovic N., "The Effectiveness of the Functional Magnetic Stimulation Therapy in Treating Sciatica Syndrome," Open Journal of Therapy and Rehabilitation 3(3):63-69 (2015).

Reaction User Manual, Viora, Doc No. MK-004 A, 2008, 53 Pages.

Remed Co Ltd K202031 510(k) Summary, Talent-Pro Electromagnetic Stimulator, 1-11 (May 2021).

Reshaping the Future of Your Practice, Cool sculpting, A Revolution in Aesthetic Fat Reduction, 2011, 10 Pages.

Riehl., M., "Chapter 3: TMS Stimulator Design" The Oxford Handbook of Transcranial Stimulation, Wasserman, E.M., ed., pp. 13-23, Oxford University Press, 26 pages, United Kingdom (2008).

Roots, H., and Ranatunga, K.W., "An Analysis of the Temperature Dependence of Force, During Steady Shortening at Different Velocities, in (Mammalian) Fast Muscle Fibres," Journal of Muscle Research and Cell Motility 29(1):9-24, Springer, Netherlands (Jun. 2008).

Ruiz-Esparza, J. and J. Barba Gomez., "The Medical Face Lift: A Noninvasive, Nonsurgical Approach to Tissue Tightening in Facial Skin Using Nonablative Radiofrequency," Dermatologic Surgery 29(4):325-332, Williams and Wilkins, United States (Apr. 2003).

Russian excerpt of Werner, R., Magnetotherapy, Pulsating energy resonance therapy, 41-67 (Jun. 2007).

Rutkove, S., "Effects of Temperature on Neuromuscular Electrophysiology," Muscle and Nerve 24(7):867-882, John Wiley and Sons, United States (Jul. 2001).

Salus Talent, a Vertice and Talos, Drott, 6 pages.

Salus Talent, Deep Penetrating Electro-Magnetic Stimulator, CR Technology, 4 pages.

Salus Talent, Deep Penetrating Electro-Magnetic Stimulator, Rehabilitation Medical Company, New choice, new satisfaction, Talent, 4 pages.

Salus Talent, Electro Magnetic Stimulator, CR Technology, 9 Pages.

Salus Talent Pop, The first sales bill, Authorization No. 20120221-41000096-66667961, 2 pages, (Feb. 2012).

Salus Talent Pro, Specification, 2 pages.

Salus, Talent Pro, The Birth of Salus Talent Pro inspired by 10 Years of Experience, Specification, Rehabilitation Medical Company, Slimon, 2 pages.

Salus, Talent Pro, The World's 1st Development 3 Tesla, 2Channel Magnetic field Therapy, Slimon , 10 pages.

Salus Talent-A, Remed, User Guide, High Intensity Electro Magnetic Field Therapy, 2017, 37 pages.

Salus Talent-Pop DOUBLE, 1 page.

Salus-Talent, Device for Deep Electromagnetic Stimulation, Nowosc, Fizjoterapia, 6 Pages.

Sargeant, A.J., "Effect of Muscle Temperature on Leg Extension Force and Short-term Power Output in Humans," European Journal of Applied Physiology and Occupational Physiology 56(6):693-698, Springer Verlag, Germany (Sep. 1987).

Schaefer, D.J., et al., "Review of Patient Safety in Time-Varying Gradient Fields," Journal of Magnetic Resonance Imaging 12:20-29, Wiley-Liss, United States (Jul. 2000).

Scientific and amp; Clinical Background of (MP)2®—A synergy between Multi polar RF and Pulsed Magnetic Field developed by Venus Concept. Prof. Yeouda Edoute M.D, Ph, D, 2 pages.

Shanghai Apolo Medical Technology Co., Ltd., K232409 510(k) Summary, Electromagnetic Stimulation Systems, (Apr. 2024), 8 pages.

Shenzhen Dongdixin Technology Co. Ltd., K210364 510(k) Summary, Migraine TENS Digital Pain Reliever, (Jun. 2021), 11 pages.

Shenzhen Hengbosi Industrial Co., Ltd., K233035 510(k) Summary, Electronic Muscle Stimulator, (Aug. 2024), 4 pages.

Shenzhen KeLiTongDa Industrial Co., Ltd., K231136 510(k) Summary, Fitness Belt (Model: KLT-07), 3 pages, (Jun. 2023).

Shimada, Y., et al., "Effects of therapeutic magnetic stimulation on acute muscle atrophy in rats after hindlimb suspension," Biomedical Research 27(1):23-27, Biomedical Research Foundation, Japan (Feb. 2006).

(56) References Cited

OTHER PUBLICATIONS

Silinskas, V., et al., "Effect of Electrical Myostimulation on the Function of Lower Leg Muscles," Journal of strength and Conditioning Research 31(6):1577-1584, Human Kinetics Pub, United States (2017).

Sport-Elec S.A., K061914 510(k) Summary, Sport—Elec, All pages (Jul. 2007).

Sport-Elec S.A., K081026 510(k) Summary, Sport—Elec, All pages (Nov. 2008).

Stallknecht, B., et al., "Are Blood Flow and Lipolysis in Subcutaneous Adipose Tissue Influenced by Contractions in Adject Muscles in Humans?," American Journal of Physiology. Endocrinology and Metabolism 292(2):E394-E399, American Physiological Society, United States (Feb. 2007).

Starbelle, PEMF Shape, Webpage, dated Feb. 10, 2020, 3 pages, available at http://www.starbelle.cn/info/PEMFShape.html.

Stedman, T.L., "Aponeurosis—Apparatus," in Stedman's Medical Dictionary, 27th Edition, Pugh, M.B., ed., pp. 113-114, Lippincott Williams and Wilkins, Baltimore, MD (2000).

Stevens, J.E., et al., "Neuromuscular Electrical Stimulation for Quadriceps Muscle Strengthening After Bilateral Total Knee Arthroplasty: A Case Series," Journal of Orthopaedic and Sports Physical Therapy 34(1):21-29, Williams And Wilkins, United States (Jan. 2004).

Storz Medical Ag, K203710 510(k) Summary, Storz Medical MAGNETOLITH Muscle Stimulator, 7 pages (May 2021).

Struppler, A., et al., "Facilitation of Skilled Finger Movements by Repetitive Peripheral Magnetic Stimulation (RPMS)—A New Approach In Central Paresis.," NeuroRehabilitation 18(1):69-82, IOS Press, Amsterdam (2003).

Struppler, A., et al., "Modulatory Effect of Repetitive Peripheral Magnetic Stimulation on Skeletal Muscle Tone in Healthy Subjects: Stabilization of the Elbow Joint," Experimental Brain Research 157(1):59-66, Springer Verlag, Germany (Feb. 2004).

Suarez-Bagnasco, D., et al., "The Excitation Functional for Magnetic Stimulation of Fibers.," Annual International Conference of the IEEE Engineering in Medicine and Biology Society, IEEE Engineering in Medicine and Biology Society, Annual International Conference, 2010:4829-4833, IEEE, United States (2010).

Super Inductive System Seat, leaflet, 2 pages (2021).

Super Inductive System Seat, User's Manual, 20 pages (2019).

Swallow, E.B., et al., "A Novel Technique for Nonvolitional Assessment of Quadriceps Muscle Endurance in Humans," Journal of Applied Physiology 103(3):739-746, American Physiological Society, United States (Sep. 2007).

SWIMS America Corp, K230167 510(k) Summary, BACK 4, (Sep. 2023), 21 pages.

Szecsi, J., et al., "A Comparison of Functional Electrical and Magnetic Stimulation for Propelled Cycling of Paretic Patients," Archives of Physical Medicine and Rehabilitation 90(4):564-570, W.B. Saunders, United States, (Apr. 2009).

Szecsi, J., et al., "Force-pain Relationship in Functional Magnetic and Electrical Stimulation of Subjects With Paresis and Preserved Sensation," Clinical Neurophysiology 121(9):1589-1597, Elsevier, Netherlands, (Sep. 2010).

Taylor, J.L, "Magnetic Muscle Stimulation Produces Fatigue Without Effort," Journal of Applied Physiology (1985) 103(3):733-734, American Physiological Society, United States, (Sep. 2007).

Tesla Stym, Iskra Medical, Tone the inner muscle with FMS Functional Magnetic Stimulation, 2013, 4 pages.

The Burn Centre Care, Education, 3 pages, printed from internet Nov. 13, 2017.

The Magstim Company Ltd, K080499 510(k) Summary, Magstim Double 70mm Air Film Coil, All pages (Dec. 2008).

The Magstim Company Ltd., K130403 510(k) Summary, Magstim D702 coil, All pages (Aug. 2013).

Theranica Bioelectronics Ltd., K223169 510(k) Summary, Nerivio, (Feb. 2023), 10 pages.

Thermi Launches Arvati, powered by Thermi, with newest advances in True Temperature Controlled Radiofrequency Technology, 5 pages (2018).

Thermi Smooth TM 250, High Power Temperature Controlled Radio Frequency, Thermi Aesthetics, 25 pages.

Thompson, M.T., "Inductance Calculation Techniques—Part I: Classical Methods," Power Control and Intelligent Motion, 25(12):40-45, (Dec. 1999) http://www.pcim.com/.

Thompson, M.T., "Inductance Calculation Techniques—Part II: Approxmiations and Handbook Methods," Power Control and Intelligent Motion, 11 pages (Dec. 1999) http://www.pcim.com/.

Tomek, J., et al., "Magnetopneumography—Incorporation of optical position reference," Journal of Electrical Engineering, All pages (2012).

Torbergsen, T., "Abstracts of the International Course and Symposium in Single Fibre EMG and Quantitative EMG Analysis. Tromsø, Norway, Jun. 4-8, 1984," Muscle and Nerve 9(6):562- 574, John Wiley and Sons, United States (Jul.-Aug. 1986).

Trifractional FAQs, http://pollogen.lifvation.com/FAQ/TriFractional%20FAQs.pdf , Aug. 2011 (4pages).

TriLipo MED Procedure, http://download.lifvation.com/Maximus_TriLipoMED_Intro.pdf , Apr. 2013, 76 pages.

TSEM Med Swiss SA, Diamagnetic Therapy: A Revolutionary Therapy, CTU Mega 20 Catalogue, dated 2016, 24 pages, Lugano Switzerland.

Turley, J., "Agilent Technologies Announces 30 MHz Function/Arbitrary Waveform Generators with Unparalleled Signal Accuracy," Elec. Eng'g J., URL: (Aug. 4, 2010), 8 pages.

Ultra Slim Professional, The very best body Contouring, Wardphotonics LLC, 2018, 16 pages.

Unique Multi-Treatment Platform For, Feminine Health, Venus Fiore, 12 pages.

Urban, J., "Magnetotherapy and Physiotherapy," 40 pages.

URO Diagnostic Clinic, Now in UDC, Automated pelvic floor muscle training, QRS International AG, 16 Pages.

U.S. Appl. No. 60/848,720, inventor Burnett, D., filed on Sep. 30, 2006 (Not Published).

U.S. Appl. No. 62/331,060, inventor Schwarz, T., filed on May 3, 2016 (Not Published).

U.S. Appl. No. 62/331,072, inventor Schwarz, T., filed May 3, 2016 (Not Published).

U.S. Appl. No. 62/331,088, inventor Schwarz, T., filed May 3, 2016 (Not Published).

U.S. Appl. No. 62/333,666, inventor Schwarz, T., filed May 9, 2016 (Not Published).

U.S. Appl. No. 62/351,156, inventor Schwarz, T., filed Jun. 16, 2016 (Not Published).

U.S. Appl. No. 62/357,679, inventor Schwarz, T., filed Jul. 1, 2016 (Not Published).

U.S. Appl. No. 62/440,905, inventors Schwarz, T. et al., filed Dec. 30, 2016 (Not Published).

U.S. Appl. No. 62/440,912, inventors Schwarz, T. et al., filed Dec. 30, 2016 (Not Published).

U.S. Appl. No. 62/440,922, inventor Schwarz, T., filed Dec. 30, 2016 (Not Published).

U.S. Appl. No. 62/440,936, inventor Schwarz, T., filed Dec. 30, 2016 (Not Published).

U.S. Appl. No. 62/440,940, inventor Schwarz, T., filed Dec. 30, 2016 (Not Published).

U.S. Appl. No. 62/441,805, inventor Prouza, O., filed Jan. 3, 2017 (Not Published).

U.S. Appl. No. 62/786,731, inventor Schwarz, T., filed Dec. 31, 2018 (Not Published).

User Guide: Mag Venture, Magpro family, MagPro R30, MagPro R30 with MagOption, MagPro X100, MagPro X100 with MagOption, MagPro software v.5.0, US-edition, MagPro family User Guide, 2010, 52 Pages.

USER Guide, Salus Talent Pro, REMED, High Intensity Electro magnetic Field Therapy -2 Channel, 2017, Version M-1.0.0, 45 pages.

USER Guide, Salus Talent, REMED, High Intensity Electro magnetic Field Therapy, Version. M- 1.0.0, 2017, 40 pages.

(56) References Cited

OTHER PUBLICATIONS

User's Manual: BTL-6000, Super Inductive System Elite, Bbtl Industries Ltd, United Kingdom, Sep. 2016, 36 pages.

User Manual: Electro-magnetic Stimulator, SALUS-TALENT, Version 1.00, Rehabilitation Medical Company,2013, 34 Pages.

User Manual: Regenetron PRO, System Information, Regenetron PRO User Manual, Nov. 2014, 7 Pages.

Vance, C., et al., "Effects of Transcutaneous Electrical Nerve Stimulation on Pain, Pain Sensitivity, and Function in People with Knee Osteoarthritis," Physical Therapy 92:898-910 (2012).

Vanquish Operator's Manual, BTL, 2012, 48 Pages.

Venus Concept Ltd., K111670 510(k) Summary, Venus Freeze (MP)2, 6 pages (Mar. 2012).

Venus Concept Ltd., K111784 510(k) Summary, Venus Swan System, 5 pages (Oct. 2011).

Venus Concept Ltd., K140629 510(k) Summary, Venus Swan (MP)2 System, 7 pages (Jun. 2014).

Venus Concept Ltd., K143554 510(k) Summary, Venus Legacy CX, 1-6, (Aug. 2015).

Venus Concept Ltd., K182094 510(k) Summary, Family of Venus RF Systems—Heal, 7 pages (May 2018).

Venus Concept Ltd., K191065 510(k) Summary, Venus Viva Device, 12 pages (Apr. 2020).

Venus Concept Ltd., K191528 510(k) Summary, Venus Legacy Pro Device, 9 pages (Sep. 2019).

Venus Concept Ltd., K201164 510(k) Summary, Venus Viva MD Device, 9 pages (Jun. 2020).

Venus Concept Ltd., K201461 510(k) Summary, Family of Venus RF Systems—Venus Freedom, 8 pages (Oct. 2021).

Venus Concept Ltd., K211461 510(k) Summary, Family of Venus RF Systems—Venus Freedom, 8 pages (Oct. 2021).

Venus Concept Ltd., K232192 510(k) Summary, Venus Versa Pro System, 11 pages (Sep. 2023).

Venus Concept Ltd., VenusFreeze MP2, User Manual, dated Jun. 2012, 46 pages.

Venus Concept Ltd., VenusViva, User Manual, dated Aug. 2013, 51 pages.

Venus Legacy, Featuring LiftFX and SculptFX, Venus Concept, Delivering the Promise, 24 pages.

Venus Legacy, User Manual International, 2009, Venus Concept, 49 pages.

Venus Swan, Experience the Difference, Venus Concept, Delivering the Promise, http://www.medicom.cz/UserFiles/File/LekarskeNenue/020Swan%20EN.pdf , 2 pages (Apr. 2016).

Venus, Venus legacy marca argentina, Oct. 14, 2014, 20 pages.

Venusfreeze, Experience the Energy, Venus Concept, Delivering the Promise, 2 pages.

Verges S., et al., "Comparison of Electrical and Magnetic Stimulations to Assess Quadriceps Muscle Function," Journal of Applied Physiology (1985) 106(2):701-710, American Physiological Society, United States, (Feb. 2009).

Wada, K., et al., "Design and Implementation of Multi-Frequency Magnetic Field Generator Producing Sinusoidal Current Waveform for Biological Researches," IEEE, 9 pages (2016).

Wanitphakdeedecha, R., et al., "Treatment of Abdominal Cellulite and Circumference Reduction With Radiofrequency and Dynamic Muscle Activation" Journal of Cosmetic and Laser Therapy 17(5):246-251, Informa Healthcare, England (2015).

Ward, A.R. and Shkuratova, N., "Russian Electrical Stimulation: The Early Experiments," Physical therapy 82(10): 1019-1030, Oxford University Press, United States (2002).

Wasilewski, M.L., Academy of Aesthetic and Anti-Aging Medicine, Application of magnetic fields with deep stimulation in the fight against local obesity of lower limbs, BTL, 2012, 4 pages.

WAT Medical Technology Inc, K172450 510(k) Summary, TENS device-HeadaTern, espresso, (Sep. 2018), 10 pages.

Web MD, what is normal body temperature? 3 pages, printed Mar. 4, 2019.

Weight to volume aluminum, 2 pages. printed from internet Sep. 25, 2018.

Weight to volume copper, 2 pages printed from internet Sep. 25, 2018.

Weiss, R.A., et al., "Induction of Fat Apoptosis by a Non-Thermal Device: Mechanism of Action of Non-Invasive High-Intensity Electromagnetic Technology in a Porcine Model," Lasers in surgery and medicine 51(1):47-53, Wiley-Liss, United States (Jan. 2019).

Weng, O., "Electromagnetic Activation of the Calf Muscle Pump," UMI Dissertation Publishing (2014).

Weyh, T., et al., "Marked Differences in the Thermal Characteristics of Figure-of-eight Shaped Coils Used for Repetitive Transcranial Magnetic Stimulation," Clinical Neurophysiology 116(6):1477-1486, Elsevier, Netherlands (Mar. 2005).

Woehrle, J., et al., "Dry Needling and its Use in Health Care—A Treatment Modality and Adjunct for Pain Management," Journal of Pain and Relief 4(5):1-3, (Aug. 2015).

Wonder Face User Manual, (2024), 18 pages with attached English-language summary and partial machine translation.

World Health Organization, "Neurological Disorders—Public Health Challenges", pp. 1-115 (2006).

World Health Organization, "The Atlas: Epilepsy Care in the World", pp. 1-96 (2005).

Yacyshy, A.F., et al., "The Inclusion of Interstimulus Interval Variability Does Not Mitigate Electrically-evoked Fatigue of the Knee Extensors," European Journal of Applied Physiology 120(12):2649-2656, Springer-Verlag, Germany (Sep. 2020).

Z Wave, Instructions for Use, Zimmer Aesthetic Division, Version 5, 44 pages.

ZAO OKB RITM, Electroneurostimulants, Transdermal Scenar-NT Instructions, All Pages (Nov. 2013).

ZAO OKB RITM, Percutaneous Electrical Stimulators With Individual Biofeedback Dosing Impact on Reflex Zones, All pages (2017).

Zelickson, B., et al., "Cryolipolysis For Noninvasive Fat Cell Destruction: Initial Results From a Pig Model," Dermatologic Surgery 35(10):1462-1470, Hagerstown, MD Lippincott, Williams and Wilkins, United States (Oct. 2009).

ZELTIQ System User Manual—Print and Binding Specifications, ZELTIQ Aesthetics, Inc, Mar. 2011, 88 pages.

Zerona, Reveal your True Shape, Product Fact Sheet, 3 pages.

Zerona R-Z6 by Erchonia, Specifications, Retrieved from the Internet: (www.myzerona.com), 2015, 1 page.

Zhang, G., et al., "A Method of Nerve Electrical Stimulation by Magnetic Induction," Annual International Conference of the IEEE Engineering in Medicine and Biology Society 2009:622-625, IEEE, United States (2009).

Zhi-De, D., "Electromagnetic Field Modeling of Transcranial Electric and Magnetic Stimulation: Targeting, Individualization, and Safety of Convulsive and Subconvulsive Applications," Academic Commons (2013).

Zhu, Y., et al., "Magnetic Stimulation of Muscle Evokes Cerebral Potentials by Direct Activation of Nerve Afferents: A Study During Muscle Paralysis, " Muscle and Nerve 19(12): 1570-1575, John Wiley and Sons, United Sates (Dec. 1996).

Zimmer MedizinSysteme GmbH, K192940 510(k) Summary, Cooltone, 14 pages (Nov. 2019).

Zimmer MedizinSysteme GmbH, K203488 510(k) Summary, emField, 9 pages (Feb. 2021).

Zimmer MedizinSysteme GmbH, K220601 510(k) Summary, CoolTone, 11 pages (Apr. 2022).

Zimmer MedizinSysteme GmbH, K230780 510(k) Summary, MFG-05, (Oct. 2023), 9 pages.

"7 Wasp-Waist Aesthetic Treatments to Try Before Summer," Hola. com, Aug. 1, 2023, (with attached machine translation); 23 pages. Available at: https://www.hola.com/belleza/caraycuerpo/20200601169177/vientre-plano-tratamientos-esteticos-bfh/.

Deleo, V., "Btl Healthcare Technologies A.S," Notice of Opposition, Patent No. EP3316962, Sep. 21, 2022, (with attached English-language translation), 36 pages.

"Deymed DuoMag XT-100 rTMS Stimulator System," uploaded Jan. 26, 2023, retrieved from: https://www.youtube. com/watch?v=l9n6S4g1sKQ, 2 pages.

"Discover How to Get a Killer Butt Without Exercise (or Surgery)" Consalud.es, Dec. 20, 2019 (with attached machine translation); 5

(56) References Cited

OTHER PUBLICATIONS pages. Available at: https://www.consalud.es/estetic/bienestar/descubre-trasero-infarto-deporte-ni-cirugia_71647_102.html.
Estivill, Silvia, "Wonder, the Aesthetic Treatment for 36,000 Muscle Contractions," Wonder Medical Technology, Jan. 20, 2020 (with attached machine translation); 6 pages. Available at: https://distritomodaweb.com/wonder-el-tratamiento-estetico-de-las-36-000-contracciones-musculares/.
"For a Flat Stomach: Good Diet and Aerobic and Anaerobic Exercise with Wonder," Inoutviajes.com, Dec. 18, 2019 (with attached machine translation); 5 pages. Available at: https://www.inoutviajes.com/noticia/11315/otras-noticias/para-un-abdomen-plano:-buena-dieta-y-ejercicio-aerobico-y-anaerobico-con-wonder.html.
"How to Get a Flat Stomach this Holiday Season," Magazineespain.com, Dec. 24, 2019 (with attached machine translation); 7 pages. Available at: https://www.magazinespain.com/abdomen-plano-fiestas-navidenas/.
"How to Increase Your Glutes Without Exercise or Surgery," Expobeautyb2b.com, No Date Available (with attached machine translation); 7 pages. Available at: https://beauty.expob2b.es/es/n-/20551/como-aumentar-los-gluteos-sin-deporte-ni-cirugia.
"Increase Your Buttocks Without Sports or Surgery," Inoutviajes.com, Dec. 5, 2019 (with attached machine translation); 5 pages. Available at: https://www.inoutviajes.com/noticia/11211/otras-noticias/aumentar-los-gluteos-sin-deporte-ni-cirugia.html.
Iskra Medical, "Functional Magnetic Stimulation," Tesla System, 4 pages (2013).
Manual of Tesla Stym device, dated Mar. 2013 (with attached English-language translation), 36 pages.
Notice of Opposition, European Patent No. EP3316962, *Fotona D.O.O.* v. *BTL Healthcare Technologies A.S.*, dated Sep. 22, 2022, 128 pages.
Photo of Facebook page, dated Sep. 23, 2013, Retrieved from the internet: https://www.facebook.com iskraMedical/pllotos/pb.100063238417700.-2207520000/1113882341970904/ftype=3, 1 page.
Photo of Facebook page, dated Mar. 26, 2015, Retrieved from: https://www.facebook.com/IskraMedical/photos/pb.100063238417700.-2207520000/1113882421970896/?typee3, 1 page.
Photo of Facebook page, dated Mar. 26, 2015, Retrieved from: https://www.facebook.com/Iskramedical/photos/pb.100063238417700.-2207520000/726831297342679/?type=3, 1 page.
Photo of Facebook page, dated Mar. 13, 2013, Retrieved from: https://www.facebook.com/IskraMedical/photos/pb.100063238417700.-2207520000/776626345696507/?type=3, 1 page.
Photo of Facebook page, dated Apr. 16, 2025, Retrieved from the internet: https://www.facebook.com iskraMedical/pllotos/pb.100063238417700.-2207520000/1113882341970904/ftype=3, 1 page.
"Presentation rTMS Deymed DuoMag XT," uploaded on Oct. 12, 2021, retrieved from: https://vwav.youtube.com/%20watch?v=sPNYsTwHtSo; 3 pages.
SIQ Test Report, Tesla Stym, dated (May 2022), 62 pages.
"The World of Aesthetics Discovers Bodybuilding, a New Era of Beauty," Beautymarket.es, Sep. 9, 2020 (with attached machine translation); 8 pages. Available at: https://www.beautymarket.es/estetica/el-mundo-de-la-estetica-descubre-la-musculacion-comienza-la-nueva-era-de-la-belleza-estetica-22668.php.
"Top List: Aesthetic Medicine Teams That Will Make a Place of Pilgrimage," Beautymed.es, Sep. 1, 2020 (with attached machine translation); 14 pages. Available at: https://www.beautymed.es/lista-top-equipos-de-medicina-estetica-que-haran-de-tu-consulta-lugar-de-peregrinacion-22591.php#.
User's Manual Magneto Stym, Magneto Stym Prestige, dated Apr. 14, 2015, 21 pages.
Video of Tesla Stym, dated Sep. 26, 2014, available at: https://www.youtube.com/watch?v=vLr2Czqv60s, 2 pages.
Wasserman, E.M., et al., "Physics and Biophysics of TMS," The Oxford Handbook of Transcranial Stimulation, Chapters 1-4, pp. 36, Oxford University Press United States (2008).

What is Air Cooling?, Supermicro, Retrieved from Internet URL: https://www.supermicro.com/en/glossary/air-cooling, pp. 1-5 (Aug. 2024).
"With 'Wonder' You Can Get a Flat Stomach and . . . a Great Butt !! " Brigida Gallego, Jan. 29, 2020 (with attached machine translation); 7 pages. Available at: https://www.periodistadigital.com/por-todo-lo-alto/20200129/con-wonder-podras-conseguir-un-abdomen-plano-y-un-buen-trasero-689404250144/.
"Wonder, or How to Increase Your Glutes Without Exercise or Surgery," Beautymarket.es, Dec. 3, 2019 (with attached machine translation); 6 pages. Available at: https://www.beautymarket.es/estetica/articulo_display.php?numero=20270.
"Wonder, the Aesthetic Treatment for 36,000 Muscle Spasms," Beautymarket.es, Jan. 20, 2020 (with attached machine translation); 8 pages. Available at: https://www.beautymarket.es/estetica/wonder-el-tratamiento-estetico-de-las-contracciones-musculares-estetica-20571.php#.
"Wonder, the Revolutionary System that Increases the Buttocks Without Exercise or Surgery," Elespanol.com, Dec. 4, 2019 (with attached machine translation); 14 pages. Available at: https://www.elespanol.com/corazon/estilo/20191204/wonder-sistema-revolucionario-aumenta-gluteos-sin-deporte/449205388_0.html.
Shandong Huamei Technology Co., Ltd., K232982 510(k) Summary, EMS Sculpt Machine, 9 pages, Nov. 2025.
CPMT Laser, K241601 510(k) Summary, EMS (FlexPulse, MagnaCore, Magnetika), 11 pages, Feb. 2025.
Fotona d.o.o., K241785 510(k) Summary, StarFormer, 13 pages, Mar. 2025.
OFAN Intelligent Technologies, K242186 510(k) Summary, Neo Sculptor, 4 pages, Sep. 2025.
Guangzhou Pinzhi Medical Technology Co., Ltd., K250033 510(k) Summary, Smart Pulse Relief, 4 pages, Apr. 2022.
Zhengzou PZ Laser Slim Technology Co., Ltd., K250038 510(k) Summary, Muscle Stimulator Device, 10 pages, May 2025.
Zimmer MedizinSysteme GmbH, K251378 510(k) Summary, CoolTone, 11 Pages, Jul. 2025.
Koutroumanidis, M, et al., "Alpha Coma EEG Pattern in Patients with Severe Covid-19 related Encephalopathy," Clinical Neurophysiology 132: 218-225, Elsevier B.V., 2021.
Editorial, "Alpha Coma in COVID Encephalopathy," Clinical Neurophysiology 132: 202-203, Elsevier B.V., 2021.
Coffey, A, et al., "Altered Supraspinal Motor Networks in Survivors of Poliomyelitis: A cortico-muscular coherence study," Clinical Neurophysiology 132: 106-113, Elsevier B.V., 2021.
Saes, M, et al., "Are early measured resting-state EEG parameters predictive for upper limb motor impairment six months poststroke? ," Clinical Neurophysiology 132: 56-62, Elsevier B.V., 2021.
Drakaki, M, et al., "Database of 25 validated coil models for electric field stimulation for TMS," Brain Stimulation 15: 697-706, Elsevier B.V., 2022.
Keijzer, H.M, et al., "Dynamic Functional Connectivity of the EEG in Relation to Outcome of Postanoxic Coma," Clinical Neurophysiology 132: 157-164, Elsevier B.V., 2021.
Bril, V, et al., "Electrophysiogical Testing in Chronic Inflammatory Demyelinating Polyneuropathy Patients treated with Subcutaneous Immunoglobulin: The Polyneuropathy and Treatment with Hizentra (PATH) Study," Clinical Neurophysiology 132: 226-231, Elsevier B.V., 2021.
Pascal, L.F., et al., "Fundamentally Altered Global- and Microstate EEG Characteristics in Huntigton's disease," Clinical Neurophysiology 132: 13-22, Elsevier B.V., 2021.
De Doncker, W., et al., "Influence of Post-stroke Fatigue on Reaction Times and Corticospinal Excitability during Movement Preparation," Clinical Neurophysiology 132: 191-199, Elsevier B.V., 2021.
Boord, M. S., et al., "Investigating how Electroencephalogram measures Associate with Delirium: A Systematic Review," Clinical Neurophysiology 132: 246-257, Elsevier B.V., 2021.
Magsood, H et al., "Safety Study of Combination Treatment: Deep Brain Stimulation and Transcranial Magnetic Stimulation," Frontiers in Human Neuroscience 14: 123, PMC, 2020.
Wasserman, E.M., "Risk and Safety or Repetitive Transcranial Magnetic Stimulation: Report and Suggested Guidelines from the

(56) References Cited

OTHER PUBLICATIONS

International Workshop on the Safety of Repetitive Transcranial Magnetic Stimulation, June 5-7. 1996," Electroencephalography and Clinical Neurophysiology 108: 1-16, Elsevier Science Ireland, 1998.
Rossi, S. et al., "Safety and Recommendations for TMS Use in Healthy Subjects and Patient Populations, with Updates on Training, Ethical and Regulatory issues: Expert Guidelines," Clinical Neurophysiology 132(1): 269-306, Elsevier, 2021.
Wagner T. et al., "Noninvasive Human Brain Stimulation," Annual Review of Biomedical Engineering 9: 527-565, 2007.
Fu, B. et al., "Efficacy and Safety of Transcranial Magnetic Stimulation for Attention-Deficit Hyperactivity Disorder: A Systematic Review andMeta-Analysis," Brain and Behavior 15(1): 1-17, 2025.
Alyagon U. et al., "Alleviation of ADHD symptoms by non-invasive right prefrontal stimulation is correlated with EEG activity," NeuroImage: Clinical 26: 102206, 2020.
Valero-Cabré A. et al., "Transcranial magnetic stimulation in basic and clinical neuroscience: A comprehensive review of fundamental principles and novel insights," Neuroscience and Biobehavioral Reviews 83: 381-404, 2017.
Klomjai W. et al., "Basic Principles of Transcranial Magnetic Stimulation (TMS) and Repetitive TMS (rTMS)," Annals of Physical and Rehabilitation Medicine 58: 208-213, 2015.
Saadati H. et al., "The Effect of rTMS with Rehabilitation on Hand Function and Corticomotor Excitability in Sub-Acute Stroke," Iranian Rehabilitation Journal 13(4): 46-52, 2015.
Ferrulli A. et al., "Weight loss induced by deep transcranial magnetic stimulation in obesity: A randomized, double-blind, sham-controlled study," Diabetes, Obesity and Metabolism 21: 1849-1860, 2019.
Matheson N.A. et al., "Understanding the Effects of Repetitive Transcranial Magnetic Stimulation on Neuronal Circuits," Frontiers in Neural Circuits 10: 67, 2016.
Squire L.R. et al., "Fundamental Neuroscience, third edition," Elsevier, 1277 pages, 2008.
Hallet M. et al., "Transcranial magnetic stimulation and the human brain," Nature 406: 147-150, 2000.
Khedr E. et al., "Short- and long-term effect of rTMS on motor function recovery after ischemic stroke," Restorative Neurology and Neuroscience 28: 545-559, 2010.
Kim S-H. et al., "The Effects of Repetitive Transcranial Magnetic Stimulation on Eating Behaviors and Body Weight in Obesity: A Randomized Controlled Study," Brain Stimulation 11(3): 528-535, 2018.
Lowe C.J. et al., "The Effects of Continuous Theta Burst Stimulation to the Left Dorsolateral Prefrontal Cortex on Executive Function, Food Cravings, and Snack Food Consumption," Psychosomatic Medicine 76: 503-511, 2014.
McLean A.L. et al., "Publication trends in transcranial magnetic stimulation: a 30-year panorama," Brain Stimulation 12: 619-627, 2019.
Miniussi C. et al., "Transcranial magnetic stimulation in cognitive rehabilitation," Neurophychological Rehabilitation 21(5): 579-601, 2011.
Dietz V. et al., "Neurorehablitation Technology," Springer, 517 pages, 2012.
Oberman L. et al., "Safety of Theta Burst Transcranial Magnetic Stimulation: A Systematic Review of the Literature," Journal of Clinical Neurophysiology 28(1): 67-74, 2011.
Rachid F., "Repetitive transcranial magnetic stimulation in the treatment of eating disorders: A review of safety and efficacy," Psychiatry Research 269: 145-156, 2018.
Rami L. et al., "The Subjective Cognitive Decline Questionnaire (SCD-Q): A Validation Study," Journal of Alzheimer's Disease 41: 453-466, 2014.
Sauvé W.M. et al., "The Science of Transcranial Magnetic Stimulation," Psychiatric Annals 44(6): 279-283, 2014.

Machado S. et al., "Repetitive Transcranial Magnetic Stimulation for Clinical Applications in Neurological and Psychiatric Disorders: An Overview," The Euroasian Journal of Medicine 45: 191-206, 2013.
Rotenberg A. et al., "Transcranial Magnetic Stimulation," Humana Press, 384 pages, 2014.
Terao Y. et al., "Basic Mechanisms of TMS," Journal of Clinical Neurophysiology 19(4): 322-343, 2002.
Pascual-Leone A. et al., "Brain Mapping: The Methods 2nd edition," Chapter 11, pp. 255-290, Elsevier, 2002.
Uher R. et al., "Effect of Left Prefrontal Repetitive Transcranial Magnetic Stimulation on Food Craving," Biological Psychiatry 58: 840-842, 2005.
Siebner H.R. et al., "How does transcranial magnetic stimulation modify neuronal activity in the brain? - Implications for studies of cognition," Cortex 45(9): 1035-1042, 2009.
Van Den Eynde F. et al., "Repetitive Transcranial Magnetic Stimulation Reduces Cue-Induced Food Craving in Bulimic Disorders," Biological Psychiatry 67(8): 793-795, 2010.
BTL Industries Inc., K211639 510(k) Summary, BTL-785W, 15 pages, Mar. 2022.
Wasserman, E.M., et al., "Physics and Biophysics of TMS," The Oxford Handbook of Transcranial Stimulation, Chapter 9, pp. 77-89, Oxford University Press United States (2008).
Wasserman, E.M., et al., "Physics and Biophysics of TMS," The Oxford Handbook of Transcranial Stimulation, Chapter 10, pp. 92-102, Oxford University Press United States (2008).
Wasserman, E.M., et al., "Physics and Biophysics of TMS," The Oxford Handbook of Transcranial Stimulation, Chapter 11, pp. 103-117, Oxford University Press United States (2008).
5Wasserman, E.M., et al., "Physics and Biophysics of TMS," The Oxford Handbook of Transcranial Stimulation, Chapter 15, pp. 171-184, Oxford University Press United States (2008).
5Wasserman, E.M., et al., "Physics and Biophysics of TMS," The Oxford Handbook of Transcranial Stimulation, Chapter 18, pp. 219-234, Oxford University Press United States (2008).
BTL Industries Inc., K222556 510(k) Summary, BTL-785x, 17 pages, May 2023.
BTL Industries Inc., K232172 510(k) Summary, BTL-785BNF Handpiece, 9 pages, Sep. 2023.
BTL Industries Inc., K243290 510(k) Summary, BTL-785BMJ, 10 pages, May 2025.
BTL Industries Inc., K233604 510(k) Summary, BTL-785Bs, 17 pages, Mar. 2024.
Tonica Elektronik A/S, K061645 510(k) Summary, MagPro R30, 6 pages, Oct. 2006.
Tonica Elektronik A/S, K071821 510(k) Summary, MCF-B65, 5 pages, Jul. 2007.
The Leading Provider of Advanced Neurostimulation Products, Magstim, 2010, 8 pages.
Magstim, K083242 510(k) Summary, Neurosign Avalanche, 8 pages, Jul. 2009.
Neuronetics Inc., K083538 510(k) Summary, Neurostar TMS Therapy System, 6 pages, Dec. 2008.
Nextim OY., K091457 510(k) Summary, Nextim Eximia Navigated Brain Stimulation System, 3 pages, Dec. 2009.
Tonica Elektronik A/S, K091940 510(k) Summary, MagPro R30, 6 pages, Mar. 2010.
Nextim OY., K112881 510(k) Summary, Nextim Navigated Brain Stimulation (NBS) System 4, 14 pages, May 2012.
Brainsway Ltd., K122288 510(k) Summary, Repetitive Transcranial Magnetic Stimulator, 11 pages, Jan. 2012.
Neuronetics Inc., K130233 510(k) Summary, Neurostar TMS Therapy System, 5 pages, Apr. 2013.
De Novo Classification Request for Brainsway Deep Transcranial Magnetic Stimulation Device, Regulatory Information, Sep. 2017. 23 pages.
Neuronetics, K133408 510(k) Summary, Neurostar TMS Therapy System, 13 pages, Mar. 2014.
Magstim, K143351 510(k) Summary, Rapid(2) Therapy System, 8 pages, May 2015.
Tonica Elektronik A/S, K150641 510(k) Summary, MagVita TMS Therapy System, 8 pages, Jul. 2015.

(56)                    References Cited

OTHER PUBLICATIONS

Tonica Elektronik A/S, K160280 510(k) Summary, MagPro R20, 8 pages, May 2016.
Neuronetics, K160703 510(k) Summary, Neurostar TMS Therapy System, 6 pages, Jun. 2016.
Neuronetics, K161519 510(k) Summary, Neurostar TMS Therapy System, 7 pages, Sep. 2016.
Tonica Elektronik A/S, K162873 510(k) Summary, MEP Monitor, 10 pages, Mar. 2017.
Magstim, K162935 510(k) Summary, Rapid2 Therapy System, 8 pages, Mar. 2017.
Tonica Elektronik A/S, K170114 510(k) Summary, Magvita TMS Therapy - W/MagPro R20, 8 pages, May 2017.
Magstim, K171051/S002 510(k) Summary, Horizon Therapy System, 9 pages, Sep. 2017.
Tonica Elektronik A/S, K171481 510(k) Summary, Magvita TMS Therapy System, 8 pages, Jun. 2017.
Nextim Plc., K171902 510(k) Summary, Nextim Navigated Brain Therapy (NBT) System 2, 10 pages, Nov. 2017.
Tonica Elektronik A/S, K171967 510(k) Summary, Magvita TMS Therapy System, 7 pages, Jul. 2017.
Tonica Elektronik A/S, K172667 510(k) Summary, Magvita TMS Therapy w/MagPro R20, 8 pages, Oct. 2017.
Brainsway Ltd., K173540 510(k) Summary, Brainsway Deep TMS System, 9 pages, May 2018.
Tonica Elektronik A/S, K173620 510(k) Summary, Magvita TMS Therapy System w/Theta Burst Stimulation, 10 pages, Aug. 2018.
Mag & More A/S, K180313 510(k) Summary, Apollo TMS Therapy System, 7 pages, May 2018.
Magstim Company Ltd., K180907 510(k) Summary, Horizon TMS Therapy System, 9 pages, Aug. 2018.
Magstim Company Ltd., K181559 510(k) Summary, Neurosign V4 Intraoperative Nerve Monitor, 8 pages, Nov. 2018.
Nextim Plc., K182700 510(k) Summary, Nextim Navigated Brain Therapy (NBT) System 2, 14 pages, Mar. 2019.
Magstim Company Ltd., K182583 510(k) Summary, Horizon TMS Therapy System, 10 pages, Mar. 2019.
Brainsway Ltd., K183303 510(k) Summary, Brainsway Deep TMS System, 10 pages, Mar. 2019.
Magstim Company Ltd., K183376 510(k) Summary, Horizon TMS Therapy System with Navigation, 12 pages, Mar. 2019.
Tonica Elektronik A/S, K193006 510(k) Summary, MagVenture TMS Therapy—for adjunctive treatment of OCD, MagVenture TMS Therapy System, 14 pages, Aug. 2020.
Brainsway Ltd., K200957 510(k) Summary, Brainsway Deep TMS System, 14 pages, Aug. 2020.
Neuronetics Inc., K201158 510(k) Summary, Neurostar Advanced Therapy, 10 pages, Nov. 2020.
The Leading Provider of Advanced Neurostimulation Products, Magstim, 2012, 8 pages.
Technical Manual Neuro-MS/D, Magnetic Stimulator, Neurosoft Ltd., 2014, 67 pages.
Magstim Rapid2 P/N 3576-23-09 Operating Manual, Magstim Ltd., Nov. 2009, 61 pages.
Nexstim, Sham Surprise shows Stroke Succeess, Apr. 2016, 14 pages.
Deep TMS System for treatment of obsessive compulsive disorder (HAC coil), Instructions for use, Brainsway, Jul. 2018, 54 pages.
MagPro family User Guide, 44 pages.
Magstim rTMS therapy, a revolutionary treatment for depression, 2014, 4 pages.
Magventure, Research, Treatment, Results, 2022, 37 pages.
Magventure News #3, Jun. 2014, 12 pages.
Magventure News #4, Nov. 2014, 12 pages.
Magventure News #6, Jul. 2015, 12 pages.
Magventure News #8, Mar. 2016, 12 pages.
Magstim: The brains behind TMS, 2017, 16 pages.
Consistent growth based on the rental model: sufficient cash available;, Brainsway, Sep. 2018, 29 pages.
Neurosoft Ltd., K133995 510(k) Summary, Neuron Spectrum 1, 50 pages, Jun. 2015.
Nexstim OYJ, Company Note, 22 p. 2018.
Now I'm a Neurostar, Neurostar, 6 p. 2017.
Transcranial magnetic stimulators attract attention, Vantage, Aug. 2018.
Rossi, S et al., "Safety, ethical considerations, and application guidelines for the use of transcranial magnetic stimulation in clinical practice and research," Clinical Neurophysiology 120: 2008-2039, Elsevier, 2009.
TMS update by Magventure, Issue 1, Jan. 2019, 20 pages.
Navigating the opportunity in depression, Nexstim, Oct. 2018. 11 pages.
Behavioral Health Market Overview, Harris Williams & Co., May 2014, 13 pages.
Annual Update, Clinical progress achieved as planned by the company, Brainsway, Mar. 2018, 9 pages.
Brainsway Ltd.: Market Trends Drive Revenue Growth, Brainsway, Aug. 2017, 56 pages.
Duomag TMS Technical Description and Instructions for use, Deymed, Feb. 2019, 87 pages.

* cited by examiner

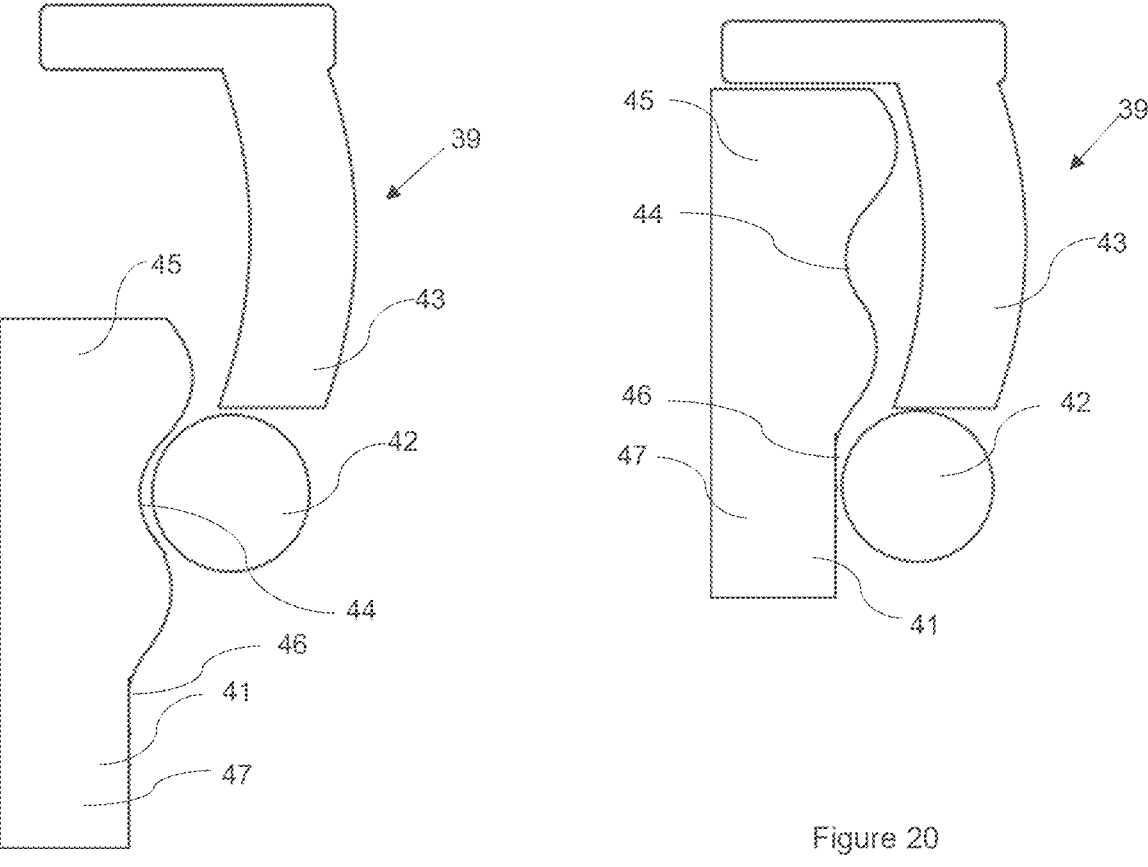
Figure 19
Figure 20
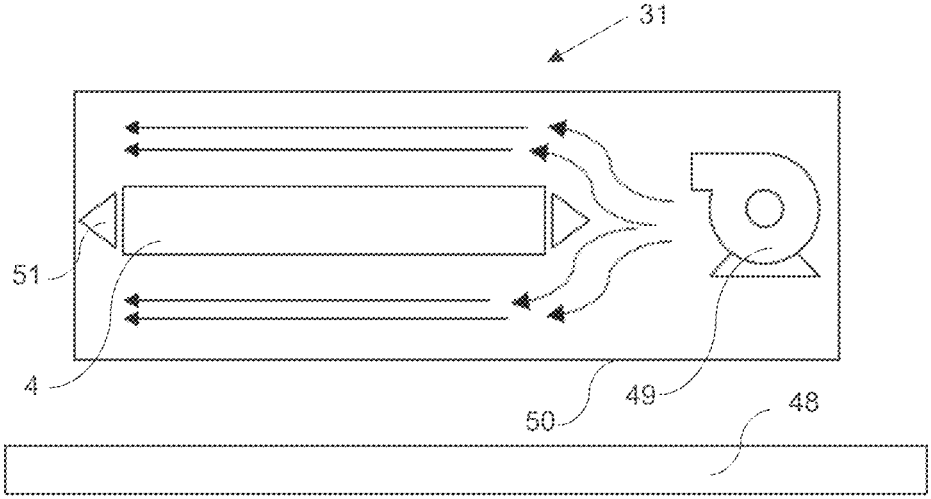
Figure 21

1

DEVICES AND METHODS FOR APPLICATION OF A MAGNETIC FIELD TO THE NERVOUS SYSTEM

CROSS REFERENCE TO RELATED APPLICATIONS

This application is a continuation of U.S. application Ser. No. 19/030,362, filed Jan. 17, 2025, which claims priority to U.S. Provisional Application No. 63/704,905, filed Oct. 8, 2024, U.S. Provisional Application No. 63/738,196, filed Dec. 23, 2024, and U.S. Provisional Application No. 63/744, 050, filed Jan. 10, 2025, all of which are hereby incorporated by reference in their entirety.

BACKGROUND

The present disclosure relates to devices and methods using the influence of magnetic field on tissue. The magnetic field may be a time-varying magnetic field.

Self-control is the ability to regulate emotions, and behavior of a human. New devices and methods are needed for promoting self-control (e.g. resisting food cravings by use of magnetic field on the brain).

A time-varying magnetic field may be applied to the head of a patient and induce electric current in at least part of a central nervous system, comprising brain and spinal cord of the patient. Transcranial magnetic stimulation may cause persistent modulation of cortical excitability as well as of other physiological, metabolic, and behavioral measures.

The induced current may be sufficient to cause depolarization of corticospinal tract neurons either directly at the axon hillock or indirectly cause depolarization of interneurons. The time-varying magnetic field may depolarize neurons transiently, but cortical excitability can be increased or decreased depending on the parameters of the stimulation. A low repetition rate such as 1 Hz or less may suppress cortical excitability. A repetition rate of 5 Hz or greater may enhance cortical excitability.

BRIEF SUMMARY

The disclosure provides a system and methods for providing a magnetic field. The magnetic field may be a time-varying magnetic field. The system may include a device or devices.

The system may include a main body, at least one connecting tube, at least one positioning arm, and at least one applicator. The devices may be configured to apply the magnetic field to the brain of the patient.

The methods include a method of finding an application position of the applicator. The method of finding the application position may be comparable or more convenient to other described methods. The application position may be suitable to apply the time-varying magnetic field to the central nervous system of the patient, e.g. a cortex such as prefrontal cortex. In some aspects, the application position may be a position in which the applicator is able to apply the time-varying magnetic field to left dorsolateral prefrontal cortex. In some aspects, the application position may be a position in which the applicator is able to apply the time-varying magnetic field to the left dorsolateral prefrontal cortex to cause the release of hormones, e.g. pleasure hormones such as dopamine, serotonin, endorphins, or oxytocin. In some aspects, the application position may be a position in which the applicator is able to apply the time-varying magnetic field to the left dorsolateral prefrontal cortex to temporarily reduce the food cravings and/or binge eating. In some aspects, the application position may be a position in which the applicator is able to apply the time-varying magnetic field to the left dorsolateral prefrontal cortex to ameliorate patient's mood.

Higher level of self-control may increase academic performance, reduce binge eating or alcohol abuse, improve relationships, and/or ameliorate positive emotions. Moreover, self-control positively influence a healthier lifestyle, including resisting the temptation of food cravings. Food cravings are defined as a strong desire or urge to eat, leading to increased dietary intake, long-term weight gain, and even binge-eating behavior. It has been indicated that by reducing food cravings, weight-loss was ameliorated, and weight re-gain prevented.

Method to enhance self-control and subsequent resistance to food cravings may be accomplished via brain stimulation, e.g. by transcranial magnetic stimulation. This stimulation may induce long-lasting changes in cortical excitability and dopamine release.

The system may be configured to apply the time-varying magnetic field to the dorsolateral prefrontal cortex (abbreviated as DLPFC) (e.g., to the left DLFPC). The system may be configured to apply the time-varying magnetic field to the left dorsolateral prefrontal cortex.

The system may be configured to apply the time-varying magnetic field to the left dorsolateral prefrontal cortex to reduce food cravings and/or binge eating.

The system may be configured to apply the time-varying magnetic field to the left dorsolateral prefrontal cortex to at least temporarily reduce food cravings and/or binge eating.

The system may be configured to apply the time-varying magnetic field to the left dorsolateral prefrontal cortex to temporarily reduce food cravings and/or binge eating.

The system may be configured to apply the time-varying magnetic field to a right dorsolateral prefrontal cortex to reduce activity of the right dorsolateral prefrontal cortex in order to food cravings and/or binge eating.

The disclosure may include a device for providing a time-varying magnetic field to the left dorsolateral prefrontal cortex in order to reduce the food cravings, wherein the device comprises an applicator comprising a positioning plate configured to be used during positioning of the applicator to the application position, wherein the positioning plate comprises a central line, and at least one visual elements.

The disclosure may include a device for providing a magnetic field to the central nervous system.

The disclosure may include a device for providing a time-varying magnetic field to the central nervous system to reduce the food cravings.

The disclosure may include a device for providing a time-varying magnetic field to the left dorsolateral prefrontal cortex to reduce food cravings.

The disclosure may include a device for providing a time-varying magnetic field to the left dorsolateral prefrontal cortex in order to reduce the food cravings, wherein the device comprises: an applicator comprising a magnetic field generating device a positioning plate configured to be used during positioning of the application to the application position, wherein the positioning plate comprises at least one visual element.

The disclosure may include a device of at least one of paragraph 9 to 15 numbered below, wherein the applicator comprises a casing having a lower side of the casing, wherein the magnetic field generating device is positioned between the one visual element and the lower side of the casing.

The disclosure may include a device for providing a time-varying magnetic field to the left dorsolateral prefrontal cortex in order to temporarily reduce the food cravings.

The disclosure may include a method of positioning of the applicator to reduce food cravings.

BRIEF DESCRIPTION OF THE FIGURES

The accompanying figures, which are incorporated herein and form a part of the specification, illustrate the present disclosure and, together with the description, further serve to explain the principles thereof and to enable a person skilled in the pertinent art to make and use the same.

FIG. 19 illustrates a lock 39 in an open position, according to some aspects.

FIG. 20 illustrates the lock of FIG. 19 in a closed position, according to some aspects.

FIG. 21 illustrates a cross-section of an exemplary applicator, according to some aspects.

4

Figure 33:
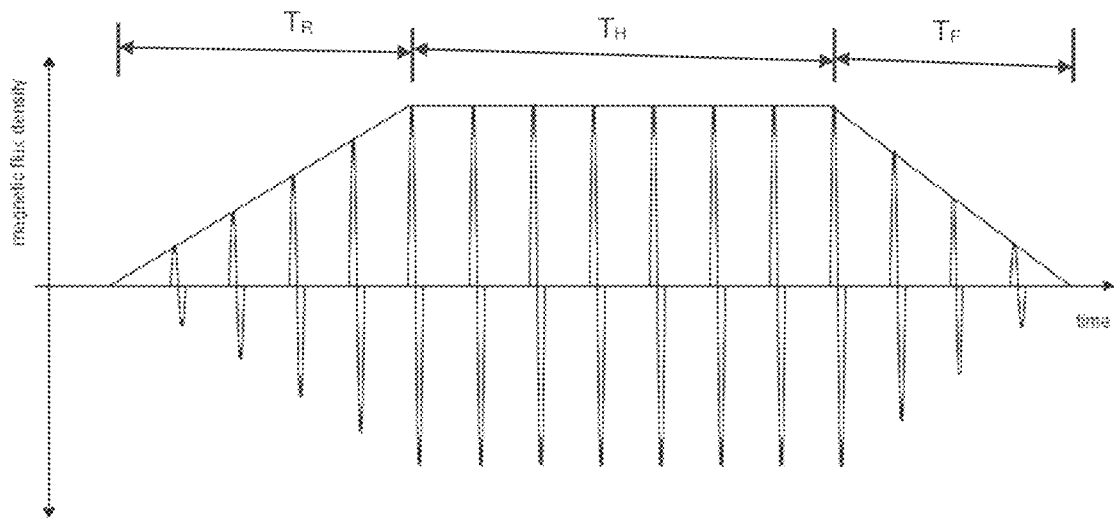

FIG. 33 illustrates an exemplary trapezoidal envelope formed by plurality of biphasic magnetic impulses having different values of magnetic flux density, according to some aspects.

Figure 34:
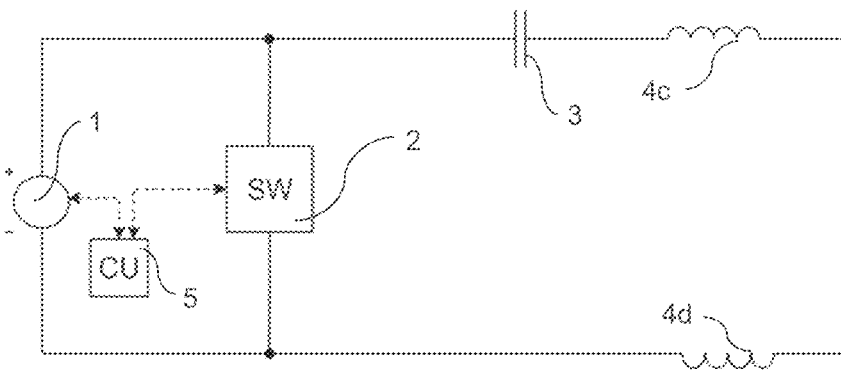
Figure 35:
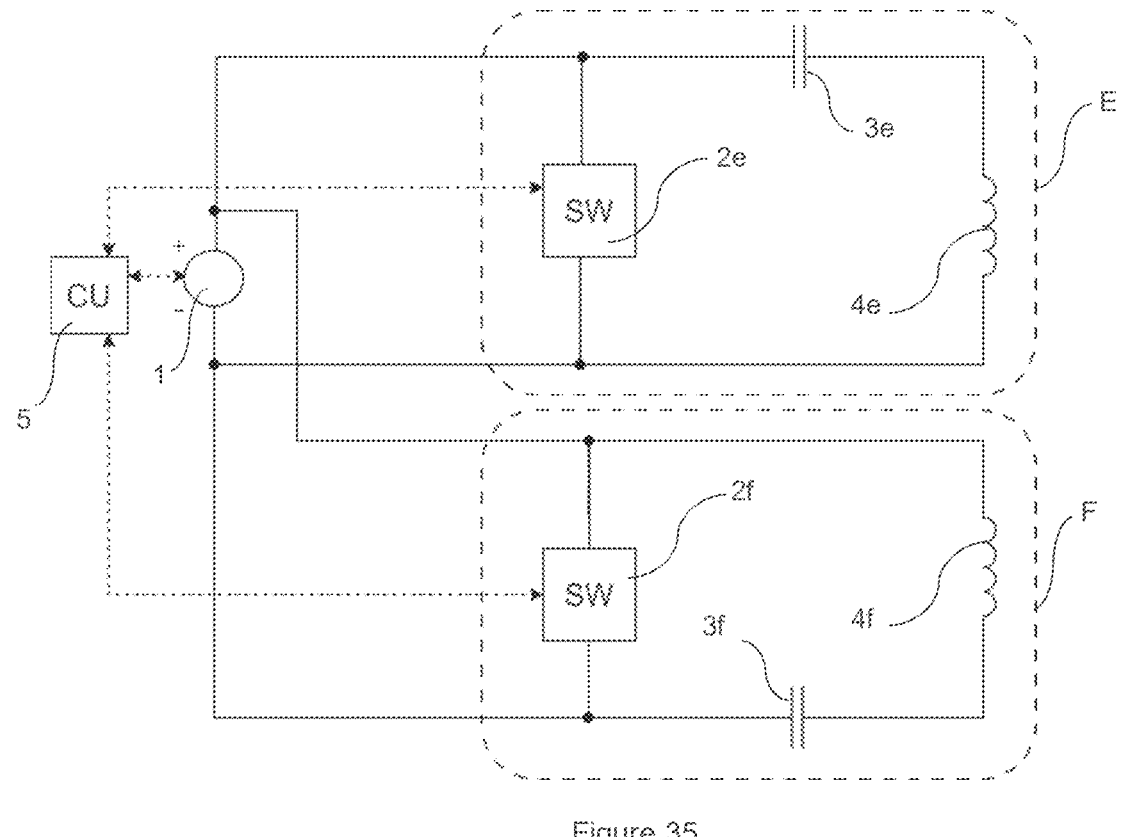
Figure 36:
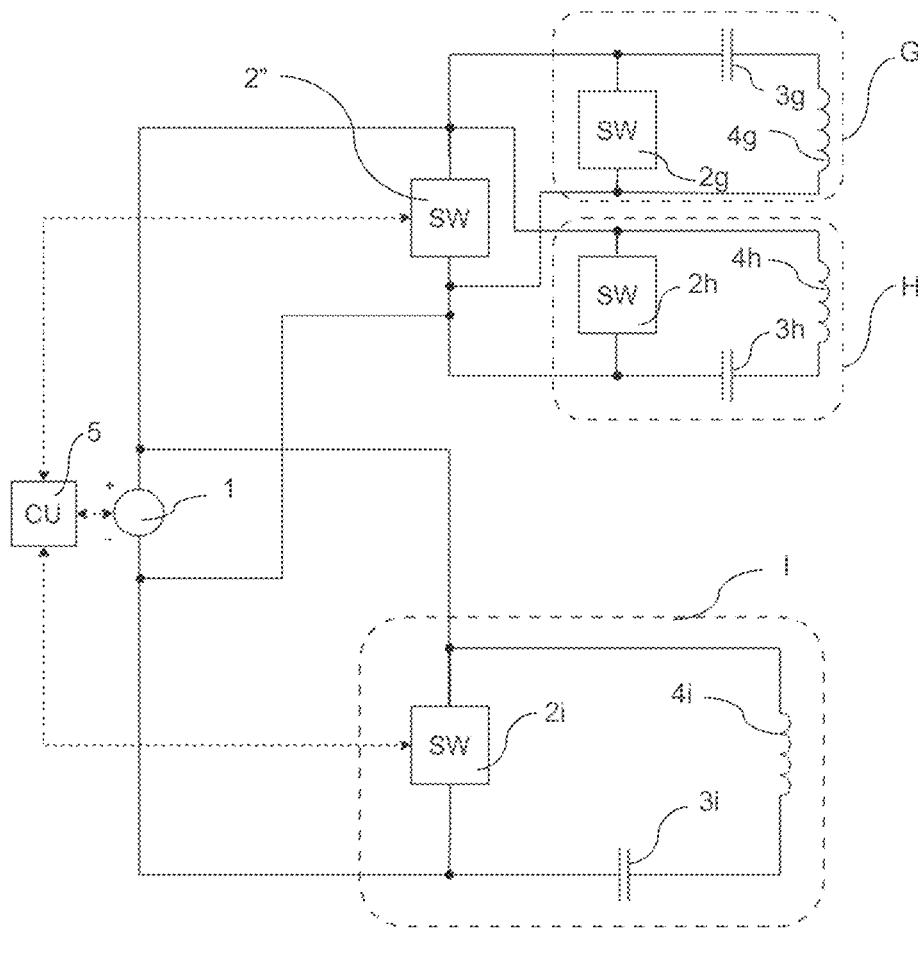

FIGS. 34, 35 and 36 illustrate exemplary magnetic circuits with a single energy source, according to some aspects.

Figure 37:
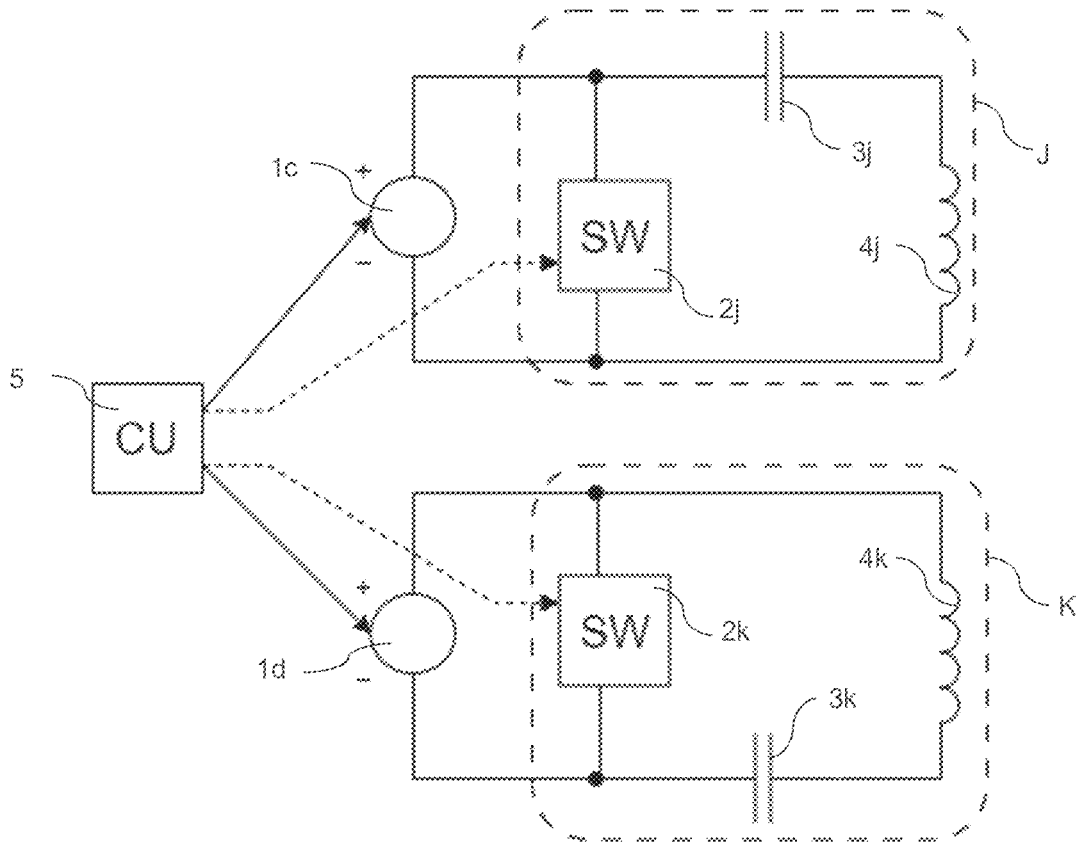
Figure 38:
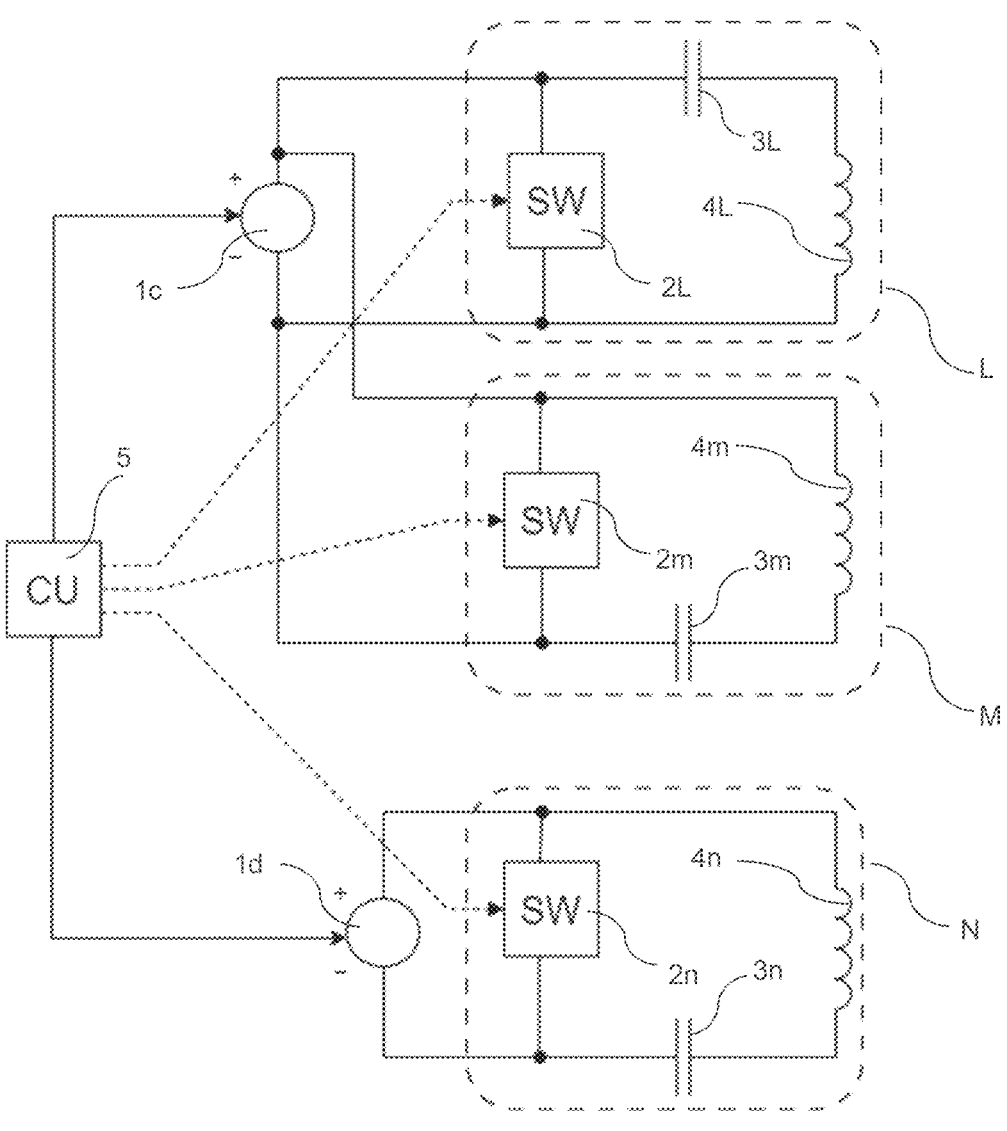

FIGS. 37 and 38 illustrate exemplary magnetic circuits with two energy sources, according to some aspects.

Figure 39:
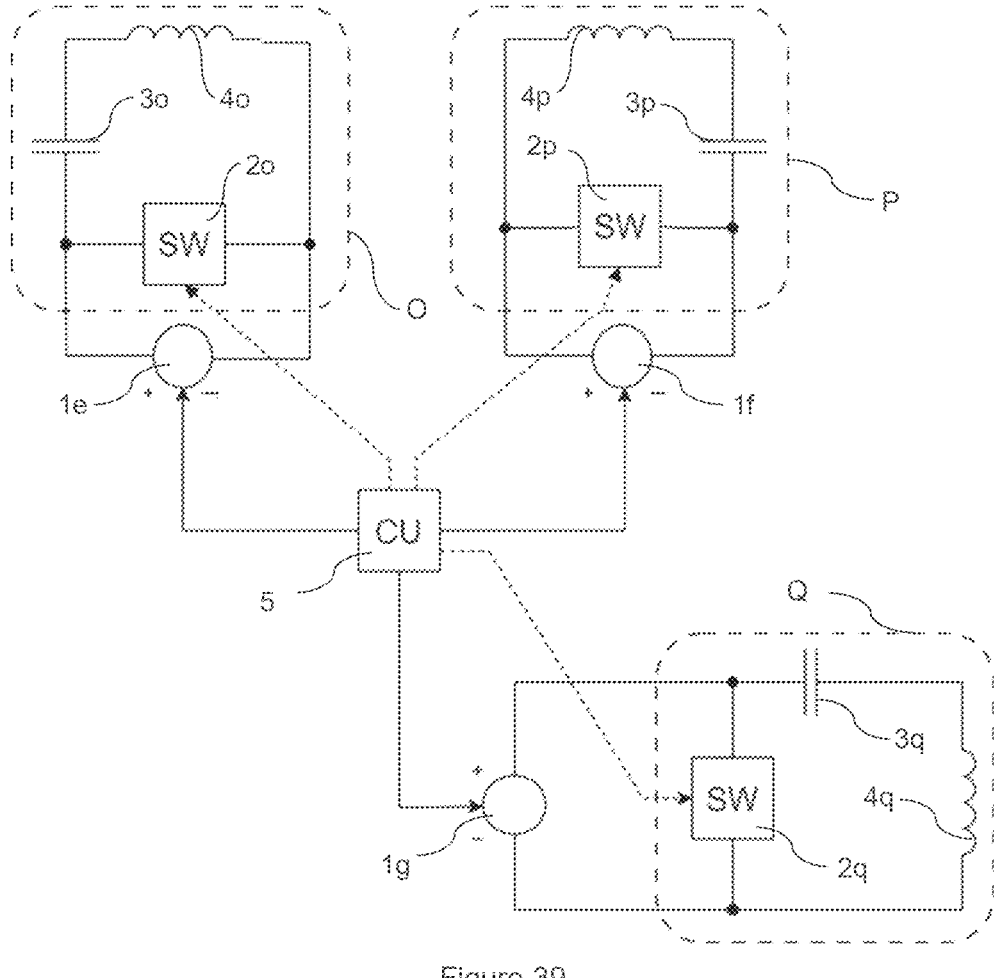

FIG. 39 illustrate exemplary magnetic circuit with three energy sources, according to some aspects.

Figure 40:
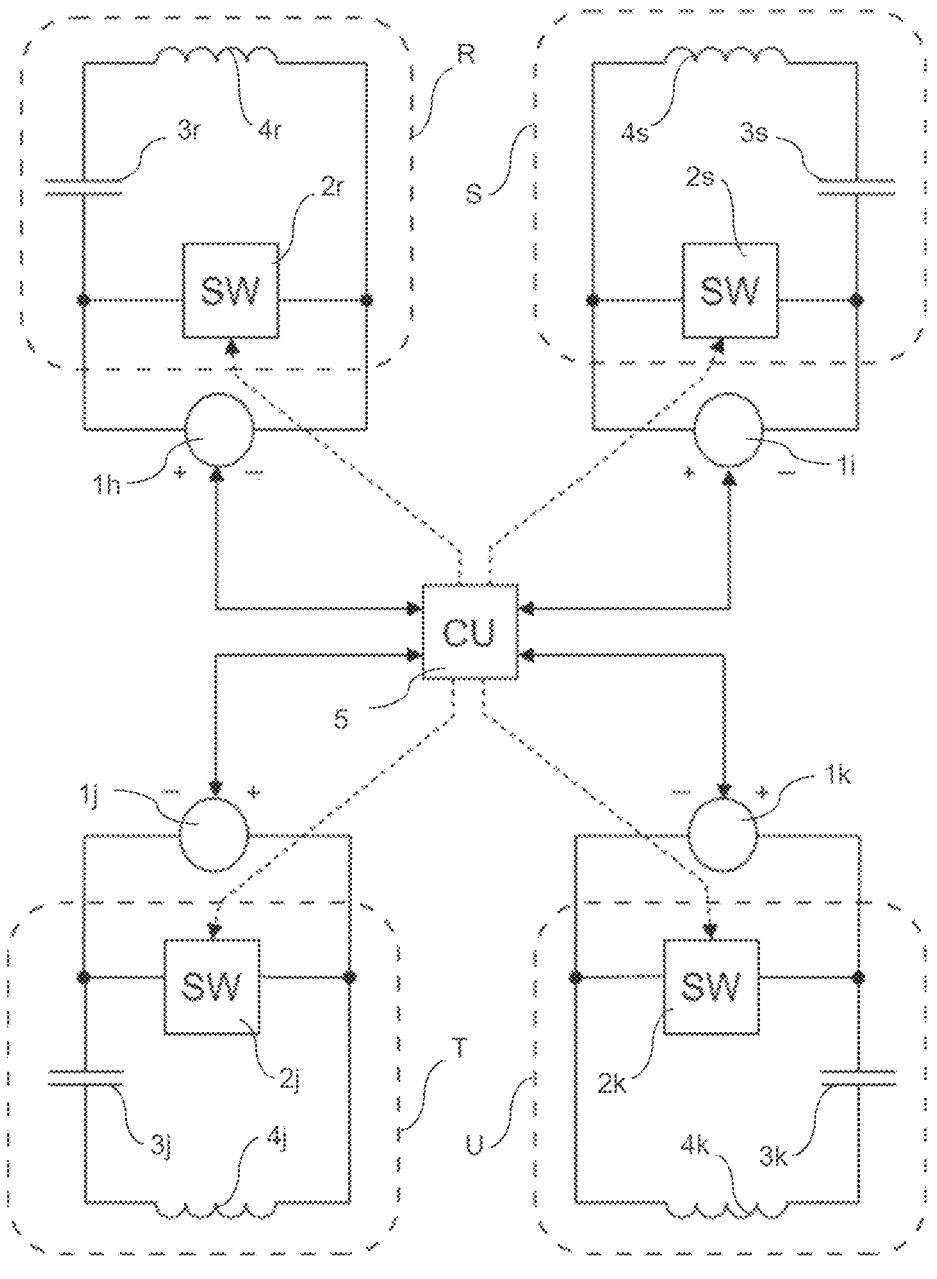

FIG. 40 illustrate exemplary magnetic circuit with four energy sources, according to some aspects.

Figure 41A:
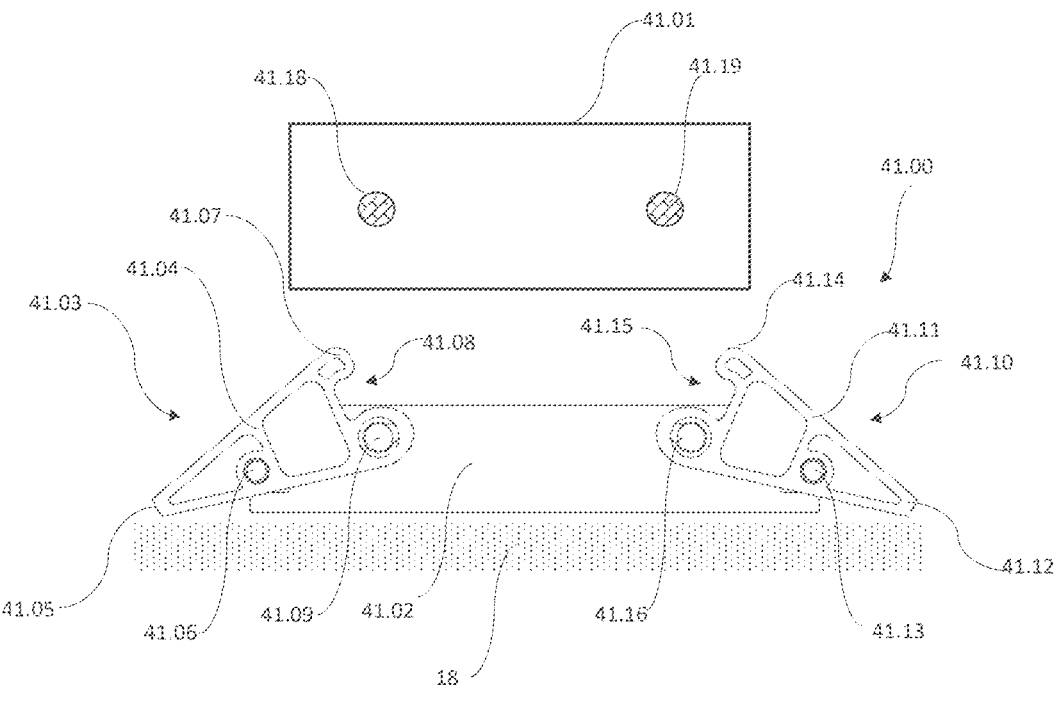
Figure 41B:
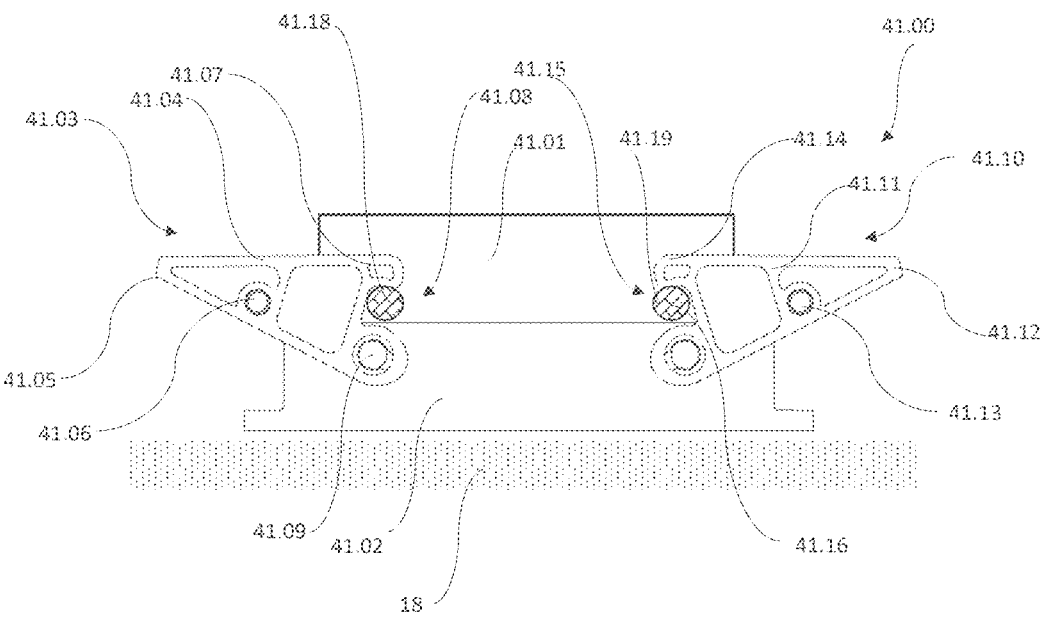

FIGS. 41*a* and 41*b* illustrate an exemplary locking mechanism for coupling the connector to the main body of the device, according to some aspects.

Figure 42:
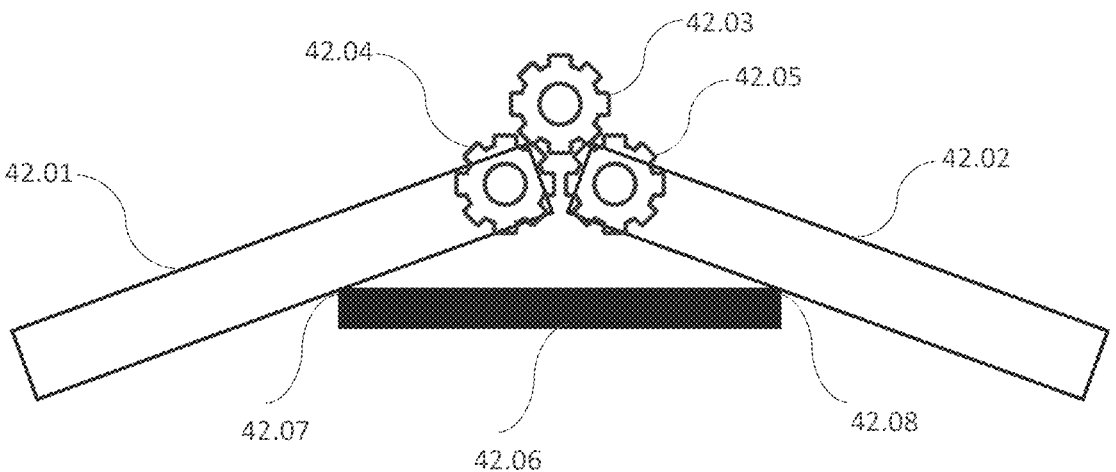

FIG. 42 illustrates an exemplary geometry changing mechanism, according to some aspects.

Figure 43A:
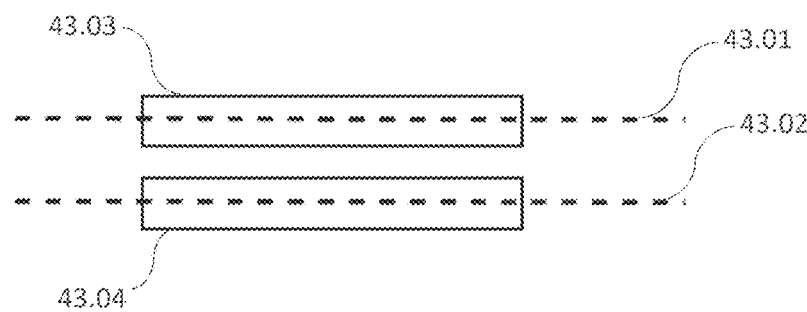
Figure 43B:
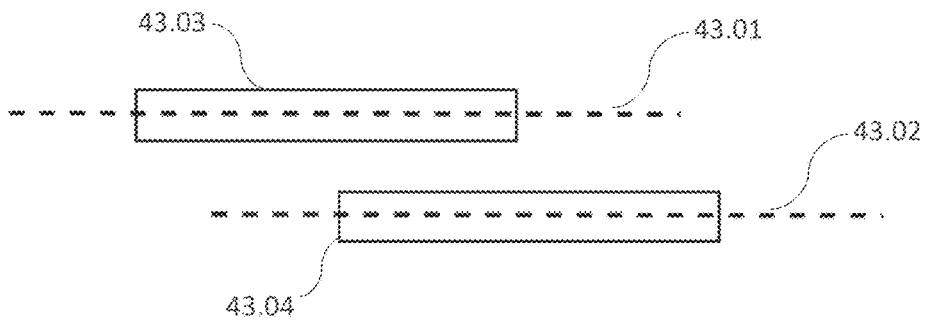
Figure 43C:
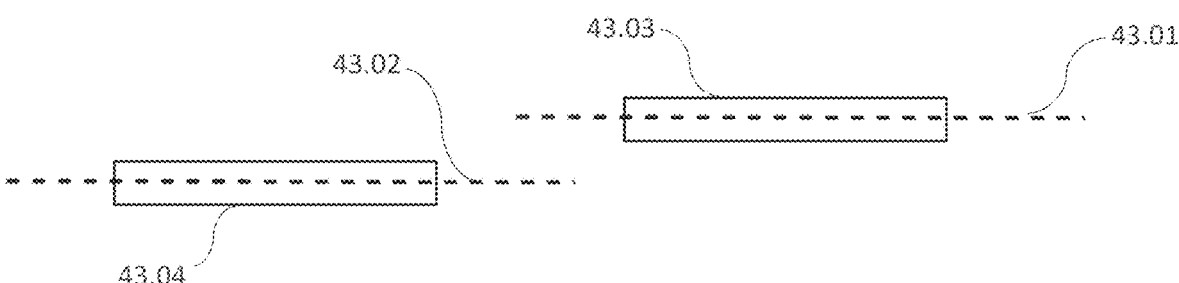

FIGS. 43*a*-43*c* illustrate exemplary orientation of two magnetic field generating devices in cross-section, according to some aspects.

Figure 44:
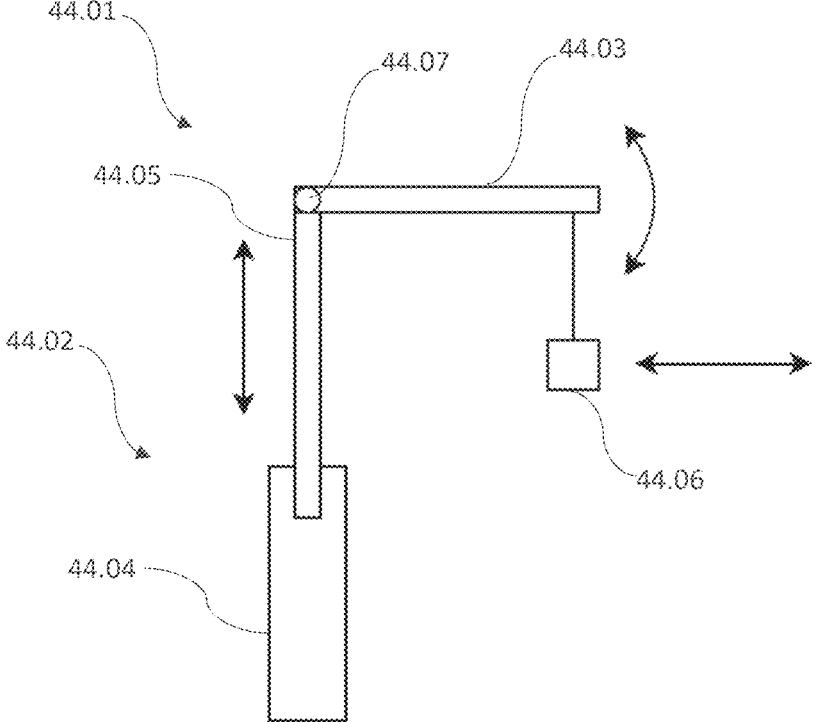

FIG. 44 illustrates an exemplary positioning stand, according to some aspects.

Figure 45A:
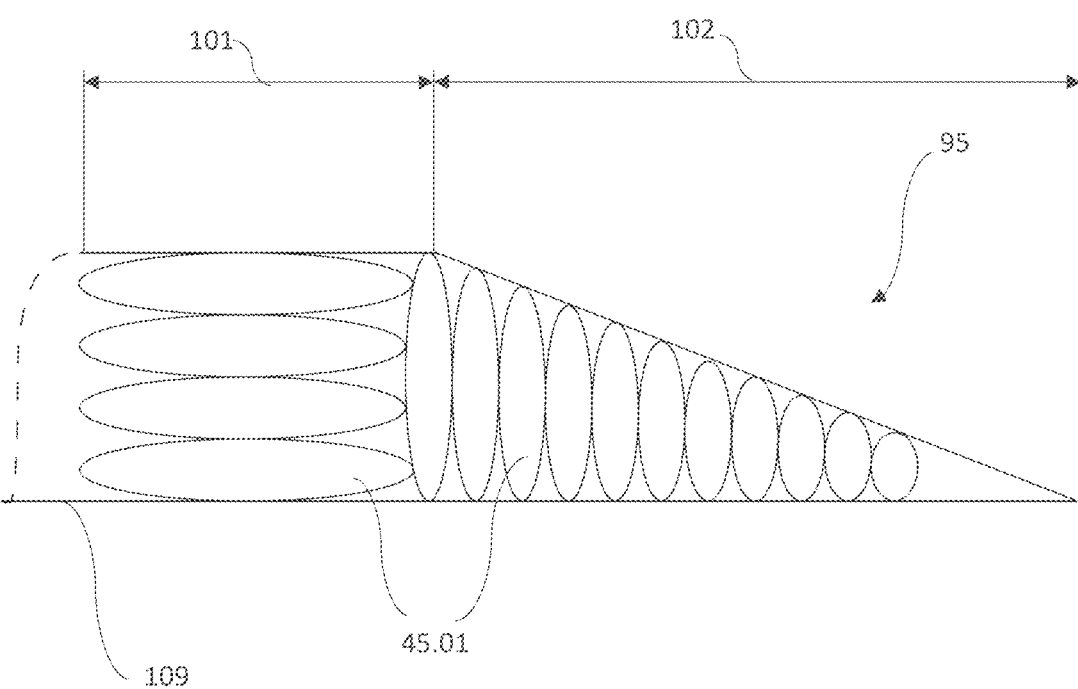
Figure 45B:
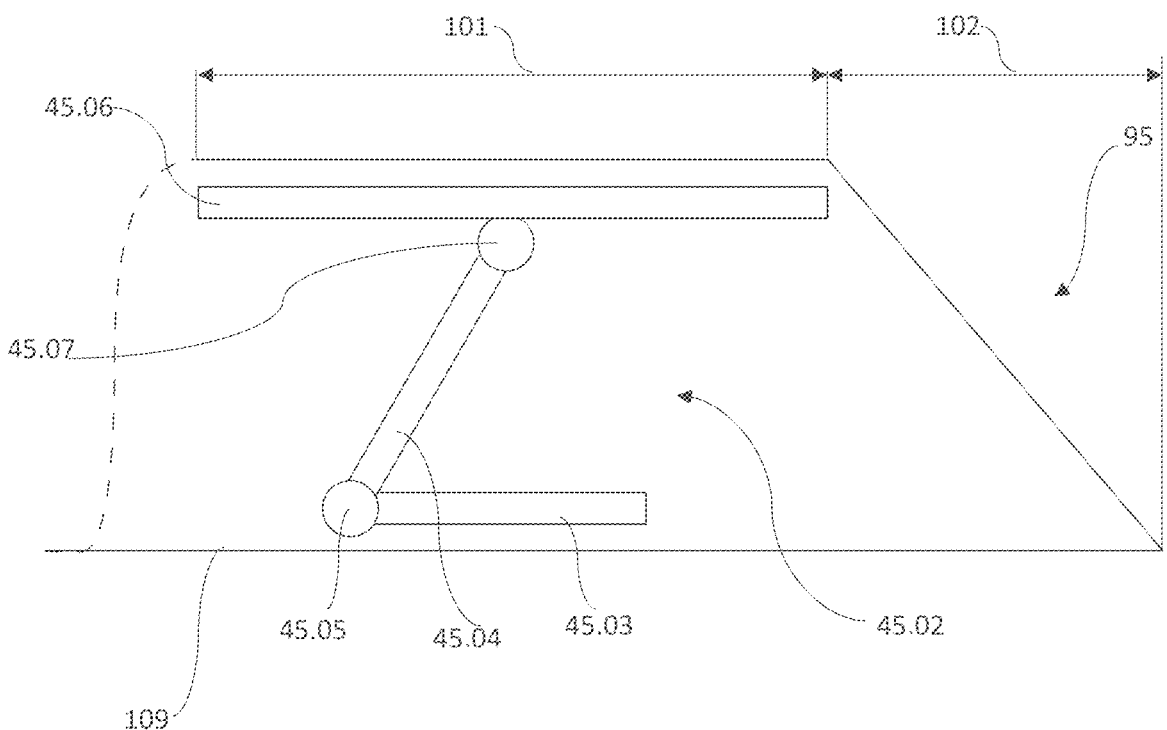
Figure 46A:
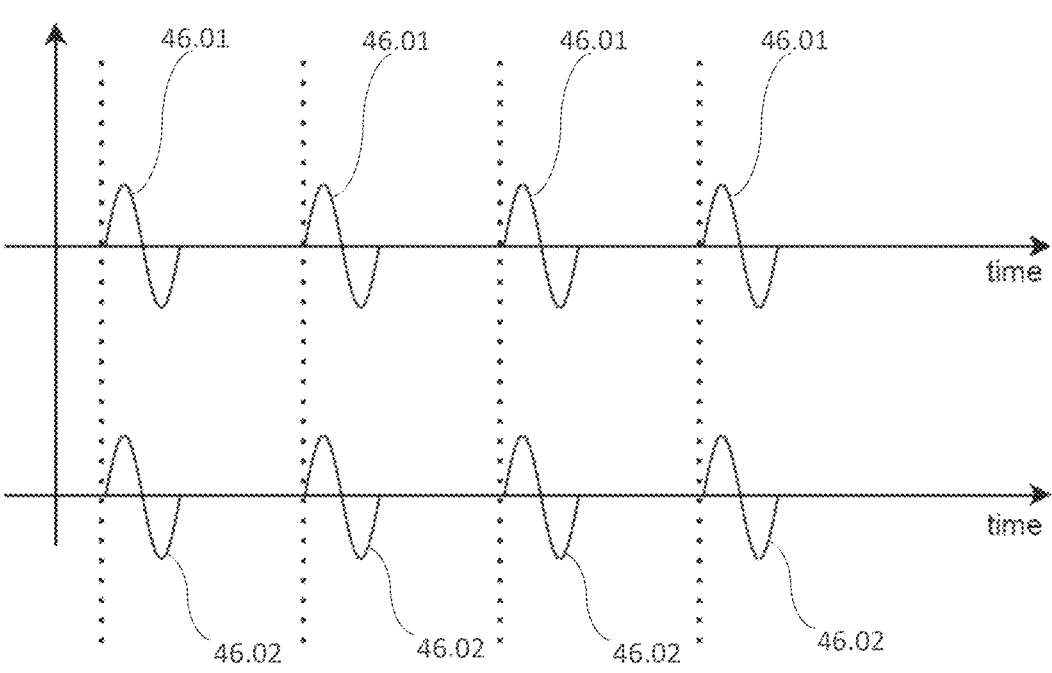
Figure 46B:
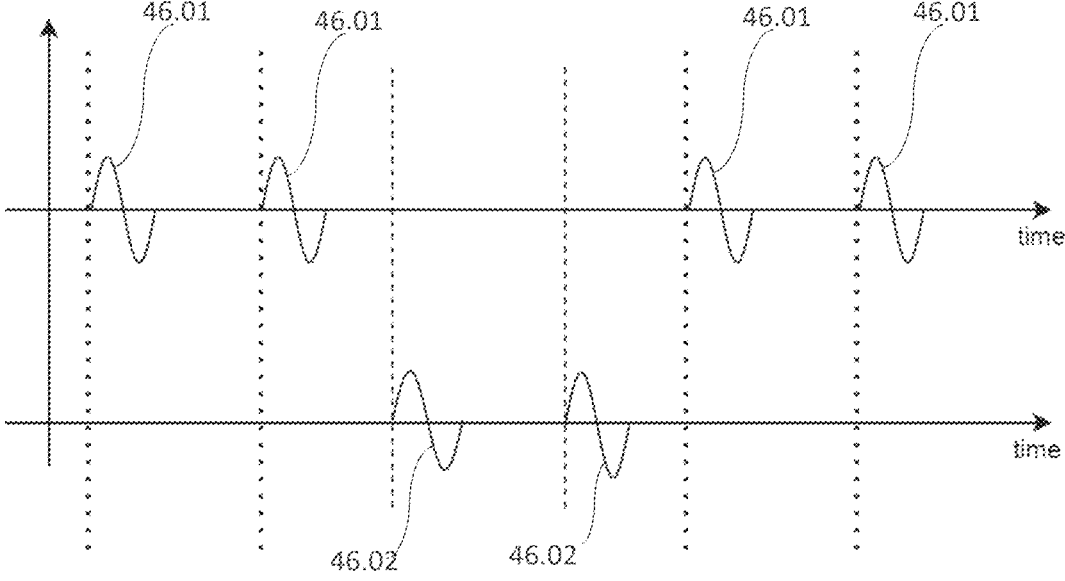
Figure 46C:
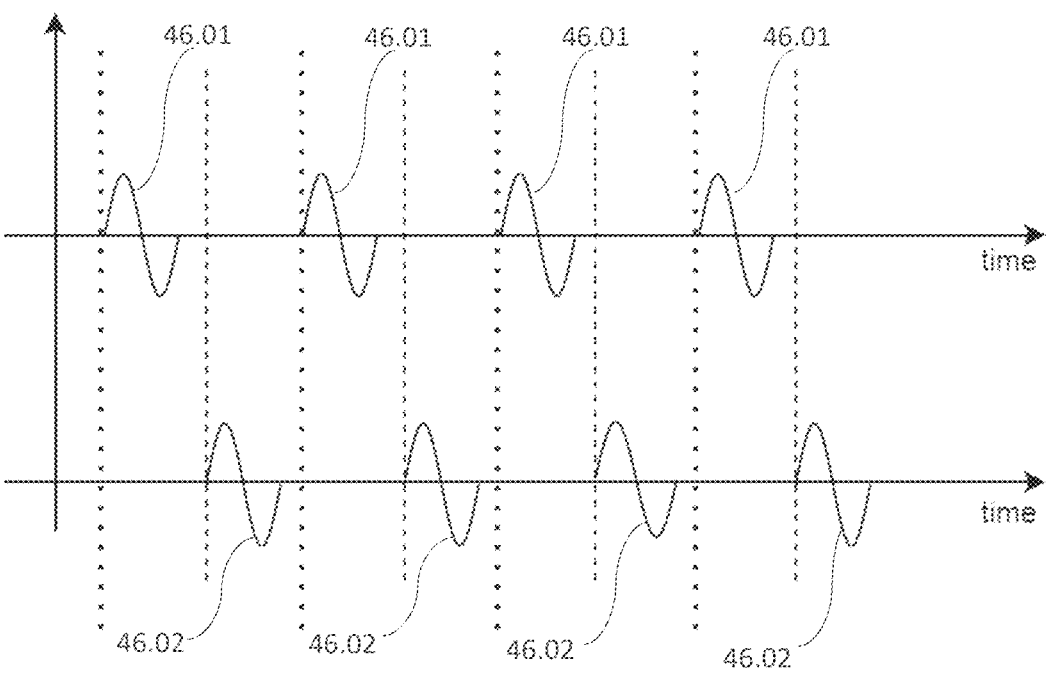
Figure 46D:
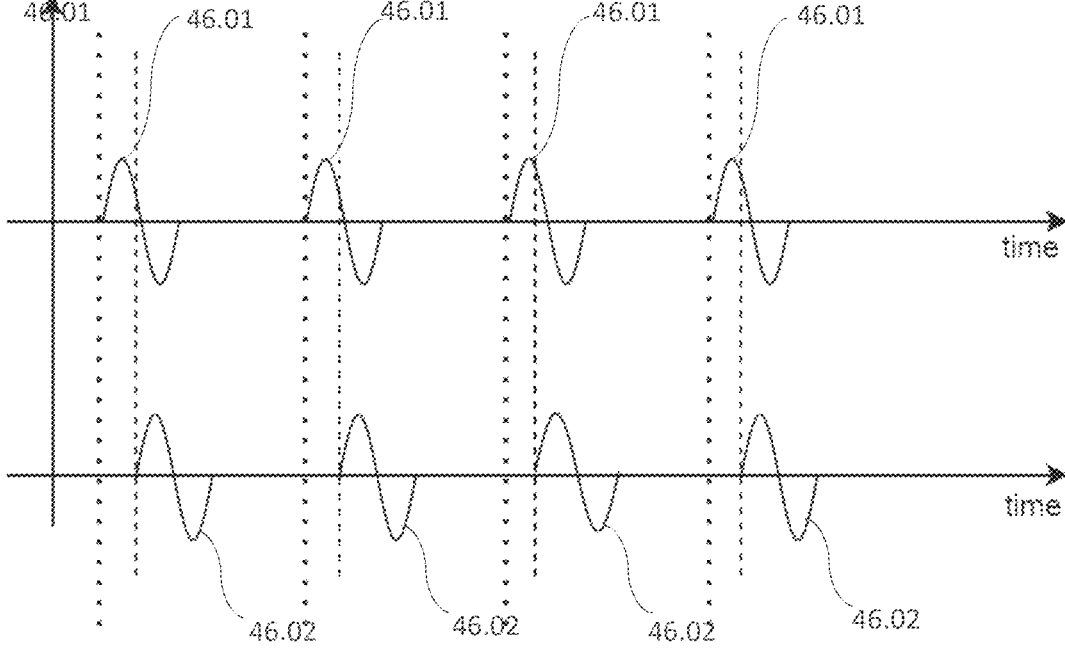

FIGS. 45*a*-45*b* illustrate cross-sections of an exemplary height adjustable pillow, according to some aspects.

FIGS. 46*a*-46*d* illustrate impulses of a magnetic fields, according to some aspects.

Figure 47:
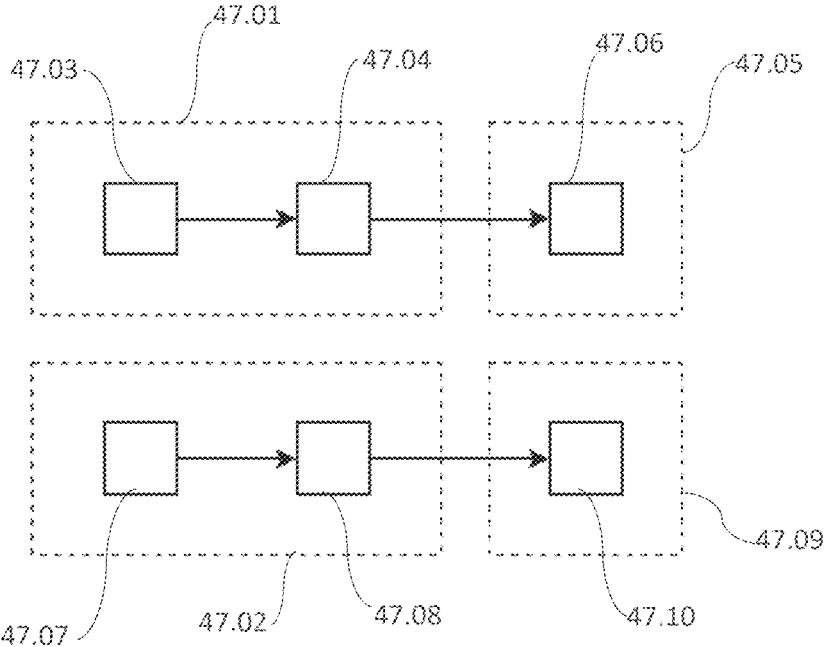

FIG. 47 illustrates a first device configured to apply magnetic field to a patient and a second device configured to apply a different energy to the patient, according to some aspects.

Figure 48A:
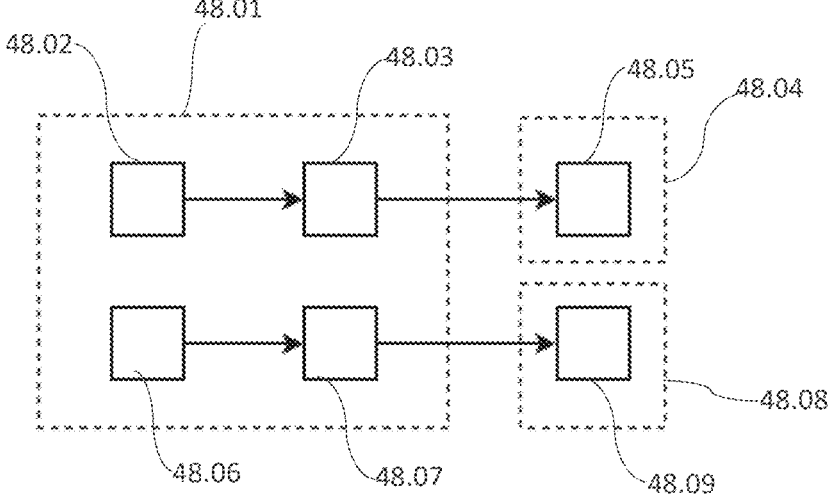
Figure 48B:
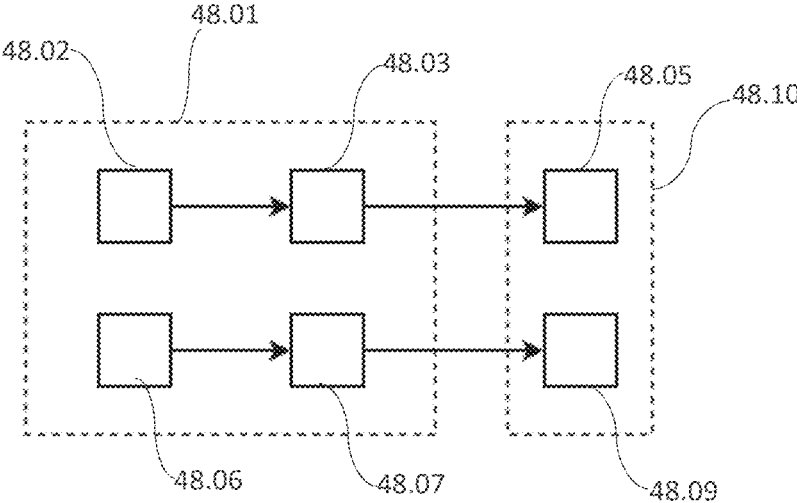

FIGS. 48*a*-48*b* illustrate a combined device, according to some aspects.

Figure 49A:
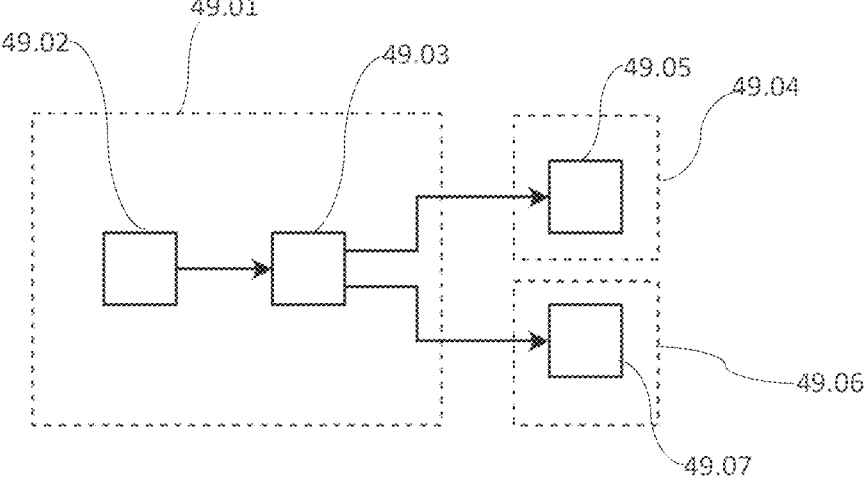
Figure 49B:
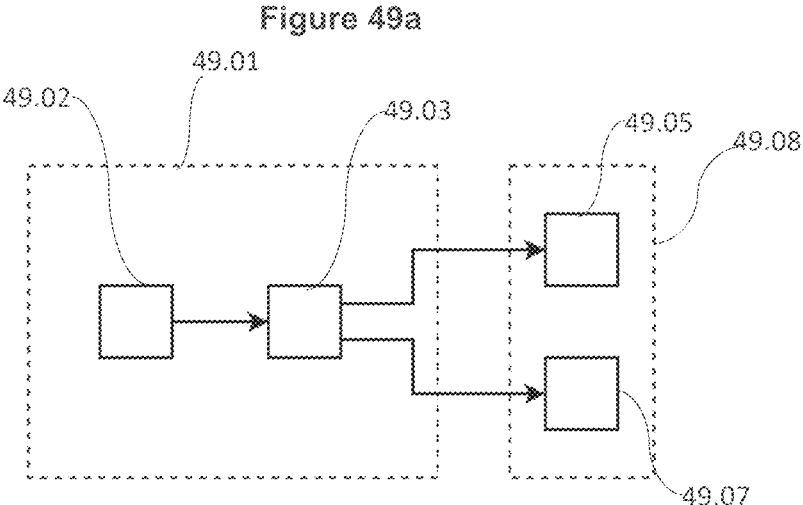

FIGS. 49*a*-49*b* illustrate a combined device, according to some aspects.

Figure 50A:
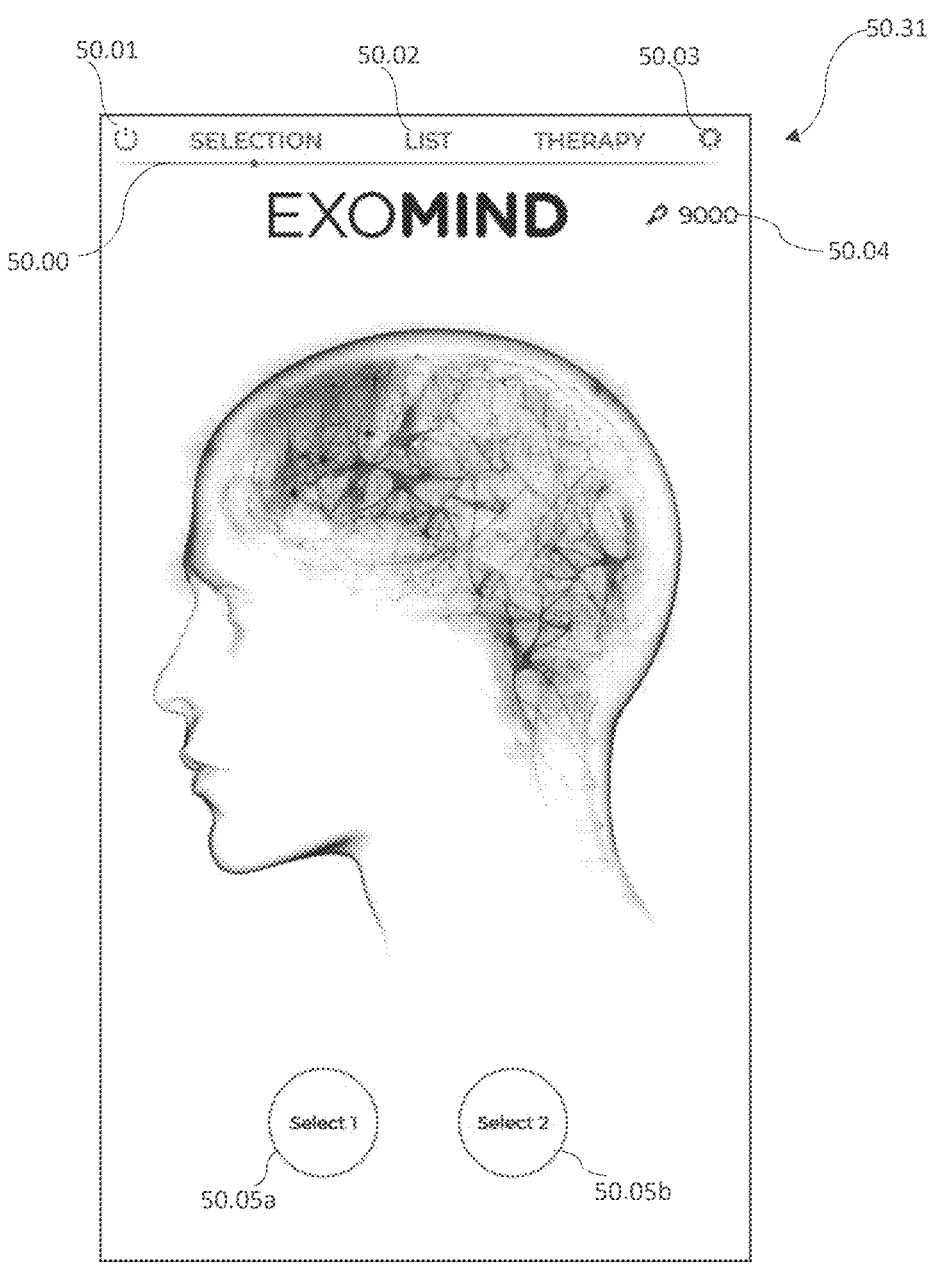
Figure 50B:
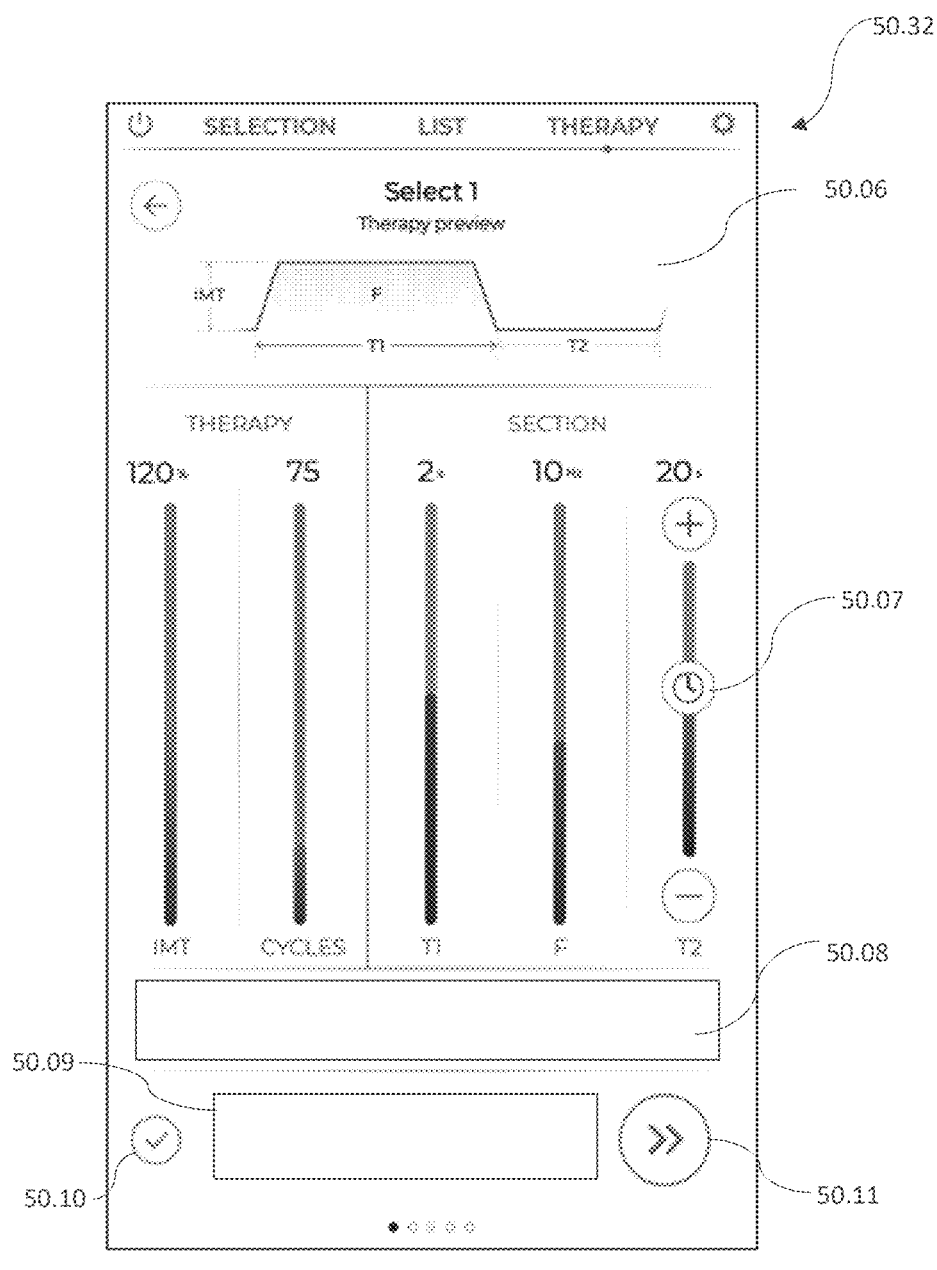
Figure 50C:
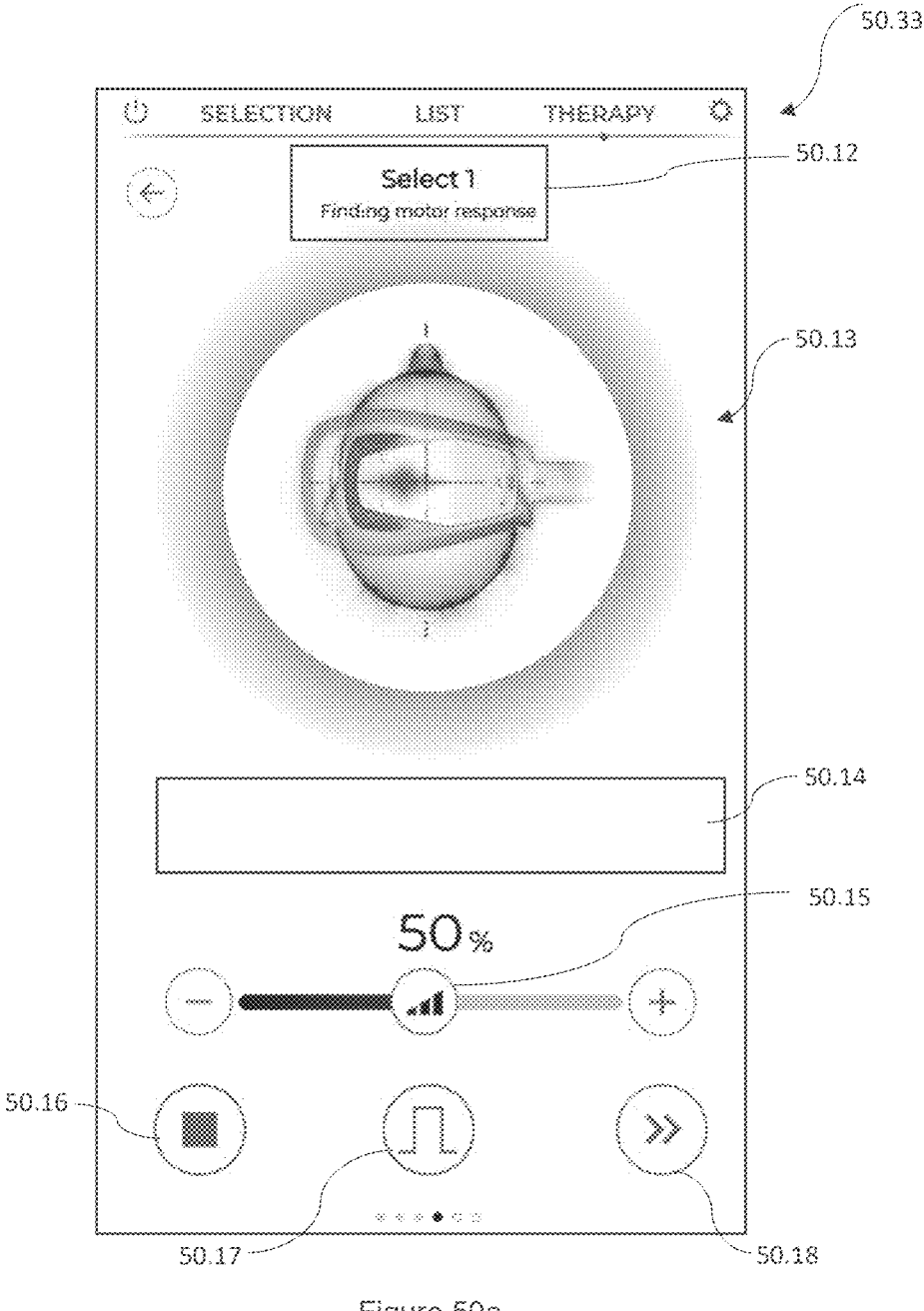

FIGS. 50*a*-50*c* illustrate an exemplary humane machine interface comprising a display, according to some aspects.

Figure 50D:
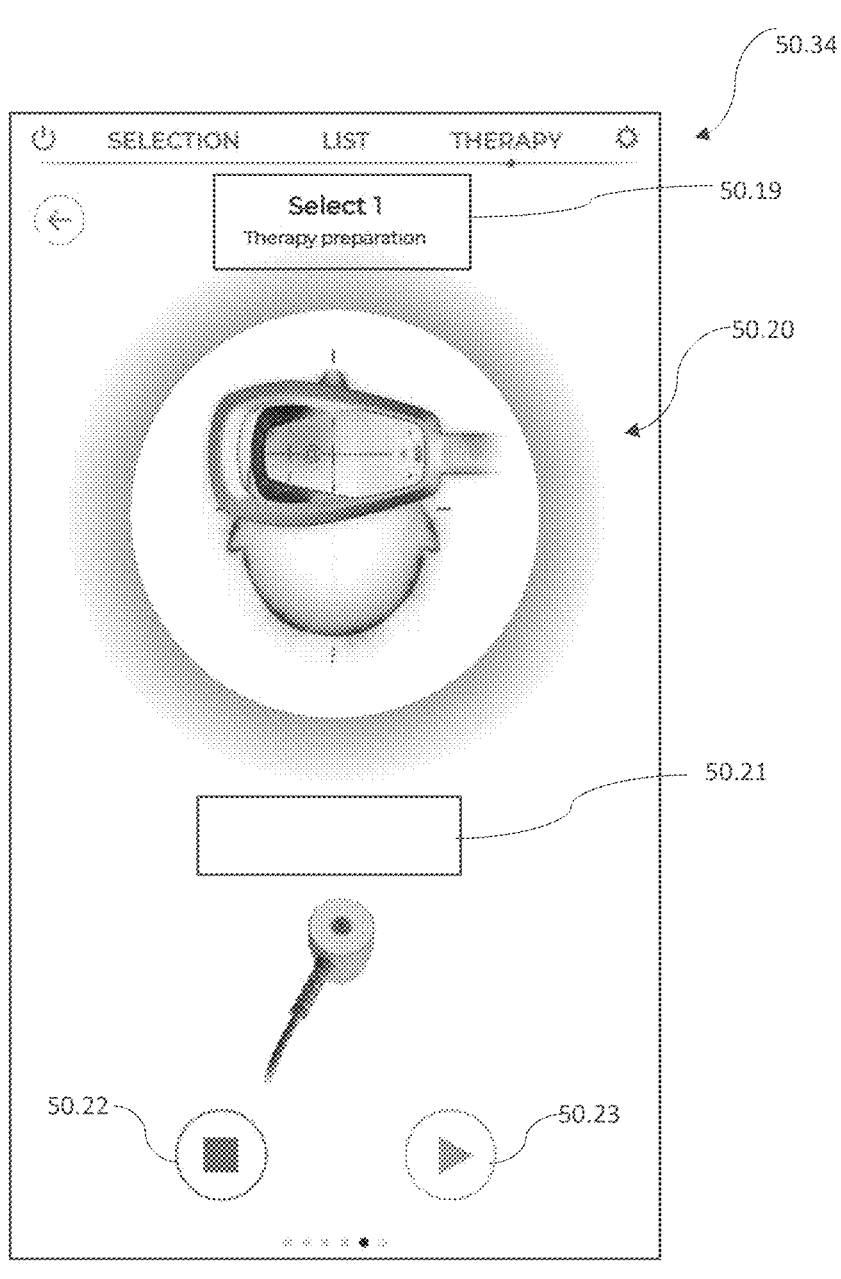

FIG. 50*d* illustrates a screen for finding a target location, according to some aspects.

Figure 50E:
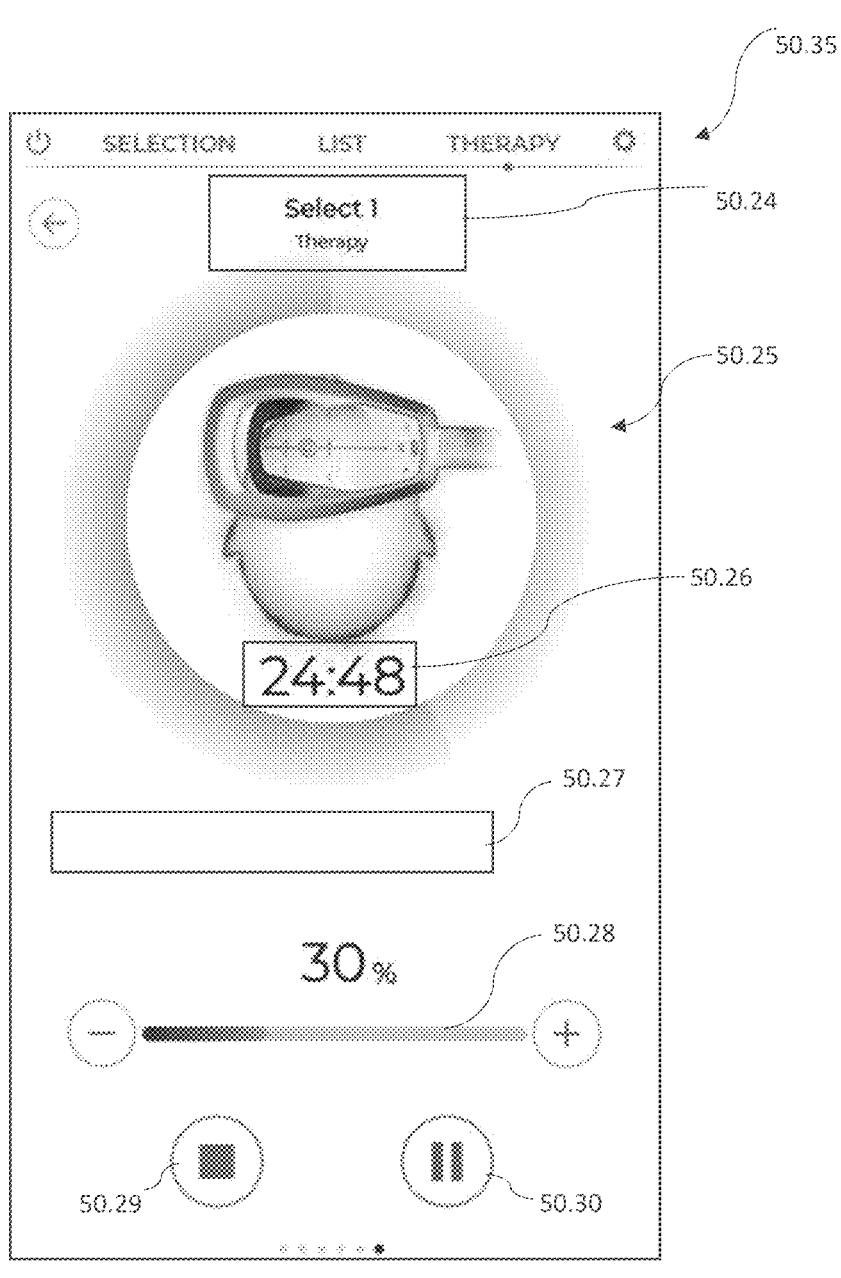

FIG. 50*e* illustrates application screen 50.35, according to some aspects.

Figure 51:
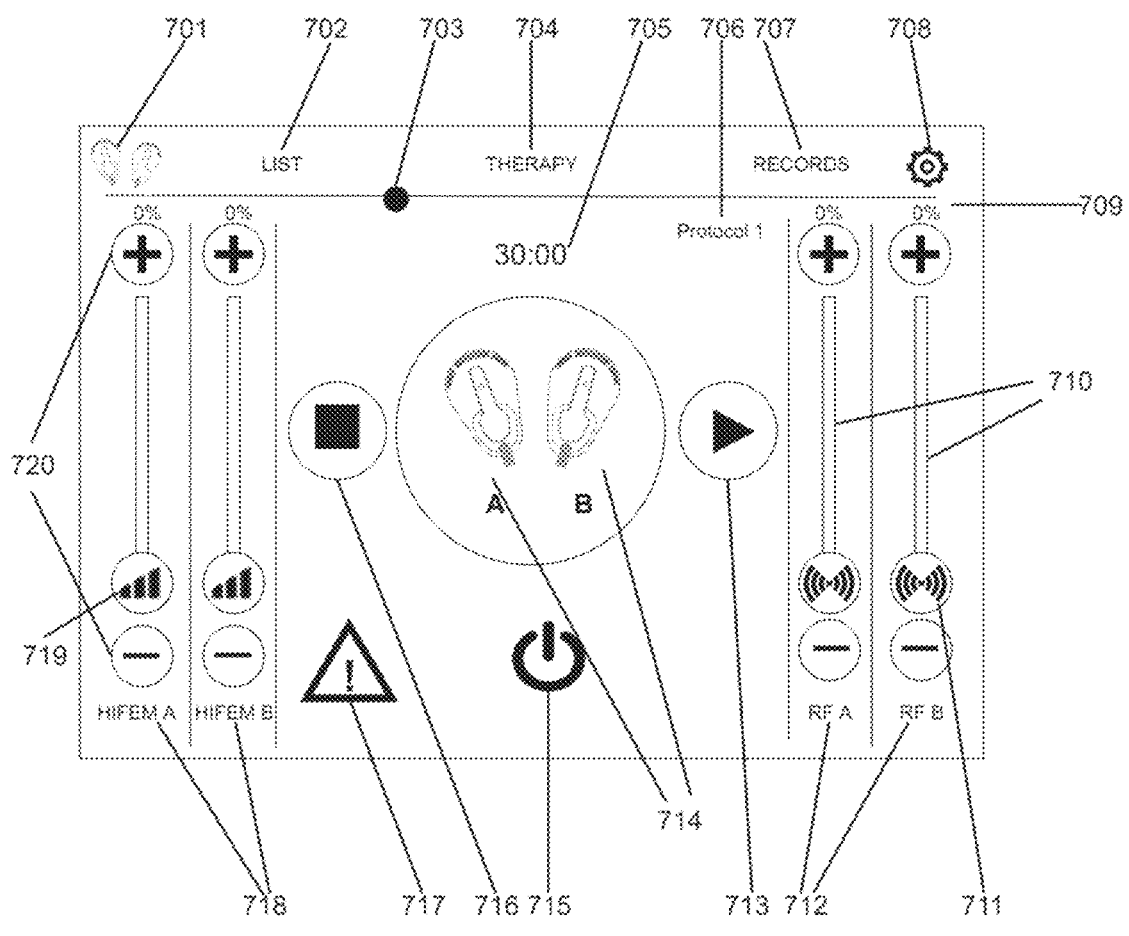

FIG. 51 shows exemplary screen of a device comprising a plurality of applicators, according to some aspects.

Figure 52:
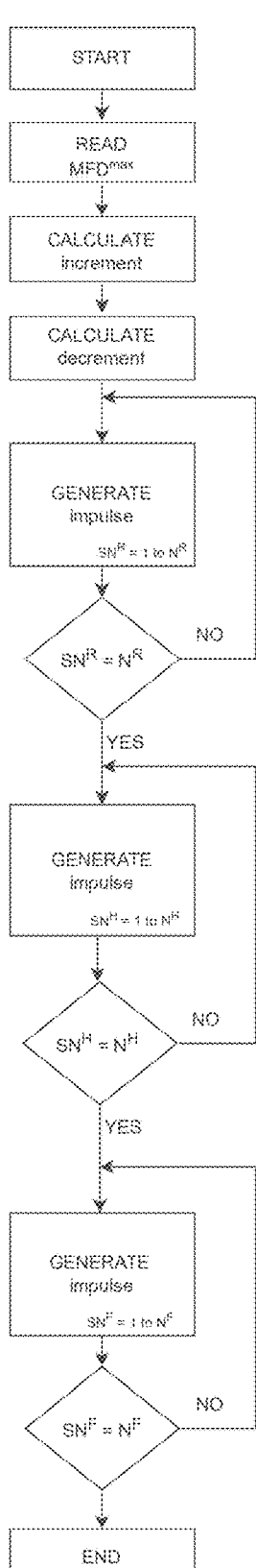

FIG. 52 illustrates a diagram for generating a trapezoidal envelope, according to some aspects.

DETAILED DESCRIPTION OF THE INVENTION

Aspects discloses herein are related to a system configured to provide a magnetic field. The magnetic field may be a time-varying magnetic field. The system may be configured to provide the magnetic field (e.g. a time-varying magnetic field) to a nervous system of a patient. The system may be configured to provide the time-varying magnetic field to a central nervous system and/or to a brain. In some aspects, the system may be configured to provide the time-varying magnetic field to a central nervous system of the patient. In some aspects, the system is configured to provide the time-varying magnetic field to a brain of the patient.

The system of the disclosure may be used for treatment and/or therapy of the patient.

The system may comprise a device (e.g., device 16). The device may include a main body (e.g., main body 18), one or more positioning arms (e.g., positioning arm 19), one or more connecting tubes (e.g., connecting tube 61), and one or more applicators (e.g. applicator 31). In some aspects, the device includes two or more applicators, three or more applicators, or four or more applicators. The device may include one main body, one positioning arm, one connecting tube, and one applicator. In some aspects, the device may include one main body and plurality of applicators, for example two, three, four or more applicators.

The main body of the device may comprise a human machine interface for setting and/or adjusting parameters, e.g. a repetition rate, a magnetic flux density, or a protocol. The human machine interface may comprise a touchscreen. The human machine interface may comprise a rotary knob, a push button, a slider, a keypad, a trackpoint, another graphic user interface, or any combination thereof. A parameter may be shown by a display (e.g. LCD screen), an LED indicator or any combination thereof.

In some aspects, the main body includes a touchscreen. The touchscreen may include on-screen information to guide the operator. In some aspects, the on-screen information guides the operator step-by-step through an entire procedure. The parameters may be set using the human machine interface (e.g., the touchscreen, buttons, or a knob on the device). Therapy and/or treatment may be started by selecting a pre-set protocol. The user may select the pre-set protocol from a list or by setting the parameters manually using the touchscreen controls. During the therapy the device may display information about the therapy and/or treatment (e.g., applied therapy type, remaining therapy time, and/or treatment parameters on the screen).

FIG. 50a-50c illustrate an exemplary humane machine interface comprising a display, according to some aspects. The display comprises a touchscreen.

The display may show a plurality of screens. The display screen may comprise a one or more sliders which of different functions. For example, slider 50.00 may be used as a navigator for selecting which screen is being used. Slider 50.00 may be moveable between several positions, each may represent one different touch screen. A first position (e.g., on the left side of the screen) may show a first screen. A second position of the slider (e.g., in the center of the screen) may show second screen.

FIG. 50a illustrates a first screen, according to some aspects. First screen 50.31 may be used for selecting treatment protocol. First screen 50.31 may include a plurality of icons. Icon 50.01 may be configured to send instruction to a control unit to turn the device into a standby mode. Standby mode may be configured to consume low power while maintaining the device in a state such that it is ready to resume full operation.

Icon 50.02 may send instructions to the control unit to display treatment parameters of protocols stored in volatile or non-volatile memory. The protocol treatment parameters may comprise a number of impulses in a train, a number of trains, a time of an inter-train period, a time of a train, an amplitude modulation, a total number of impulses applied in a protocol or a time duration of the protocol.

Icon 50.03 may send instruction to the control unit to display a setting(s) of the device. The settings of the device may be adjusted by operator. The settings may include, but is not limited to, sound control, language selection, account selection, service setting, or information about hardware or firmware.

Icon 50.04 may display a number of remaining impulses. The number of remaining impulses may decrease to 0. The 0 value of remaining impulses may refer to service control necessary to verify hardware components (e.g., magnetic field generating device, energy storage device). The number of remaining impulses may refer to credits used for treatment. The credits may be used for billing information. The number of remaining impulses may refer to lifespan of the magnetic field generating device.

Icons 50.05a and 50.05b may be configured to send instructions to the control unit to select a preset treatment protocol. Each treatment protocol may comprise a set of instructions to generate a predefined plurality of magnetic impulses of predefined parameters. Parameters may include repetition rate, number of impulses in train, modulation of impulses in train, etc.

A position of slider 50.00 may correspond to a step of setting the protocol. Setting the protocol may be done by operator using the user interface. The process of protocol setting may comprise selecting a protocol, defining a motor threshold value of magnetic flux density, and starting the protocol.

FIG. 50b illustrates second screen 50.32, according to some aspects. The second screen 50.32 may display summary of the protocol.

The summary of the protocol may comprise a visualization field of bursts including a train and inter-train period. Slider 50.07 may be used for adjusting the inter-train period. The inter-train period may be adjusted by tapping icon "+" or "−".

The summary of the protocol may comprise a first text field 50.08 including information such as a total number of pulses, treatment duration, or a range of motor threshold value of magnetic flux density.

Second screen 50.32 may comprise a second text field 50.09 including disclosure referring to use of the device. The disclosure may refer to instructions which may be followed by operator. The screen may further comprise safety icon 50.10 which may be checked to continue the Protocol setting. Icon 50.11 may confirm set treatment parameters and send instructions to the control unit to display the next screen.

FIG. 50c illustrates third screen 50.33, according to some aspects. The third screen 50.33 may be configured to find a motor threshold value magnetic flux density. Third screen 50.33may comprise text field 50.12 showing the selected protocol and a step of the treatment.

Third screen 50.33may comprise visualization 50.13 step of finding motor threshold value (e.g., finding position of applicator). The visualization may be a static image or dynamic animation.

Third screen 50.33 may comprise text field 50.14 including instructions for operator such as how the applicator may be positioned to determine a motor threshold value of magnetic flux density.

The third screen may comprise slider 50.15 used for visualizing a value of magnetic flux density generated by the magnetic field generating device. Slider 50.15 may be moveable between two positions. A first position of the slider may refer to 0% referring to generating no magnetic flux density. A second position of the slider may refer to 100% of the maximal value of magnetic flux density generated by the magnetic field generating device. For example, the 100% may be equal to 5 Tesla in an embodiment where the magnetic field generating device is capable of generating 5 Tesla. A 1% value may be offset, e.g. the offset of the 1% may be in a range of 0.01 Tesla to 1 Tesla, in a range of 0.1 Tesla to 0.9 Tesla, in a range of 0.2 Tesla to 0.8 Tesla, in a range of 0.5 Tesla to 0.8 Tesla, or in a range of 0.25 Tesla to 0.7 Tesla. A value XY of currently generated magnetic flux density may be shown in % above the slider. The magnetic flux density may be adjusted by touching slider 50.15 and sliding in a side-to-side direction. For example, sliding to the left may lower the magnetic flux density, and sliding to the right may increase the magnetic flux density. The magnetic flux density may be adjusted by touching the icons "+" and "−". The touchscreen may send instructions to the control unit to adjust the magnetic flux density accordingly.

The value of generated magnetic flux density may be represented by chroma or color saturation. Lower values of the magnetic flux density may be represented by bright colors, whereas higher values of the magnetic flux density may be represented by colors of higher saturation. The color may be of a single wavelength. Alternatively the value of magnetic flux density may be represented by different colors, i.e. color of different wavelengths. Lower values of magnetic flux density may be represented by colors of shorter wavelengths and higher values of magnetic flux density may be represented by colors of longer wavelengths.

The third screen may comprise icon 50.16 used for sending instructions to the control unit to cease the protocol setting.

The third screen may comprise icon 50.17 used for sending instructions to the control unit to generate magnetic impulse.

The third screen may comprise confirm icon 50.18 used for confirming the motor threshold value of magnetic flux density and proceeding to next screen.

FIG. 50*d* illustrates a screen for finding a target location, according to some aspects. Fourth screen 50.34 may be configured to find a position of the applicator adapted to apply time-varying magnetic field to target location.

Fourth screen 50.3 may comprise text field 50.19 showing the selected protocol and a step of the treatment.

Fourth screen 50.3 may comprise visualization 50.20 depicting a step of finding a position of the applicator. The visualization may by a static visual, or dynamic animation.

Fourth screen 50.3 may comprise text field 50.21 including instructions to verify the protocol using a safety button. The safety button may be configured to be pressed by the patient. For example, the patient may press the safety button if they experience discomfort. The safety button may cease the protocol.

Fourth screen 50.3 screen may comprise an Icon 50.22 used for sending instructions to the control unit to cease the protocol.

Fourth screen 50.3 may comprise icon 50.23 for confirming the protocol settings and starting the protocol.

FIG. 50*e* illustrates application screen 50.35, according to some aspects. Application screen 50.35 may be configured to display actual treatment parameters. The treatment parameters may include remaining time and applied value of magnetic flux density. The applied value of magnetic flux density may be associated with a motor threshold value of magnetic flux density.

Application screen 50.35 may comprise text field 50.24 showing the selected Protocol and a step of the treatment.

Application screen 50.35 may comprise visualization 50.25 of an applicator position.

Application screen 50.35 may comprise text field 50.26 including treatment time. The time may be time remaining to the end of the treatment.

Application screen 50.35 screen may comprise text field 50.27 comprising instructions to the operator indicating how to adjust the magnetic flux density during the protocol.

Application screen 50.35 may comprise bar 50.28 configured to visualize the magnetic flux density applied to the patient. The magnetic flux density may be adjusted by operator via using icons "+" and "−".

Application screen 50.35 may comprise icon 50.29 for sending instructions to the control unit to cease the protocol.

Application screen 50.35 may comprise icon 50.30 for sending instructions to the control unit to pause the protocol. Icon 50.30 may be used for continuing the paused protocol. For example, icon 50.30 may be a"PAUSE" symbol for pausing the protocol. In some embodiments, icon 50.30 may be a "PLAY" symbol for continuing the protocol. Icon 50.30 may alter between these two symbols (e.g., play and pause).

Application screen 50.35 may comprise time XY. The time indicator may show remaining time of the protocol. Alternatively, the time indicator may show an actual time of the Protocol. Alternatively, the time indicator may show the actual time of the protocol, and remaining time of the protocol.

FIG. 51 shows exemplary screen of a device comprising a plurality of applicators, according to some aspects. At least one applicator may comprise a magnetic field generating device. At least one applicator may use a different source of energy. Alternatively, at least one applicator may comprise a magnetic field generating device and a different source of energy. The screen may display one or more applicator symbols 701. Applicator symbols 701 and their respective colors may represent connection quality, number and/or type of available or connected applicators, additional treatment devices connected to main unit 11 and/or involved in the treatment. List 702 may redirect to a page or different display layout where a list of treatment protocols may be recorded or adjusted. List 702 of treatment protocols may include one or more predetermined values of one or more treatment parameters (e.g., intensity of magnetic field, intensity of different energy, intensity of magnetic impulses, intensity of magnetic pulses, pulse duration, burst duration, composition of individual burst, duty cycles, shape of envelope, time of treatment, composition of treatment parts, threshold temperature of the biological structure during the treatment, and/or other parameters). The list of treatment parameters may include one or more saved treatment protocols optimized for individual patients or body area of a patient. After choosing the treatment protocol, the treatment parameters may be optimized by user. Furthermore, the treatment parameters may be adjusted by choosing additional patient parameters, such as patient body type (e.g. skinny, slim, average weight, overweight, or obese), or a patient's BMI, gender, age group (e.g., younger than 30, 30-39, 40-49, 50-59, and 60 and older). The treatment parameters may be additionally optimized by selecting part of a treatment protocol.

Figures 7, 8, 9:
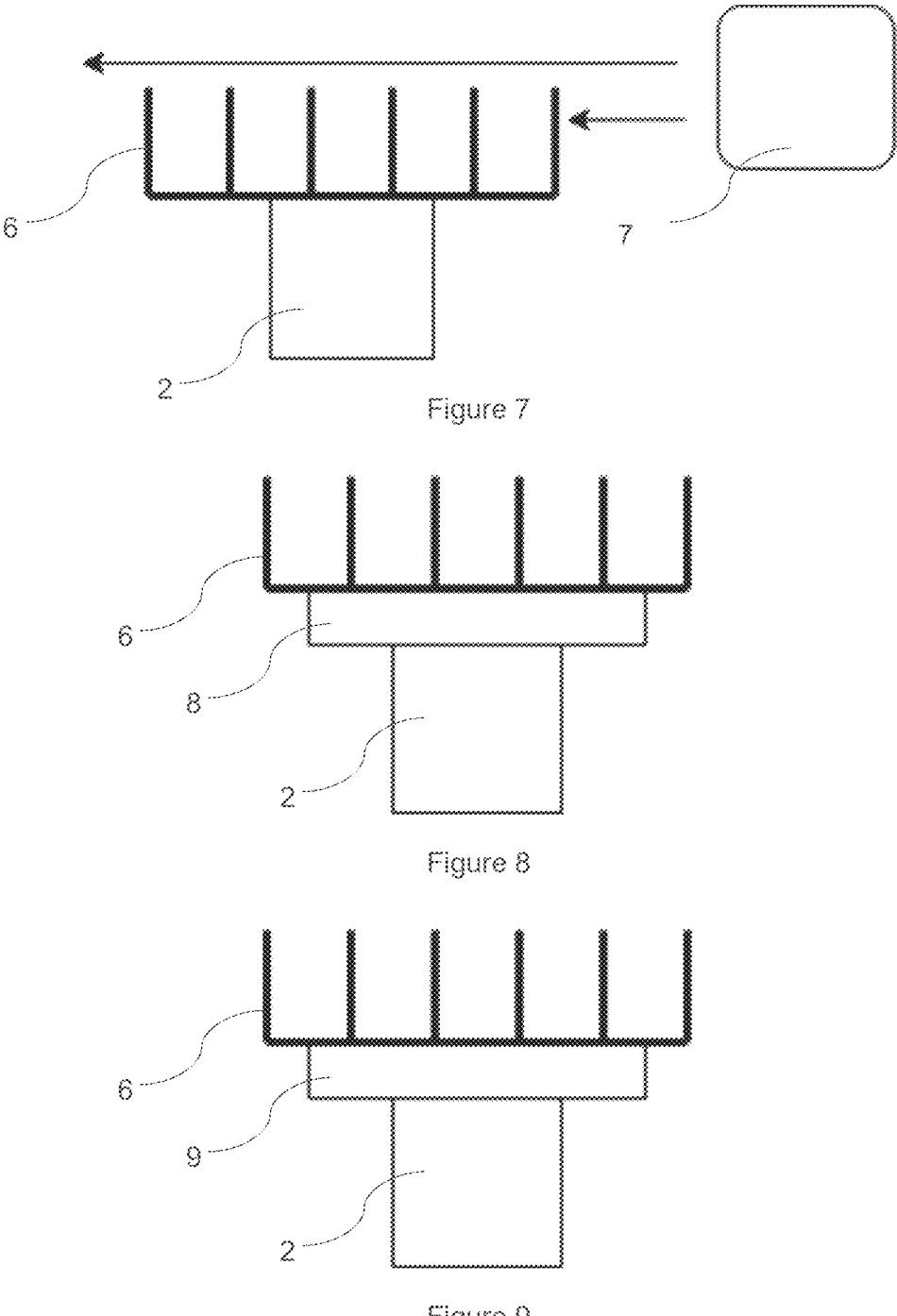
FIGS. 7-13 illustrate exemplary systems for cooling the switching device, according to some aspects.

Therapy icon 704 may represent the interface illustrated in FIG. 7. Timer 705 may represent a treatment duration, remaining time of the treatment, and/or lapsed time of the treatment. The "Protocol 1" icon 706 may illustrate the number of a selected, currently applied, or prepared protocol. The "records" 707 icon may redirect to another page of the interface including a recorded history of treatments, information regarding treated patients, information regarding a billing and renting system, information regarding billing information and/or credit cost of the treatment. The "records" 707 icon may display how many credits are left on a credit account, how many credits were spent, how long the treatment device was used, and/or other billing information. An icon illustrated by a symbol "setting" 708 may redirect a user to a setting of the treatment device including the setting of a melody and/or intensity of the sound produced by the device and/or brightness of the display. The sound produced by the treatment device and/or brightness of the display may be different before and/or during the treatment. The interface displayed when "setting" 708 icon is clicked may also enable the user to change a date, time, language, type and/or parameters of connection between the main unit and the applicator, the additional treatment device, and/or the communication device. The "setting" 708 interface may include icons for starting a calibration and functionality scan of the treatment device and its connected parts. The "setting" 708 interface may provide software information, software history and/or software actualization, a button for contacting service and/or sending error protocol, type of operation mode (e.g. "basic" or "expert" including additional settings of the treatment device), possibility to recharge credits for treatments, restoring to the device to factory setting, and/or other settings.

Intensity indicator 709 may be illustrated in the form of percentile, number, power and/or in another format. Intensity indicator 709 may be located adjacent to an icon that may adjust the intensity of the treatment energy source. Intensity indicator 709 may be located under, over and/or in an icon (e.g. as a number in intensity bar 710) and/or as another visualization that may adjust the intensity of the treatment energy source. Each intensity bar 710 representing one treatment energy source of provided energy (e.g. a magnetic field, a different energy) may have its own intensity indicator 709. The treatment device may include multiple applicators 51.10, for example, a first applicator A and a second applicator B may be connected to the main unit of the treatment device. In this way, applicators A and B may be applied to different muscles in the same muscle group or to a pair of muscles, such as a left and right buttock, left and right sides of an abdomen, a left and right thigh, among other paired muscles or cooperating muscles. The number of connected applicators and/or additional treatment devices providing the treatment energy may be lower or higher than two.

As shown in FIG. 51, each applicator may provide magnetic treatment 718 (left HMI part marked as HIFEM A and HIFEM B for the purpose of Figure) and/or an treatment by different energy 712 (right screen part marked as RF A and RF B for the purpose of FIG. 51).

The intensity of each magnetic field and/or different energy source may be independently regulated. By scrolling magnetic intensity scroller 719 and/or different energy intensity scroller 711 through intensity bars 710. One or more scrollers or intensity bars may be moved independently or may be moved together with another scroller or intensity bar in order to regulate a plurality of magnetic fields, plurality of different energies together and/or plurality of different energies and magnetic fields provided by the one applicator together. One or more scrollers or intensity bars may be controlled independently or may be moved together with another scroller or intensity bar in order to regulate a plurality of magnetic fields, plurality of different energies together and/or plurality of different energies and magnetic fields provided by two applicators together. One or more intensity bars 710 may be distinguished by a color and may be adjusted by intensity scroller 719 or 711 and/or by an intensity buttons 720. Intensity buttons 720 may change (e.g. increase or decrease) an RF field and/or a magnetic field intensity by a fixed increment, such as 1% or 2% or 5% or 10% or in a range from 1% to 10% or in a range from 1% to 5% of maximal possible field intensity. An intensity of the magnetic field and/or the different energy may be adjusted independently for each treatment energy source. The intensity of the magnetic field and/or different energy may be adjusted by selection and/or connection of one or more applicators, additional treatment devices and/or treatment energy sources.

The operation of one or more different energy sources and/or magnetic field generating devices may be synchronized and may be controlled by one, two or more intensity scrollers 719 and/or intensity buttons 720. The treatment may be started by start button 713 that may be automatically (e.g. after starting the treatment) changed into a pause button. The treatment may be restarted and/or stopped by stop button 716 during the treatment. The interface may also show an indicator of a discomfort button 717 that may be activated by the patient through a remote control, for example, when the treatment is uncomfortable. When the discomfort button 717 is activated the treatment may be automatically and immediately interrupted (e.g. paused or stopped). When the discomfort button 717 is activated the treatment device may provide a human perceptible signal including an audible alert, including a sound. Further, the human perceptible signal may include a visual alert, such as a flashing color. Based on the discomfort of the patient, the user may adjust the treatment parameters or treatment protocol, attachments or couplings of the applicator. The interface may also include a software power switch 715 to switch the treatment device on or off.

As shown in FIG. 51, the screen may include two intensity bars 710 for treatment by different energy sources and two intensity bars 710 for treatment by magnetic fields. Further, the screen may include two intensity scrollers 711 for treatment by different energy sources and two intensity bars 719 (e.g. 719) for treatment by magnetic field. Furthermore, the screen may include four intensity buttons for different energy treatments and four intensity buttons 720 for magnetic treatment. One intensity scroller, one intensity bar, and/or two intensity buttons may be provided for one treatment circuit. Therefore, the FIG. 51 may show the screen of treatment device including two treatment circuits for different energy treatments and two treatment circuits for magnetic treatments.

The main body may include a top side, a front side, and a rear side.

The human machine interface may be positioned on a top side of the main body of the device.

The main body may include a front side. The front side of the device may include an on-off button. In some aspects, the on-off button is configured to turn the device on and off. Further the front side may include a stop button that can be used to immediately stop the operation of the device (e.g., if an emergency situation occurs, such as a sudden uncomfortable application of a time-varying magnetic field). In some aspects, the device is configured to immediately stop the operation of the device when the stop button is pressed).

The main body may include a rear side. The rear side of the main body may include a ventilation grid, one or more applicator connectors, a port for external communication (e.g. USB port), and/or a connector for a positioning arm.

At least one applicator connector may be used for connecting the applicator (e.g., via the connecting tube) to the main body. In some aspects, the applicator connector may be e.g. a socket. The applicator connector (e.g. socket) may include a locking structure. The applicator may be removable from the applicator connector (e.g. socket) using the locking structure. The locking structure may be a bayonet mechanism or a lever mechanism. In some aspects, the locking structure may be a pin type, or it may include a screw for coupling the applicator connector (e.g. socket) to the main body.

FIGS. 41a and 41b illustrate a locking mechanism for coupling a connector to the main body of the device. The locking mechanism may comprise a socket, a first lever and a second lever. The connector may comprise a first protrusion on a first side and a second protrusion on a second side.

FIG. 41a illustrates locking mechanism 41.00 in an open position when connector 41.01 is released from socket 41.02, or when connector 41.01 is freely connected the socket 41.02 but connector 41.01 is not secured. First lever 41.03 may include first plate 41.04. First plate 41.04 may comprise first edge 41.05, first magnetic element 41.06, first apex 41.07, and first concavity 41.08. First apex 41.07 may be above first concavity 41.08, and opposite to first edge 41.05. First lever 41.03 may be coupled to socket 41.02 by first hinge 41.09 and configured to enable rotational movement of first plate 41.04 between a first (e.g., open) position and second (e.g., locked) position.

Second lever 41.10 may include second plate 41.11. Second plate 41.11 may comprise second edge 41.12, second magnetic element 41.13, second apex 41.14, and second concavity 41.15. Second apex 41.14 may be above second concavity 41.15, and opposite to second edge 41.12. Second lever 41.10 may be coupled to socket 41.02 by second hinge 41.16 configured to enable rotational movement of second plate 41.11 between third (e.g., open) position and fourth (e.g., locked) position. The movement of first plate 41.04 and second plate 41.11 between open and locked positions may be manual.

First hinge 41.09 and second hinge 41.16 may be symmetrically positioned on respective sides of socket 41.02. Second lever 41.10 may be coupled to socket 41.02 on opposite sides of socket 41.02 with respect to first lever 41.03.

Connector 41.01 may comprise a first protrusion and a second protrusion.

Connector 41.01 may be configured to be inserted into socket 41.02. Socket 41.02 may be connected to main body 18 by screws (not shown)

First plate 41.04 may be in the first position and the second plate 41.11 may be in the third position when connector 41.01 is out of the socket 41.02. Alternatively connector 41.01 may be inserted in socket 41.02 but connector 41.01 may not be secured in socket 41.02 and may be freely detachable out of socket 41.02. First magnetic element 41.06 may be configured to attract first plate 41.04 to the screw to maintain first plate 41.04 in a first position close to the device 18 when connector 41.01 is out of socket 41.02 or not secured in socket 41.02. Second magnetic element 41.13 may be configured to attract second plate 41.11 to the screw to maintain second plate 41.11 close to the device 18 when connector 41.01 is out of socket 41.02 or not secured in socket 41.02.

First plate 41.04 may be in the second position and second plate 41.11 may be in a fourth position when connector 41.01 is inserted into socket 41.02 and is secured within socket 41.02. The first protrusion may be within first concavity 41.08 and the second protrusion may be within second concavity 41.15. First apex 41.07 may be above the first protrusion and second apex 41.14 may be above the second protrusion to prevent connector 41.01 to be pulled out of socket 41.02.

The first and second magnetic members attract respective lever to socket 41.02 when connector 41.01 is out of socket 41.02. First 41.10 and second lever 41.10 may be attracted to socket 41.02 by magnetic force so that socket 41.02 is comfortably accessible by connector 41.01.

In some aspects, the socket may include a magnetic member with opposite polarity with respect to the magnetic member in the first and second levers to attract the respective lever while the connector is released out of the locking mechanism.

In some aspects, the magnetic member may be replaced by any suitable quick lock-release member (e.g. a high friction element).

The device may be movable (e.g., the device may be mobile). Movable casters may be positioned on a lower side of the main body, close to the floor. The casters may be swivel casters. Each caster may include a wheel and a brake. The brake may be configured to disable movement of the caster and maintain the device in a stable position without movement. The brake may be manually operated. The brake may be operated by foot of the operator to enable free operation of the device by both hands. The brake may be locked before treatment to provide the stable position of the device to provide stable and/or uninterrupted operation with the applicator, the human machine interface, and/or the positioning arm.

The brake of the caster may be movable in two positions. In a first position, the brake may not contact the wheel so that the wheel may be unlocked and may be freely moveable. In a second position, the brake may contact the wheel so that the wheel may be in a locked position and movement of the wheel may be disabled. Each wheel brake may be independently operated. Brakes of the wheels may be foot-operated separately. The brake may be locked by being stepped on, and unlocked by being pulled out.

In some aspects, the wheels may be operated by a wheel lock. The wheel lock may include a crank and a system of a plurality of levers, springs and/or moveable members. In some aspects, the wheels may be braked and released electronically. A control unit may control the movement of the wheels independently or synchronously.

The device may include a circuit configured to generate a time-varying magnetic field. Such circuit may be called a magnetic circuit within this disclosure.

The magnetic circuit may include a connection to a power supply (not shown), an energy source, a switching device, an energy storage device, and a magnetic field generating device. The energy source, the switching device, and the energy storage device may be positioned in the main body. The magnetic field generating device may be positioned in the applicator. Various aspects of the magnetic circuits are described within the disclosure. The features of the magnetic circuit within these various aspects may include same characteristics described below.

The power supply may be a standard power grid via e.g. a household plug.

The energy source may be AC power supply such as transformer, a DC power supply such as a linear power supply, a switched mode power supply, a programmable power supply, and/or a regulated power supply capable of providing constant voltage or current.

The switching device may be a diode, a MOSFET, a JFET, a IGBT, a BJT, a thyristor, a triac, and/or any combination thereof. The switching device may be combination of a thyristor and a diode. In some aspects, the switching device may include both a thyristor and a diode. In some aspects, the switching device may include a thyristor configured to enable a discharge of the capacitor to the magnetic field generating device. In some aspects, the switching device may include a diode configured to enable current flow from the magnetic field generating device to the capacitor such that the capacitor is recharged.

The energy storage device may be a capacitor. The capacitor may be an electrolytic capacitor (e.g. an aluminium capacitor, a tantalum capacitor, a manganese capacitor and/or a niobium capacitor), a supercapacitor, a ceramic capacitor or any other suitable type of the capacitor.

A capacitance of the energy storage device may be in the range of 5 nF to 100 mF, in the range of 25 nF to 50 mF, in the range of 100 nF to 10 mF, in the range of 1 μF to 1 mF, or in the range of 5 to 500 μF.

An inductance of the magnetic field generating device may be in the range of 1 nH to 50 mH, in the range of 50 nH to 10 mH, in the range of 500 nH to 1 mH, or in the range of 1 uH to 500 μH.

The energy storage device may be charged on a voltage. In some aspects, the voltage in a range of 100 V to 20 kV, in a range of 200 V to 15 kV, in a range of 300 V to 10 kV, in a range of 400 V to 8 kV, in a range of 500 V to 6 kV, in a range of 750 V to 4 kV, or in a range of 1000 V to 2 kV.

The energy storage device may discharge a current pulse. In some aspects, the current pulse is in a range of 100 A to 20 kA, in a range of 250 A to 15 kA, in a range of 500 A to 10 kA, in a range of 750 A to 8 kA, in a range of 1000 A to 6 kA, in a range of 1200 A to 5 kA, or in a range of 1500 A to 4 kA.

The magnetic field generating device may be a magnetic coil.

Operation of the magnetic circuit may be controlled by one or more control units. Each control unit may comprise at least one of a microprocessor, field programmable gate array, digital signal processor, application specific integrated circuit, and/or printed circuit board.

Figure 1:
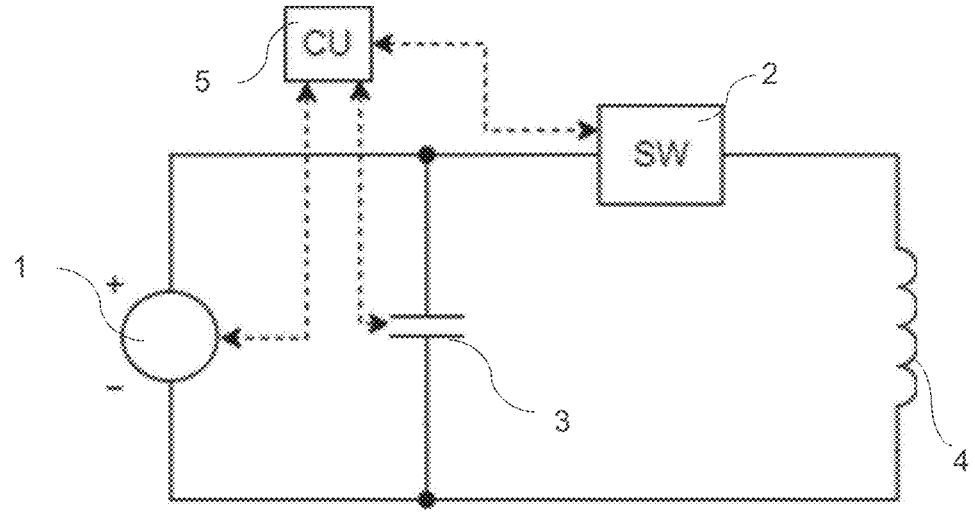
FIGS. 1, 2, 3, 4, and 5 illustrate exemplary magnetic circuits, according to some aspects

FIG. 1 illustrates a magnetic circuit according to some aspects. The magnetic circuit may be configured to connect to a power supply (connection and power supply not shown), an energy source 1, a switching device 2, an energy storage device 3, and a magnetic field generating device 4. The energy source 1, the switching device 2, the energy storage device 3 and the control unit 5 may be positioned in the main body. The magnetic field generating device 4 may be positioned in the applicator 31.

In some aspects, the control unit 5 operates the energy source 1 to charge the energy storage device 3 when the switching device 2 is switched off. The control unit 5 may operate the switching device 2 to be switched on and/or to discharge energy from the energy storage device 3 to the magnetic field generating device 4 to generate an impulse of the time-varying magnetic field. Then the control unit 5 may operate the switching device 2 off to enable to recharge energy losses caused during generating the impulse of the time-varying magnetic field.

The magnetic circuit may include a protective resistor and/or a protective circuit for protecting the energy source 1 from the high voltage and/or current pulse during discharging period (for example, when the switching device 2 is on). The protective circuit may be used for recuperation of the energy, which can be used for recharging the energy storage device 3.

Figure 2:
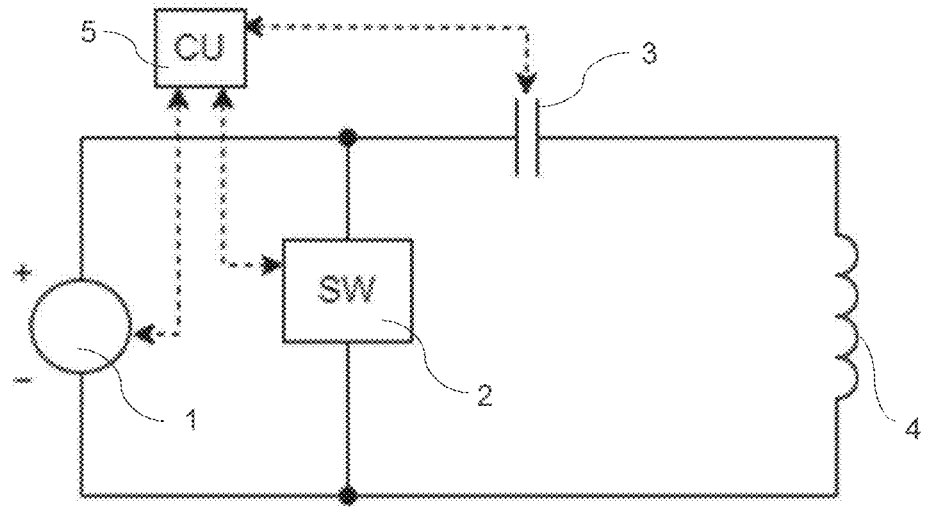

FIG. 2 illustrates a magnetic circuit according to some aspects. The magnetic circuit includes a connection to a power supply (connection and power supply is not shown), an energy source 1, a switching device 2, an energy storage device 3, and a magnetic field generating device 4. The energy source 1, the switching device 2 the energy storage device 3 and the control unit 5 may be positioned in the main body. The magnetic field generating device 4 may be positioned in the applicator 31.

The magnetic field generating device 4 and the energy storage device 3 may be in serial connection, and together in parallel connection with the switching device 2. Such connection of the switching device 2 enables direct connection of the magnetic field generating device 4 and the energy storage device 3 so energy from the energy storage device 3 flows to the magnetic field generating device 4 to generate a time-varying magnetic field.

The control unit 5 may operate the energy source 1 to charge the energy storage device 3 via the magnetic field generating device 4 when the switching device 2 is switched off. The control unit 5 may operate the switching device 2 such that the switching device 2 is switched on to discharge energy from the energy storage device 3 to the magnetic field generating device 4 to generate the impulse of time-varying magnetic field. The switching device 2 may be switched on for a time period of one impulse. During this period a controlled shorting of the energy source 1 may be executed to protect the energy source 1 from the high voltage/current pulse. Then the control unit 5 may turn the switching device 2 off to recharge energy losses caused during generating the impulse of the time-varying magnetic field.

In some aspects, the device may include a plurality of magnetic field generating devices for applying time-varying magnetic fields to multiple target locations of the patient, e.g. left and right side of the patient.

Figure 3:
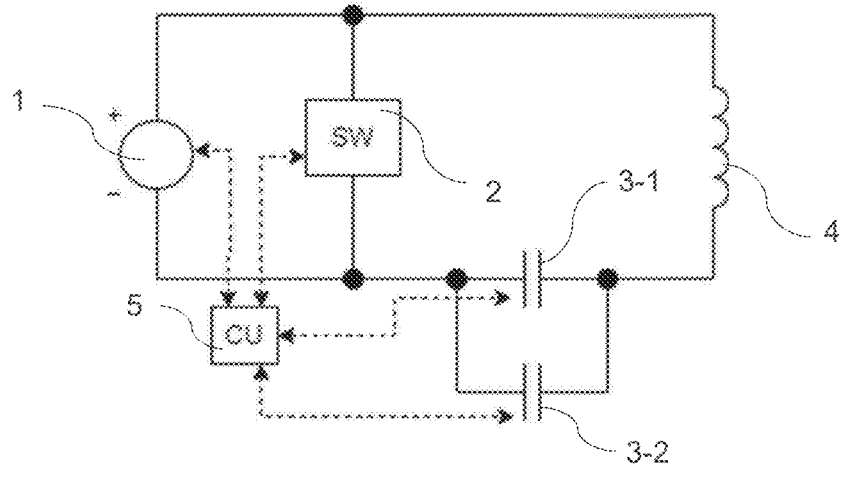

FIG. 3 illustrates a magnetic circuit according to some aspects. The magnetic circuit may include a connection to a power supply (connection and power supply is not shown), an energy source 1, a switching device 2, a first energy storage device 3-1, a second energy storage device 3-2 and a magnetic field generating device 4. The energy source 1, the switching device 2, the first energy storage device 3-1, and the second energy storage device 3-2 may be positioned in the main body. The magnetic field generating device 4 may be positioned in the applicator.

Figure 4:
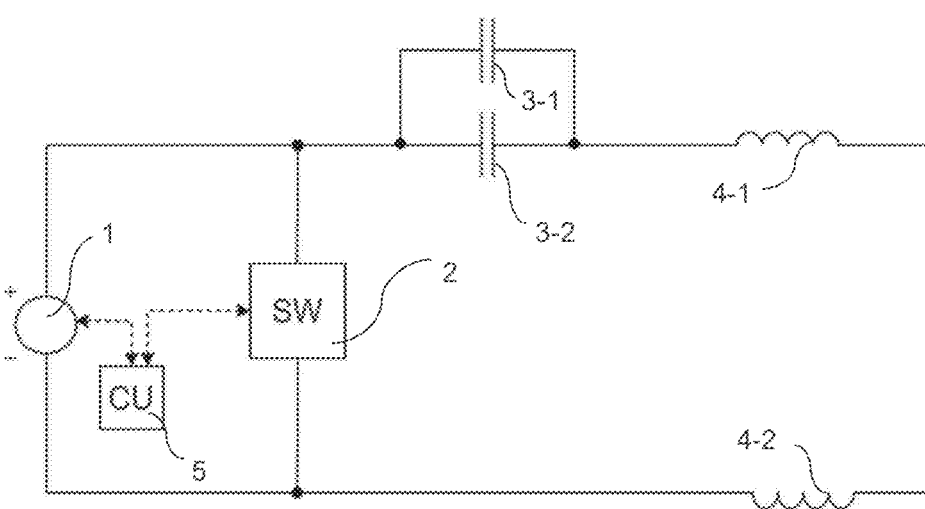

FIG. 4 illustrates a magnetic circuit according to some aspects. The magnetic circuit may use a single energy source 1 for generating simultaneous time-varying magnetic fields via two magnetic field generating devices, 4-1 and 4-2. The magnetic circuit may include the energy source 1, switching device 2, two energy storage devices 3-1 and 3-2, and two magnetic field generating devices 4-1 and 4-2 and the control unit 5. Magnetic field generating devices 4-1 and 4-2 may be connected in series. The energy storage devices 3-1 and 3-2 may be charged by energy source 1. Switching device 2 may be switched to enable discharge the charged energy storage device 3-1 and energy storage device 3-2 to the magnetic field generating device 4-1 to generate first time-varying magnetic field and to the magnetic field generating device 4-2 to generate a second time-varying magnetic field. In some aspects, the magnetic field generating devices 4-1 and 4-2 may be connected in parallel. The control unit 5 may be configured to control the operation and/or the state of energy source 1, the switching device 2 and/or the energy storage devices 3-1 and 3-2.

The magnetic circuit of FIG. 4 may comprise two magnetic field generating devices 4-1 and 4-2. The magnetic field generating device 4-1 and the magnetic field generating device 4-2 may be positioned in a single applicator, In some aspects, the magnetic field generating device 4-1 may be positioned in a first applicator, while the magnetic field generating device 4-2 may be positioned in a second applicator. When plurality of applicators are used, the applicators may be independently positioned.

The magnetic field generating device 4-1 may generate a time-varying magnetic field with equal treatment parameters to the magnetic field generating device 4-2.

Use of two energy storage devices (e.g. 3-1 and 3-1 shown in FIGS. 3 and 4) in the magnetic circuit may be beneficial. When single energy storage device with higher capacitance is present, its capacitance may be significantly decreased over time and the generated magnetic impulses may not have the required magnetic flux density value. Replacing a single energy storage devices with two energy storage devices 3-1 and 3-2, wherein sum of capacitance of the energy storage devices 3-1 and 3-2 is same as the capacitance of single energy storage device may avoid this situation. In case of an aluminum capacitor, the capacitance of single energy storage device with higher capacitance may be significantly decreased overtime by destruction and/or vaporization of an aluminum oxide layer of such capacitor by repeated recharge of high amount of electrical energy.

A sum of the capacitance of the first energy storage device 3-1 and the second energy storage device 3-2 may be in a range of 1 microFarad to 1000 microFarad, 10 microFarad to 950 microFarad, 12 microFarad to 800 microFarad, 20 microFarad to 700 microFarad, 20 microFarad to 600 micro-Farad, 30 microFarad to 500 microFarad, or 30 microFarad to 250 microFarad. In some aspects, the capacitance of first energy storage device 3-1 and the second energy storage device 3-2 may be equal. In some aspects, the capacitance of the first energy storage device 3-1 is different than the capacitance of the second energy storage device 3-2. In some aspects, the capacitance of each of the first energy storage device 3-1 and the second energy storage device 3-2 is in a range of 0.5 microFarad to 500 microFarad, 5 microFarad to 475 microFarad, 6 microFarad to 400 micro-Farad, 10 microFarad to 350 microFarad, 10 microFarad to 300 microFarad, 15 microFarad to 250 microFarad, or 15 microFarad to 125 microFarad. The capacitance of the first energy storage device 3-1 may be same or different compared to the capacitance of the second energy storage device 3-2. In some aspects, the sum of the capacitance of the first energy storage device 3-1 and the second energy storage device 3-2 is 120 microFarad, the capacitance of the first energy storage device 3-1 is 60 microFarad, and the capacitance of the second energy storage device 3-2 is 60 micro-Farad. In some aspects, the sum of the capacitance of the first energy storage device 3-1 and the second energy storage device 3-2 is 120 microFarad, the capacitance of the first energy storage device 3-1 is 40 microFarad, and the capacitance of the second energy storage device 3-2 is 80 micro-Farad.

Figure 5:
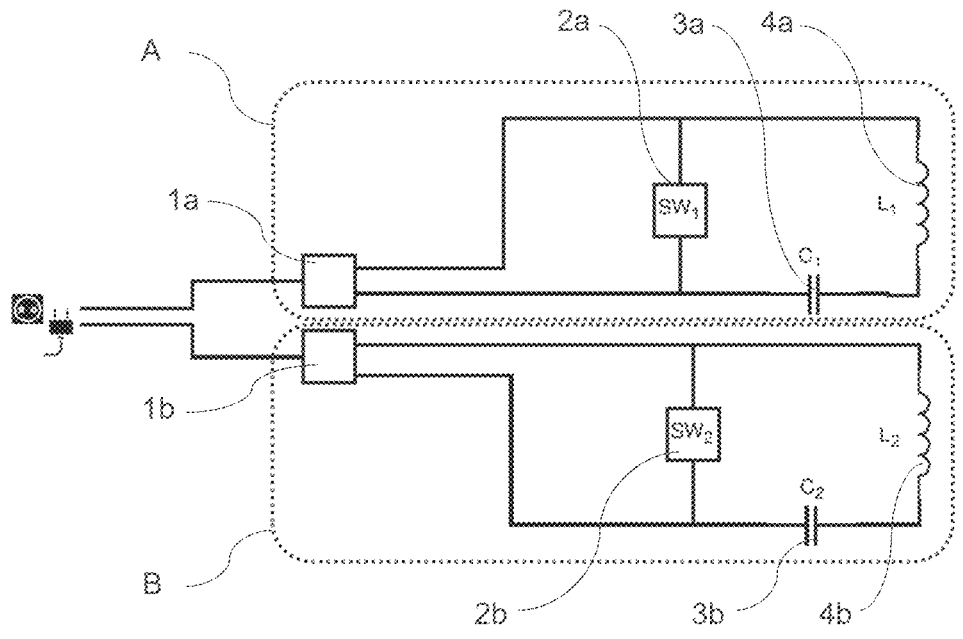

FIG. 5 illustrates a magnetic circuit according to some aspects that includes two independent subcircuits A and B (dotted lines). The subcircuit A may include an energy source 1a, a switching device 2a, an energy storage device 3a, and a magnetic field generating device 4a. The subcircuit B may include an energy source 1b, a switching device 2b, an energy storage device 3b, and a magnetic field generating device 4b.

The subcircuit A may generate the time-varying magnetic field independently of the subcircuit B. The magnetic circuit may generate the magnetic field of one subcircuit while the second circuit is off. For example, the subcircuit A may generate the magnetic field while the subcircuit B is turned off. In some aspects, the subcircuit B may generate the magnetic field while the subcircuit A is turned off. Further, operation of the subcircuit A may alternate with operation of the subcircuit B.

The subcircuit A may generate the first magnetic field of equal treatment parameters as the second magnetic field generated by the subcircuit B. Both magnetic subcircuits may be set up individually or synchronously. Each of magnetic field generating device 4a or magnetic field generating device 4b may generate respective time-varying magnetic field at the same time without necessity of alternating the magnetic field generating devices during the treatment.

In some aspects, the subcircuit A may generate magnetic field of treatment parameters different from magnetic field generated by the subcircuit B. In some aspects, the magnetic impulse generated by the subcircuit A may be shifted with respect to the magnetic impulse generated by the subcircuit B.

The subcircuit A may generate a time shifted time-varying field with respect to time-varying magnetic field generated by subcircuit B.

The magnetic circuit may include a plurality of energy storage devices providing energy to the magnetic field generating device in order to enable higher energy pulse to be provided to the magnetic field generating device. In some aspects, at least one energy storage device may provide energy to magnetic field generating devices. In some aspects, both magnetic subcircuits may include a common energy source.

The control unit may control providing energy from the at least one energy storage device to the plurality of magnetic field generating devices in order to generate a plurality of magnetic impulses by each magnetic field generating device. All magnetic field generating devices of the plurality of magnetic field generating devices may generate magnetic field within the treatment without any operator input.

The generated magnetic impulse may be monophasic or biphasic. In some aspects, polyphasic impulse may be used (e.g. impulse having more than one positive and more than one negative period, wherein the polyphasic impulse is continuous). The magnetic impulse may be sinusoidal. In some aspects, a shape of the impulse may be adjusted according to the patient's needs by using a specialized circuit comprising inductors and/or capacitors.

As previously mentioned, the device may include a control unit. The control unit may include and/or execute a plurality of instructions for operating the device. The instructions may include instructions to turn on the device, receive operator's input, monitor, and/or operate hardware components such as the energy source, energy storage device or the switching device, store treatment protocols, generate new treatment protocols, and/or perform a calibration process.

The control unit may include a set of instructions for determining correctness of generated magnetic impulses, controlling hardware components and/or disabling treatment (e.g., if an error occurs). Further, the control unit may notify an operator about an occurrence of a hardware error or upcoming maintenance.

The device may include a memory for storing the protocols, a predefined value of the voltage waveform, calibration value of impulses and/or others. The memory may comprise non-volatile memory such as HDD, SSD, flash memory, ROM or NVRAM, and volatile operating memory such as RAM, cache memory, register or virtual memory.

The device may include a system of monitoring quality of generating magnetic impulse. In such case, the control unit may calibrate the device before each treatment. Control unit may be configured to send instructions to the energy source to charge the energy storage device using a predefined value. Then the control unit may send instruction to the switching device to discharge the energy storage device to the magnetic field generating device to generate the magnetic impulse. The voltage waveform measured on the energy storage device may be measured by the control unit and/or via A/D converter and then the voltage waveform may be compared with a reference voltage waveform stored in a memory of the device. The control unit may send instruction to start treatment when the correct waveform is generated. Otherwise, the operation of the device may be disabled.

In some aspects, the control unit may include algorithm for monitoring quality of generated impulse. A voltage may be measured on the energy storage device by the control unit via the A/D converter. The voltage waveform may be compared with a reference voltage waveform measured during a calibration of the device. A correlation coefficient of measured voltage waveform and the reference voltage waveform may be calculated. The control unit may send an instruction to start treatment when the value of the correlation coefficient is in predefined range. Otherwise the operation of the device may be disabled. The correlation coefficient may be independent of a value of the time-varying magnetic field, or it may depend only on the waveform shape of the magnetic impulse.

As previously mentioned, the device may include at least one magnetic field generating device. The magnetic field generating device may be a magnetic coil. The magnetic field generating device may include a plurality of conductors. In some aspects, a single conductor may be used. In some aspects, the conductor may have a round cross-section. In some aspects, the conductor may have circular or oval cross-section. The conductor may comprise a wire. In some aspects, the wire is bare. In some aspects, the wire is insulated. The magnetic field generating device may comprise multiple loops of wire. One loop of wire may be referred to as a turn. A plurality of turns which forms the magnetic coil may be called a winding.

A diameter of the conductor may be in a range of 0.005 mm to 20 mm, in a range of 0.05 mm to 15 mm, in a range of 0.1 mm to 10 mm, in a range of 0.2 mm to 8 mm, in a range of 0.5 mm to 6 mm, in a range of 1 mm to 5 mm, in a range of 0.01 mm to 0.5 mm, or in a range of 0.05 mm to 1 mm.

In some aspects, a cross-section of the conductor may be non-circular (e.g. square, rectangular or hexagonal). A length of one side of the conductor may be in a range of 0.005 mm to 30 mm, in a range of 0.05 mm to 20 mm, in a range of 0.1 mm to 15 mm, in a range of 0.2 mm to 12 mm, in a range of 0.5 mm to 10 mm, in a range of 0.75 mm to 8 mm, in a range of 0.005 mm to 0.5 mm, in a range of 0.1 mm to 0.5 mm, or in a range of 2 mm to 15 mm.

In some aspects, an area of cross-section of the conductor may be in a range of $0.00001 \text{ mm}^2$ to $0.0001 \text{ mm}^2$, in a range of $0.001 \text{ mm}^2$ to $0.02 \text{ mm}^2$, in a range of $0.1 \text{ mm}^2$ to $3 \text{ mm}^2$, in a range of $10 \text{ mm}^2$ to $50 \text{ mm}^2$, in a range of $75 \text{ mm}^2$ to $200 \text{ mm}^2$, in a range of $250 \text{ mm}^2$ to $500 \text{ mm}^2$, in a range of $0.00001 \text{ mm}^2$ to $300 \text{ mm}^2$, or in a range of $1 \text{ mm}^2$ to $150 \text{ mm}^2$.

The magnetic field generating device may include a litz-wire including a plurality of insulated wires. The magnetic field generating device may be circular or non-circular. The magnetic field generating device may be planar.

In some aspects, the magnetic field generating device may be of various shapes, e.g. oval, rectangular, Figure-8, V-shape etc.

In some aspects, a plurality of magnetic field generating devices may be used for applying time-varying magnetic fields to different target locations. In some aspects the time-varying magnetic fields may be applied laterally to corresponding brain parts (e.g. to left DLPFC and right DLPFC). In some aspects, the time-varying magnetic fields may be applied to different brain parts (e.g. to frontal cortex and to parietal cortex).

In some aspects, the magnetic field generating device may be non-planar, e.g. convex or concave. The magnetic field generating device may be double cone magnetic coil.

The concave magnetic field generating device may ensure closer contact of surface of the magnetic field generating device to patient's head.

In some aspects, the magnetic field generating device may be of variable inductance. The inductance may be varied by adjusting the shape of magnetic field generating device (e.g. from circular to non-circular such elliptic), adjusting the active number of turns, inserting a core (e.g. ferromagnetic core), changing the radius (e.g. inner and outer), creating an inter-turn gap and/or combination thereof. In some aspects, inductance of a plurality of magnetic field generating devices positioned one above another may be changed by adjusting a distance between the magnetic field generating devices.

In some aspects, the magnetic field generating device may be actively bent to vary the inductance. The magnetic field generating device may be resilient or flexible. In some aspects, the magnetic field generating device may be rigid or partially rigid with flexible part. The flexible part may create a cross section through a center of the magnetic field generating device. In some aspects, the flexible part may be any intersection of the magnetic field generating device.

A geometry changing mechanism may enable adjusting a geometry of the magnetic field generating device. The geometry changing mechanism may include an effector configured to exert a force to part of the magnetic field generating device. The force may bend the magnetic field generating device. The geometry changing mechanism may include at least one actuator. The at least one actuator may be rotational (e.g. a gear). The gear may be operated manually or it may be coupled to motor to be operated electronically. In some aspects, the actuator may be translational (e.g. linear). The linear actuator may be operated manually or electronically. A motion of the actuator may simultaneously adjust a mutual orientation of left and right portions of the magnetic field generating device. In some aspects, the actuator may not move a part of the magnetic field generating device. For example, the actuator may only move the left part of the magnetic field generating device to change orientation of the left part with respect to the right part. Similarly, the actuator may only move the right part of the magnetic field generating device to change orientation of the right part with respect to the left part FIG. 42 illustrates exemplary geometry changing mechanism comprising first moveable part 42.01, second moveable part 42.02, and central gear 42.03. First moveable part 42.01 includes first gear 42.04. Second moveable part 42.02 includes second gear 42.05. Magnetic field generating device 42.06 may be coupled to first moveable part 42.01 at point 42.07 and to second moveable part 42.02 at point 42.08. First gear 42.04 and second gear 42.05 may be coupled to central gear 42.03. Central gear 42.03 may enable change of mutual orientation of first moveable part 42.01 and second moveable part 42.02 via a geometry changing mechanism. The inductance of magnetic field generating device 42.06 may vary by adjusting mutual orientation of first moveable part 42.01 and second moveable part 42.02.

In some aspects, the magnetic field generating device may be below the geometry changing mechanism and the geometry changing mechanism may adjust mutual orientation of the first portion of the magnetic field generating device and the second portion of the magnetic field generating device by exerting force. The effector may include a counterpart below the central portion of the magnetic field generating device.

Noted above, the magnetic field generating device may include a loop of wire configured to be turned. In some aspects, the magnetic field generating device may vary inductance by changing a number of active turns. A terminal connected to the magnetic field generating device may be moveable along lateral axis such that the current provided between terminals may vary by a number of turns. The current may be provided to the magnetic field generating device between the terminals. A maximal number of active turns may position the terminals such that they are coupled to an edge of the magnetic field generating device.

In some aspects the magnetic field generating device may comprise a magnetic core. The magnetic core may be made of ferromagnetic material, soft iron, silicon steel, nickel-iron alloy, AlNiCo or cobalt-iron. In some aspects, a permanent magnet may be used (e.g. rare earth magnet such as made of neodymium or samarium-cobalt). The magnetic core may be of various shape such as a rod shape, conic shape, toroidal, E-shape, U-shape or C-shape. The inductance of the magnetic field generating device may be adjusted by at least partially inserting the magnetic core into the core of the magnetic field generating device.

Figure 6:
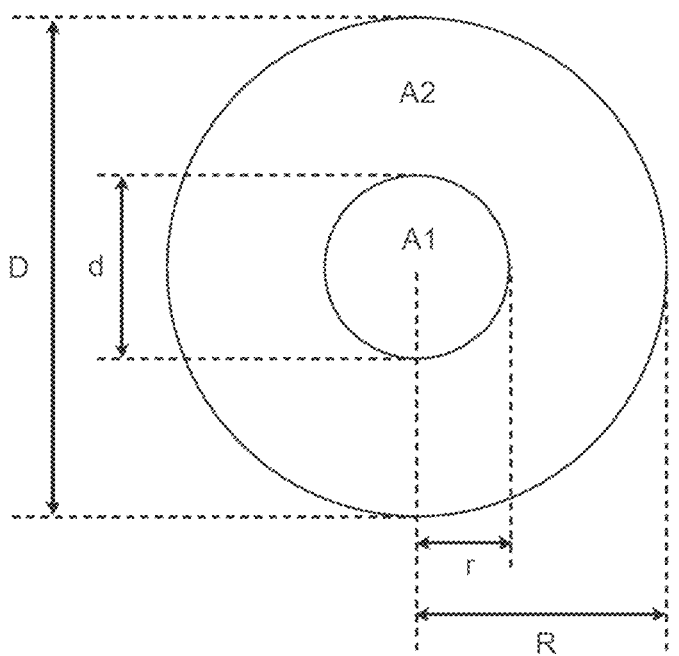
FIG. 6 illustrates an exemplary magnetic field generating device, according to some aspects.

FIG. 6 illustrates a floor projection of an exemplary circular planar magnetic field generating device. The circular planar magnetic field generating device may be characterized by dimensions including an outer diameter D, an inner diameter d, an inner radius r and an outer radius R. The magnetic field generating device is further characterized by an area A1 and an area A2. The area A1 is associated with dimensions r and d. The area A1 may include no winding. The area A1 may include a core of the magnetic field generating device. The core may be an air core. In some aspects, the core may include material with high magnetic permeability such as iron, steel, ferromagnetic material or ferrite. The area A2 is associated with dimensions R and D.

The dimension r may be in a range of 1% to 99%, 2% to 95%, or 3% to 80%, 4% to 60%, or 6% to 50%, or 7% to 40% of the dimension R. The dimensions of r and R may be used for achieving convenient shape of the generated magnetic field.

In some aspects, the diameter D is 100 mm and the dimension r is 10% of the dimension R. In such aspects, the dimension R is 50 mm and the dimension r is 5 mm.

The area A2 may include a winding. The winding may include a conductor (e.g. wire) or a plurality of conductors. The conductor may be insulated. Each conductor of the plurality of conductors may be insulated. The winding may be tightly arranged, e.g. without any gap between turns of conductors. A conductor may touch an adjacent conductor. The winding area A2 may be at least 0.99 cm$^2$. The winding area A2 may be in the range of 0.99 to 7900 cm$^2$, 4 to 7900 cm$^2$, 9 to 1950 cm$^2$, 15 to 975 cm$^2$, or 45 to 450 cm$^2$.

In some aspects, the winding may include a gap between turns of conductors. The gap between turns of conductors may be up to 50%, 25%, 15%, 10%, 5%, 1%, 0.5%, or 0.1% of the of the difference between R and r.

A total surface area of the magnetic field generating device (e.g. the sum of surface of areas A1+A2) may be at least 1 cm$^2$. The total surface area of the magnetic field generating device may be in the range of 1 cm$^2$ to 8000 cm$^2$, 5 cm$^2$ to 8000 cm$^2$, in the range of 10 cm$^2$ to 2000 cm$^2$, in the range of 20 cm$^2$ to 1000 cm$^2$, or in the range of 50 cm$^2$ to 500 cm$^2$.

The device may provide the magnetic field having a magnetic fluence. The magnetic fluence is defined by Equation 1.

$$MF = B_{PP} \cdot A_{MFGD}$$
<div align="right">Equation 1</div> where: MF is magnetic fluence [T·cm$^2$]; B$_{PP}$ is maximal peak to peak magnetic flux density generated by the magnetic field generating device [T]; A$_{MFGD}$ is area of the magnetic field generating device [cm$^2$].

The magnetic field generating device may generate the time-varying magnetic field of the magnetic fluence in a range of 5 T·cm$^2$ to 40000 T·cm$^2$, in a range of 5 T·cm$^2$ to 40000 T·cm$^2$, in the range of 10 T·cm$^2$ to 20000 T·cm$^2$, in the range of 25 T·cm$^2$ to 5000 T·cm$^2$, or in the range of 50 T·cm$^2$ to 1500 T·cm$^2$.

The device may magnetic field having a winding magnetic fluence. The winding magnetic fluence is defined by Equation 2.

$$WMF = B_{PP} \cdot A_2$$
<div align="right">Equation 2</div> where: WMF is winding magnetic fluence [T·cm$^2$]; B$_{PP}$ is maximal peak to peak magnetic flux density generated by the magnetic field generating device [T]; A$_2$ is winding area of the magnetic field generating device [cm$^2$].

The magnetic field generating device may generate the time-varying magnetic field with the winding magnetic fluence of at least 5 T·cm$^2$, 10 T·cm$^2$, 15 T·cm$^2$, or 20 T·cm$^2$. In some aspects, the magnetic field generating device may generate the time-varying magnetic field with the winding magnetic fluence in a range of 5 T·cm$^2$ to 40000 T·cm$^2$, in a range of 40 T·cm$^2$ to 40000 T·cm$^2$, in a range of 40 T·cm$^2$ to 20000 T·cm$^2$, in a range of 50 T·cm$^2$ to 10000 T·cm$^2$, in a range of 75 T·cm$^2$ to 7500 T·cm$^2$, in a range of 100 T·cm$^2$ to 5000 T·cm$^2$, in a range of 150 T·cm$^2$ to 2750 T·cm$^2$, in a range of 200 T·cm$^2$ to 2000 T·cm$^2$, or in a range of 275 T·cm$^2$ to 1500 T·cm$^2$.

The device may include a plurality of magnetic field generating devices (e.g. two or more, three or more, four or more). The magnetic field generating devices may be connected in parallel and placed one above the other in mutually parallel planes. Generated time-varying magnetic fields by such structure may be equal to a time-varying magnetic field generated by a single magnetic field generating device having equal inductance to each of the plurality of parallel magnetic field generating devices. Energy losses of parallel magnetic field generating devices may be lower compared to the single magnetic field generating device.

The plurality of magnetic field generating devices may be mutually oriented in a first plane and a second plane, where the second plane may be above the first plane. A first magnetic field generating device and second magnetic field generating device may be partially overlapping with respect to a floor projection as shown in FIG. 43a. In some aspects, the first magnetic field generating device and the second magnetic field generating device may be positioned mutually above on another with respect to a floor projection as show in FIG. 43b. In some aspects, first magnetic field generating device may be spaced apart from the second magnetic field generating device in floor projection as shown in FIG. 43c. The summed magnetic fields from the first and second magnetic field generating devices may include two peaks of the magnetic flux density. The peaks may correspond to the peak of the magnetic field generated by respective magnetic field generating device. For example, a first peak may correspond to the peak of a first magnetic field from the first magnetic field generating device and a second peak may correspond to the peak of a second magnetic field from the second magnetic field generating device.

The plurality of magnetic field generating devices may be mutually oriented by an angle. The angle may be convex or concave. The mutual orientation may cause respective magnetic fields of each magnetic field generating device to focus on a target biological structure. As a result, the target biological structure in the focus may be treated. Each of the magnetic field generating device may include a core.

The device may provide a combination of magnetic fields with different types of energy. The different types of energy may induce heat in a brain. The different type of energy may be generated by a mechanical source (e.g. shock-wave or ultrasound), by an optical source, or a radiofrequency source. The mechanical source positioned within the device may provide ultrasound and/or shock waves. The optical source positioned within the device may emit laser, visible light, ultraviolet light, infrared light, and/or X-ray. The radiofrequency source may provide radiofrequency field. In some aspects, the source of different type energy may be out of the device, e.g., in different device generating the different type of energy.

The operation of the device may generate heat. The device and/or its components may be cooled. A component may include any part of the device. At least part of the device may be cooled.

Operation of the switching device may generate heat. Overheating of the switching device may be prevented by cooling the switching device.

The switching device may be cooled by a flow of a cooling medium. The cooling medium may be directed to the switching device by a fluid mover, e.g. a blower, a ventilator, a fan, and/or a pump. As the switching device may be positioned within the main body, the fluid mover configured to provide cooling of the switching device may be positioned in the main body. The cooling medium may be a fluid such as liquid (e.g. water, oil) or gas. In some aspects, the cooling medium is air. The heated cooling medium is directed from the switching device to heat exchanger or out of the device to remove heat from the switching device. Temperature of the switching device may be higher than temperature of cooling medium. The heat may be dissipated by use of a heat exchanger, e.g. a heat sink. The heat exchanger may be comprise large surface area in contact with the cooling medium. The heat exchanger may comprise a heat sink comprising a plurality of ducts.

FIG. 7 illustrates cooling device for cooling the switching device. The cooling device may include switching device 2, a fan 7, and the heat exchanger 6 may be positioned in the main body of the device. The switching device 2 may be coupled to the heat exchanger 6. The heat exchanger 6 may comprise a heat sink comprising plurality of ducts (as shown in the FIG. 6). The surface of the heat sink may be cooled by air provided by the fan 7. The fan 7 may direct the air in the direction of the heat sink 6, as depicted by the arrows.

FIG. 8 illustrates another cooling device for cooling of switching device. The cooling device may include a heat pipe 8 between the switching device 2 and a heat exchanger 6. The heat pipe 8 may be coupled to the heat exchanger 6 to transfer heat generated by the switching device 2 to the heat exchanger 6. The heat pipe 8 may include a hollow tube with a liquid cooling medium. The liquid cooling medium may boil on contact surface with the switching device 2, evaporate, and becomes a gaseous cooling medium. The phase transition may remove heat from the switching device 2. The gaseous cooling medium may move along the heat pipe to the heat exchanger 6 to be cooled and to be transited back to liquid cooling medium. The liquid cooling medium may be directed back to vicinity of the switching device 2. Such cooling medium having two phase transition in such case may be water, alcohol, tetrafluoroethane, isobutan, propane, any freon, mercury or any combination thereof.

FIG. 9 illustrates another cooling device for the switching device. The cooling device may include heat exchanger 6 and an active cooling element 9 such as a thermoelectric element, e.g. Peltier cooler. The active cooling element 9 may be coupled to the switching device 2 directly or by a material with high heat conductivity, e.g. silver, copper, gold, aluminum, or a thermal paste. The control unit may control the active cooling element 9 to create a temperature gradient. In case of the Peltier element, the Peltier element may be cooler on the side coupled to the switching device 2 to cool the switching device 2 (e.g., reduce the temperature of switching device 2). The Peltier element may have a higher temperature on its second side coupled to the heat exchanger 6, so that the temperature of heat exchanger 6 is increased. Excessive heat in the heat exchanger 6 may be removed by at least one approach, such as by directing air.

Figure 10:
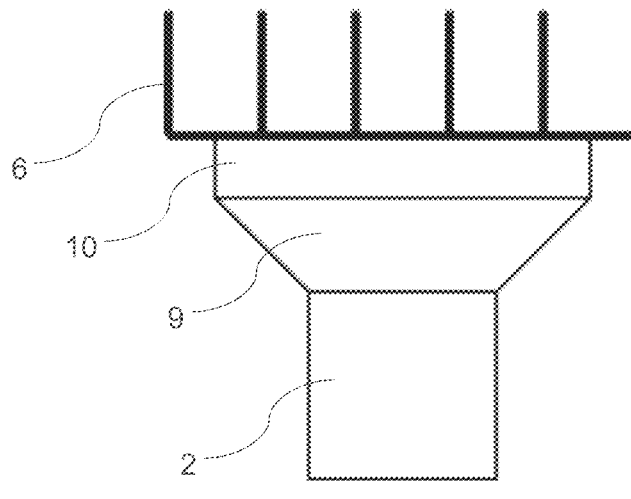

FIG. 10 illustrates another cooling device for cooling of the switching device. The cooling device may include a passive cooling element 10 between the active cooling element 9 and heat exchanger 6. The active cooling element 9 (e.g. Peltier element) may be larger than the switching device 2. The passive cooling element 10 may be made of a material of high thermal conductivity. The passive cooling element 10 may be a block of material having a conical shape and a first contact surface with a smaller section area and a second contact surface with larger section area. The first contact surface of the smaller section area may be coupled to the switching device 2 and the second contact surface of the larger section area may be coupled to active cooling element 9. The passive cooling element 10 may increase an active surface of the active cooling element 9 and substantially increase effectivity of cooling of the switching device 2. The active cooling element 9 may be coupled to the heat exchanger 6. Cooling power may be power used for controlling heat removing device and for controlling the Peltier element. Cooling by this approach may be more efficient than cooling by active cooling element 9 only.

Figure 11:
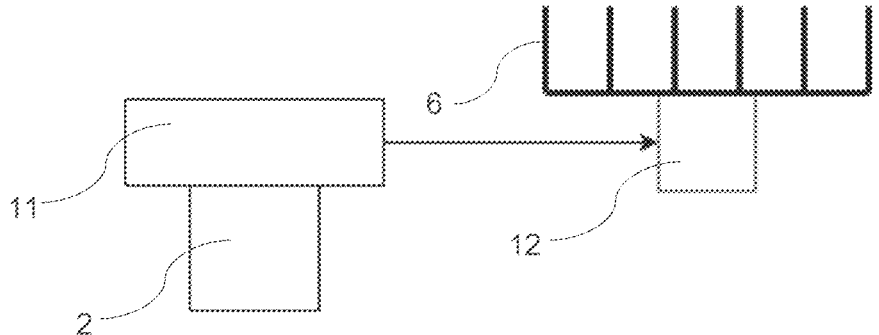

FIG. 11 illustrates another cooling device for cooling of the switching device. The cooling device may include a chiller 11. The chiller 11 may be coupled to the switching device 2 by a heat conductor 12, which transfers heat generated by the switching device 2 to the chiller 11. The heat conductor 12 may be material with high thermal conductivity. The chiller 11 may be coupled to the heat exchanger 6. The chiller 11 may remove heat from the switching device 2 via contact surface. The chiller 11 may be a device and/or material using vapor compression and/or absorption refrigeration cycles. The chiller 11 may cool the switching device 2 to very low temperatures, e.g. about 0° C.

Figure 12:
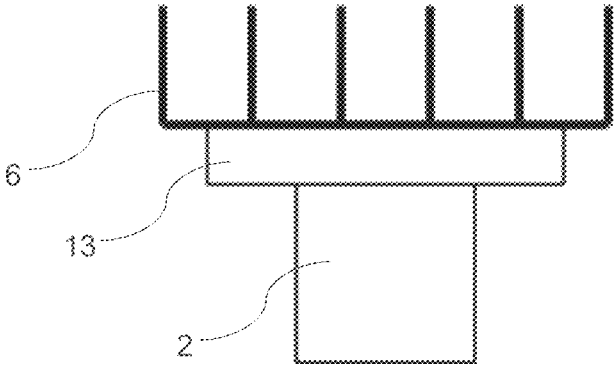

FIG. 12 illustrates another cooling device for cooling the switching device. The cooling device may include a Stirling engine 13. The Stirling engine 13 may include working gas (e.g. outer air, helium, carbon dioxide, etc.). A first contact surface of the Stirling engine 13 may be coupled to the switching device 2 to heat the working gas. The Stirling engine 13 may convert pressure changes of the working gas to mechanical work during a cooling process of the heated cooling medium. The mechanical work may be used e.g. for removing heat from the heat exchanger 6. Such cooling may cool the switching device 2 to very low temperatures below 0° C. (e.g., −120° C.). The Stirling engine may provide power to fluid mover.

Figure 13:
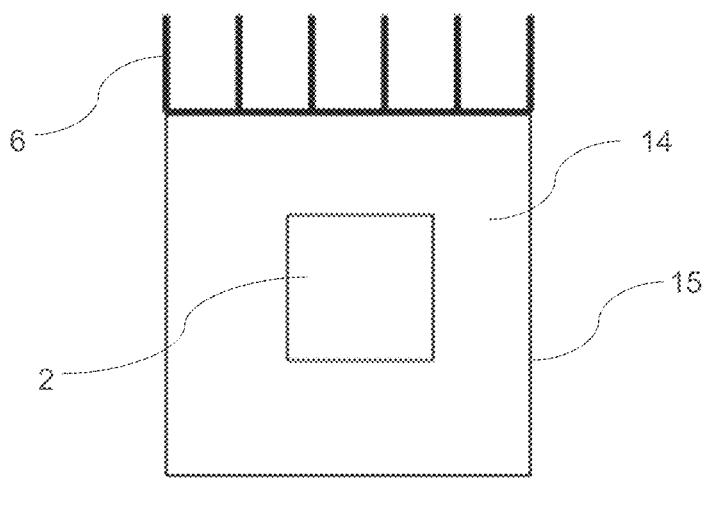

FIG. 13 illustrates an cooling device for cooling the switching device. cooling device may include a two-phase cooling medium 14. The switching device 2 and the two-phase cooling medium 14 may be positioned in a tank 15 including cooling medium 14. The switching device 2 may be submerged in the cooling medium 14. The two-phase cooling medium 14 may be a fluid with low boiling temperature. Temperature of the switching device may be higher than temperature of two-phase cooling medium 14. The switching device 2 may be cooled to a boiling temperature of the two-phase cooling medium 14. The two-phase cooling medium 14 may have infinite electric resistance, so it is safe for the patient. The two-phase cooling medium 14 may be e.g. a fluorocarbon-based fluid such as 3M Novec™. The two-phase cooling medium 14 may change phase from liquid to gas as it is heated by operation of the switching device 2, so the switching device 2 is cooled by phase change of the two-phase cooling medium 14. The gaseous phase of two-phase cooling medium 14 changes its phase from gas to liquid by cooling on a contact surface of the tank 15 coupled to the heat exchanger 6. The tank 15 may further comprise conduits for contacting the surface of the heat exchanger 6.

The device may include a positioning arm providing mechanical connection between the main body and the applicator. The positioning arm may support the applicator during positioning of the applicator before and/or during the generation of the magnetic field by the magnetic field generating device. The positioning arm may be configured to direct support of the applicator, to provide easier operation with the applicator and/or to provide stable position of the applicator during the use of the device.

The positioning arm may comprise two connectable parts, one on each end of the positioning arm. A first end may be connected to a rear side of the main body of the device. A second end of the positioning arm may be connected to the applicator.

The positioning arm may be attached to the main body of the device. The positioning arm may be used for positioning the applicator to the patient. The positioning arm may include a plurality of degrees of freedom (e.g. two, four, five, six or eight) to enable precise positioning of the applicator to the patient. The positioning arm may have a first end and a second end opposite the first end. The applicator may be coupled to the positioning arm on the second end of the positioning arm, and the positioning arm may be coupled to the main body at the first end of the positioning arm.

Figure 14:
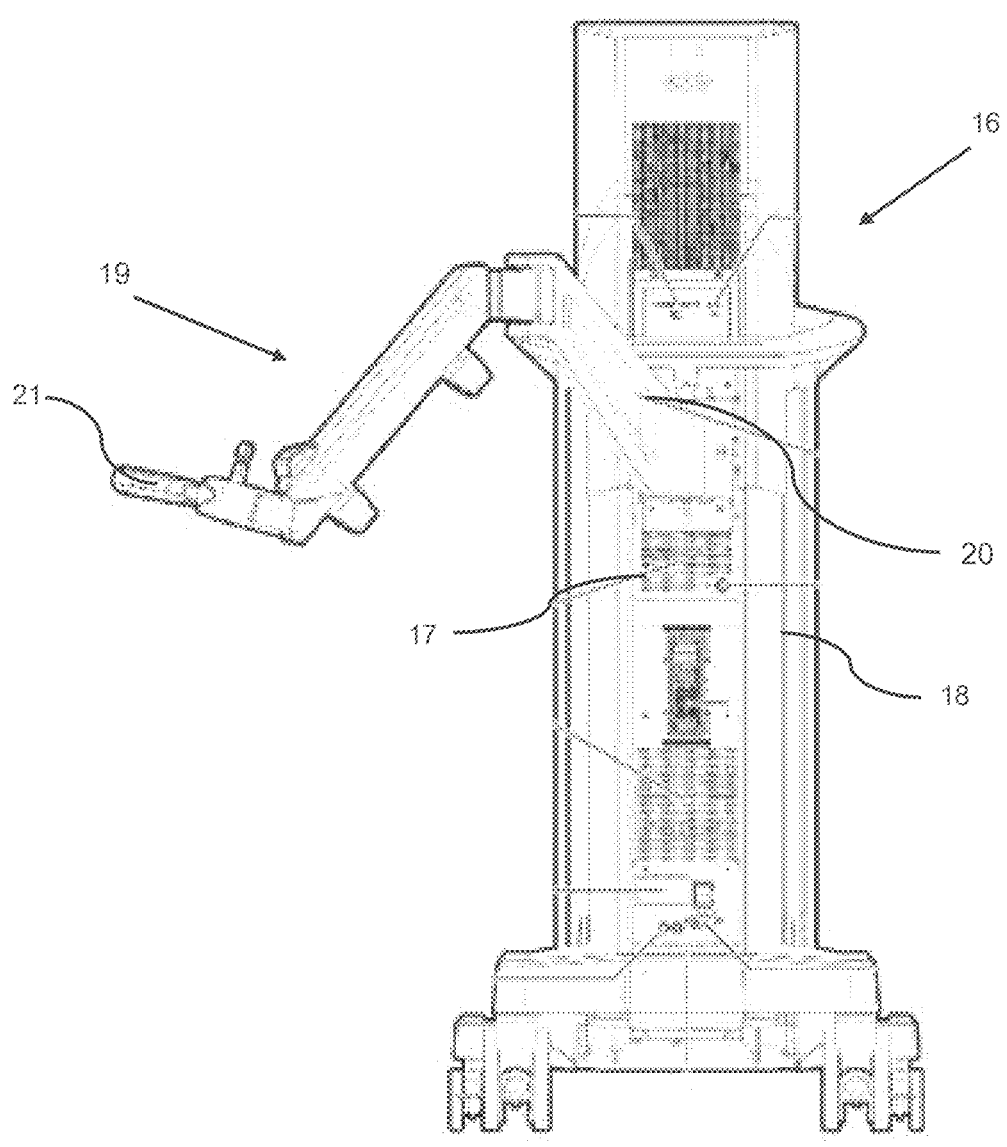
FIG. 14 illustrates a rear view of an exemplary main body of a device, according to some aspects.

FIG. 14 illustrates exemplary rear side 17 of the main body 18 of the device 16, wherein the positioning arm 19 is coupled to the rear side 17 of the main body 18. The positioning arm 19 is attached to the device 16 at first end 20 of the positioning arm 19. The second end 21 of the positioning arm 19 is configured to be connected to the applicator.

Figure 15:
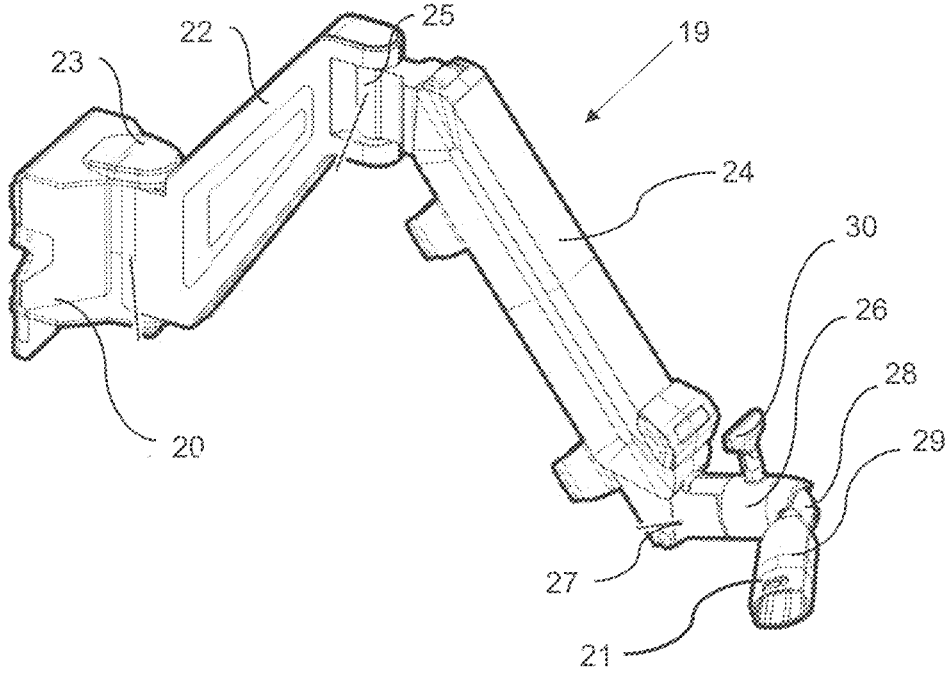
FIG. 15 illustrates a view of an exemplary positioning arm, according to some aspects.

FIG. 15 illustrates exemplary positioning arm 19 with a first end 20 and a second end 21. The positioning arm 19 may comprise four links enabling positioning of the applicator. The link may include a rigid material (e.g. metal and/or plastic material). The first link 22 may be coupled to the main body of the device by a first gudgeon 23 (e.g. roll gudgeon) positioned of the first end of the first link 22. Connection by the first gudgeon 23 may enable rotation of the positioning arm 19 in horizontal plane. The first link 22 may provide basic elevation of the applicator in a direction to the patient. A second link 24 may be coupled to first link 22 by a second gudgeon 25 (e.g. roll gudgeon) positioned between the second end of the first link 22 and the first end of the second link 24. The second gudgeon 25 may enable rotation of the second link 24 in horizontal plane of the second link 24. A third link 26 may be coupled to the second link 24 by a third gudgeon 27 (e.g. roll gudgeon) positioned between the second end of the second link 24 and the first end of the third link 26. The second end of the third link 26 may comprise a ball joint 28 enabling rotation of a fourth link 29. A fourth link 29 may be coupled to the second end of the third link 26 by a ball joint 28 positioned between the second end of the third link 26 and the first end of the fourth link 29. The ball joint 28 may be locked in a static position. In some aspects, the ball joint 28 may be locked by a locking screw 30. In some aspects, applicator may be removably coupled to the positioning arm. In some aspects, the fourth link 29 may comprise a locking mechanism for removable coupling of the applicator to the positioning arm 19. The locking mechanism may be positioned on a second end of the fourth link 29. The second end of the fourth link 29 may be opposite to the first end of the fourth link 29.

Figure 16:
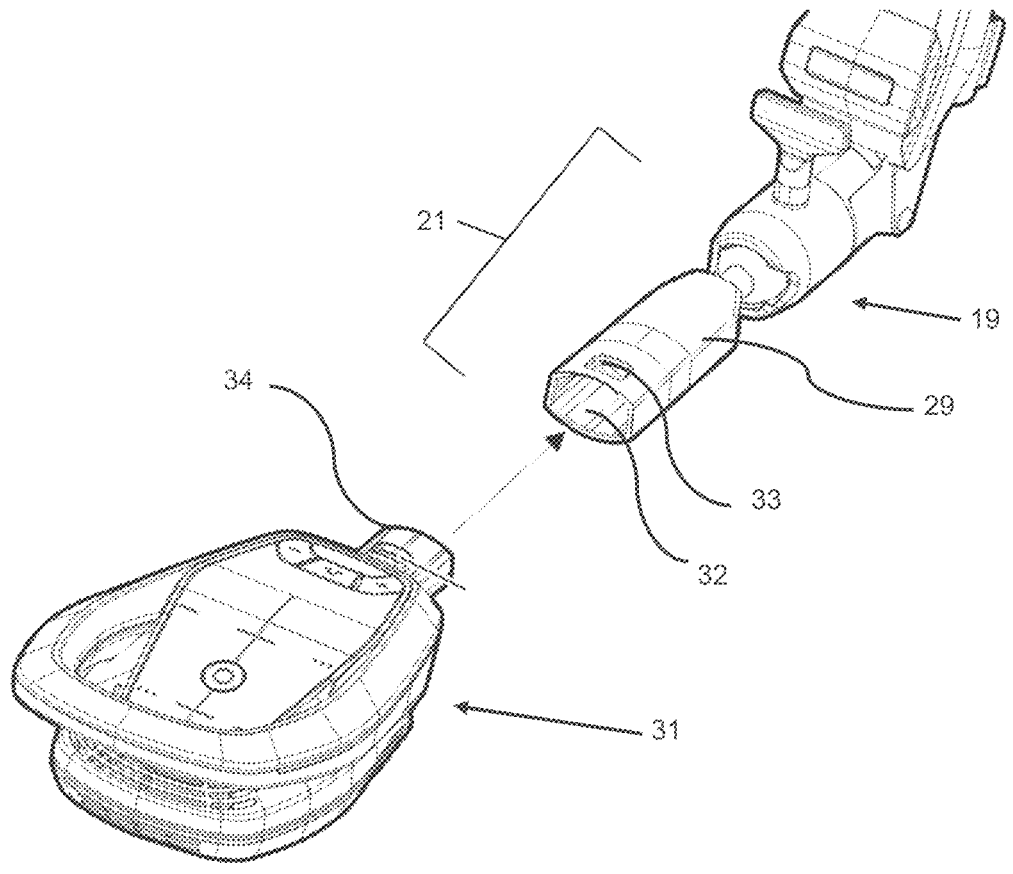
FIG. 16 illustrates a view of the connection of an exemplary positioning arm with an exemplary applicator, according to some aspects.

FIG. 16 illustrates the exemplary connection of the applicator 31 with the positioning arm 19. The applicator 31 may be removably attached to the positioning arm 19. In some aspects, the positioning arm 19 includes a sleeve 32 at the second end 21 of the positioning arm 19. In some aspects, sleeve 32 may be hollow. The fourth link 29 is positioned on the second end 21 of the positioning arm 19. The sleeve 32 may be configured to be connected to the applicator 31. The sleeve 32 may include a gap 33 for removable attachment of the applicator 31 to the positioning arm 19. The connection of the applicator 31 to the positioning arm 19 may be enabled by a locking mechanism. The locking mechanism according to some aspects is depicted on FIG. 16. The applicator 31 may include a latching member 34 biased by a resilient member (e.g. spring). The latching member 34 may be adapted to fit the gap 33 in the sleeve 32 at the second end 21 of the positioning arm 19. The applicator 31 may be attached to the positioning arm 19 by inserting (depicted by an arrow in FIG. 16) the applicator 31 into the sleeve 32 and locking the latching member 34 in the gap 33. Applicator 31 may be removed by pressing the latching member 34 and pulling the applicator 31 from the sleeve 32.

The positioning arm may comprise six degrees of freedom to enable precise positioning of the applicator.

Figure 17:
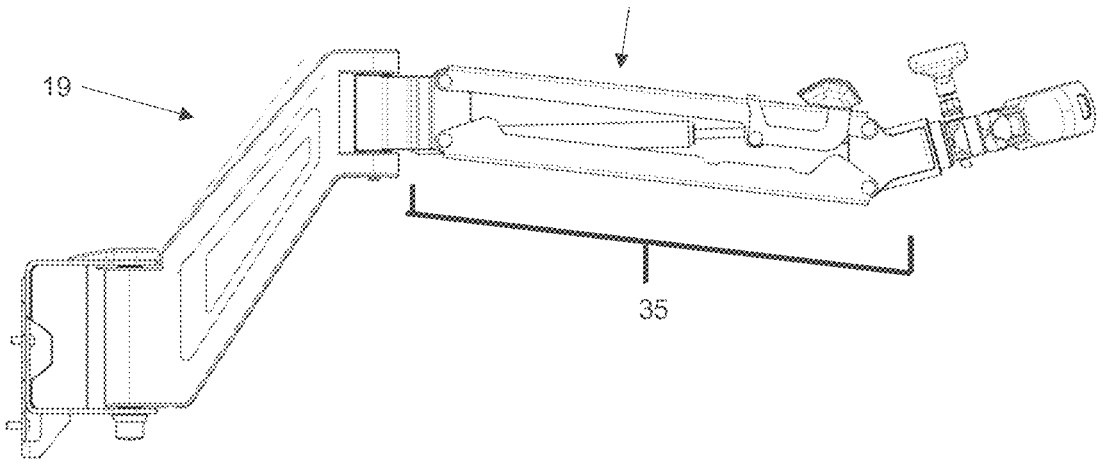
FIG. 17 illustrates another view of an exemplary positioning arm, according to some aspects.

The second link 24 of the positioning arm 19 may include a parallelogram mechanism. In some aspects, the parallelogram mechanism is configured to provide movement of the second link 24, e.g. in vertical axis. FIG. 17 illustrates an exemplary parallelogram mechanism 35 as part of the second link 24 of the positioning arm 19.

Figure 18:
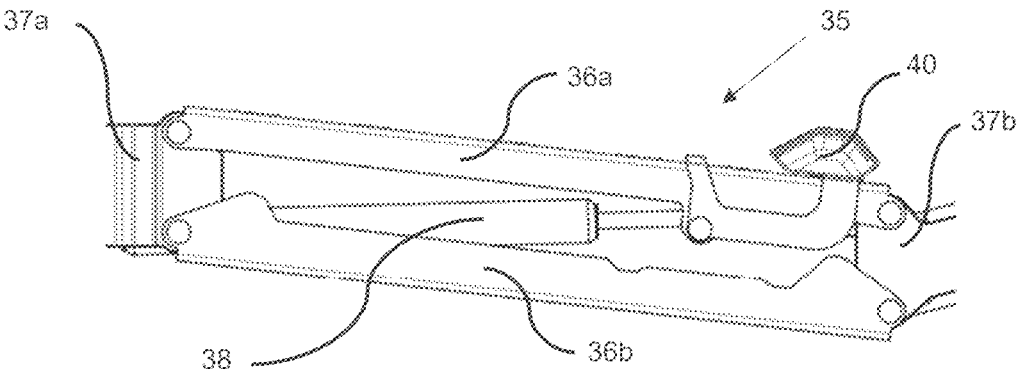
FIG. 18 illustrates a view of a parallelogram mechanism, according to some aspects.

FIG. 18 illustrates the exemplary parallelogram mechanism 35. The parallelogram mechanism 35 may comprise at least one pair of sublinks and at least one pair of frames. For example, the parallelogram mechanism 35 may comprise two sublinks 36a and 36b and two frames 37a and 37b. Movement of the sublinks 36a and 36b in mutually parallel planes may provide sufficient distance in-between the sublinks 37a and 37b. The sublink 36a and sublink 36b may be mutually parallel in each position of the movement of the parallelogram mechanism. The frame 37a and the frame 37b may be mutually parallel in each position of the movement of the parallelogram mechanism 35. The sublink 36a may be connected to the frame 37a and the frame 37b. The sublink 36b may be connected to the frame 37a and the frame 37b. A distance on the frame 37a between connections of sublink 36*a* and sublink 36*b* to the frame 37*a* may be equal to a distance between connection of the sublink 36*a* and the sublink 36*b* on the frame 37*b*.

The positioning arm 19 may comprise a resilient element 38 to enable elevation and positioning of the applicator. The resilient element may include a sliding piston. The resilient element may be a gas spring, oil spring and/or a hydro-pneumatic suspension gas spring including oil chamber. In some aspects, the resilient member may include a mechanical spring (e.g. coil spring, torsion spring, tension spring or leaf spring).

FIGS. 17 and 18 show the resilient element 38 positioned in the second link in the parallelogram mechanism 35. The resilient element 38 is shown to be connected to the parallelogram mechanism 35 on two opposite ends in diagonal corners by mechanical coupling enabling rotation. The resilient element 38 is shown to be connected by connection to two diagonal corners. First diagonal corner may include a connection of the sublink 36*b* to the frame 37*a*, while the second diagonal corner may include a connection of the sublink 36*a* to the frame 37*b*.

The lowest position of the positioning arm may compress a gas within the resilient element to a highest pressure. Energy of compressed gas may compensate for a weight of applicator so the applicator is easy to position by the operator.

The positioning arm 19 may comprise a lock 39. In some aspects, the lock is configured to lock the spring positioned of the second link. The lock may maintain a steady position of the applicator and/or the second link. The lock may ensure that a position (e.g. an elevation) of the second link is fixed. A locked position of the lock disables the movement of the spring so the position of the second link (e.g. elevation) and/or applicator cannot be changed. An unlocked position of the lock may release the gas to enable changing the position (e.g. elevation) of the second link and/or applicator.

FIG. 19 schematically illustrates a lock 39 in open position, while the FIG. 20 illustrates the lock 39 in closed position. The lock 39 may comprise a locking member 41, a rotating member 42, a moveable member 40, and a pulling member 43. Lock 39 may be controlled by manual movement of the moveable member 40 along the second link of the positioning arm. The moveable member 40 as shown in FIG. 18.

The moveable member 40 may be connected to the pulling member 43. The pulling member 43 is coupled to a rotating member 42 on a lower end of the pulling member 43. The rotating member 42 slides along a contact surface of the locking member 41. The locking member 41 may have a round recess 44 on upper side 45 and flat portion 46 on its lower side 47. In some aspects, the locking member may include a first recess (e.g. round recess) on its upper side 45 and a second recess (e.g. round recess) on its lower side 47. The rotating member 42 may be moveable between two positions. The lock 39 may be unlocked when the rotating member is in the round recess. Oppositely the lock 39 may be locked when the rotating member substantially contacts the flat portion.

In some aspects, the moveable member 40 and pulling member 43 may form one member.

In some aspects the lock may be replaced by a worm gear.

In some aspects the applicator may be positioned by a positioning stand. The positioning stand may be external such that it is not part of the device's main body. FIG. 44 illustrates positioning stand 44.01 may include vertical stand 44.02 and horizontal rod 44.03. Vertical stand 44.02 may comprise first part 44.04 and second part 44.05. First part 44.04 may be hollow to enable second part 44.04 to be moveable inside first part 44.04 in a vertical direction to adjust the height of positioning stand 44.01. Applicator 44.06 may be moveable in a direction along horizontal rod 44.03. Positioning stand 44.01 may comprise joint 44.07 coupling second part 44.05 of vertical stand 44.02 to horizontal rod 44.03. The joint may enable tilting of horizontal rod 44.03 with respect to second part 44.05 of vertical stand 44.02 such that applicator 44.06 may be moved.

The horizontal rod may be permanently fixed to the vertical rod. In some aspects, the horizontal rod may be detachably coupled to the vertical rod by any suitable manner (e.g. by screw, bolt, pin, bayonet or any quick release mechanism). The horizontal rod may be extendable to enable position the applicator in a horizontal plane. In some aspects, the horizontal rod may comprise rails. The applicator may be moved along the rails in the horizontal plane.

The applicator may be fixed or removably coupled to a second end of the horizontal rod. In some aspects, the applicator may be attached to the horizontal rod by a hanging member.

The horizontal rod may comprise a counterbalance on a first end of the horizontal rod. The counterbalance may compensate a gravitational force of the applicator. The counterbalance may provide comfortable positioning of the applicator by operator.

In some aspects, the horizontal rod may be coupled to the vertical rod by a hinge. The hinge may be used to adjust the applicator's position.

The weight of the applicator may be compensated by a counterweight on a different side of the positioning arm.

In some aspects, the device may not include a positioning arm.

The device may comprise a connecting tube 61. The connecting tube may comprise wiring configured to transfer energy pulses from the energy storage device to the magnetic field generating device in order to generate the magnetic impulses. The connecting tube may be flexible. In some aspects, the connecting tube may include a fluid conduit. The fluid conduit may be coupled to a source of fluid within the main body of the device. The source of fluid may include a cooling medium, e.g. a fluid or a liquid such as water or oil. The cooling medium may be directed via the fluid conduit to into the applicator to cool the magnetic field generating device. The fluid may be directed to the applicator by a suitable fluid mover, e.g. a pump.

As mentioned previously, the device may include the applicator. The applicator may include a casing, one or more magnetic field generating devices, one or more fluid movers and a fastening member. In some aspects, the applicator may include a casing, one magnetic field generating device, one fluid mover and one or more fastening members. In some aspects, the applicator may include a casing, one magnetic field generating device, two fluid movers and one or more fastening members. In some aspects, the applicator may include a casing, two magnetic field generating devices, one fluid mover and one or more fastening members. In some aspects, the applicator may include a casing, two magnetic field generating devices, two fluid movers and one or more fastening members. In some aspects, the applicator may include a casing, two magnetic field generating devices, four fluid movers and one or more fastening members.

The applicator may be connected to the main body of the device by a connecting tube. The connecting tube may also include wiring coupled to the control unit of the device. The connecting tube may also include wiring coupled to the energy storage device of the device and to the magnetic field generating device. The magnetic field generating device may be cooled. The casing may be manufactured from plastic or any other suitable material.

The fluid mover positioned in the applicator may have different function from the fluid mover positioned in the main body. The fluid mover positioned in the applicator may provide cooling of the magnetic field generating device, while the fluid mover positioned in the main body may provide cooling of the switching device. The fluid mover positioned in the applicator may pull the air to the applicator from the outside of the device. When two fluid movers are positioned within the applicator, both fluid movers may pull air to the applicator from the outside of the device.

FIG. 21 illustrates a cross-section of the applicator 31 positioned in a vicinity of body 48 of the patient. The applicator 31 may include the magnetic field generating device 4 and a casing 50. The applicator 31 may further comprise the fluid mover 49 and at least one fastening member 51 for connection of the magnetic field generating device 4 to the casing 50 of the applicator 31. The fastening member 51 may be made of a resilient material (e.g. rubber, polyurethane, thermoplastic elastomer, PVC, or others). In some aspects, rigid material may be used as fastening member 51 as well. The fastening member 51 may be coupled to an outer perimeter of the magnetic field generating device 4. In some aspects, fastening member 51 may be coupled to lower or upper side of the magnetic field generating device 4. The fastening member 51 may connect the magnetic field generating device 4 to the casing 50 of the applicator 31 in at least one point.

In some aspects, the fastening member 51 may surround the magnetic field generating device 4 to couple the magnetic field generating device 4 to the casing 50 on entire perimeter of the magnetic field generating device 4.

The fastening member 51 may maintain the magnetic field generating device 4 spaced apart from the casing 50 of the applicator 31 so that cooling medium may flow between the casing of the applicator and the magnetic field generating device.

At least one fluid mover 49 may be positioned in the applicator 31. In some aspects, two fluid movers 49 may be positioned within the applicator. At least one fluid mover 49 may be placed at a position around the perimeter of magnetic field generating device 4. In some aspects, the fluid mover may be positioned in a different plane oriented to the plane of the magnetic field generating device 4 by an angle. The fluid mover 49 may be a device for directing the cooling medium into the casing 50 of the applicator (e.g., a blower, a fan, a pump, or a compressor). The cooling medium may be a fluid such as air (e.g., air from outside of the applicator) or any other gaseous medium. When air is used as the cooling medium, it may be air from outside of the applicator drawn in by one or more fluid movers 49 through one or more inlets into the casing of the applicator 31, directed by the fluid mover 49 within a vicinity of the magnetic field generating device 4 and directed out of the applicator 31 through one or more one outlet. The fluid mover 49 positioned at a position around the perimeter of the magnetic field generating device 4 may not be interfered with by the magnetic field generated by the magnetic field generating device 4.

In some aspects, the fluid mover 49 may be positioned above or below the magnetic field generating device 4 in sufficient distance to prevent negative influence of the magnetic field generated by the magnetic field generating device 4.

Fluid mover 49 may be arranged at a position around a perimeter of magnetic field generating device 4 to direct air to bypass the magnetic field generating device 4 over an upper side and/or a lower side of the magnetic field generating device 4. The lower side of the magnetic field generating device 4 may be positioned closer to the body 48 of the patient. The arrows indicate the air flow through the applicator 31. FIG. 21 shows that air may flow over an upper side of the magnetic field generating device 4 and a lower side of the magnetic field generating device 4.

The outer air may be precooled before entering the casing 50 of the applicator 31. Air may be precooled by an air cooling element using refrigeration. An inlet for directing the air to the casing of the applicator may be placed at a position around a perimeter of the magnetic field generating device 4, to remove heat from the magnetic field generating device 4. The fluid mover 49 may be positioned at the position around a perimeter of the magnetic field generating device 4 and close to the inlet. One or more ducts may be positioned between the inlet and the fluid mover 49. An outlet for directing the heated air out of the casing 50 may be on an opposite side of the casing 50 with reference to the inlet to enable the air to flow in a direction parallel to the magnetic field generating device 4. The outlet may be on an upper side of the applicator to direct the heated air from the applicator in a direction from the patient. Either inlet or outlet may include a plurality of holes for unimpeded airflow.

Figure 22:
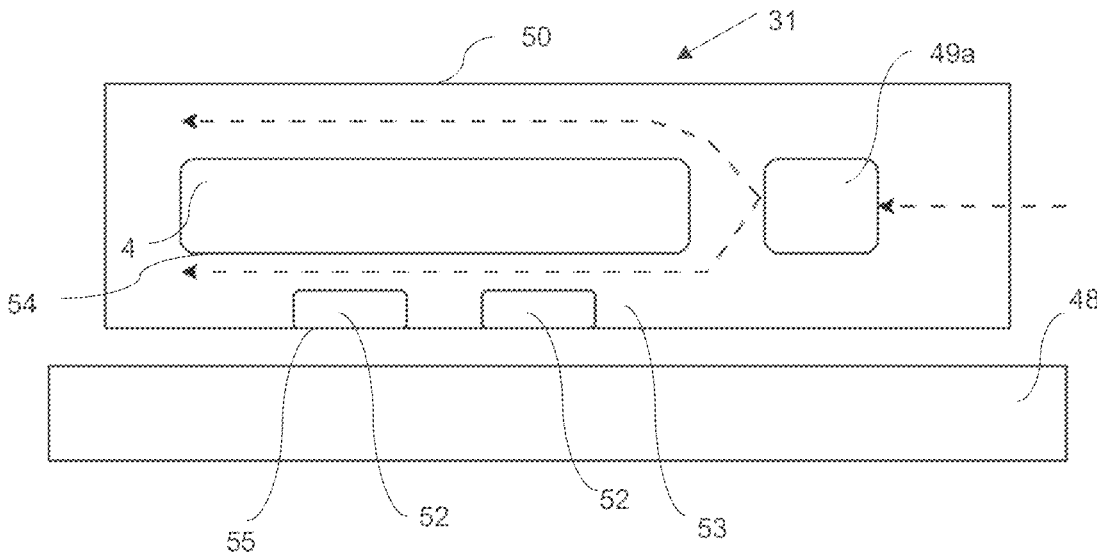
FIG. 22 illustrates a cross-section of an exemplary applicator, according to some aspects.
Figure 23:
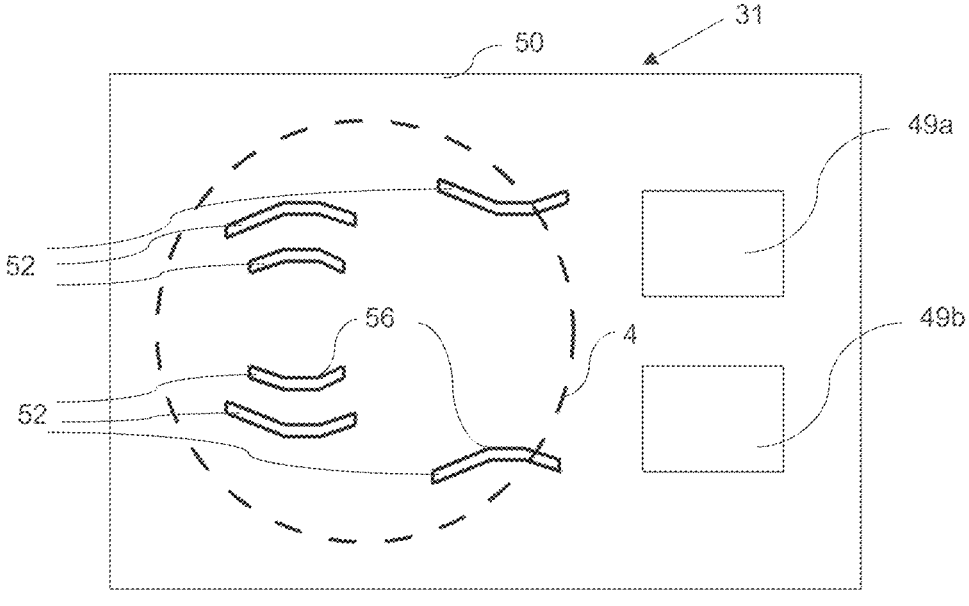
FIG. 23 illustrates a cross-section of an exemplary applicator from the applicator's floor projection, according to some aspects.

FIG. 22 illustrates a cross-section of another exemplary applicator. FIG. 23 illustrates a cross-section of same exemplary applicator as in 22 in view from below. In this aspect, the applicator may include two fluid movers 49, fluid mover 49a and fluid mover 49b. Fluid mover 49a and/or 49b may be a fan. From the view of the FIG. 22, second fluid mover 49b is positioned behind the first fluid mover, so only one fluid mover 49a is visible. Fluid movers may be configured to provide cooling of the magnetic field generating device 4. Arrows represents direction of the air directed by the fluid movers, wherein air is depicted to be drawn into the applicator by fluid movers and directed then around the magnetic field generating device 4. Applicator 31 may further comprise one or more barriers 52. In some aspects, barriers 52 may be configured to reduce the size of the air flow path and thus increase the speed by which air moves around magnetic field generating device 4. In some aspects, barriers 52 are positioned in a lower space 53, wherein the lower space is positioned between the lower side 54 of the magnetic field generating device and the casing 50. In some aspects, the barriers 52 direct the air in higher speed around the magnetic field generating device 4. The barriers may be made of a rigid material (e.g., plastic, metal or any other suitable material). The function of the barrier may include further direction of air within the lower space 53 provided by the fluid movers in a vicinity of the of magnetic field generating device 4.

In some aspects, the barrier 52 may be made of plastic. In some aspects, the barrier 52 may be made of a resilient material such as rubber. In some aspects, a resilient material reduces vibration caused by the magnetic field generating device to reduce vibrations, e.g. a noise heard as clicking sound. The barriers may be coupled to the lower side 55 of the casing 50.

As can be seen in the FIG. 23 showing bottom up view of exemplary applicator 31, the barrier 52 includes a longer side 56 positioned along the direction of the air. The barrier 52 may be at least partially positioned below the magnetic field generating device 4. The barrier 52 may be positioned at least partially between the magnetic field generating device 4 and the patient.

In some aspects, the applicator may include one or more barriers 52 positioned in the upper space between the upper side of the magnetic field generating device and the casing 50.

In some aspects, the applicator may not include a fluid mover. The cooling medium may be a liquid, e.g. (oil or water).

The applicator may be connected to the main body by the connecting tube. The connecting tube may be used for providing additional or alternative type of cooling. The connecting tube may include a fluid conduit directing a cooling medium from a source of the cooling medium to the magnetic field generating device to remove heat generated by the magnetic field generating device. The fluid conduit may be connected to a source of cooling medium. The source of cooling medium may include oil, water gas or any other suitable cooling medium.

The device may include an applicator including a plurality of magnetic field generating devices, e.g. two or more. The applicator may comprise a positioning mechanism including mechanical member enabling mutual positioning of the magnetic field generating devices within the applicator.

A positioning element may be used for adjusting a distance between the magnetic field generating devices within the applicator. The positioning element may comprise for example a mechanical slider, such as a screw driven linear slider. Also, the positioning element may be rotational to adjust mutual orientation of the magnetic field generating devices. The rotational positioning element may comprise a joint or a gear.

The applicator may be hand-held applicator.

Figure 24:
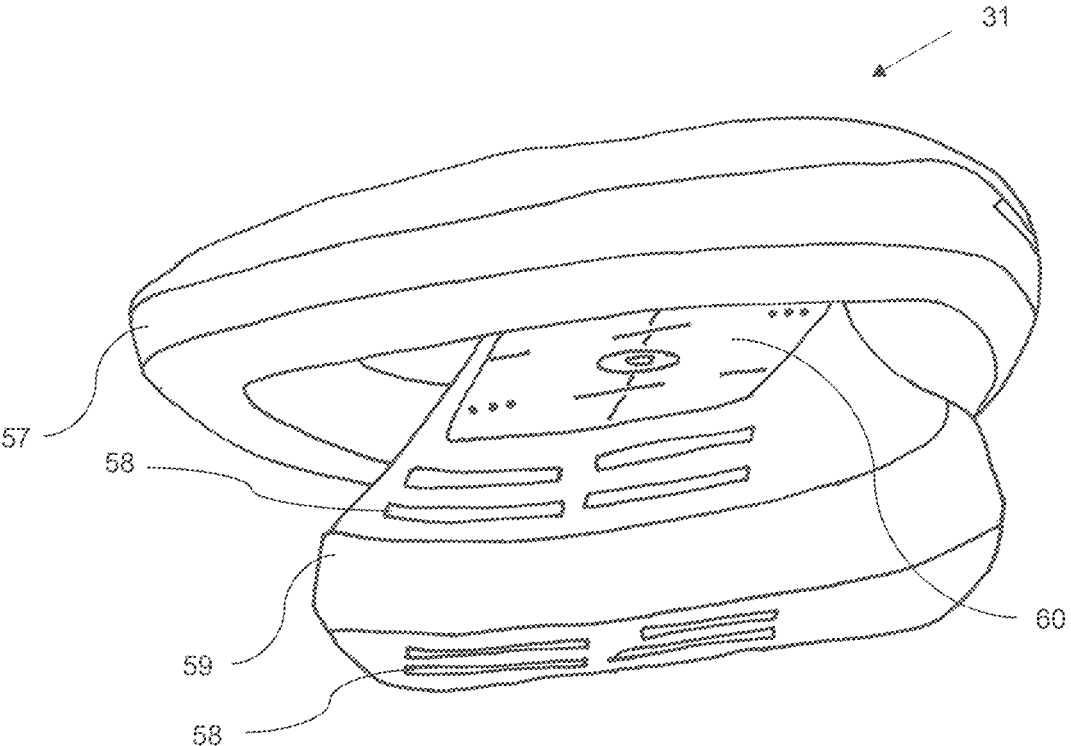
FIG. 24 illustrates a front perspective view of an exemplary applicator, according to some aspects.
Figure 25:
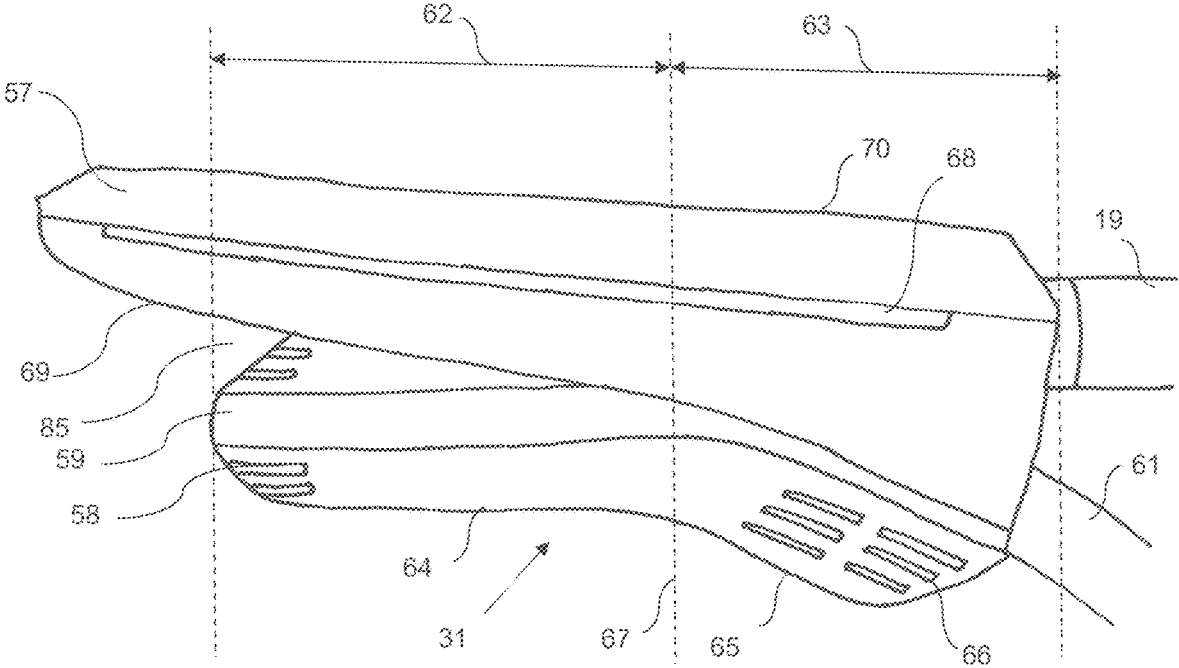
FIG. 25 illustrates a side view of an exemplary applicator, according to some aspects.
Figure 26:
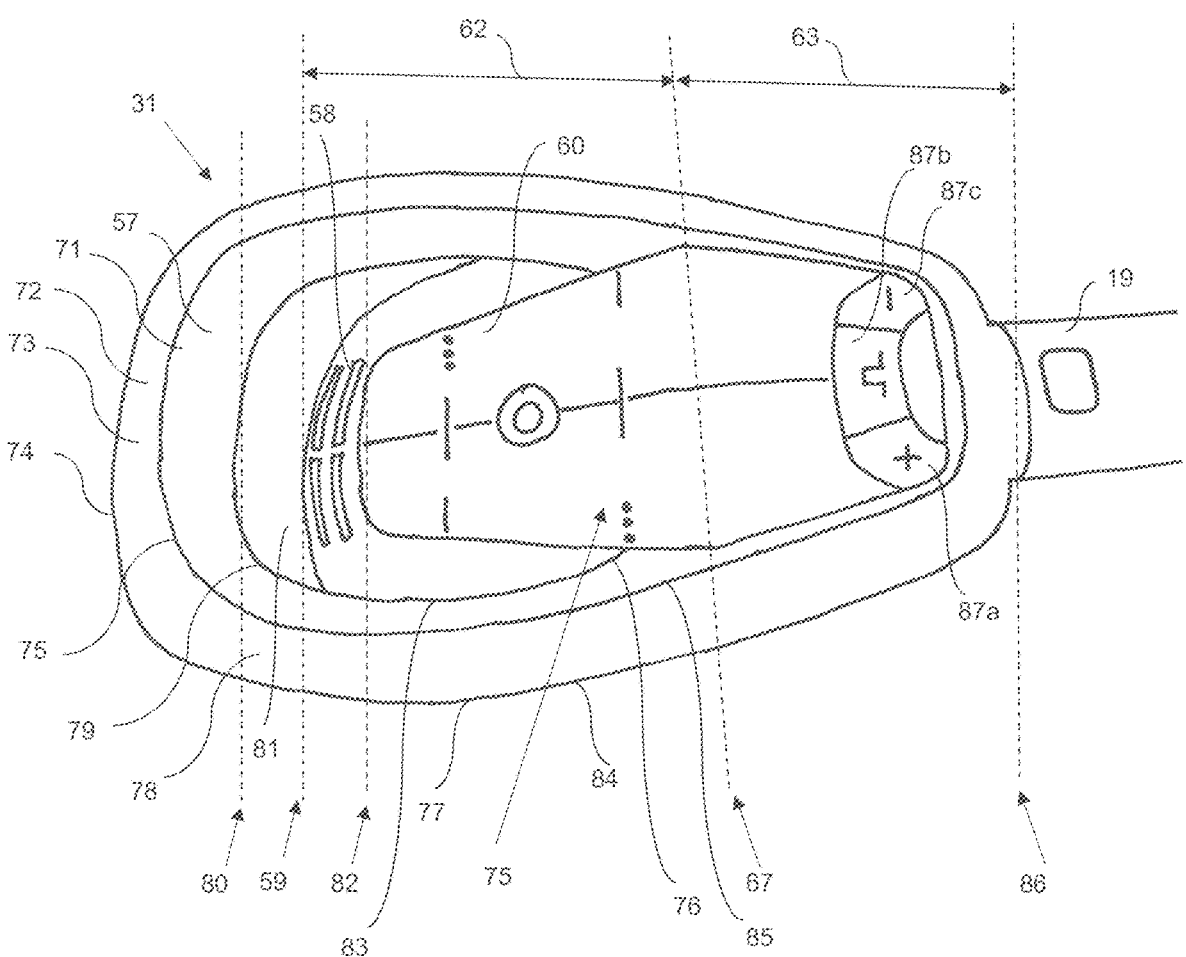
FIG. 26 illustrates a top view of an exemplary applicator, according to some aspects.

FIGS. 24, 25 and 26 illustrate exemplary applicator.

The applicator 31 may comprise application part 62, non-application part 63 and handle 57. Further, the applicator 31 may comprise a positioning plate 88 shown partly in FIG. 24 and fully in FIGS. 26 and 27.

Application part 62 of the applicator 31 comprise a magnetic field generating device and an outlet 58. Non-application part 63 does not comprise a magnetic field generating device. Upper side of application part 60 may be substantially planar. The magnetic field generating device may be in a plane substantially parallel to lower side of application part 64.

The back portion of non-application part 86 may include a first part of connector connecting the positioning arm 19 and the connecting tube 61 to the applicator 31. Within the connector, connection of the applicator 31 to the connecting tube 61 may be positioned under connection of the applicator 31 to the positioning arm 19 in order to enable comfortable positioning of the applicator 31. Contact of connecting tube 61 and the positioning arm 19 may be avoided during positioning of the applicator 31. The applicator 31 may be free to move.

In some aspects, tilted part of the back side of applicator 31 comprises an inlet 66 for directing air into the applicator 31. The inlet 66 comprises one or more holes.

The lower side of the non-application part 65 may be substantially planar. The lower side of non-application part 65 may comprise an inlet 66. The lower side of non-application part 65 may be spaced from the upper side of non-application part 70 by a distance in a range of 10 mm to 250 mm, in a range of 30 mm to 230 mm, in a range of 50 mm to 210 mm, in a range of 60 to 180, in a range of 65 to 160, in a range of 70 mm to 200 mm, or in a range of 50 mm to 150 mm. The lower side of non-application part 65 and the upper side of non-application part 70 may be mutually oriented in two planes spaced apart and defined by an angle in a range of 5° to 85°, in a range of 5° to 75°, in a range of 5° to 70°, in a range of 5° to 65°, in a range of 6° to 60°, in a range of 6° to 50°, or in a range of 8° to 30°. Orientation and distance of the upper side of the non-application part 70 and lower side of the non-application part 65 may provide space for fluid mover 25 positioned inside the non-application part 63. The operating buttons 87a, 87b and 87c may be positioned over and/or above the inlet 66 and the fluid mover 49. Buttons 87a, 87b and 87c may be sufficiently close to each other to enable comfortable adjusting value of magnetic flux density and providing single pulses using only one hand.

The lower side of the non-application part 65 and the lower side of the application part 64 may be mutually oriented in two planes spaced apart and defined by an angle in a range of 90° to 180°, in a range of 95° to 175°, in a range of 100° to 170°, in a range of 105° to 165°, in a range of 110° to 160°, in a range of 120° to 150°, or in a range of 130° to 160°. Such orientation may be designed for substantial positioning of the applicator 31 (including application part 62 and non-application part 63) to a head of a patient.

The upper side of the non-application part 70 may be aligned with a plane of top handle portion 85. The upper side of the non-application part 70 and the upper side of the application part 60 may be positioned in two mutually different planes defined by a concave angle in a range of in a range of 100° to 170°, in a range of 120° to 160°, in a range of 130° to 150°, or in a range of 145° to 175°. The angle may be defined in a fall-edge 67, where the applicator 31 and positioning plate bends. A distance between the fall edge 67 and the back portion of the non-application part 86 may be in a range of 10 mm to 250 mm, in a range of 25 mm to 225 mm, in a range of 50 mm to 210 mm, in a range of 50 mm to 200 mm, in a range of 60 mm to 180 mm, in a range of 65 mm to 175 mm, in a range of 75 mm to 150 mm, in a range of 100 mm to 150 mm, or in a range of 55 mm to 85 mm.

A distance between a front upper side of the application part 82 and the fall-edge 67 may be in a range of 25 mm to 350 mm, in a range of 50 mm to 300 mm, in a range of 75 mm to 250 mm, in a range of 100 mm to 200 mm, in a range of 110 mm to 175 mm, or in a range of 120 mm to 155 mm.

A front application part 59 is in a plane parallel to the plane of upper side of application part 60. These planes are spaced apart in a distance in a range of 1 mm to 50 mm, in a range of 2 mm to 40 mm, in a range of 4 mm to 30 mm, in a range of 5 mm to 20 mm, or in a range of 7.5 mm to 15 mm. The distance may be between the front upper side of application part 82 and a front application part 59 measured in top view. The applicator 31 may comprise the outlet 58 between front upper side of application part 82 and the front application part 59. Such orientation of the outlet 58 enables to direct air away from the patient. The outlet 58 is on opposite side of the applicator 31 with respect to the inlet 66. Such configuration enables to direct air in a direction parallel to the magnetic field generating device 4.

The handle 57 may form an opening 81 on the upper side of the applicator. The handle 57 may extend over at least application part 62 of the applicator 31.

The outer contour of the handle 57 may comprise a first outer handle portion 84 extending in a direction corresponding with a shape of the upper side of non-application part 70. The first outer handle portion 84 may be bended to a third outer handle portion 78 via a second outer handle portion 77.

The first outer handle portion 84 may be oriented with the third outer handle portion 78 in an angle in a range of 130° to 185°, in a range of 135° to 180°, in a range of 140° to 185°, in a range of 145° to 185°, or in a range of 165° to 179°.

In some aspects, the first handle portion and the third handle portion may not be oriented by an angle, e.g. third handle portion and first handle portion are one piece.

First handle portion may be configured to couple the handle to the applicator. The handle 57 may comprise a plurality of portions, e.g. two three, four or more. A first portion may be configured to couple the handle to the applicator (positioning plate). A second portion may couple the first portion to a third portion, wherein the third portion may be configured to be distanced from the positioning plate. The third portion may be coupled to gripping portion.

Dimension of the first, second and third portions may establish a distance of the gripping portion from the applicator plate. A distance of the gripping portion and the applicator plate may be at least 10 mm to enable easy griping the gripping portion by a hand of the operator. Each portion of the handle may include an inner portion and outer portion. Inner portion may be positioned closer to the center of the applicator.

The outer contour of the handle 57 may correspond to inner contour of the handle 57. A first inner handle portion 76 may be parallel to the first outer handle portion 84, a second inner handle portion 83 may be parallel to the second outer handle portion 77 and a third inner handle portion 79 may be parallel to the third outer handle portion 78. Inner and outer handle portions are in a plane. A distance of respective inner handle portion and outer handle portion may be in a range of 1 mm to 75 mm, in a range of 5 mm to 60 mm, in a range of 10 mm to 50 mm, in a range of 15 mm to 40 mm, or in a range of 20 mm to 50 mm (measured in said plane) A distance between left and right second inner handle portions may be in a range of 25 mm to 300 mm, in a range of 50 mm to 250 mm, in a range of 75 mm to 200 mm, in a range of 100 mm to 175 mm, or in a range of 100 mm to 150 mm. A distance between cut edge 75 and front application part 59 may be in a range of 50 mm to 400 mm, in a range of 75 mm to 300 mm, in a range of 100 mm to 250 mm, in a range of 120 mm to 200 mm, or in a range of 125 mm to 150 mm.

Front inner handle portion 80 may be spaced apart from the front outer handle portion 73 by a distance in a range of 1 mm to 75 mm, in a range of 5 mm to 60 mm, in a range of 10 mm to 50 mm, in a range of 15 mm to 40 mm, or in a range of 20 mm to 50 mm. A front handle portion may rise in front handle rising portion 71 from the front inner handle portion 80 to the front top handle portion 73 and may fall from the front top handle portion 73 to the front outer handle portion 73. An angle between rising plane of front handle rising portion 71 and falling plane of falling edge of handle 72 may be in a range of 60° to 150°, in a range of 65° to 145°, in a range of 75° to 140°, in a range of 85° to 135° or in a range of 90 to 125°.

The front lower handle portion 69 of the handle may be substantially planar and may be oriented to the upper side of application part 60 in a convex angle in a range of 5° to 90°, in a range of 8° to 80°, in a range of 10° to 65°, in a range of 12° to 45°, or in a range of 15° to 35°.

A mutual orientation of the front inner handle portion 80 with the front outer handle portion 73, a distance between them, and a distance between front top handle portion 73 and the front lower handle portion 69 may be designed to be comfortably gripped by the operator to enable comfortable and correct positioning of the applicator.

From a perspective of the operator's hand, the front handle rising portion 71 may be contacted by metacarpus, the falling edge of handle 72 may be contacted by proximal phalanxes and the front lower handle portion 69 by middle phalanx. Distal phalanxes contacts front inner handle portion 80.

A distance between front application part 59 and front inner handle portion 80 may be in a range of 0.5 mm to 250 mm, in a range of 1 mm to 100 mm, in a range of 5 mm to 80 mm, in a range of 10 mm to 75 mm, in a range of 15 mm to 60 mm, in a range of 20 mm to 50 mm, or in a range of 25 mm to 40 mm measured in floor plan of top of the applicator top view. A distance between front application part 59 and lower side of the application part 64 may be in a range of 10 mm to 250 mm, in a range of 20 mm to 200 mm, in a range of 25 mm to 175 mm, in a range of 50 mm to 150 mm, or in a range of 70 mm to 100 mm measured in side view. This mutual orientation of the handle 57 and distances between handle 57 and the application part 62 may enable comfortable gripping the handle 57 such that the handle 57 may be fully gripped by operator's hand.

Upper side of application part 60 may be configured to be positioned away from the patient.

The handle 57 may further comprise a lighting element 68. The lighting element emits light during treatment. The lighting element may be a light emitting diode. The lighting element may be positioned along the length of the handle 57

The handle may form a concavity 85 with the application part.

Non-application part of the applicator may comprise a fluid mover e.g. blower or fan. Upper side of the non-application part is substantially planar. The upper side of the non-application part may comprise positioning plate and an applicator user interface. In some aspects, the applicator user interface comprises one or more buttons. In some aspects, the buttons may include a single impulse button 87b for providing a single magnetic impulse. Further, increase button 87a and decrease button 87c may be configured to regulate magnetic flux density (through communication with the control unit). The upper side of the non-application part 70 may comprise positioning plate and buttons. Buttons may include a single impulse button 87b for providing a single magnetic impulse. Further, increase button 87a and decrease button 87c may be configured to regulate magnetic flux density (e.g. through communication with the control unit). The buttons may be close to the back portion of non-application part 86. Position of buttons may enable an operator to use one hand only to provide single magnetic impulses with different value of magnetic flux density in order to find the motor threshold. The operator may adjust magnetic flux density, apply single magnetic impulses and adjust position of the applicator by using only single hand.

The upper side of the applicator 31 positioned further from the patient may comprise a positioning plate comprising markers (e.g. visual element described below) for comfortable positioning of the applicator 31. The markers may be visually distinctive and comprise for example a carving, recess and/or color different from the rest of the applicator and/or positioning plate. Colors may be interpreted as a surface reflecting a specific wavelength and/or spectra in band between 380 nm and 750 nm, e.g. blue in a range of 450 nm to 495 nm or red in a range of 620 nm to 750 nm. Markers may be of various shape, for example linear, circular, dot, arrow, cross, pointer hand, or triangle.

In some aspects, the applicator may comprise a positioning system on the applicator's surface. The positioning system may comprise at least two markers positioned on the applicator's surface to enable comfortable positioning of the applicator. The markers may be on any visible surface of the applicator (e.g. on top of the applicator, or around perimeter of the applicator). A first marker may be in a direction configured to be oriented towards an ear of the patient and a second marker may be in a direction configured to be oriented towards a nose of the patient. The first and second markers may be dot, line, arrow, pictogram, or any other visual indicator. The first and the second markers may be lines, where the first marker may be perpendicular to the second marker.

In some aspect operating member may be positioned proximate to the positioning plate. The operating member may be configured to send instruction to control unit to generate impulse and/or adjust magnetic flux density. The operating member may be e.g. button, rotary knob, track point, slider, touchscreen or any other user interface.

Figure 27:
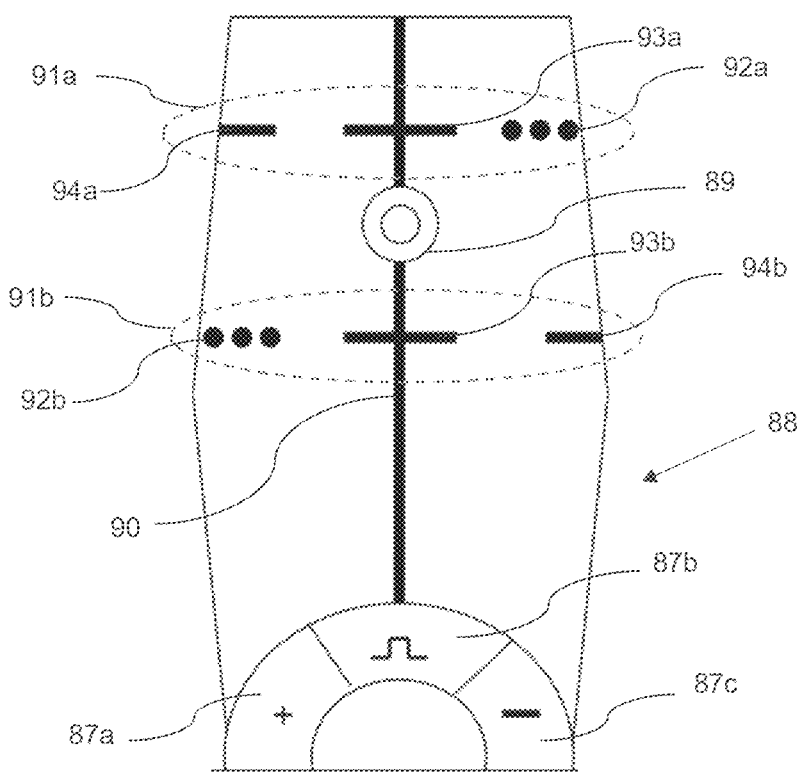
FIG. 27 illustrates a scheme of an exemplary positioning plate, according to some aspects.

FIG. 27 illustrates an exemplary positioning plate 88 with buttons 87a, 87b and 87c. The positioning plate 88 may include at least one visual element. The visual elements may include a central visual element (e.g., double circle mark), a center line, a first visual element, a second visual element, a third visual element, a fourth visual element, a fifth visual element and/or sixth visual element.

A central visual element 89 (e.g. double circle mark) may be present on the upper side of the applicator and/or on the positioning plate. The central visual element 89 may refer to a center of magnetic field generating coil, wherein the magnetic field generating device is positioned within the casing below the central visual element 89. Alternatively the positioning plate may lack central visual element 89.

A center line 90 in a direction from back side of applicator to front side of applicator extends from the operating buttons to the front of the upper side of the application part and intersects the central visual element 89. This line is to be aligned with left ear and right ear of the patient to set the magnetic field generating coil to correct lateral position to find motor threshold point.

Two markers 91a and 91b may be positioned laterally to the central visual element 89. First marker 91a includes a first visual element 92a, a second visual element 93a and a third visual element 94a. In some aspects, the first visual element 92a may be a triple dot mark, the second visual element 93a may be a line mark and the third visual element 94a may be a short line. Second cross mark 91b includes a fourth visual element 92b, a fifth visual element 93b and a sixth visual element 94b. In some aspects, the fourth visual element 92b may be a triple dot mark, the fifth visual element 93b may be a line mark and the sixth visual element 94b may be a short line.

Alternatively markers 91a and/or 91b may include a line perpendicular to center line 90.

First visual element 92a and/or fourth visual element 92b may be aligned with corresponding pillow visual element on a positioning pillow, which maintains patient's head in stable position. The second visual element 93a crossing the center line 90 may provide a line between the first visual element 92a and the third visual element 94a. The fifth visual element 93b crossing the center line 90 may provide a line between the fourth visual element 92b and sixth visual element 94b. The third visual element 94a and/or the sixth visual element 94b positioned close to edge of the upper side of the application part may be aligned toward the patient's nose in a treatment position. The third visual element 94a may be on an opposite side from the first visual element 92a. The sixth visual element 94b may be on an opposite side from the fourth visual element 92b. Markers 91a and 91b may be positioned in a single linear direction. The second visual element 93a crossing the center line 90 may be between the first visual element 92a and third visual element 94a. The fifth visual element 93b crossing the center line 90 may be between the fourth visual element 92b and the sixth visual element 94b. The third visual element 94a and the first visual element 92a may be on an opposite side of the upper side of the application part. The sixth visual element 94b and the fourth visual element 92b may be on opposite side of the upper side of the application part. Marker 91a may be on a different side of central visual element 89 than marker 91b. Both marker 91a and marker 91b may be mutually oriented upside-down. Such position of marker 91a and marker 91b enables versatile positioning for left-handed operator and/or for right-handed operator. The position of the magnetic field generating coil may be identical when the positioning the applicator is executed by a left-handed or a right-handed operator, when respective visual element are aligned according to positioning method described within this disclosure.

In some aspects, the applicator may be positioned by using a laser beam or by using a transparent window.

The front application part 59 may be spaced apart from a lower side of the application part 64 by a distance in a range of 0.1 mm to 100 mm, in a range of 0.5 mm to 80 mm, in a range of 1 mm to 75 mm, in a range of 5 mm to 60 mm, in a range of 10 mm to 50 mm, or in a range of 12 mm to 25 mm. The lower side of the application part 64 may include a sphere carving-in. The carving-in sphere may correspond with a shape of at least a part of a surface of a patient's head. The rest of the lower side of the application part 64 may be planar.

In some aspects, the lower side of the application part may be moveable with respect to the upper side of the application part 60. Such movability may enable the magnetic field generating device to be sufficiently close to the patient's head. The magnetic field generating device may be fixed to the lower side of the application part from inside of the applicator.

The moveable lower side of the application part may be coupled to the non-application part by a mechanism enabling partial tilting of the application part with respect to a non-application part, e.g., a joint with restricted range of movement.

In some aspects, a lower side of the application part may be coupled to an upper side of the application part by a member configured to distance the lower side of the application part and the upper side of the application part. The member may be resilient (e.g. a spring, silicon, rubber or elastic fiber such as polypropylene, polyester or elastane). In some aspects, the member enabling distancing the lower side of the application part and the upper side of the application part may be rigid (e.g., a self-winding rope). The member may maintain the lower side of the application part against gravitation force to be in a distance. The gravitation force may extend the member such that the distance between the lower application part and the upper application part increases. When the applicator contacts the patient the member may shorten or be compressed to maintain contact with the patient's head, even though the upper side of application part slightly moves. The distance between the lower application part and the upper application part may be shorter than when the applicator is not in contact with the patient. Such mechanism may be positioned directly in a positioning arm to provide the same functionality as the member for distancing the lower side of the application part. In some aspects, a rigidity of the end link of fourth link 29 may be below 500 MPa. In some aspects, stiffness of the last joint may be in a range of $10^3$ N/m to $10^9$ N/m, in a range of $10^4$ N/m to $10^8$ N/m, or in a range of $10^6$ N/m to $10^8$ N/m.

In some aspects, a proximity sensor may be used for monitoring proximity of applicator from patient's head. The proximity sensor detect a distance between the patient and the lower part of the applicator. A signal corresponding to a distance of the applicator from the patient's head may be sent to control unit. The control unit may adjust a value of magnetic flux density based on the distance change to maintain a predefined magnetic flux density value. For example, a first value of magnetic flux density at a first distance may induce equal electric current to a second value magnetic flux density at a second distance different from the first distance. The proximity sensor may be inductive, capacitive. ultrasonic, infrared, photoelectric, magnetic electric (e.g. Hall sensor), or any other type of proximity sensor. If the proximity sensor is an inductive proximity sensor, a metallic member may be placed onto patient's head.

In some aspects, an optical proximate sensor, e.g. infrared or photoelectric, may be in the lower part of the applicator. The optical proximate sensor may include an emitter and a receiver. The emitter may emit optical waves directed towards the patient's head. The receiver may detect infrared optical waves reflected by the patient's head. A reflective member may be placed on the patient's head to reflect the optical waves towards the receiver. The receiver may generate an electric signal based on the received optical waves. The signal may be directed to the control unit.

In some aspects, the optical wave may be directed towards the patient's head via optical fiber. The distance may be measured by an optical sensor detecting time of flight between the emitter and receiver. The time of flight may be measured as time difference between emitting a pulse of the optical waves and detecting the pulse by the receiver.

In some aspects an ultrasound proximity sensor may be used. The emitter may emit an ultrasound wave which may be reflected by patient's head. The receiver may detect and measure the reflected ultrasound waves to determine a distance between the applicator and patient's head. The ultrasound proximity sensor may generate an electric signal corresponding to the distance of the lower side of the applicator. The electric signal may be directed to the control unit.

In some aspects, a ball and at least one accelerometer may be used for monitoring position change for adjusting the value of the magnetic flux density. The ball may change position as the applicator is moved. The accelerometer may determine a motion of the ball based on measured voltage. The measured voltage may correspond position change.

The accelerometer may have three axes. In some aspects, a plurality of single axis accelerometers may be used. The plurality of single axis accelerometers may measure the motion in mutually oriented axes defined by an angle. The angle may be in a range from 75° to 115°. In some aspects, three single axis accelerometers may be mutually oriented as three different faces of virtual cube, where the walls share one common vertex.

The device may comprise a positioning pillow. In some aspects, the positioning pillow may not be a component of the device, but the positioning pillow may be delivered with a device. In some aspects, the positioning pillow may be delivered separately.

The positioning pillow may be made of foam, e.g., memory foam or latex foam. The positioning pillow may be anatomically shaped. In some aspects, the positioning pillow may be made of polyester fiber-fill, or a combination with other materials used for manufacturing pillows, or any other biocompatible material adapted to be easily cleaned.

Figure 28:
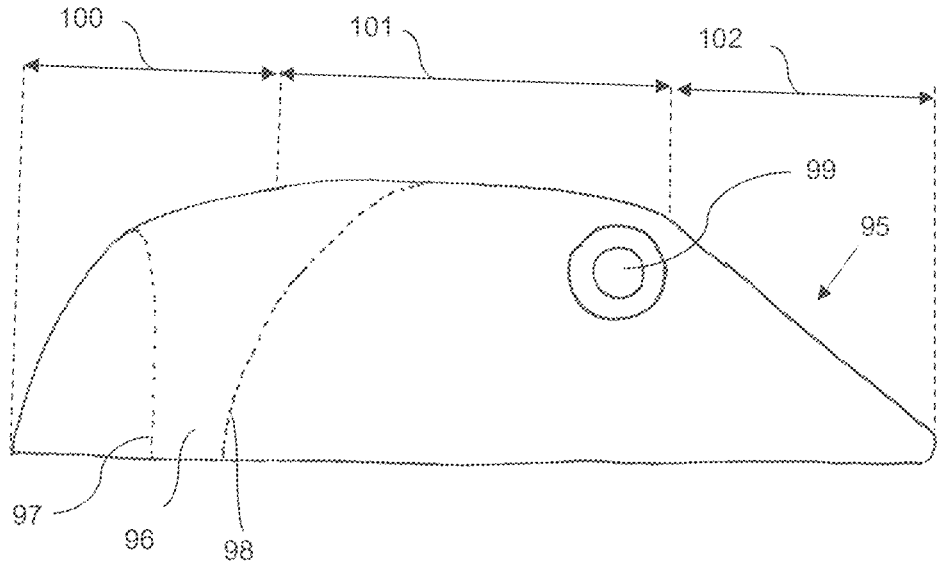
FIG. 28 illustrates a side view of an exemplary positioning pillow, according to some aspects.

FIG. 28 illustrates a side view of the positioning pillow 95 (full line). The height increasing portion 102 may increase from the front side to the top portion. The central portion 101 may be substantially flat and may comprise the highest point. Height decreasing portion 100 goes from central portion 101 to the pillow rear side 104 of the positioning pillow 95. The height decreasing portion 100 may be separated from the height increasing portion 102 by the central portion 101. The height increasing portion 102 may be configured to support at least part of patient's back and/or neck.

Dotted line illustrates inner surface of recess 96 ending in orifice. (described below) Shape of recess 96 may be designed to maintain patient's head in stable position. At least part of patient's crown (corona capitis or vertex) fits into the recess 96 such that the head may be maintained in the recess 96 by gravitational force. The recess 96 includes front portion and rear portion opposite the front portion. The recess rear portion 97 increases from the orifice toward positioning pillow rear part 106 to prevent sliding of head upward. The front recess portion increases from recess toward recess front portion 98 to prevent sliding of head downward.

The positioning pillow 95 further includes a pillow locking element 99 on each side. The pillow locking element 99 may comprise a magnetic counterpart to fit another magnetic part in a belt used for maintaining the applicator close to the patient's head. Only one locking element on one side may be used during treatment. Presence of two locking elements (one on each side) may provide free use for left-handed or right-handed operator.

The height of the positioning pillow may be adjustable. The positioning pillow may comprise a height adjusting member (e.g. at least one inflatable cell, or rigid positioning plate). The height adjustable member may be inside the positioning pillow. The at least one inflatable cell may be inflated to increase the height of the positioning pillow, or deflated to decrease the height of the positioning pillow. The profile of the positioning pillow may be adjusted by a plurality of inflatable cells according to the patient's needs. An inflatable cell may be inflated actively or passively prior positioning the patient. An inflatable cell may be actively inflated after positioning the patient on the positioning pillow. The inflatable cell may comprise a resilient member (e.g. a spring) which may be compressed by a weight of the patients head. In some aspects, the inflatable cell may comprise a resilient porous material such as foam which may include a full volume of air during in relaxed state (e.g., before positioning the patient) and may be partially deflated by force exerted by positioning the patient's head onto the positioning pillow.

FIG. 45*a* illustrates a cross-section of exemplary height adjustable pillow comprising a plurality of inflatable cells 45.01 inside pillow 95. Inflatable cells 45.01 may be vertically oriented within height increasing portion 102, and horizontally oriented within central portion 101.

In some aspects, the rigid positioning plate coupled to platform 109 may be used. The positioning plate may adjust the height of the pillow by translational or rotational motion. The positioning plate may be coupled to platform 109 by a height adjusting column propelled or by a linear actuator. The positioning plate may be coupled to platform 109 by an angle adjusting mechanism.

The angle adjusting mechanism may be manual, semi-manual or electric. An Automatic angle adjusting mechanism may include electronic components such as an actuator. In some aspects, a rotary electric actuator, such as a stepper motor or servomotor, may be used. A manual angle adjusting mechanism may comprise a rotational member controlled by an operator or the patient. The rotational member may be gripped by the operator. The rotational member may turn the positioning plate with respect to the platform 109. A friction between the positioning plate and the platform may be sufficient to prevent free collapsing of the positioning plate onto the platform. The rotational member may be circular or oval shaped.

FIG. 45b illustrates a cross-section of exemplary height adjustable pillow comprising height adjusting mechanism. Height adjusting mechanism 45.02 may comprise platform lever 45.03, height adjusting lever 45.04, and upper plate 45.06 with sliding member 45.07. Platform lever 45.03 may be in contact with platform 109 of pillow 95. Platform lever 45.03 and height adjusting lever 45.04 may be connected by joint 45.05 enabling mutual rotational movement. Rotation in joint 45.05 may be configured to change mutual orientation of platform lever 45.03 and height adjusting lever 45.04. The mutual orientation may be defined by an angle in joint 45.05. Height adjusting lever 45.04 may comprise sliding member 45.07 configured to be moved along horizontal plate 45.06. The movement of sliding member 45.07 along horizontal plate 45.06 may be configured to adjust the height of central portion 101.

In some aspects, an angle adjusting mechanism may include a lever and at least one spring. The spring may be a radial spring. The radial spring may provide a highest position for the positioning plate. The radial spring may be compressed. The lever may enable compressing of the positioning plate. For example, the lever may comprise a gear part and may lock a counter-gear part on the positioning plate. The joint of the positioning plate and the platform may include the radial spring such that the radial spring automatically releases the positioning plate to the highest position.

Figure 29:
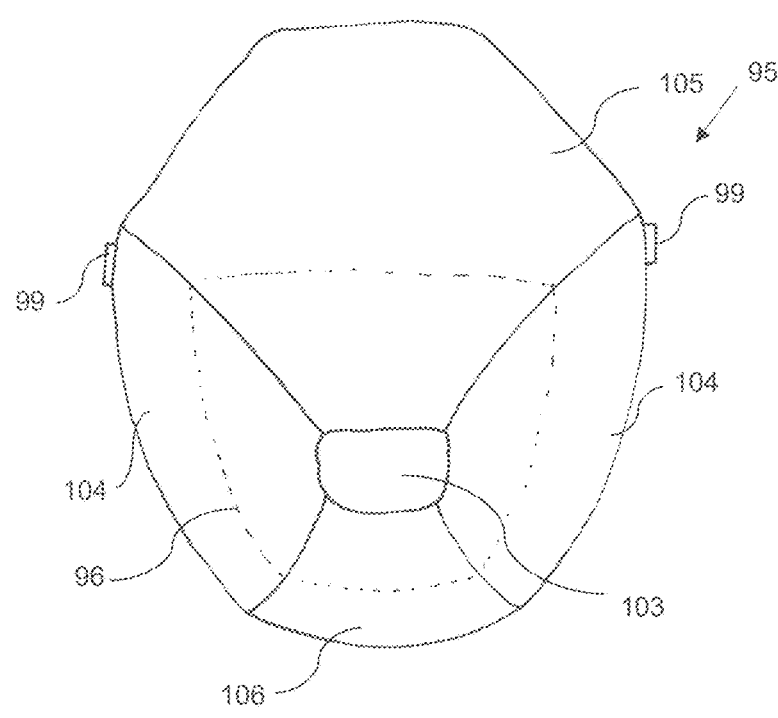
FIG. 29 illustrates a top view of an exemplary positioning pillow, according to some aspects.

FIG. 29 illustrates top view of the positioning pillow 60. The positioning pillow includes substantially flat front part and substantially oval head maintaining part. The head maintaining part may include a recess 96 (enclosed by dotted line) with orifice 103 (full line). The orifice 103 may extend from top portion to the opening in a platform 109. The orifice 103 fits at least part of the patient's head, e.g. vertex, parietal region, occipital region etc. The orifice 103 maintains the patient's head in stable position. Side walls of the orifice 103 are configured to prevent lateral motion (e.g. shifting of patient's head), pillow front part 105 may be configured to prevent downward movement of the head and pillow rear part 106 may be configured to prevent upward movement of the head. Conical surfaces of the orifice 103 are adapted to fit any scale of head. In some aspects, recess may be dome shaped, conic dome shaped or oval shape shaped.

Figure 30:
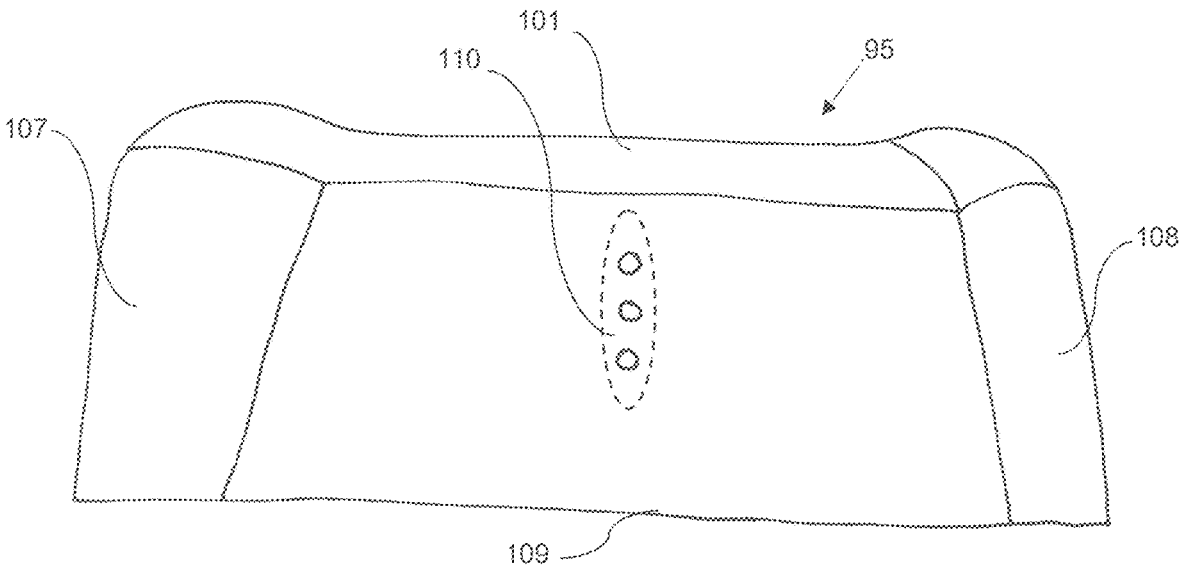
FIG. 30 illustrates a rear view of an exemplary positioning pillow, according to some aspects.

FIG. 30 illustrates the positioning pillow 95 from a rear view. The positioning pillow 95 may include left side wall 107 and right side wall 108 oriented in convex angle with respect to the platform 109 of the positioning pillow 95. The convex angle may provide sufficient lateral stability for the positioning pillow 95. Decreasing portion may be configured to provide sufficient comfortable for the patient during maintaining patient's head. Central portion 101 may be substantially flat in a plane parallel to platform 109.

The positioning pillow 95 may include at least one marker. In some aspects, a plurality of markers may be used, e.g. two, three, four or more. Markers may be used for positioning the patient and/or positioning the applicator with respect to the patient to correct treatment position. In one aspect back portion includes a marker in center. The marker should be aligned with corresponding marker on applicator. For example, the positioning pillow 95 may include a pillow visual element 110. During the positioning of the applicator, the pillow visual element 110 may be aligned with the first visual element or fourth visual element shown on the positioning plate of the applicator.

The device may comprise a belt. The belt may be used for maintaining the applicator close to the patient's head.

The applicator may be maintained close to the patient's head by a belt.

The belt may be coupled to a handle of the applicator through an opening of the applicator. A length of the belt may be adjustable. The length may be adjusted by a mechanical member (e.g. pin-type buckle, side-release buckle, cam buckle or ladder lock slider). In some aspects, the length of the belt may be adjusted via a Velcro.

The belt may be made of a flexible and resilient material such as flexible fabric or elastic textile. The belt may be made of easily cleanable material such as silk, nylon, polyester, elastane, polyethylene or polypropylene.

The belt may be operatively coupled to the positioning pillow from the side.

The first end of the belt may be coupled to the positioning pillow through pillow locking element, while the second end may be loose. During positioning of the applicator, the second end of the belt may be placed through the opening of the applicator and joined with the first end.

The belt may comprise a magnetic part to be inserted into the pillow locking element in the side portion of the positioning pillow. The pillow locking element may comprise a magnetic counterpart. The belt may be coupled by placing the magnetic part to the pillow locking element such that it may be attracted by the counterpart in the pillow locking element. The belt may be released out of the connected position by exerting force in a direction from the hole. The exertion force may be greater than the attracting force to release the belt from the hole.

The positioning pillow may comprise holes including counterparts on both sides to be coupled by left-handed and by right-handed operators.

In some aspects, the belt may be coupled to the positioning pillow by a different manner, e.g. Velcro, press stud, buckle or other mechanical mechanism. In some aspects, the belt may be may be coupled by a threaded fastener, snap-fit fastener, clamp, buckle, or latching mechanism.

In some aspects, the applicator may be maintained to the patient by a mechanical member (e.g. a U-shaped member). The mechanical member may be coupled to the applicator and the patient. For example, a first part of a U-shape may be coupled to the applicator and a second part of the U-shape may be coupled to the patient. The second part may be coupled below the patient's head. The U-shape member may comprise a first portion and a second portion. The first portion may be coupled to the positioning pillow or it may be positioned below the pillow. The second portion may be over the patient's head.

In some aspects, the applicator may be put down onto the patient to maintain the contact by gravitational force.

The applicator may be positioned proximate to the patient. As used here, proximate to includes both contactless and in actual contact with the skin of the patient. The applicator may be positioned in a distance in a range of 0.1 mm to 50 mm or 0.5 to 25 mm or 1 mm to 10 mm from the patient's skin.

In some aspects, the applicator may be in contact with the patient. In some aspect, the applicator may be in contact with the head of the patient. In some aspect, the applicator may be in contact with hair of the patient. In some aspect, the applicator may be in contact with a skin of the patient.

In some aspects, the applicator may be in indirect contact with the patient via a bolus. The bolus may be filled with a material, preferably a fluid, influencing time-varying magnetic field. In some aspects, the bolus may be transparent for time-varying magnetic field. The bolus may be used for distancing the applicator from the patient's body to enable to treat the patient by smaller amount of magnetic flux density. The bolus may be used for treatment of the patient with smaller magnetic flux density than is minimum magnetic flux density generated by device Devices of the disclosure may provide application of time-varying magnetic field to specific brain areas.

Devices of the disclosure may provide application of the time-varying magnetic field to prefrontal cortex. Prefrontal cortex may comprise the cortical networks that support behavioral regulation, for example integration of cognitive processes including attention, working memory and/or inhibitory control. Provided time-varying magnetic field may enhance neuronal activity in the prefrontal cortex to reduce food craving.

The dorsolateral prefrontal cortex may mediate appropriate cognitive strategies necessary to inhibit food-evoked visceral cravings (e.g., secondary to exposure to palatable food and food cues such as food advertisements), thus preventing overindulgence in the absence of physiological energy deficit. In addition, the dorsolateral prefrontal cortex may implement cognitive control by modulating dopamine neurotransmission in the ventromedial prefrontal cortex ventral tegmental area, and nucleus accumbens, resulting in the inhibition of inappropriate responses, devaluation of immediate appetitive rewards, and the implementation of goal-directed behaviors. The dorsolateral prefrontal cortex is a critical functional node for the downregulation of the rewarding properties of energy-dense foods, inhibiting impulsive food consumption in the absence of a physiological energy deficit, thereby enabling individuals to exert control over their consumptive behaviors.

The most anterior part of the frontal cortex (e.g., the prefrontal cortex) contains the cortical networks that support behavioral regulation (e.g., the integration of cognitive processes including attention, working memory, and inhibitory control). Specifically, dietary self-regulation refers to an individual's ability to exert conscious control over food choice and consumption.

Application of time-varying magnetic field to brain of patient may influence production of pleasure hormones, e.g. dopamine, serotonin, endorphins and/or oxytocin. Release of pleasure hormones may help the patient to suppress negative emotions.

Devices of the disclosure may provide application of the time-varying magnetic field to dorsolateral prefrontal cortex, which is area of the prefrontal cortex.

Devices of the disclosure may apply time-varying field to the patient to provide treatment and/or provide therapy to and/or to alleviate and/or to relieve different illnesses, physical states neuropsychiatric disorders or mental and behavioral disorders.

Devices of the disclosure may apply time-varying field to the patient to reduce food cravings and/or binge eating Devices of the disclosure may apply time-varying magnetic field to the patient to temporarily reduce food cravings and/or binge eating The neuropsychiatric disorder, mental disorders and/or behavioral disorders may include major depressive disorder, depression, bipolar disorder/mania, schizophrenia, obsessive compulsive disorder (OCD), post-traumatic stress disorder (PTSD), mania and/or other mood disorders), panic disorder, generalized anxiety, phobic disorders (e.g. panic disorder, phobia or social phobia), pain (e.g. migraine, trigeminal neuralgia), chronic pain disorders (e.g. neuropathic pain such as pain due to diabetic neuropathy, and idiopathic pain disorders such as fibromyalgia and regional myofascial pain syndromes), substance-related disorders (dependence and abuse and withdrawal diagnoses for alcohol, cocaine, amphetamine, caffeine, nicotine, *cannabis*), food related disorder (e.g. binge eating, food cravings such as sugar/salt or fried food), cravings or reward driven behaviors (e.g. associated with an addiction to legal or illegal drugs, gambling, sex), attention deficit/hyperactivity disorder (ADHD), Tourette's syndrome, dissociative disorders, neurodegenerative disease (e.g. Alzheimer's disease, Parkinson's disease, dementia and nerve injury, Amyotrophic Lateral Sclerosis (ALS), Huntington disease, or Multiple Sclerosis (MS)), epilepsy, magnetic seizure therapy (MST), essential tremor, head injury; primary sleep disorders (insomnia, hypersomnia, circadian rhythm sleep disorder), rehabilitation following stroke (neuro plasticity induction), spinal cord injury and regeneration/rehabilitation, premenstrual dysphoric disorder (PMS), dysphagia, aphasia, stuttering, tinnitus and/or cognitive enhancements.

In some aspects, the devices of the disclosure may be configured to apply time-varying field to the patient to provide treatment to major depressive disorder, depression, obsessive compulsive disorder, food cravings and/or binge eating.

In some aspects, the devices of the disclosure may be configured to apply time-varying field to the patient to provide reduction of major depressive disorder, depression, obsessive compulsive disorder, food cravings and/or binge eating.

In some aspects, the devices of the disclosure may be configured to apply time-varying field to the patient to provide temporary reduction of major depressive disorder, depression, obsessive compulsive disorder, food cravings and/or binge eating.

In some aspects, the devices of the disclosure may be configured to apply time-varying field to the patient to provide temporary reduction food cravings and/or binge eating.

In some aspects, the devices of the disclosure may be configured to apply time-varying field to the patient to provide improvement of mental well-being, major depressive disorder, depression, obsessive compulsive disorder, food cravings and/or binge eating.

In some aspects, the devices of the disclosure may be configured to apply time-varying field to the patient to provide increase of mental well-being and/or will power.

In some aspects, the devices of the disclosure may be configured to apply time-varying field to the patient to provide relieve of major depressive disorder, depression, obsessive compulsive disorder, food cravings and/or binge eating.

In some aspects, the devices of the disclosure may be configured to apply time-varying field to the patient to provide alleviate of major depressive disorder, depression, obsessive compulsive disorder, food cravings and/or binge eating.

The methods using the device may include application of the magnetic field to a target location. The devices may be configured to apply the magnetic field to the target location. The target location may be a location in the body of the patient, e.g. central nervous system including a brain and a spinal cord. The target location may be reached by the magnetic field generated by the magnetic field generating device positioned in the applicator. In order to reach the target location by the magnetic field, the applicator may be positioned in a target location.

The target location may comprise the left dorsolateral prefrontal cortex, a right dorsolateral prefrontal cortex, a temporal lobe and other parts of the central nervous system.

When temporal lobes are target locations, two applicators of the device may be used.

The application position is the position of the applicator, where the applicator is able to apply the time-varying magnetic field to reach the target location.

The application position may comprise a position over dorsolateral prefrontal cortex, called as DLFPC position. The DLPFC position may be the application positon suitable for application of the magnetic field to the left dorsolateral prefrontal cortex.

The method of treatment and/or therapy using the device may include method of finding the DLPFC position of the applicator in relation to the head of the patient to apply the time-varying magnetic field to the left dorsolateral prefrontal cortex. The DLPFC position may be suitable for providing time-varying magnetic field to provide treatment and/or therapy. The DLPFC position may be suitable to apply the time-varying magnetic field to the brain of the patient. In some aspects, the DLPFC position may be a position in which the applicator is able to apply the time-varying magnetic field to the left dorsolateral prefrontal cortex. In some aspects, the DLPFC position may be a position in which the applicator is able to apply the time-varying magnetic field to the left dorsolateral prefrontal cortex to reduce the food cravings and/or binge eating.

In some aspects, the patient may be laid down on the patient support. In some aspects, the patient may be seated.

The method of finding the DLPFC position may result in setting the applicator in a position suitable for application of time-varying magnetic field to dorsolateral prefrontal cortex, e.g. left dorsolateral prefrontal cortex. The method of finding an DLPFC position may result in setting the applicator in a position above the head of the patient and/or dorsolateral prefrontal cortex.

The method of finding the DLPFC position may include multiple steps.

In a first step of the method of finding the DLPFC position, patient's head may be set into the positioning pillow such that the patient's crown is positioned in the recess of the positioning pillow and top of patient's head is towards pillow visual element.

Figure 31:
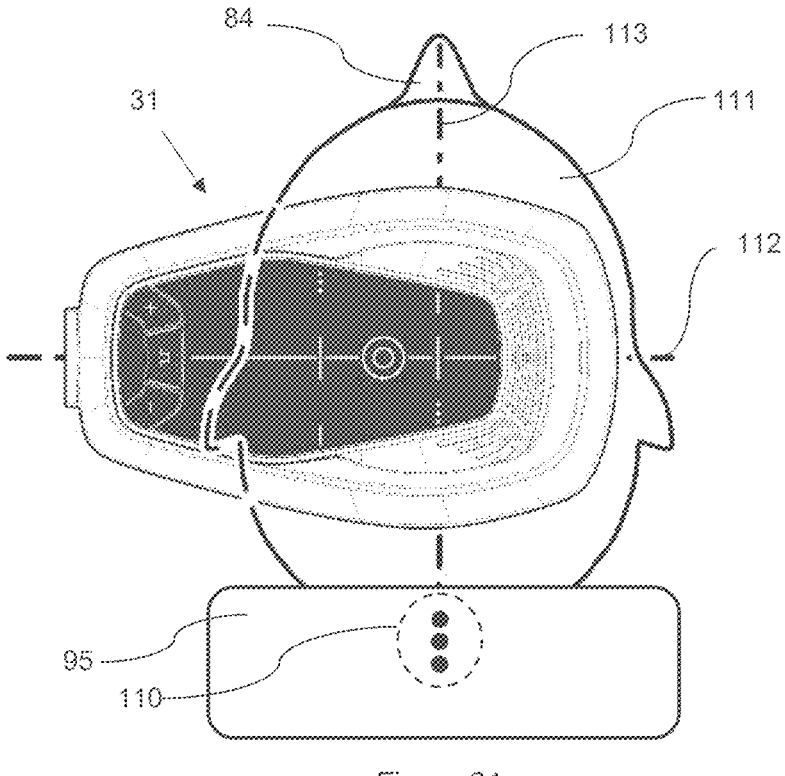
FIG. 31 illustrates a second step of a method of finding an application position of the applicator, according to some aspects.

The FIG. 31 shows a second step of the method of finding the DLPFC position of the applicator. In the second step, the applicator may be positioned proximate to patient's head 111 such that the first visual element 92a on the positioning plate of the applicator is aligned with the pillow visual element 110 of the positioning pillow 95. The third visual element 64a may be directed toward a nose 114 of the patient along a direction of nose-crown axis 113. The third visual element 94a may be directed toward a nose 114 of the patient in median plane. The central line of the positioning plate may be aligned with line in a direction of ear-ear axis 112. The direction of ear-ear axis 112 may include a direction earlobe to earlobe, so the central line of the positioning plate may be aligned with line in a direction of earlobe to earlobe. In some aspects, the direction of ear-ear axis 112 may include eardrum to eardrum, so the central line of the positioning plate may be aligned with line in a direction of eardrum to eardrum. In some aspects, the direction of ear-ear axis 112 may include ear canal to ear canal, so the central line of the positioning plate may be aligned with line in a direction of ear canal to ear canal.

The at least one visual element may be aligned with any other anatomical structure, e.g. eye, nose, ear, earlobe, part of eyebrow, malar process, zygoma etc.

In this position, a central visual element 89 (e.g. the double circle mark) over center of magnetic field generating device may be targeted over a region where a motor threshold value of magnetic flux density may be determined.

The second step of the method of finding the DLPFC position results in the applicator being positioned above and/or in a vicinity of the motor cortex. The second step of the method of finding the DLPFC position further results in the applicator being able to provide time-varying magnetic field in order to find a motor threshold. In an exemplary application, the applicator may provide single magnetic impulses in order to find a sufficient value of magnetic flux density via the application of time-varying magnetic field to the motor cortex of the brain.

As can be seen from the FIG. 31, only a part of positioning plate may be used during the method to find the DLPFC position. To be specific, only the first visual element 92a, the second visual element 93a and the third visual element 64a of marker 91a are used, together with center line 90 (for reference numbers, please see the FIG. 18). Second marker 91b with the fourth visual element 92b, the fifth visual element 93b and the sixth visual element 94b may not be used in the shown aspect. The use of first marker 91a for the second step illustrated in FIG. 22 may be for a right-handed operator. Second marker 91b may be reserved for left-handed operator.

The second step of the method of finding the DLPFC position results in the applicator being positioned above and/or in a vicinity of the motor cortex.

In case of left-handed operator, the applicator itself will be rotated by angle of 180°, so the fourth visual element 92b will be close to the pillow visual element positioned on the positioning pillow.

In a third step of the method of finding the DLPFC position the value of magnetic flux density referred as motor threshold may be found by using operating buttons button 87b. 87a (plus) or 87c (minus) close to back portion of the non-application part. Further a button 87b (single impulse) may be used for applying single magnetic impulses to the motor cortex to establish value of magnetic flux density referred as the motor threshold.

The third step may include using button 87b to apply a single magnetic impulse to the patient. Based on the response of the patient's finger (e.g. thumb), the value of magnetic flux density may be increased by use of the button 87a and/or decreased by use of the button 87c.

The motor threshold value may be a value of magnetic flux density applied to the motor cortex sufficient to induce electric current of sufficient value to induce the lowest level of stimulation to cause a muscle contraction of the patient's thumb. The thumb may be contralateral. The muscle contraction may include a twitch. The motor threshold value may be used to detect that time-varying magnetic field is set at sufficient value of the magnetic flux density to reach the brain. The motor threshold value may be found by increasing magnetic flux density until the patient's finger twitches. In some aspects, the motor threshold value may be accurately determined by repetitively using buttons 87a, 87b and/or 87c. A value of the magnetic flux density causing the motor threshold (e.g., the motor threshold value) may be stored in volatile memory.

In some aspects, the treatment device may generate a pretreatment sequence. The pretreatment sequence may include a train of impulses. A repetition rate be low (e.g. 1 Hz, or 0.5 Hz). A magnetic flux density of subsequent impulses may be gradually increased until the operator determines the motor threshold value has been reached. The increase of the magnetic flux density may be linear. An increase step may be in a range from 0.01 T to 0.2 T, in a range from 0.05 T to 0.15 T, in a range from 0.015 T to 0.1 T, or in a range from 0.025 to 0.085 T. In some aspects, the increase step may be in a range from 1% to 5% of the maximal magnetic flux density generated by the treatment device. In some aspects the increase of the magnetic flux density may be exponential such that the magnetic flux density increase faster in lower values and slower in the greater values. In some aspects, the exponential increase may be a step of 3% of the maximal magnetic flux density generated by the treatment device in a range from 30% to 60%, and a step of 1% for magnetic flux density in a range from 80% to 100% of the maximal magnetic flux density generated by the device.

In some aspects, the pretreatment sequence may generate a train of pulses of constant repetition rate while the magnetic flux density of individual impulses may be adjusted by the operator.

A value of the magnetic flux density causing motor threshold may be stored in volatile memory.

The third step of the method of finding the DLPFC position results in the applicator being positioned above and/or in a vicinity of the motor cortex further with the operator having knowledge of the motor threshold value.

Figure 32:
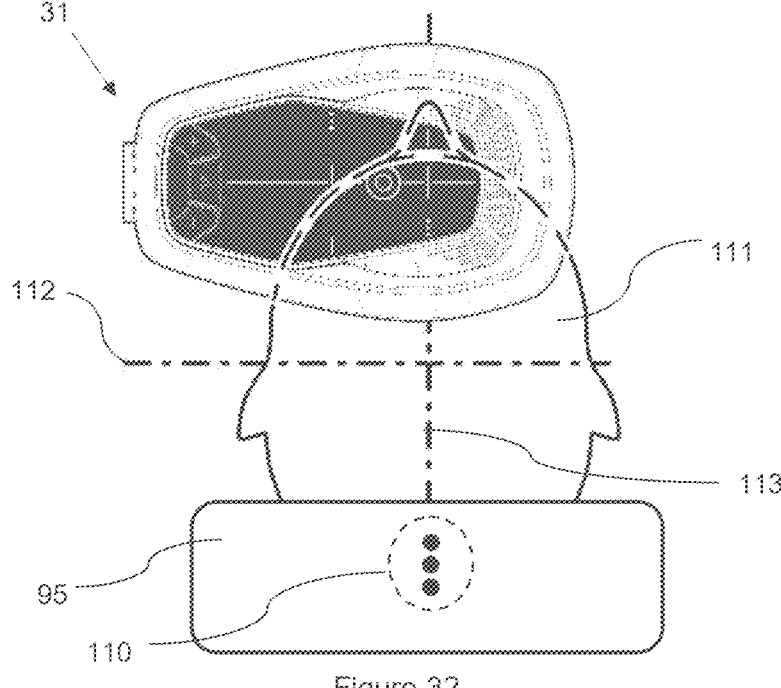
FIG. 32 illustrates a fourth step of a method of finding an application position of the applicator, according to some aspects.

The FIG. 32 shows a fourth step of the method of finding the DLPFC position of the applicator.

In a fourth step of the method of finding the DLPFC position the applicator may be moved forward toward a nose of the patient. The applicator may be moved in such way, that the line defined by marker 91a (and the third visual element 64a) is still pointing towards the nose of the patient and the first visual element 92a on applicator is aligned with pillow visual element on the positioning pillow. The applicator may be moved in direction of the nose-crown axis 113. The applicator may be moved in this direction but around the shape of patient's head 111. The applicator may be moved in the parasagittal plane. The applicator may be moved in this direction for a distance in a range from 2 to 10 cm, 3 cm to 9 cm, or 5 cm to 7 cm. In some aspects, the applicator may be moved in the direction of nose to a distance in a range from 5 cm to 7 cm. A suitable measuring instrument may be used such as a length gauge.

Further, the fourth step may be described in following way. As the motor threshold value is established, the fourth step may include shifting the applicator toward the patient's nose in the same parasagittal plane where the motor threshold magnetic flux density was established.

The fourth step of the method of finding the DLPFC position results in the applicator being positioned above and/or in a vicinity of the left dorsolateral prefrontal cortex, further with the operator having knowledge of the value of magnetic flux density (e.g., the motor threshold value).

The previously described four steps of the method of finding the DLPFC position may be used for a new patient.

The operator may plan to find the DLPFC position on the head of the patient, who was treated before by at least one round of application of time-varying magnetic field from the devices of the disclosure in the same place of stimulation (e.g. hospital, clinic or beauty salon). In that case, the third step of the method of finding the DLPFC position may be omitted, since the operator already remembers and/or noted the motor threshold value of the patient. Also, the motor threshold value may be stored in memory of the device and used by the control unit.

The described method of finding the DLPFC position may be better suited for easier and faster positioning of the applicator than other methods, for example use of a targeting cap or a laser beam. The method of finding the DLPFC position may not require use of targeting cap and/or use of laser beam. Because of use of the positioning plate positioned on the applicator, the does not require use of targeting cap and/or use of laser beam.

In some aspects, the applicator may be coupled to the patient's head by a headband including at least one marker. In some aspects, the applicator may be positioned via a plurality of elastic bands comprising at least one marker, e.g. head band around head and cross-bands through centre, first cross-band may be aligned with ear-ear axis, second cross-band may be aligned with axis vertex-nose. First cross-band may include marker referring to position to find moto threshold. Second cross-band may include a marker for finding the target location.

In some aspects, two applicators may be used. A first applicator may be used to find the target location and correct position of the positioning arm. As the positioning arm may be fixed then the first applicator (preferably having light weight) may be replaced by second applicator. The first applicator and the second applicator has magnetic field generating devices of equal parameters and size. The first applicator may be light weight, e.g. without active cooling. Second applicator may be heavier than the first applicator, e.g. it may include actively cooled coil. The second applicator may comprise magnetic field generating device cooled by liquid, e.g. by water or oil.

After finding the DLPFC position, the method of treatment or use of the device may include application of a time-varying magnetic field to the dorsolateral prefrontal cortex.

The time-varying magnetic field may be applied to the target location in train of subsequent impulses forming an envelope. The envelope may comprise a first time period when a plurality of impulses is generated and with an amplitude of magnetic flux density of the sequential impulses increasing to form an envelope. Envelope may be increasing or decreasing. The control unit sends instruction to energy source to provide energy to energy storage device to be charged to a value Q1. Then the control unit sends instruction to switching device to be switched to discharge the energy storage device to the magnetic field generating device generate an impulse of the magnetic field. The switching device may be switched on for a time period of one impulse. Then the switching device may be switched off and the control unit sends instruction to the energy source to charge the energy storage device on a value Q2, wherein the value of Q2 may be greater than the value Q1. The process of switching and generating the magnetic field may be repeated. The process of sequential charging with increasing value of Q may be repeated until Qn equals to value for generating amplitude of the magnetic flux density equal to the maximal value of the envelope. The increase quotient may be constant for generating linear or non-linear (e.g. exponential) changing envelope. The quotient may be positive to generate increasing envelope. The quotient may be negative for generating decreasing envelope.

The first time period may be fixed. The control unit may adaptively adjust the quotient based on the motor threshold value. The control unit may adaptively adjust rate of increasing/decreasing envelope following the patient's need.

The target location may be susceptible to stimulation by application of higher magnetic flux density.

The time-varying magnetic field may be applied to the patient using the motor threshold value. In some aspects, the value of magnetic flux density applied to dorsolateral prefrontal cortex may be the result of a multiplication of the motor threshold value by a scaling factor. The scaling factor may be greater than 100% of the motor threshold value, such a 110%, 120%, or 140%. In some aspects, the scaling factor may be less than 100% of motor threshold value, such as 90%, 85%, 80%, 70%, or 60%. When the scaling factor is 100%, the value of magnetic flux density applied to brain may be identical to the motor threshold value. When the scaling factor is 120%, the value of magnetic flux density applied to brain is 1.2× higher than the motor threshold value. When the scaling factor is 80%, the value of magnetic flux density applied to brain is result of 0.8× multiplication of the motor threshold value Sub-therapeutic magnetic impulses may be of equal effect as therapeutic magnetic impulses. As the magnetic flux density is lowered, the more energy may be required for generating time-varying magnetic field. Therapeutic impulses may be impulses of the time-varying magnetic field with a magnetic flux density of at least a motor threshold value, e.g. motor threshold, or 120% motor threshold. Sub-therapeutic impulses may be impulses of the time-varying magnetic field with a magnetic flux density below a motor threshold value, e.g. 80% motor threshold, or 60% of motor threshold.

The control unit may send instructions to an energy source to repetitively charge the energy storage device, and send instructions to the switching device to be switched to discharge the energy from the energy storage device to the magnetic field generating device to repetitively generate magnetic impulses. The sequential impulses of the magnetic field may be assembled to form a trapezoidal envelope.

FIG. 33 illustrates an exemplary trapezoidal envelope formed by a plurality of magnetic impulses (e.g. biphasic magnetic impulses) having different values of magnetic flux density. The vertical axis may represent a magnetic flux density. The horizontal axis may represent time. $T_R$ may be the time of increasing amplitude of magnetic flux density, e.g. the amplitude of the magnetic flux density of plurality of sequential impulses may increase. $T_H$ may be the time of maximal amplitude of magnetic flux density, e.g. the amplitude of the magnetic flux density of plurality of sequential impulses may be constant. $T_F$ may be the time of decreasing amplitude of magnetic flux density, e.g. the amplitude of the magnetic flux density of plurality of sequential impulses may decrease. A sum of $T_R$, $T_H$ and $T_F$ may be a trapezoidal envelope duration. In some aspects, $T_R$ lasts 0.7 second, $T_H$ lasts 0.2 second, and $T_F$ lasts 1.1 second to establish trapezoidal envelope duration.

Use of the trapezoidal envelope in the protocol may decrease energy consumption. The stimulation caused by trapezoidal envelope may be equal to stimulation caused by a rectangular envelope. Use of trapezoidal envelope in the protocol may reduce the requirements to cool the magnetic field generating device and/or switching device due to lower energy consumption during generating the trapezoidal shape in comparison with rectangular envelope. Further, the resistive losses may be reduced due to lower temperature of the magnetic field generating device. Time-varying magnetic fields applied in trapezoidal envelopes may be more comfortable for the patient compared to rectangular envelopes.

FIG. 52 illustrates a diagram for generating a trapezoidal envelope. FIG. 52 may be exemplary application of FIG. 33. An initial value of magnetic flux density may be constant for all patients. The initial value of the magnetic flux density may be equal to a terminal value of magnetic flux density. Alternatively, the initial value of magnetic flux density may be different from the terminal value of magnetic flux density. Both of the initial value of the magnetic flux density and the terminal value of the magnetic flux density may be lower than the value of magnetic flux density of an impulse generated during time $T_H$.

The time durations $T_R$, $T_H$ and $T_F$ may be fixed such that the time durations may be equal for all patients. The time durations $T_R$, $T_H$ and $T_F$ may remain the same for all motor threshold values of magnetic flux density.

The control unit may read motor threshold value of magnetic flux density from volatile memory. The control unit may calculate a maximal value of magnetic flux density generated during the time of $T_H$. The maximal value of the magnetic flux density may depend on a scaling factor. The maximal value of magnetic flux density during $T_H$ is given by Equation 3.

$$MFD^{max} = MFD^{MT} \cdot SF \qquad \text{Equation 3}$$

where $MED^{max}$ is maximal value of magnetic flux density [T] during $T_H$; $MFD^{MT}$ is motor threshold value of magnetic flux density [T]; and SF is scaling factor.

The control unit may calculate an increment. The increment may depend on a repetition rate of impulses, time duration $T_H$, a motor threshold value of magnetic flux density, or a number of impulses generated during time duration $T_H$. The increment is given by Equation 4

$$I = MFD^{max} / N^R \qquad \text{Equation 4}$$

where I is increment [T]; $MED^{max}$ is a maximal value of magnetic flux density [T] during $T_H$; $N^R$ is number of impulses generated during $T_H$.

The control unit may calculate a decrement. The decrement may depend on a repetition rate of impulses, time duration $T_H$, motor threshold value of magnetic flux density, or number of impulses generated during time duration $T_H$. The decrement is given by Equation 5

$$D = MFD^{max} / N^F \qquad \text{Equation 5}$$

where D is decrement [T]; $MED^{max}$ is maximal value of magnetic flux density [T] during $T_F$; $N^F$ is number of impulses generated during $T_F$.

The control unit may send instructions to an energy source to charge an energy storage device to be discharged through the switching device to the magnetic field generating device to generate an impulse of the magnetic field. Impulses during $T_R$ are generated with a magnetic flux density given by Equation 6

$$MFD = I \cdot SN^R \qquad \text{Equation 6}$$

where MFD is a magnetic flux density of the impulse [T]; I is increment [T]; and $SN^R$ is serial number of impulse generated during $T_R$.

The control unit may send instructions to an energy source to charge an energy storage device to be discharged through the switching device to the magnetic field generating device to generate an impulse of the magnetic field. Predefined number NH of impulses is generated during $T_H$. Each impulse during $T_H$ has an equal magnetic flux density irrespective of its serial number $SN^{HH}$. Impulses during $T_H$ are generated with a magnetic flux density given by Equation 7

$$MFD=MFD^{max} \qquad \text{Equation 7}$$

where MFD is magnetic flux density of the impulse [T]; and $MED^{max}$ is maximal value of magnetic flux density [T].

The control unit may send instructions to an energy source to charge an energy storage device to be discharged through the switching device to the magnetic field generating device to generate an impulse of the magnetic field. Impulses during $T_F$ are generated with a magnetic flux density given by Equation 8

$$MFD=MFD^{max}-(D \cdot SN^F) \qquad \text{Equation 8}$$

where MFD is magnetic flux density of the impulse [T]; $MFD^{max}$ is maximal value of magnetic flux density [T]; D is decrement [T]; and $SN^F$ is serial number of impulse generated during $T_F$.

The trapezoidal envelope may provide enhanced stimulation by the magnetic impulse applied to the target location. The target location may be stimulated by sub-therapeutic impulses and by therapeutic impulses. The sub-therapeutic impulses may increase the patient's comfort during the treatment. The biological structures may be stimulated by gradually increasing and/or decreasing impulses such that the biological structure may be treated more effectively. The increasing and/or decreasing impulses may influence the biological structures smoothly and the stimulation may be unobtrusive for the patient.

The trapezoidal envelope may be applied to a target location of the patient to by the applicator. The increasing portion of the trapezoidal envelope may induce increasing stimulation by increasing sub-therapeutic impulses to the therapeutic impulses. The stimulation by sub-therapeutic impulses may increase susceptibility of the biological structure (e.g., cell, neuron or spinal fluid) in the target location. The stimulation by therapeutic impulses may cause a strong stimulation of the biological structure. The increasing sub-therapeutic impulses may induce the biological structures in the target location to be receptive for the treatment by therapeutic impulse.

A plurality of impulses with equal value of magnetic flux density may be applied to the target location to cause strong stimulation after the stimulation by impulses with sequentially increasing magnetic flux density. The therapeutic impulses may sufficiently stimulate the biological structure in the target location to induce an electric current in the target location.

The target biological structure may be stimulated by impulses with sequentially decreasing the magnetic flux density after a last impulse of the plurality of impulses. The plurality of impulses may have equal magnetic flux density. The impulses with decreasing magnetic flux density may include therapeutic impulses causing strong stimulation and sub-therapeutic impulses. The sub-therapeutic impulses with decreasing magnetic flux density may continually restore the biological structure and balance natural activities while stimulating by sub-therapeutic impulses.

The device may provide a protocol during operation. The protocol may be stored in the memory of the device and used by the control unit.

The device may provide a protocol including time-varying magnetic field including magnetic impulses and a repetition rate. The repetition rate may be defined as number of magnetic impulses per second. The repetition rate may be in a range of 0.1 Hz to 1000 Hz, 0.1 Hz to 700 Hz, 0.1 Hz to 500 Hz, or 0.1 Hz to 200 Hz. The cooling of switching device described within the disclosure may allow for use of higher repetition rates.

A repetition rate of impulses may vary during a train. Modulation in the repetition rate may be in a trapezoidal envelope. The repetition rate may increase or decrease in a range from 1 Hz to 150 Hz, in a range from 2 Hz to 100 Hz, in a range from 3 Hz to 50 Hz, in a range from 5 Hz to 30 Hz, or in a range from 1 Hz to 25 Hz. The repetition rate may increase for a time period in a range from 0.1 s to 20 s, in a range from 0.2 s to 10 s, in a range from 0.3 s to 7 s, in a range from 0.5 s to 5 s, or in a range from 0.5 s to 15 s. The repetition rate with a constant repetition rate may be generated for a time period in a range from 0.2 s to 30 s, in a range from 0.5 s to 20 s, in a range from 0.7 s to 15 s, in a range from 1 s to 10 s, or in a range from 0.5 s to 7 s. In some aspects, the increasing repetition rate may be from 15 Hz to 20 Hz for 0.7 s, generating impulses of 20 Hz for 0.3 s and decreasing repetition rate from 20 Hz to 15 Hz for 1 s.

The device may provide a protocol including time-varying magnetic field including magnetic impulses. The impulses may have the same or different values of the magnetic flux density. At least two magnetic impulses within one session may have same magnetic flux density values. The magnetic flux density may be measured by a fluxmeter on the outer surface of the applicator, between the magnetic field generating device and the patient. In some aspects, the magnetic flux density may be derived via a voltage on a capacitor and/or by a control unit. The device may provide the time-varying magnetic field having a magnetic flux density in a range of 0.1 Tesla to 10 Tesla, 0.1 Tesla to 8 Tesla, 0.1 Tesla to 5 Tesla, 0.1 Tesla to 4 Tesla, 0.1 Tesla to 3.8 Tesla, 0.25 Tesla to 8 Tesla, 0.25 Tesla to 5 Tesla, 0.25 Tesla to 4 Tesla, 0.25 Tesla to 3.8 Tesla, 0.5 Tesla to 8 Tesla, 0.5 Tesla to 5 Tesla, 0.5 Tesla to 4 Tesla, or 0.5 Tesla to 3.8 Tesla. In some aspects, the device may provide the time-varying magnetic field having a magnetic flux density in a range from 0.1 Tesla to 7 Teslas, in a range from 0.2 Tesla to 5 Tesla, in a range from 0.4 Tesla to 4 Tesla, or in a range from 0.7 Tesla to 2.5 Tesla.

The device may provide a protocol including time-varying magnetic field with same or various value of magnetic flux density. The time-varying magnetic field may include a plurality of magnetic impulses. The magnetic impulse may have impulse width. The impulse width may be in a range of 1 us to 1000 μs, 10 us or 700 μs, 100 us to 600 μs, or 200 us to 400 μs.

The time-varying magnetic field may be generated with a maximal value of the magnetic flux density derivative may be up to 5 MT/s, e.g. in a range of 0.3 to 800 kT/s, in a range of 0.5 to 400 kT/s, in a range of 1 to 300 kT/s, in a range of 1.5 to 250 kT/s, in a range of 2 to 200 kT/s, or in a range of 2.5 to 150 kT/s. In exemplary applications the maximal value of the magnetic flux density derivative may be in a range of 5 kT/s to 100 kT/s, in a range of 10 kT/s to 50 kT/s, or in a range of 20 kT/s to 40 kT/s. The value of magnetic flux density derivative may correspond to induced current within the tissue.

The time-varying derivative of the magnetic flux density is defined by Equation 9.

$$dB/dt, \qquad \text{Equation 9}$$

where: dB is magnetic flux density [T]; dt is time derivative [s]. The time-varying magnetic field may be applied to the patient during a treatment lasting in a range from days or weeks, such as in a range from 1 day to 10 weeks, in a range from 5 days to 6 weeks, in a range from 1 week to 5 weeks, in a range from 2 to 4 weeks, or in a range from 1 week to 3 weeks.

The treatment may include a plurality of treatment sessions. A treatment session may be one application of a treatment protocol. The treatment session may last in a range from 1 min to 240 min, in a range from 5 min to 100 min, in a range from 10 min to 60 min, in a range from 15 min to 30 min, or in a range from 20 min to 45 min.

The protocol may include at least one train, wherein the train is a group of at least two magnetic impulses, e.g. 2, 10, 20, 40, 50, 100 or 1000. The train may include a plurality of impulses in a range from 2 to 1000, in a range from 5 to 500, in a range from 10 to 250, in a range from 50 to 100, or in a range from 20 to 45. The protocol may include at least one burst, wherein the burst includes a train with an inter-train pause, wherein the inter-train pause may comprise no generated magnetic impulses. The device may not apply the time-varying magnetic field during the inter-train pause. The inter-train pause period may be between the trains.

A plurality of impulses may be applied during the treatment session such as in a range from 50 to 20,000, in a range from 1000 to 20,000, in a range from 2000 to 15,000, or in a range from 7500 to 12,500.

A total number of impulses for treatment may be in a range from 1000 to 50,000, in a range from 7500 to 40,000, in a range from 15,000 to 30,000, or in a range from 18,000 to 25,000.

The number of impulses in sequential trains may increase during the treatment. In some aspects, the repetition rate of impulses in the train may increase. In some aspects, the time duration of the train may increase. In some aspects, number od impulses in sequential trains, the repetition rate in train or time duration of trains may increase within the treatment. Increasing the number of impulses in sequential train may increase susceptibility of the biological structure in the target location such that the later trains of the treatment may include the highest number of the impulses to cause the greatest stimulation. The treatment may be sufficiently comfortable because increasing number of the impulses in sequential trains may condition the biological structure to the high number of impulses.

An exemplary Protocol 1 includes plurality of trains, wherein one train lasts for 4 seconds and inter-train pause lasts for 11 seconds. Repetition rate of magnetic impulses may be 10 Hz. The exemplary protocol 1 may provide 3000 magnetic impulses during a treatment session. The exemplary protocol 1 may provide 75 trains during a treatment session. Scaling factor may be 120%, therefore the applied value of magnetic flux density is 20% greater than the motor threshold value. The exemplary protocol 1 may be used for treatment of the major depressive disorder.

An exemplary Protocol 2 includes plurality of trains, wherein one train lasts for 2 seconds and an inter-train pause lasts for 20 seconds. Repetition rate of magnetic impulses may be 20 Hz. The exemplary protocol 2 may provide 2000 magnetic impulses during a treatment session. The exemplary protocol 2 may provide 50 trains during a treatment session. Scaling factor may be 100%, therefore the applied value of the magnetic flux density is identical as the motor threshold value. The exemplary protocol 2 may be used for treatment of the obsessive compulsive disorder.

An exemplary Protocol 3 includes two different repetition rates of 18 Hz and 20 Hz. Magnetic impulses may be applied in bursts, wherein each burst may comprise one train of magnetic impulses, and one inter-train pause. Initial part of the exemplary protocol 4 may comprise a burst comprising train lasting 2 second with magnetic impulses having the repetition rate of 18 Hz, and an inter-train period lasting 6 seconds. After the initial part, the Protocol 4 may comprise a main part. The main part may comprise bursts including trains lasting 2 second and inter-train pauses lasting 5 seconds. During the main part, the repetition rate of the magnetic impulses may be alternated, such that the one burst includes magnetic impulses with repetition rate of 18 Hz, while a subsequent burst includes magnetic impulses with repetition rate of 20 Hz. The total number of magnetic impulses applied during a treatment session may be 9764. Scaling factor may be 100%, therefore the applied value of the magnetic flux density is identical as the motor threshold value.

An exemplary Protocol 4 includes three different repetition rates of 12 Hz, 15 Hz and 18 Hz. Magnetic impulses are applied in bursts, wherein each burst may comprise one train of magnetic impulses, and one inter-train pause. The exemplary Protocol 5 may comprise bursts including trains lasting 1.9 second and inter-train pauses lasting 5 seconds. A first burst includes a first train including 24 magnetic impulses having the repetition rate of 12 Hz, a second burst includes a second train including 30 magnetic impulses having the repetition rate of 15 Hz and a third burst includes a third train including 36 magnetic impulses having the repetition rate of 18 Hz. The first burst, second burst and third burst may be repeated in sequence during the protocol. First train, second train and third tram may comprise magnetic impulses forming a trapezoidal envelope. In this envelope, time of increasing magnetic flux density may be 0.7 second, time of maximal value of magnetic flux density may be 0.2 second and time of decreasing magnetic flux density may be 1.1 second. The total number of magnetic impulses applied during a treatment session may be 6300. The scaling factor may be 70%, therefore the applied value of magnetic flux density may be 70% of motor threshold value. The applied value of magnetic flux density may be 30% below motor threshold. The exemplary protocol 5 may be used for treatment of the binge eating or food cravings.

An exemplary Protocol 5 includes trains of single repetition rate lasting 3 seconds with inter-train pause 10 seconds, e.g., trains lasts 13 seconds.

An exemplary Protocol 6 includes trains of three different repetition rates 12 Hz, 15 and 18 Hz. Each train lasts 2 seconds and inter-train pause lasts 5 seconds. The scaling factor may be 100%, therefore the applied value of magnetic flux density applied to the patient equals to the motor threshold value.

An exemplary protocol 7 includes plurality of trains, wherein one train lasts for 2 seconds and an inter-train pause lasts for 10 seconds. The repetition rate of magnetic impulses may be 10 Hz. The exemplary protocol 8 may be used for treatment of the binge eating or food cravings.

An exemplary Protocol 8 may include a plurality of clusters, each cluster including a plurality of trains. Exemplary protocol 8 may include impulses of repetition rate 50 Hz. Each train lasting 60 ms may be followed by 140 ms of inter-train pause. The cluster lasting 2 seconds may comprise 10 trains. The clusters may be generated with inter-cluster pauses lasting 8 seconds each. Protocol 8 may provide 600 impulses in 3 minutes. The protocol may be used for food cravings, or depression.

An exemplary Protocol 9 may include a plurality of trains including impulses of repetition rate 50 Hz. A Train may last 60 ms, followed by 200 ms of inter-train pause. The protocol may provide 600 impulses in 40 seconds.

An exemplary Protocol 10 may include a plurality of trains with three different repetition rates: 20 Hz, 17 Hz and 50 Hz. Trains may be repeatedly applied, a train of 20 Hz may be followed by a train of 17 Hz, followed by a train of 50 Hz. Then another train of 20 Hz, a train of 17 Hz, and 5 trains of 50 Hz may applied. A train of 20 Hz may last 2 seconds followed by an inter-train pause of 10 seconds. A train of 17 Hz may last 2 seconds followed by an inter-train pause lasting 8 seconds. A cluster may include trains of repetition rate of 50 Hz includes 5 trains lasting 100 ms each, followed by a 200 ms inter-train pause. The pause between the cluster and train of 20 Hz may last 12 seconds. The Protocol 10 may be used for treatment of OCD, food cravings, or chemical substance addiction (e.g., nicotine, alcohol or drugs).

An exemplary Protocol 11 may include trains of 18 Hz and trains with impulses modulated in a repetition rate. The train of 18 Hz may last 2 seconds. A train with a modulated repetition rate may begin with impulses of 15 Hz and have a repetition rate gradually increasing to 20 Hz. Increasing repetition rate may last 1 second and then a repetition rate may be maintained at 30 Hz while a magnetic flux density of sequential impulses may decrease for a time period of one second.

The time-varying magnetic field may be applied to laterally corresponding target locations of brain, e.g. left dorsolateral prefrontal cortex and/or right dorsolateral prefrontal cortex. Application to laterally corresponding target locations may increase stimulation on the patient and/or provide different effects of the stimulation.

The device may provide time-varying magnetic field with higher repetition rate to left target location of the brain and time-varying magnetic field with lower repetition rate to right target location, e.g. 20 Hz to left location and/or 1 Hz to right location. The left location might be activated by a high repetition rate while the right location might be inhibited. Such approach might enhance treatment results and/or provide different effects of the stimulation.

The system of this disclosure may be used for complex treatment and/or therapy of the patient. The system may enhance effect of improving visual appearance by synergic effect of applying time-varying magnetic fields to a patient's muscles and/or brain.

The time-varying magnetic field may be applied to a muscle o cause a muscle contraction. Repetitive muscle contraction may be used for muscle toning, improving muscle strength and/or reducing adipose cells by increasing metabolism in and/or in a vicinity of the muscle. The body region may comprise a patient's abdomen, buttock, thigh, calf, bra fat, body handle, chin, arm or shoulder.

Additionally the time-varying magnetic field applied to the patient's brain may suppress food cravings to reduce food intake. The use of the device may reduce the patient's weight and form a healthy shape the patient's body through different applications of time-varying magnetic field(s).

In one aspect the system of the disclosure may include two separate devices. A first device may be a muscle stimulation device, and a second may be a transcranial magnetic device. The muscle stimulating device may apply a time-varying magnetic field to the muscle of the patient to cause a muscle contraction of the muscle in the body region. Further the muscle contraction may increase muscle tone and/or reduce adipose cells in natural way. The transcranial magnetic device may apply time-varying magnetic field to the patient's brain to reduce food cravings. The muscle stimulation device may include at least one applicator. The transcranial magnetic device may include at least one applicator.

The muscle stimulation device may include two applicators, each including one magnetic field generating device. The transcranial magnetic device may include a single applicator including one magnetic field generating applicator.

In some aspects, the applicator of the transcranial magnetic device may include a plurality of magnetic field generating devices, e.g. two, three or more.

In some aspects, the transcranial magnetic device may include a plurality of applicators, e.g. two or more.

In some aspects the system may include one combined device. The combined device may apply time-varying magnetic fields to both the patient's muscle and brain. The combined device may include one or more applicators. The combined device may include at least two applicators. The combined device may include three, four or more applicators.

The combined device may include two applicators. The first applicator may be configured to apply a time-varying magnetic field to a body region of the patient to cause a muscle contraction in the body region. The second applicator may be used for applying time-varying magnetic field to the patient's brain.

The combined device may include three applicators.

In some aspects, when the combined device includes three applicators, the first applicator and the second applicator may be configured to apply a time-varying magnetic field to the body region of the patient to cause muscle contraction in the body region. The first applicator and the second applicator may be positioned independently. The first applicator and the second applicator may be positioned laterally on the patient, e.g. the first applicator may be positioned on left part of patient's abdomen or buttock and the second applicator may be positioned on right part of patient's abdomen or buttock. Each of two applicators may be used for a different body region. In some aspects, two applicators may be positioned on left and right extremities of the patient such as arms, thighs, calves. In some aspects, two applicators may be positioned in different body regions. The third applicator may be used for applying time-varying magnetic field to the patient's brain.

The combined device may include four applicators.

In some aspects, the first applicator and the second applicator may be configured to apply the time-varying magnetic field to one or more muscles of the patient to cause muscle contractions in a body region. The first applicator and the second applicator may be positioned separately. The first applicator and the second applicator may be positioned laterally on the patient, e.g. the first applicator may be positioned on left part of patient's abdomen or buttock and the second applicator may be positioned right part of patient's abdomen or buttock. The first applicator and the second applicator may be used for different body regions. The third and fourth applicators may be used for applying time-varying magnetic fields to the patient's brain. The third applicator and the fourth applicator may apply time-varying magnetic field to different brain regions. The third and fourth applicators may apply respective time-varying magnetic field to laterally corresponding brain regions. In some aspects, the third and fourth applicators may be focused to a single location of the brain.

Each pair of the applicators may be laterally coupled to the patient.

The combined device may include at least one energy source for providing energy to plurality of magnetic field generating devices for generating time-varying magnetic field.

FIGS. 34, 35 and 36 illustrate aspects of magnetic circuits using one single energy source for both possible treatments, e.g. muscle and brain.

FIG. 34 schematically illustrates a magnetic circuit according to some aspects using single energy source for generating simultaneous time-varying magnetic fields by two magnetic field generating devices. The combined device includes the energy source 1, energy storage device 3, switching device 2 and two magnetic field generating devices 4c and 4d and the control unit 5. Magnetic field generating devices 4c and 4d are connected in serial connection. The energy storage device 3 may be charged by energy source 1. Switching device 2 may be switched to enable discharge of the charged energy storage device 3 to the magnetic field generating device 4c to generate a first time-varying magnetic field and to the magnetic field generating device 4d to generate a second time-varying magnetic field.

First time-varying magnetic field generated by magnetic field generating device 4c may be applied to a body region to cause muscle contraction, while the second time-varying magnetic field generated by magnetic field generating device 4d may be applied to a brain of the patient. In some aspects, the magnetic field generating devices 4c and 4d may be connected in parallel. The control unit 5 may be configured to control the operation and/or the state of energy source 1, the switching device 2 and/or the energy storage device 3.

Magnetic circuit of FIG. 34 may be configured to include multiple magnetic field generating devices. For example, as depicted in FIG. 25a, the magnetic circuit may comprise two magnetic field generating devices 4c and 4d. Magnetic field generating device 4c may be positioned in a first applicator, while the magnetic field generating device 4d may be positioned in a second applicator. The first applicator may be used for transcranial magnetic stimulation and the second applicator may be used for muscle stimulation. The applicators may be independently positioned.

The magnetic field generating device 4c may generate a time-varying magnetic field with equal treatment parameters as the magnetic field generating device 4d.

The magnetic field generating device 4c may generate a time-varying magnetic field with at least one different treatment parameter than the magnetic field generating device 4d. The treatment parameter may be an impulse duration or magnetic flux density. In some aspects, the magnetic flux density may be different, while the repetition rate of magnetic impulses of both time-varying magnetic fields may be equal.

FIG. 35 illustrates a magnetic circuit according to some aspects of a combined device including one energy source and two magnetic field generating devices. The exemplary combined device of FIG. 35 includes two magnetic subcircuits E and F. Subcircuit E (dash line) includes energy storage device 3e, a switching device 2e and magnetic field generating device 4e. Subcircuit F (dash line) includes energy storage device 3f, a switching device 2f and magnetic field generating device 4f. Both magnetic field generating subcircuits E and F are powered by one energy source 1. The magnetic field generating subcircuit E generates a time-varying magnetic field independently from the magnetic circuit F. Magnetic field generating device 4e generates a time-varying magnetic field configured to be applied to a muscle and magnetic field generating device 4f generates time-varying magnetic field configured to be applied to a brain. Treatment parameters such as repetition rate and magnetic flux density of time-varying magnetic field generated by subcircuit E are independent of parameters corresponding to subcircuit F. Parameters of the time-varying magnetic field generated by magnetic field generating device 4e may differ from treatment parameters of the time-varying magnetic field generated by magnetic field generating device 4f. The control unit 5 may be configured to control the operation and/or the state of energy source 1, switching devices 2e and 2f and/or energy storage devices 3e and 3f.

In some aspects, each of the subcircuits E and F may include an additional magnetic field generating device to generate an additional time-varying magnetic field. A plurality of magnetic field generating devices in one subcircuit may be connected in parallel or in series to generate a plurality of time-varying magnetic fields having equal treatment parameters.

Magnetic circuit shown on FIG. 35 may comprise two magnetic field generating devices 4e and 4f and may be suitable for a combined device including a plurality of magnetic field generating devices. Magnetic field generating device 4e may be positioned in a first applicator, while the magnetic field generating device 4f may be positioned in a second applicator. The first applicator may be used for transcranial magnetic stimulation and the second applicator may be used for muscle stimulation. The applicators may be independently positioned.

FIG. 36 illustrates a magnetic circuit according to some aspects that includes energy source 1 for magnetic field generating devices 4g, 4h, and 4i.

The magnetic circuit includes a single energy source and three magnetic subcircuits G, H and I. Subcircuit G (dash line) includes switching device 2g, energy storage device 3g and magnetic field generating device 4g. The subcircuit H (dash line) including switching device 2h, energy storage device 3h and magnetic field generating device 4h. Energy storage devices 3g and 3h are charged by energy source 1. The switching device 2g may be switched to discharge the energy storage device 3g to magnetic field generating device 4g to generate a first time-varying magnetic field. The switching device 2h may be switched to discharge energy storage device 3h to magnetic field generating device 4h to generate a second time-varying magnetic field. The switching device 2" may be configured to control charging of energy storage devices 3g and 3h. When the switching device 2" is switched on, energy storage devices 3g and 3h may be charged. When the switching device 2" is switched off, energy storage devices 3g and 3h may not be charged The subcircuit I (dash line) includes, switching device 2i, energy storage device 3i and magnetic field generating device 4i. The energy storage device 3i may be charged by energy source 1. The energy storage device 3i may be discharged to magnetic field generating device 4i when the switching device 2i is switched on. The magnetic field generating device 4i generates a third time-varying magnetic field.

The control unit 5 may be configured to control the operation and/or the state of energy source 1, switching devices 2h and 2i and/or energy storage devices 3h and 3i.

The time-varying magnetic field generated by magnetic field generating device 4g may be generated independently of the time-varying magnetic field generated by magnetic field generating device 4h. The repetition rate of time-varying magnetic field generated by magnetic field generating device 4g may be different from the time-varying magnetic field generated by the magnetic field generating device 4h. At least one treatment parameter of the time-varying magnetic field generated by subcircuit G may be independent from treatment parameters of the time-varying magnetic field generated by subcircuit H.

Magnetic circuit shown on FIG. 36 may comprise three magnetic field generating devices and may be suitable for a combined device including a plurality of magnetic field generating devices. Magnetic field generating device 4g may be positioned in a first applicator, magnetic field generating device 4h may be positioned in a second applicator, while the magnetic field generating device 4i may be positioned in a third applicator. The applicators may be independently positioned. In some aspects, magnetic field generating devices 4g and 4h may be in one applicator.

The applicators may be used for different therapies. For example, the first applicator including magnetic field generating device 4g and the second applicator including magnetic field generating device 4h may be used for muscle stimulation, while the third applicator including magnetic field generating device 4i may be used for transcranial magnetic stimulation of brain. In some aspects, the first applicator includes magnetic field generating device 4g may be used for transcranial magnetic stimulation of brain, while the second applicator including magnetic field generating device 4h and the third applicator including magnetic field generating device 4i may be used for may be used for muscle stimulation. In some aspects, the first applicator including magnetic field generating device 4g and the second applicator including magnetic field generating device 4h may be used for transcranial magnetic stimulation of brain, while the third applicator including magnetic field 4i generating device may be used for muscle stimulation.

Further, first and second applicators for muscle stimulation may be mutually interconnected by a movement structure such that a position of the applicators may not be mutually independent. The movement structure may include one or more joints or gears. Movement of the applicators used for muscle stimulation may be independent from the applicator used for transcranial stimulation.

In some aspects, the magnetic circuit may include a first applicator including a magnetic field generating device configured to generate the time-varying magnetic field to stimulate the brain, and second applicator including two magnetic field generating device configured to generate the time-varying magnetic field to provide muscle stimulation.

The combined device may include two energy sources. Both energy sources and magnetic circuits may be controlled by one or more control units.

FIG. 37 illustrates a magnetic circuit according to some aspects that includes two energy sources. The magnetic circuit includes an energy source 1c and an energy source 1d and two subcircuits J and K.

The subcircuit J includes switching device 2j, energy storage device 3j and magnetic field generating device 4j. The energy storage device 3j may be charged by energy source 1c. Operation of energy source 1c may be monitored and controlled by control unit 5. The switching device 2j may be switched on to discharge energy storage device 3j to magnetic field generating device 4j to generate a time-varying magnetic field. Switching of switching device 2j may be under control of control unit 5.

The subcircuit K includes switching device 2k, energy storage device 3k and magnetic field generating device 4k.

The energy storage device 3k may be charged by energy source 1d. Operation of energy source 1d may be monitored and controlled by control unit 5. The switching device 2k may be switched on to discharge energy storage device 3k to the magnetic field generating device 4k to generate a time-varying magnetic field. Switching of switching device 2k may be under control of the control unit 5.

The subcircuit J (dash line) generates the time-varying magnetic field to be applied to brain, while the subcircuit K (dash line) generates the time-varying magnetic field to be applied to the body to cause a muscle contraction. Any part of the magnetic circuit and/or subcircuits J and K may be controlled and/or adjusted by the control unit 5.

Operation of the subcircuit J may be independent from operation of the subcircuit K. At least one treatment parameter of the time-varying magnetic field generated by subcircuit J may be independent from treatment parameters of the time-varying magnetic field generated by subcircuit J.

The time-varying magnetic field generated by magnetic field generating device 4j may be generated independently from the time-varying magnetic field generated by magnetic field generating device 4k. Repetition rate of the time-varying magnetic field generated by magnetic field generating device 4j may be different from the time-varying magnetic field generated by the magnetic field generating device 4k. At least one treatment parameter of the time-varying magnetic field generated by subcircuit J may be independent from treatment parameters of the time-varying magnetic field generated by subcircuit K.

Magnetic field generating device 4j may be positioned in a first applicator, while the magnetic field generating device 4j may be positioned in a second applicator. The first applicator may be used for muscle stimulation, while the second applicator may be used for transcranial magnetic stimulation of brain. The applicators may be independently positioned.

FIG. 38 illustrates a magnetic circuit according to some aspects that includes two energy sources. The magnetic circuit includes an energy source 1c and an energy source 1d and three subcircuits L, M and N. Operation of energy source 1c and energy source 1d may be monitored and controlled by control unit 5. The magnetic circuit may include three magnetic field generating devices.

The magnetic circuit includes an energy source 1c, an energy source 1d and three magnetic subcircuits L, M and N. Subcircuit L (dash line) includes switching device 2L, energy storage device 3L and magnetic field generating device 4L. The subcircuit M (dash line) including switching device 2m, energy storage device 3m and magnetic field generating device 4m. Energy storage devices 3L and 3m may be charged by the energy source 1c. The switching device 2L may be switched to discharge energy storage device 3L to magnetic field generating device 4L to generate a first time-varying magnetic field. The switching device 2m may be switched to discharge energy storage device 3m to magnetic field generating device 4m to generate a second time-varying magnetic field.

The subcircuit part N (dash line) includes energy storage device 3n, switching device 2n and magnetic field generating device 4n. The energy storage device 3n may be charged by energy source 1d. The energy storage device 3n may be discharged to magnetic field generating device 4n when the switching device 2n may be switched. The magnetic field generating device 4n generates a third time-varying magnetic field to be applied to brain. Switching of switching devices 2L, 2m and 2n may be controlled by the control unit 5.

The time-varying magnetic field generated by magnetic field generating device 4k may be generated independently of the time-varying magnetic field generated by magnetic field generating device 4m. Repetition rate of time-varying magnetic field generated by magnetic field generating device 4k may be different from the time-varying magnetic field generated by the magnetic field generating device 4m. At least one treatment parameter of the time-varying magnetic field generated by subcircuit L may be independent from treatment parameters of the time-varying magnetic field generated by subcircuit M.

Magnetic field generating device 4L may be positioned in a first applicator, the magnetic field generating device 4m may be positioned in a second applicator and the magnetic field generating device 4n may be positioned in a third applicator. The applicators may be independently positioned.

The applicators may be used for different therapies. For example, the first applicator including magnetic field generating device 4L and the second applicator including magnetic field generating device 4m may be used for muscle stimulation, while the third applicator including magnetic field generating device 4n may be used for transcranial magnetic stimulation of brain. In some aspects, first applicator including magnetic field generating device 4L may be used for transcranial magnetic stimulation of brain, while the second applicator including magnetic field generating device 4m and the third applicator including magnetic field generating device 4n may be used for may be used for muscle stimulation. In some aspects, the first applicator including magnetic field generating device 4L and the second applicator including magnetic field generating device 4m may be used for transcranial magnetic stimulation of brain, while the third applicator including magnetic field 4n generating device may be used for muscle stimulation.

The combined device may include three energy sources. All energy sources and magnetic circuits may be controlled by one or more control units.

First energy source may provide energy for generating time-varying magnetic field to be applied to brain. Second energy source and third energy source may provide energy for generating time-varying magnetic fields to be applied to body region to cause muscle contraction.

FIG. 39 illustrates a magnetic circuit according to some aspects that includes three independent energy sources. The magnetic circuit includes an energy source 1e, an energy source 1f and an energy source 1g and three subcircuits O, P and Q. Operation of the energy source 1e, the energy source 1f and the energy source 1g is monitored and controlled by control unit 5. The magnetic circuit includes three magnetic field generating devices.

The magnetic circuit may include an energy source 1e, an energy source 1f, an energy source 1g and three magnetic subcircuits O, P and Q. Subcircuit O (dash line) includes switching device 20, energy storage device 30 and magnetic field generating device 40. The subcircuit P (dash line) may include switching device 2p, energy storage device 3p and magnetic field generating device 4p. The subcircuit Q (dash line) may include switching device 2q, energy storage device 3q and magnetic field generating device 4q. When energy source 1e charges the energy storage device 30, the switching device 20 may be switched to discharge the energy storage device 30 to magnetic field generating device 40 to generate a first time-varying magnetic field. When energy source 1f charges the energy storage device 3p, the switching device 2p may be switched to discharge the energy storage device 3p to magnetic field generating device 4p to generate a second time-varying magnetic field. When energy source 1g charges the energy storage device 3q, the switching device 2q may be switched to discharge the energy storage device 3q to magnetic field generating device 4q to generate a third time-varying magnetic field. Switching of switching devices 20, 2p and 2q may be controlled by the control unit 5.

The time-varying magnetic field generated by magnetic field generating device 40 may be generated independently on time-varying magnetic field generated by magnetic field generating device 4p and/or 4q. Repetition rate of time-varying magnetic field generated by magnetic field generating device 40 may be different from time-varying magnetic field generated by the magnetic field generating device 4p and/or 4q. At least one treatment parameter of the time-varying magnetic field generated by subcircuit O may be independent from treatment parameters of the time-varying magnetic field generated by subcircuit P and/or Q.

Magnetic field generating device 40 may be positioned in a first applicator, the magnetic field generating device 4p may be positioned in a second applicator and the magnetic field generating device 4q may be positioned in a third applicator. The applicators may be independently positioned.

Applicators may be used for different therapies. For example, the first applicator including magnetic field generating device 40 and the second applicator including magnetic field generating device 4p may be used for muscle stimulation, while the third applicator including magnetic field generating device 4q may be used for transcranial magnetic stimulation of brain. In some aspects, the first applicator including magnetic field generating device 40 and the second applicator including magnetic field generating device 4p may be used for transcranial magnetic stimulation of brain, while the third applicator including magnetic field generating device 4q may be used for muscle stimulation.

The combined device may include four energy sources. All energy sources and magnetic circuits may be controlled by one or more control units.

FIG. 40 illustrates a magnetic circuit according to some aspects that includes four independent energy sources. The magnetic circuit includes an energy source 1h, an energy source 1i, an energy source 1j and an energy source 1k and three subcircuits R, S, T and U. Operation of the energy source 1h, the energy source 1i, the energy source 1j and the energy source 1k is monitored and controlled by control unit 5. The magnetic circuit includes four magnetic field generating devices.

Subcircuit R (dash line) may include switching device 2r, energy storage device 3r and magnetic field generating device 4r. When energy source 1h charges the energy storage device 3r, the switching device 2r may be switched to discharge the energy storage device 3r to magnetic field generating device 4r to generate a first time-varying magnetic field. The subcircuit S (dash line) may include switching device 2s, energy storage device 3s and magnetic field generating device 4s. When energy source 1i charges the energy storage device 3s, the switching device 2s may be switched to discharge the energy storage device 3s to magnetic field generating device 4s to generate a second time-varying magnetic field. The subcircuit T (dash line) may include switching device 2t, energy storage device 3t and magnetic field generating device 4t. When energy source 1j charges the energy storage device 3t, the switching device 2t may be switched to discharge the energy storage device 3t to magnetic field generating device 4t to generate a third time-varying magnetic field. The subcircuit U (dash line) including switching device 2u, energy storage device 3u and magnetic field generating device 4u. When energy source 1k charges the energy storage device 3u, the switching device 2u may be switched to discharge the energy storage device 3u to magnetic field generating device 4u to generate a fourth time-varying magnetic field . . . . Switching of switching devices 2r, 2s, 2t and 2u may be controlled by the control unit 5.

The time-varying magnetic field generated by magnetic field generating device 4r may be generated independently of time-varying magnetic field generated by magnetic field generating device 4s, 4t and/or 4u. Repetition rate of the time-varying magnetic field generated by magnetic field generating device 4r may be different from the time-varying magnetic field generated by the magnetic field generating device 4s, 4t and/or 4u. At least one treatment parameter of the time-varying magnetic field generated by subcircuit R may be independent from treatment parameters of the time-varying magnetic field generated by subcircuit S, T and/or U.

Magnetic field generating device 4r may be positioned in a first applicator, the magnetic field generating device 4s may be positioned in a second applicator, the magnetic field generating device 4t may be positioned in a third applicator and the magnetic field generating device 4u may be positioned in a fourth applicator. The applicators may be independently positioned.

Applicators may be used for different therapies. For example, the first applicator including magnetic field generating device 4r and the second applicator including magnetic field generating device 4s may be used for muscle stimulation, while the third applicator including magnetic field generating device 4t and the fourth applicator including magnetic field generating device 4t may be used for transcranial magnetic stimulation of brain. In some aspects, the first applicator including magnetic field generating device 4r, the second applicator including magnetic field generating device 4s and the third applicator including magnetic field generating device 4t may be used for muscle stimulation, while the fourth applicator including magnetic field generating device 4t may be used for transcranial magnetic stimulation of brain. In some aspects, the first applicator including magnetic field generating device 4r, the second applicator including magnetic field generating device 4s and the third applicator including magnetic field generating device 4t may be used for transcranial magnetic stimulation of brain, while the fourth applicator including magnetic field generating device 4t may be used for muscle stimulation.

Impulses of the first magnetic field and the second magnetic field may be generated with a time shift within one pulse such that the impulse of the second magnetic field may be generated between the start of two subsequent impulses of the first magnetic field as shown in FIGS. 46a-46d.

As depicted in FIG. 43a, the impulses of first magnetic field 46.01 may be generated simultaneously with impulses of second magnetic field 46.02.

As depicted in FIG. 43b, the impulses of first magnetic field 46.01 may be generated sequentially with impulses of second magnetic field 46.02.

As depicted in FIG. 43c, the impulses of first magnetic field 46.01 may be generated time-shifted with impulses of second magnetic field 46.02.

As depicted in FIG. 43d, the impulses of first magnetic field 46.01 may be generated partially overlapping with impulses of second magnetic field 46.02.

All types of generation may be provided by the device during one treatment session.

In some aspects, a method for applying a time-varying magnetic field to a patient may use a device comprising an energy source, a capacitor, a switching device, and a magnetic field generating coil in an applicator. The energy source may charge the capacitor. The switching device may be switched on and the capacitor may be discharged to the magnetic field generating coil to generate the time-varying magnetic field. The switching device may be switched off to stop providing current from the capacitor to the magnetic field generating coil. The capacitor may be recharged by the energy source. The impulse of the time-varying magnetic field may have a magnetic flux density in a range of 0.1 Tesla to 10 Tesla, the impulses may be repeated with a repetition rate in a range of 0.1 Hz to 1000 Hz, the impulse may last a time period of an impulse duration in a range of 1 us to 1000 μs, and a maximal value of a magnetic flux density derivative of the impulse may be in a range of 0.3 kT/s to 800 kT/s. The patient may be positioned on a positioning pillow comprising at least one marker. The applicator may be positioned proximate to a head of the patient. A first marker of the applicator may be aligned with at least one anatomical structure of the patient to find an area of a motor cortex. A second marker on the applicator may be aligned with the at least one marker on the pillow. A first operating button may be pressed to generate a single impulse, the operating button may be on the applicator, and the operating button may be pressed by the operator. A second operating button may be pressed by the operator to increase a value of the magnetic flux density of sequential impulses up to an establish motor-threshold value of the magnetic flux density. The applicator may be shifted in a direction toward the patient's nose, approximately 2 cm to 10 cm, to be over a target location, alternatively the applicator may be shifted in any other direction, the direction may correspond with any anatomical structure, or the applicator may not be shifted. The applicator may be coupled to the patient's head by a belt. A first end of the belt may be inserted through an orifice of the applicator to the belt itself and may be attached to itself anywhere along the belt. A second end of the belt may be coupled to the positioning pillow. The protocol may start and a plurality of trains of impulses may be applied to the target location. A train may comprise a plurality of impulses. The train may be modulated in amplitude of the magnetic flux density into a trapezoidal envelope. Electric current may be induced in the target location.

In some aspects, a device may be configured to generate a time-varying magnetic field. The device may comprise a main body, a positioning arm, and an applicator. A control unit, an energy source, a capacitor, a switching device may be within the main body. The positioning arm may comprise a plurality of links and a plurality of joints. Each joint may be configured to change a mutual orientation of the plurality of links. At least one link may comprise a parallelogram mechanism. The applicator may be operatively connected to the positioning arm by a locking mechanism comprising a latching member in the applicator. The latching member may be adapted to fit a gap in the positioning arm. The gap may be in a sleeve at an end of the positioning arm. The end of the positioning arm may be distant from the main body. The applicator may comprise a casing, a magnetic field generating coil, and a fluid mover. The magnetic field generating coil and the fluid mover may be within the casing. The casing may comprise a lower side configured to be positioned to the patient; an upper side configured to be positioned away from the patient, wherein the upper side is on an opposite side of the applicator with respect to the lower side; a non-application part comprising the fluid mover; and an application part comprising the magnetic field generating coil arranged such that the fluid mover is configured to direct an outer air in a direction along a surface of the magnetic field generating coil in a direction. The device may comprise a connecting tube configured to connect the applicator to the main body. The casing may include a first end and a second end. The first end may comprise at least one operating member configured to generate an impulse or adjust a magnetic flux density. The second end may form a handle adapted to be held by a hand of an operator. The handle may form an orifice configured to receive a belt adapted to maintain the applicator proximate to the patient.

In some aspects, the device may be configured to generate a time-varying magnetic field. The device may comprise a main body, a positioning arm, and an applicator. The main body may comprise a control unit, an energy source, a capacitor, and a switching device. The control unit may be configured to regulate the energy source to charge the capacitor. The switching device may be configured to discharge the capacitor to a magnetic field generating coil to generate a time-varying magnetic field. The device may further include a positioning arm comprising a first end connected to the main body, and a second end distant from the main body. The applicator may be removably attached to the positioning arm by a locking mechanism. The applicator may comprise the magnetic field generating coil. The applicator may further include a lower side configured to be positioned in contact with the patient; an upper side configured to be positioned distant from the patient. The upper side may comprise a positioning plate comprising a positioning system with at least one marker configured to be aligned with at least one anatomical structure. The at least one marker may comprise a center line adapted to be aligned with an ear of the patient, and a cross-line adapted to be positioned in a direction of the nose of the patient. The cross-line may be aligned with a marker on a positioning pillow. The device may be configured to generate a protocol comprising a plurality of impulses of the time-varying magnetic field assembled into trains, wherein each train may comprise at least two impulses. At least one train may comprise a plurality of impulses of a different magnetic flux density. The impulses may form a trapezoidal envelope.

Combination

The transcranial magnetic stimulation may be combined with the application of different treatment energy types. Brain treatment may use different types of energy to induce a synergistic effect. The different types of energy may be at least one of the following: electric current, mechanical waves such as audible sound or ultrasound, optical waves such as infrared light, visible light or ultraviolet light, radio waves, microwaves, radiofrequency waves X-ray or gamma rays, and any combination thereof.

The magnetic field and different treatment energy may be applied to the same treatment location. The treatment location may be an area of the skull over which the generator of the different type of energy is placed to stimulate the target location.

Alternatively a different treatment location may also be targeted by the different type of energy, e.g. one energy generator may be over forehead and second energy generator be over vertex.

Alternatively the different treatment energy may be applied to a single treatment location but a different target location. For example, the magnetic field may be applied to a cortex while a different type of energy may be applied through the cortex to a deeper neural structure (e.g. the thalamus).

Pairing treatment by magnetic fields and different energy types may induce enhanced treatment effects (e.g. migraines may be relieved faster, or binge eating may be reduced faster). The different types of energy may stimulate the brain via different mechanisms of action to induce similar effects as treatment by a magnetic field. The |

The target location may be stimulated by a direct electric current.

The direct electric current may be applied to the brain via a plurality of electrodes attached to patient's head. Two or more electrodes may be used. Multiple pairs of electrodes may be used for treatment of lateral target locations (e.g., left prefrontal cortex and right prefrontal cortex).

Direct current may modulate neuron excitability via altering resting membrane neuron potentials. For example, the direct current may influence firing of neurons. The direct electric current applied by a node may depolarize the membrane and increase neuronal excitability. The direct electric current applied by a cathode may hyperpolarize the membrane and reduce excitability of the neuron (e.g., an overactive region may be suppressed).

The direct electric current may improve synaptic connections or large neural networks. Further production of neurotransmitters may be influenced for enhancing brain function (e.g., glutamate, GABA or dopamine). In some aspects the direct electric current may influence a mood of the patient.

An amplitude of the alternating electric current may be in a range from 0.1 mA to 10 mA, in a range from 0.2 mA to 7 mA, in a range from 0.5 mA to 5 mA, or in a range from 1 mA to 2 mA.

The electric current density may vary depending on a surface of electrode in a range from 0.01 mA/cm$^2$ to 1 mA/cm$^2$, in a range from 0.02 mA/cm$^2$ to 0.75 mA/cm$^2$, in a range from 0.03 mA/cm$^2$ to 0.25 mA/cm$^2$, or in a range from 0.05 mA/cm$^2$ to 0.1 mA/cm$^2$.

The application of direct electric current may last in a range from 1 min to 240 min, in a range from 5 min to 120 min, in a range from 10 min to 90 min, in a range from 15 min to 60 min, or in a range from 20 min to 40 min.

Treatment by a magnetic field and direct electric current may be used for treating depression or chronic pain. In some aspects, combined treatment by the magnetic field and direct electric current may improve cortical plasticity, stroke recovery, and cognitive functions such as learning or memory.

Mechanic Energy

One or more devices may be used for treatment by a magnetic field and mechanical waves. In some aspects the device may include the magnetic field generating device and at least one mechanical waves generating device. Alternatively one device may include the magnetic field generating device and second device may include at least one mechanical waves generating device.

Mechanical waves may be applied to the brain. The mechanical waves may be applied continuously or in a pulse regime.

Acoustic

The device may comprise a generator of audible mechanical waves, such as a speaker, buzzer, tuning fork, musical instrument such as string instrument or drum, whistle, or piezoelectric transducer. The generator may refer to hardware components in FIGS. 47, 48a, 48b, 49a and 49b.

A target location may be stimulated by audible mechanical waves. The audible mechanical waves may have a frequency in a range from 18 Hz-20 KHz.

The audible mechanical waves may primarily influence a temporal lobe comprising an auditory cortex, and secondarily the audible mechanical waves may influence a frontal cortex, prefrontal cortex, or deeper structures such as an amygdala.

The device may be configured to provide the audible mechanical waves to at least one of following: a temporal lobe, an auditory cortex, a frontal cortex, prefrontal cortex, or an amygdala.

The audible mechanical waves may influence the brain's natural response to auditory stimuli to promote synchronization of brain waves to enhance neuroplasticity and mental well-being.

The device may comprise headphones or earplugs. The audible mechanical waves may be applied to the patient via headphones or earplugs. The audible mechanical waves may be applied via a stereo. Alternatively, the generator of the audible mechanical waves may be attached to a belt or helmet. Alternatively, the generator of the audible mechanical waves may be integral part of a belt or helmet.

Binaural Beat

In some aspects, audible mechanical waves of different frequencies are simultaneously applied to ears of patient. These two audible mechanical waves of two different frequencies are translated by the brain as a third audible mechanical waves with a frequency that equals to a difference of frequencies of audible mechanical waves applied to the patient. For example first frequency may be 400 Hz and second frequency may be 430 Hz, wherein the brain interprets them as a sound with frequency of 30 Hz. A frequency of applied audible mechanical waves may be in a range from 50 Hz to 2 kHz, in a range from 100 Hz to 1500 Hz, in a range from 200 Hz to 1000 Hz or in a range from 300 Hz to 500 Hz.

The difference of frequencies depends on treatment effect below.

Audible mechanical waves of frequency difference in a range from 0.5 Hz to 4 Hz may be used for improving sleep, pain management or relaxing the patient. The audible mechanical waves of frequency difference may regulate hormones, e.g. production of human growth hormone or DHEA, or reduction of cortisol.

Audible mechanical waves of frequency difference in a range from 4 Hz to 8 Hz may be used for relaxing the patient, deep meditation or reducing stress.

Audible mechanical waves of frequency difference in a range from 8 Hz to 12 Hz may be used for relaxing the patient, meditation or accelerating learning.

Audible mechanical waves of frequency difference in a range from 12 Hz to 30 Hz may be used for task focusing, analytical capabilities or solving problems.

Audible mechanical waves of frequency difference in a range from 30 Hz to 100 Hz may be used for increasing concentration or memory synchronization.

Applying of audible mechanical waves with different frequency may be in a range from 10 min to 120 min, in a range from 15 min to 90 min, in a range from 20 min to 60 min or in a range from 30 min to 60 min.

Harmonic

In another aspect the audible mechanical waves may be applied to both ears of the patient with equal frequency. Alternatively the audible mechanical waves may be applied to one ear only.

The audible mechanical waves may be of single frequency or the frequency may vary to generate different tones. Tone may be audible mechanical wave of constant frequency. The tones may be composed to synchronize a natural sound or a sequence, e.g. a melody. The group of tone may be of single constant frequency repeated in time. Repetition time may be in a range from 0.1 s to 60 s, in a range from 0.2 s to 45 s, in a range from 0.5 s to 30 s, in a range from 1 s to 15 s or in a range from 3 s to 10 s.

A frequency may be in a range from 1 Hz to 10 kHz, in a range from 20 Hz to 1 kHz, in a range from 40 Hz to 10 kHz, in a range from 50 Hz to 750 Hz or in a range from 100 Hz to 500 Hz.

Application of mechanical waves with audible frequency may be used for treatment of tinnitus, meditation, emotion, stress relieve, relaxation, anxiety or cognitive enhancement.

In some aspects, the device may be configured to apply combination of magnetic field, audible mechanical waves and electric current. Application of audible mechanical waves and electric current may substantially influence somatosensory pathway. The electric current may be applied via electrode to patient's tongue. Such combined application may reduce tinnitus.

In some aspects at least one sensor may be used for measuring physiological signal of the patient, e.g. EEG, EEG, heartbeat, HRV or any other. The sound may be synchronize with the measured signal to influence brain waves.

Ultrasound

A target location may be stimulated by ultrasonic mechanical waves, i.e. with a frequency over 20 kHz. The ultrasonic mechanical wave may be referred as ultrasound wave.

The device may comprise a generator and an ultrasound generating device. The ultrasound generating device may be e.g. piezoelement, magnetostrictive element, electrodynamic converter, or capacitive microgenerator. The generator may refer to hardware components in FIGS. 47, 48*a*, 48*b*, 49*a* and 49*b*.

The device may be configured to apply the ultrasound wave may be applied to at least of the following: cortex, e.g. somatosensory cortex, motor cortex, prefrontal cortex, or deep brain structure such as thalamus.

The device may be configured to apply ultrasound wave be applied in focused manner.

Application of ultrasound wave may induce a pressure to cell membrane to modulate ion channels such that generation of action potential may be increased or decreased. Ultrasound waves may modulate activity of peripheral nerves and/or spinal reflexes.

A frequency of the ultrasound waves may vary based on intended penetration, i.e. depth of the treated target location. The frequency may be constant during the treatment or the frequency may vary. The frequency may vary during the treatment continuously between two limit frequencies (lowest frequency and highest frequency). In some aspects, the frequency may vary in trains of different frequency, the trains may be repeated with a specific period. Variation of the frequency may be controlled or provided by a control unit of the device.

The device may be configured to apply ultrasound waves having frequency may be in a range from 20 kHz to 5 MHz, in a range from 100 kHz to 3 MHz, in a range from 500 kHz to 1 MHz, or in a range from 250 kHz to 700 kHz.

The ultrasound wave may be applied in trains of continual application of ultrasound wave, i.e. the ultrasound wave is not interrupted. Train may last a time duration in a range from 1 μs to 50 s, in a range from 5 μs to 25 s, in a range from 100 μs to 15 s, in a range from 1 s to 20 s.

A repetition rate of the trains may be in a range from 0.1 Hz to 250 Hz, in a range from 0.5 Hz to 150 Hz, in a range from 1 Hz to 100 Hz, in a range from 20 Hz to 75 Hz in a range from 40 Hz to 50 Hz.

The ultrasound wave may be generated by one or more ultrasound generating device, e.g. piezoelement. Number of ultrasound generating devices may be in a range from 2 to 1000, in a range from 5 to 512, in a range from 10 to 256, in a range from 32 to 128, or 4 to 16.

The ultrasound generating device may be coupled to the patient in a helmet or an adjustable belt, e.g. headband. In some aspects the ultrasound generating device may be on a positioning arm.

A power density applied to the patient by the ultrasound generating device may be in a range from 0.1 W/cm² to 1 kW/cm².

High power ultrasound waves may be applied to brain to cause permanent effect by coagulation of cellular proteins and/or thermal coagulation. Power density of high power ultrasound waves may be in a range from 200 W/cm² to 1000 W/cm², in a range from 350 W/cm² to 800 W/cm², in a range from 500 W/cm² to 650 W/cm².

Power density of medium power ultrasound waves may be in a range from 200 W/cm² to 100 W/cm², in a range from 180 W/cm² to 120 W/cm², in a range from 160 W/cm² to 140 W/cm².

Power density of low power ultrasound waves may be in a range from 0.01 W/cm² to 100 W/cm², in a range from 0.1 W/cm² to 70 W/cm², in a range from 0.5 W/cm² to 50 W/cm², or in a range from 0.1 W/cm² to 2 W/cm².

The application of ultrasound wave may be used for improving cognitive function, neuromodulation, treatment of neurological disorders and/or therapeutic intervention of neurological disease.

Shockwave

One or more devices may be used for treatment by magnetic field and shock waves. The device may be configured to provide shock waves to the target location.

A target location may be stimulated by mechanical waves, i.e. non-linear pressure wave with high peak pressure followed by low tensile amplitude, short rise time, and short time duration of pulse. The shock wave may comprise a positive phase and a negative phase.

The positive phase refers to mechanical force applied to the target location. Negative phase may generate cavitation and following implosion of bubbles caused by cavitation generates second wave.

The shock wave may be focused or radial.

The shock waves may be generated by electrohydraulic principle, electromagnetic principle, piezoelectric principle or ballistic principle.

The generator may refer to hardware components in FIGS. 47, 48a, 48b, 49a and 49b.

A depth of penetration of shock wave may be affected by skull.

The device may be configured to apply shock wave to target location in motor cortex for promoting neuroplasticity, moto function (e.g. after stroke), or post-traumatic brain injury.

The shock wave may be applied to target location in somatosensory cortex for modulating pain pathways to manage chronic pain.

The shock wave may be applied to target location in temporal cortex to reduce tinnitus. Alternatively memory may be improved.

The shock wave may be applied to target location in deep brain structure in hippocampus for improving learning, memory, or neuroprotection against Alzheimer's disease. The stimulation may be indirect via increase blood flow, or neuronal network changes.

The shock wave may be applied to target location in deep brain structure in basal ganglia for treating of Parkinson's disease or motor functions. The stimulation may be indirect via inducing of neovascular or anti-inflammatory effect.

The shock wave may be applied to target location in deep brain structure in cerebellum for enhancing movement coordination, balance or fine motor function.

The applicator comprising shockwave generating element may be positioned from below of the skull in occipital region.

The frequency of generating shock wave may in a range from 0.1 Hz to 100 MHz, in a range from 100 Hz to 70 MHz, in a range from 1 kHz to 50 MHz, in a range from 25 kHz to 10 MHz, in a range from 100 kHz to 900 kHz, or in a range from 150 kHz to 20 MHz.

The shock wave may comprise one shock pulse.

A shock wave pulse duration of the shock wave may be around 10 ms.

Repetition rate of shock wave pulses may be up to 250 Hz and it may vary based on therapy effect. Following repetition range may overlap in a range from 1 Hz to 2 Hz.

A repetition rate in a range from 1 Hz to 10 Hz may penetrate deeper structures to improve angiogenesis and promote vascular remodeling.

A repetition rate in a range from 10 Hz to 20 Hz may increase neuroplasticity and may be used for pain management. Alternatively it may be used for treating depression, anxiety or neurodegenerative diseases.

A repetition rate in a range from 20 Hz to 30 Hz may have low penetration and may stimulate superficial structures, e.g. cortex such as motor cortex or sensory cortex. It may be used for treatment of migraine, headache, neuropathic pain or it may locally activate neurons.

Higher repetition rates e.g. in a range from 30 Hz to 80 Hz may rapidly modulate neuronal activity. It may be used for treatment of tinnitus or it may enhance cognitive functions.

A peak high pressure amplitude may be in a range from 0.5 MPa to 150 MPa, or in a range from 1 MPa to 120 MPa, in a range from 5 MPa to 100 MPa.

A low tensile pressure amplitude may be in a range from 250 Pa to 25 MPa, in a range from 1 kPa to 15 MPa, in a range from 25 kPa to 15 MPa, in a range from 100 kPa to 800 kPa, or in a range from 500 kPa to 7 MPa.

Energy of the shock pulse may be in a range from 10 mJ to 1000 mJ, in a range from 25 mJ to 600 mJ, in a range from 50 mJ to 400 mJ, in a range from 100 mJ to 200 mJ, or in a range from 64 mJ to 256 mJ.

Application of shock wave may be used for cognitive enhancement, functional brain stimulation. Alternatively it may be used for treatment of depression, anxiety, neurodegenerative diseases such as Parkinson or Alzheimer, or chronic headaches.

Light

One or more devices may be used for treatment by magnetic field and light. In some aspects the device may include the magnetic field generating device and at least one light generating device. Alternatively one device may include magnetic field generating device and second device may include at least one light generating device.

The device may be configured to apply light to the target location.

The device may be configured to apply light of various wavelengths.

The device may comprise one or more light generating devices, e.g. visible light generating device, infrared light generating device and/or ultraviolet light generating device. The light generating device may be e.g. a bulb, incandescent bulb, light emitting diode (LED), fluorescent lamp, laser or laser diode, electric discharge source, incandescent source, electroluminescence source or flashlight. A generator configured to generate energy for light generating device may refer to hardware components in FIGS. 47, 48*a*, 48*b*, 49*a* and 49*b*.

Treatment effect depends on wavelength of the light. Light from visible spectra are mainly intended to treat mental state of patient and providing well-being. Light from infrared spectrum are mainly intended to directly stimulate target location to stimulate metabolism of cells.

The applicator comprising may be in a form of helmet, googles, glasses, frame of glasses, or a headband. In some aspects applicator comprising earplug or headphone may comprise light generating device to apply light to ear of the patient. The light generating device may be removably attached to the applicator, or it may be integral part of the applicator. In some aspects, light generating device may be external of the applicator, e.g. applicator may be a headband or helmet comprising light generating device for applying the light.

VIS

A treatment by light from visible spectra may be applied into eyes of the patient. Light may be transmitted to retina causing biological signal directed to occipital lobe to visual cortex. The biological signal may be electric signal, or chemical signal.

The light may influence circadian rhythm, sleep cycle, or mood, boost energy of the patient during insufficient daylight, and reduce jet-lag.

Blue light may decrease melatonin production to not feel tired.

Light may influence mitochondrial function, e.g. ATP production. It may improve blood flow and increase oxygenation of brain cells.

The device may comprise visible light generating device. The visible light generating device may be multispectral, or single wavelength light generating device. In some aspects, visible light generating device may comprise a light emitting diode. One or a more of visible light generating device may be used to generate visible light and apply the visible light to brain of the patient. A number of visible light generating device may be in a range from 1 to 1000, in a range from 2 to 750, in a range from 10 to 500, in a range from 50 to 200, or in a range from 5 to 30. The visible light generating devices may be positioned in a pattern or randomly. The visible light generating devices may generate visible light in a predetermined randomly or in pattern, the pattern may repeated. Visible light may be applied continuously or in pulses. A repetition rate of the visible light may be in a range from 0.1 Hz to 250 Hz, in a range from 0.5 Hz to 100 Hz, in a range from 1 Hz to 50 Hz, in a range from 5 Hz to 20 Hz, or in a range from 10 Hz to 30 Hz.

A wavelength of visible light generated by visible light generating device may be in a range from 300 nm to 850 nm, or in a range from 380 nm to 800 nm. Applied visible optical waves differs following intended treatment effect.

Visible light with wavelength in a range from 400 nm to 600 nm may be used for influencing circadian rhythm (it does not affect directly the brain but sleep-awake pattern). Wavelength in a range from 450 nm to 550 nm may be used as well. It may be generally blue light or green light. In some aspects, a white light may be added to the single wavelength light.

Visible light with wavelength in a range from 600 nm to 700 nm may be applied to brain directly via scalp. It may be used for increasing blood flow, ATP production, relaxing the patient or meditation. In some aspects, the visible light may be mixed with light of NIR spectra to promote increasing blood flow.

A visible light intensity may be equivalent to 10,000 lux. In some aspects, the light intensity may be in a range from 1 lux to 10000 lux, in a range from 1 lux to 1000 lux, in a range from 50 lux to 700 lux, in a range from 100 lux to 500 lux, in a range from 200 lux to 400 lux, or in a range from 120 lux to 250 lux.

An applicator comprising visible light generating device may be in a form of display on positioning arm in front of the patient or display coupled to a band to be coupled to the patient. The display may be in sufficient distance from patient's face, e.g. in a range from 1 cm to 100 cm, in a range from 3 cm to 50 cm, in a range from 5 cm to 30 cm, or in a range from 10 cm to 20 cm.

The light may be applied to the patient for a time period lasting in a range from 1 min to 240 min, in a range from 5 min to 120 min, in a range from 10 min to 60 min, or in a range from 15 min to 45 min.

In some aspects, the light may be applied to patient's cavity of the head, e.g. ear. Applied visible light may comprise monochromatic blue enriched by white light to ear of the patient to influence circadian areas to treat insomnia, seasonal affective disorder, Parkinson's disease, ADHD, traumatic brain injury, post-traumatic stress disorder, or mood of the patient.

Treatment by magnetic field and light may be used for improving neuroplasticity or memory by generating new connections, treatment on anxiety or brain trauma, memory.

Infra

A treatment by light from infrared (abbreviated as IR) spectra may be applied to the patient.

IR light may be transmitted to a scalp of the patient and penetrate the skull and biological structures below the skull.

The device may be configured to apply the IR light to the scalp of the patient, where the IR light may penetrate to or into part at least one of the following: a frontal lobe, temporal lobe, parietal lobe, an occipital lobe, a frontal cortex, prefrontal cortex, motor cortex, subcortical structures such as hippocampus or thalamus.

IR light may be applied to a cavity of the patient (e.g., ear, nose or mouth). The IR optical waves may be applied to the olfactory bulb.

IR light may stimulate mitochondrial metabolism to produce more ATP, increase blood flow in the brain, and influence molecular channels in cells. In some aspects, IR light may stimulate expression of a neurotrophic factor to support neurogenesis or repair neural cells. In some aspects, IR light may promote vasodilatation to increase cerebral blood flow and brain oxygenation. In some aspects, IR light may regulate dopamine release.

The IR light generating device may be configured to provide multispectral optical waves, or single wavelength optical waves. In some aspects, an IR light emitting diode may be used.

One or a plurality of IR light generating devices may be used to generate IR light and apply the IR light to a brain of the patient. A number of IR light generating device may be in a range from 1 to 1024, in a range from 5 to 750, in a range from 20 to 512, in a range from 50 to 256, or in a range from 8 to 32. IR light generating devices may be positioned in a pattern or randomly. IR light generating devices may generate IR optical waves in a predetermined pattern or randomly. The pattern may repeated. Optical waves may be applied continuously or in pulses. A repetition rate of the pulses may be in a range from 0.1 Hz to 250 Hz, in a range from 0.5 Hz to 100 Hz, in a range from 1 Hz to 50 Hz, in a range from 5 Hz to 20 Hz, or in a range from 10 Hz to 40 Hz. A low repetition rate may be used for relaxing the patient. In some aspects, a high repetition rate may be used for improving cognitive function and memory. A high repetition rate may be in a range from 50 Hz to 250 Hz, in a range from 75 Hz to 200 Hz, or in a range from 100 Hz to 150 Hz.

A wavelength of IR light generated by IR light generating device may be in a range from 750 nm to 1500 nm, be in a range from 800 nm to 1100 nm, or be in a range from 810 nm to 850 nm.

In some aspects, IR-B with a wavelength in a range from 1500 nm to 3 μm, or IR-C with a wavelength in a range from 3 μm to 1 mm may be used.

IR light with a wavelength in a range from 750 nm to 1500 nm may be applied to brain directly via the scalp. It may be used for increasing blood flow, ATP production, and relaxing the patient or meditation. In some aspects the IR optical waves may be mixed with optical waves of NIR spectra (e.g., in a range from 750 nm to 2500 nm) to increase blood flow. Alternatively, it may help the patient to relax.

A device may be configured to provide different optical waves. IR light may be applied with visible optical waves. For example IR light may be directed through the skull while visible light (e.g., red light with wavelength in a range from 600 nm to 780 nm) may be applied through a retina of the patient. Application of IR light may alternate with application of visible light for a predetermined period. The period may last in a range from 1 s to 60 min, in a range from 30 s to 45 min, in a range from 1 min to 30 min, or in a range from 10 min to 15 min.

An intensity of IR light may be in a range from 1 mW/cm$^2$ to 1 W/cm$^2$, in a range from 5 mW/cm$^2$ to 500 mW/cm$^2$, in a range from 10 mW/cm$^2$ to 300 mW/cm$^2$, in a range from 50 mW/cm$^2$ to 200 mW/cm$^2$.

The device may comprise an applicator providing IR light. The applicator providing IR light may be in a form of a helmet, earplugs, a headband or a clip coupled to nose. Alternatively, the applicator providing IR light may be coupled to a positioning arm. The IR light generating device may be detachably coupled to the applicator or it may be an integral part of the applicator.

The IR light may be applied to the patient for a time period lasting in a range from 1 min to 240 min, in a range from 5 min to 120 min, in a range from 10 min to 60 min, or in a range from 15 min to 45 min.

Treatment by magnetic field and infrared light may be used for improving cognitive functions, neuroplasticity, or memory by generating new connections. In some aspects application of IR light may be used for treating neurodegenerative disease (e.g., Alzheimer or Parkinson), traumatic brain injury, stroke, or mood disorder (e.g. depression or anxiety).

Thermal

One or more devices may be used for treatment by a magnetic field and thermal energy. In some aspects the device may include the magnetic field generating device and at least one device configured to generate thermal energy to be applied to the patient to heat and/or cool a target location. Alternatively, one device may include the magnetic field generating device and a second device may include at least one device configured to generate thermal energy to be applied to the patient to heat and/or cool the target location.

The device may be configured to provide heat to a target location. Heating of the target location may be direct by application of treatment energy (e.g., electromagnetic waves, optical waves, or mechanical waves). Heating may increase blood flow or promote release of a neurotrophic factor supporting neurogenesis and neuronal repair. Increased blood flow may increase oxygenation, nutrient delivery, or metabolites removed from the neural structures.

In some aspects the target location may be heated indirectly by increased blood flow to the target location by stimulation of different parts of brain. This approach may be generally used for treating deep neural structures.

In some aspects, shallow target location (e.g., the cortex) may be heated conductively. Heat may be applied to the brain via the skull to heat a cerebrospinal fluid. Alternatively, the brain may be heated via heat applied at or below the occipital region to increase temperature of blood flowing to the brain.

The TMS may be combined with application of a magnetic field to different biological structures (e.g., peripheral neural structure, or neuromuscular plate). The different biological structure may be in different body regions than the head of the patient (e.g., abdomen, buttock, arms, or legs such as thighs or calf).

The magnetic field applied to the body region may induce an electric current in the neuromuscular plate to cause a muscle contraction in the body region. The muscle contraction may improve muscle volume, tone, or strength. In some aspects, adipose cells may be reduced by the muscle contractions.

Combination of TMS and application of magnetic field to the body region to cause muscle contraction may induce significant improvement of visual appearance of the patient. The visual appearance may be improved by a combined treatment of two different approaches. TMS may influence the patient's diet by reducing food cravings. Treatment by the magnetic field causing muscle contractions may reduce adipose cells and improve muscle.

The application of the magnetic field to the body region and TMS may occur simultaneously. In some aspects, the magnetic field may be applied to the body region to cause muscle contraction prior to or after TMS, within one treatment session. In some aspects, treatment by the magnetic field may be applied to muscle and may alternate with TMS. The treatments may be applied periodically such as once or twice a week. In some aspects, treatments may be applied 3, 4, 5 or more times a week.

In some aspects, a magnetic field may be applied to a brain of the patient and a second magnetic field may be applied to the body region of the patient to cause a muscle contraction in the body region.

The magnetic field applied to the brain may be applied in a first protocol including a plurality of trains of impulses of the magnetic field. The plurality of trains may include first trains of impulses with a first repetition rate and second trains of impulses with a second repetition rate. The first repetition rate may be different from the second repetition rate. The trains of impulses may be modulated in amplitude of sequential impulses into an envelope. The envelope may be trapezoidal. The first protocol may be applied to the brain for a time period in a range from 10 min to 30 min. A number of impulses applied to the brain may be in a range from 9000 to 11000.

The magnetic field applied to the body region may be applied in a second protocol including a plurality of trains of impulses of the magnetic field. The plurality of trains may include a third train of impulses with a third repetition rate, a fourth train of impulses with a fourth repetition rate, and a fifth train of impulses with a fifth repetition rate. The fourth repetition rate may be higher than the third repetition rate. The fifth repetition rate may be lower than each of the third repetition rate and the fourth repetition rate. The third and fourth trains of impulses may be modulated in amplitude of sequential impulses into a trapezoidal envelope. The fifth train of impulses may include impulses of equal amplitude of magnetic flux density. The second protocol may be applied to the body region for a time period in a range from 15 min to 45 min. A number of impulses applied to the body region may be in a range from 15000 to 30000. Each train may cause muscle contraction in the body region.

Example 1

A clinical test was performed to demonstrate the effect of an exemplary device of the disclosure and exemplary method of the disclosure providing transcranial magnetic stimulation on the food cravings.

The purpose of the test was to gather clinical evidence that the device of the disclosure is able to provide a temporary reduction of food cravings in healthy subjects who have food cravings periods at least 3-5 times per week. Further, the purpose of this test was to assess the participants' satisfaction with the therapy. Furthermore, the purpose of this test to assess how comfortable the therapy is.

Method

The test included 23 subjects (8 males and 15 females) of ages ranging from 23-71 years. All subjects enrolled voluntarily and signed a consent form.

The subjects were required to complete four to six treatment visits and two follow-up visits. Four to six treatments were delivered, one treatment session per day. The treatments were delivered twice a week, 2-3 days apart.

The left dorsolateral prefrontal cortex area of the brain was stimulated with a protocol comprising 120 trains of 2 second duration with 10 second inter-train pause administered at a repetition rate of magnetic impulses of 10 Hz. The intensity of magnetic flux density was carefully set according to the patient's feedback, but never exceeded 100% of the individual's motor threshold. The parameters of the treatment were adjusted according to patient feedback and comfort.

Examination for possible adverse effects was done before and after each visit. With the second follow-up visit, the subject's participation in the test was finished. The duration of participation from baseline visit to completion was approximately 3 months.

Clinical results were collected by two methods, one objective and one subjective.

Objective Method

The body weight measurement was conducted in order to document the subject's weight and calculate the Body Mass Index.

Subjective Method

Subjective method comprised the subject's self-report by plurality of questionniares.

A first questionnaire called Food Craving Questionnaire-Trait (FCQ-T) measured the frequency and intensity of food cravings experiences in general. The questionnaire had 39 items and response categories range from "1=never" to "6=always". There were no inverted items. Responses to all items were summed up for a total score. Thus, higher scores represent more frequent and intense food cravings. The Food Craving Questionnaire-Trait was handed to the subjects at 1-month follow-up visit The second questionnaire was a Satisfaction questionnaire. The satisfaction questionnaire was given to every subject who completed the treatment. Subjects were answering the therapy comfort questionnaire using a 5-point scale ranging from strong agreement (very satisfied with the therapy outcome) to strong disagreement (very unsatisfied with therapy outcome). The satisfaction questionnaire was handed to the subjects at 1-month follow-up visit.

The third questionnaire was a Therapy Comfort questionnaire. The 5-point Likert scale questionnaire and a numerical analog pain scale (0-10) was used for evaluating the comfort during the treatment sessions. The therapy comfort questionnaire was handed to the subjects at the last therapy visit.

Results

A first result was derived from a statistical analysis of the Food Craving Questionnaire-Trait (FCQ-T) questionnaire. As mentioned previously, higher scores represent more frequent and intense food cravings. Using paired t-test, the data analysis showed significant (P<0.001) reduction in FCQ-T score at 1-month follow-up compared to the baseline score. Mean reduction of FCQ-T score was 59.3 points, CI [42.21; 76.40]. The Wilcoxon signed-rank test comparing the reduction of FCQ-T score [reduction of FCQ-T score=baseline FCQ-T score-1-month follow-up FCQ-T score] of all subjects to the suggested threshold of 19 points, showed significant (P<0.001) result. The lower bound of the 95% CI of the mean reduction achieved in this test was 42.21 points, safely exceeding this criteria. This result demonstrates the clinical significance of was achieved. The summary of the FCQ-T score are shown in table 1:

TABLE 1

| Summary of the FCQ-T score. | | |
| --- | --- | --- |
| FCQ-T score (points) | Baseline | 1-month follow-up |
| Average ± SD | 165.3 ± 29.2 | 106.0 ± 35.7 |
| [95% CI] | [152.7; 177.9] | [90.6; 121.4] |
| Min-Max | 99-204 | 61-184 |

Another result was derived from statistical analysis of the Satisfaction questionnaires. At 1-month follow-up, the substantial majority of subjects reported their satisfaction with the therapy outcomes as 20 (86.96%) subjects answered "strongly agree" or "agree" to the question "I am satisfied with the treatment results." (Q1); 17 subjects (x.91%) answered "strongly agree" or "agree" to the question "My food cravings have improved after the treatments" (Q2); 18 subjects (78.26%) answered "strongly agree" or "agree" to the question "My urge to overeat is reduced after treatments" (Q3); and 15 subjects (65.22%) answered "strongly agree" or "agree" to the question "My well-being is improved after the treatments." (Q4). Summary of the satisfaction questionnaires is shown in following table 2:

TABLE 2

Subject's answers to the 5-point Likert scale satisfaction questionnaire at 1-month follow-up.

| Scoring | 1-month responses | | | |
| --- | --- | --- | --- | --- |
| | Q1 (N, %) | Q2 (N, %) | Q3 (N, %) | Q4 (N, %) |
| Strongly agree | 9 (39.13%) | 8 (34.78%) | 6 (26.09%) | 7 (30.43%) |
| Agree | 11 (47.83%) | 9 (39.13%) | 12 (52.17%) | 8 (34.78%) |
| Neither agree nor disagree | 0 (0.00%) | 3 (13.04%) | 1 (4.35%) | 3 (13.04%) |
| Disagree | 3 (13.04%) | 3 (13.04%) | 4 (17.39%) | 4 (17.39%) |
| Strongly disagree | 0 (0.00%) | 0 (0.00%) | 0 (0.00%) | 1 (4.35%) |
| Overall satisfaction | 20 (86.96%) | 17 (73.91%) | 18 (78.26%) | 15 (65.22%) |

Another result was derived from statistical analysis of the Therapy comfort questionnaires. In total 20 subjects (87.0%) "agreed" or "strongly agreed" with the statement "I found the treatment comfortable". The summary of the subject's answers to the therapy comfort questionnaire can be found in Table 3

TABLE 3

Subject's answers to the 5-point Likert scale Therapy Comfort Questionnaire.

| Scoring | Patient's responses (N, %) |
| --- | --- |
| Strongly Agree | 5 (21.7%) |
| Agree | 15 (65.2%) |
| Neither Agree Nor Disagree | 2 (8.7%) |
| Disagree | 1 (4.3%) |
| Strongly Disagree | 0 (0.0%) |
| TOTAL Agreed | 20 (87.0%) |

Another results was derived from statistical analysis of the Therapy comfort questionnaires questions related to pain sensation. Pain sensation assessed by 10-point analogue scale yielded an average score of 2.3+1.9 points with a 95% CI [1.5; 3.1]. Scores of 20 (86.96%) subjects fell into the none to mild pain range (0-3), while 1 (4.35%) subject reported a pain level of 5 points, referring to the moderate pain, and 2 (8.70%) subjects reported a pain level of 7 points, referring to the severe pain. The summary of the subject's answers to the therapy comfort questionnaire can be found in Table 4 below.

TABLE 4

Subject's answers to the 10-point numerical analogue pain scale.

| Scale | Patient's response (N, %) | Pain level (N, %) |
| --- | --- | --- |
| 0 | 3 (13.04%) | None total: 3 (13.04%) |
| 1 | 4 (17.39%) | Mild total: 17 (73.91%) |
| 2 | 9 (39.13%) | |
| 3 | 4 (17.39%) | |
| 4 | 0 (0.00%) | Moderate total: 1 (4.35%) |
| 5 | 1 (4.35%) | |
| 6 | 0 (0.00%) | |
| 7 | 2 (8.70%) | Severe total: 2 (8.70%) |
| 8 | 0 (0.00%) | |
| 9 | 0 (0.00%) | |
| 10 | 0 (0.00%) | |

Further, body weight data were analyzed. In 18 out of 23 patients (78.26%) weight loss was reported at 1-month follow-up. Subsequently, it was whether the patients' weight changed from the baseline value. The one-way repeated measures ANOVA revealed a significant result (P<0.001) and Tukey's post hoc tests demonstrated that there was a statistically significant change in weight between baseline value and value measured at 1-month follow-up visit. Average weight reduction at 1-month follow-up was 1.5 kg (95% CI [0.3; 2.7]). Correspondingly, a statistically significant reduction was also observed in BMI values at 1-month follow-up visit compared to baseline values. Average BMI reduction at 1-month follow-up was 0.5 kg/m2 (95% CI [0.1; 0.9]).

In this test, 23 subjects received the complete set of test treatments with the investigated device and completed the test. Throughout the whole test no adverse events were documented by the investigator and/or staff in the subjects who underwent treatments with the device of disclosure. The therapies were perceived as comfortable by a substantial majority of patients as 87.0% of subjects "agreed" or "strongly agreed" with the statement "I found the treatment comfortable", and the same percent of subjects fell into none (0) or mild pain range.

The device of this disclosure may be a non-invasive tool for the temporary reduction of food cravings, which is safe and effective Based on the results of this clinical test, the treatment with the device of disclosure has shown to be safe and effective for temporary reduction of food cravings. The reduction of the Food Craving Questionnaire-Trait score at 1-month follow-up was found both statistically and clinically significant. Average reduction of the Food Craving Questionnaire-Trait score was 59.3 points. Overall, the test results were accompanied with high subject satisfaction levels. The outcomes of the treatment outweighed the potential risks since no adverse event was found during the course of the test and the therapy was perceived as comfortable by most of the patients.

Thus, novel devices and methods have been shown and described. Various changes and substitutions may of course be made without departing from the spirit and scope of the disclosure. The disclosure, therefore, should not be limited, except by the following claims and their equivalents.

Paragraph 1: A device for providing a magnetic field to the central nervous system.

Paragraph 2: A device for providing a time-varying magnetic field to the central nervous system to reduce the food cravings.

Paragraph 3: A device for providing a time-varying magnetic field to the left dorsolateral prefrontal cortex in order to reduce the food cravings.

Paragraph 4: A device for providing a time-varying magnetic field to the left dorsolateral prefrontal cortex in order to reduce the food cravings, wherein the device comprises: an applicator comprising a magnetic field generating device a positioning plate configured to be used during positioning of the application to the application position, wherein the positioning plate comprises a central line, an at least visual element.

Paragraph 5: The device of paragraph 4, wherein the magnetic field generating device is positioned between the positioning plate and the body of a patient.

Paragraph 6: The device of paragraph 4, wherein the magnetic field generating device is positioned between the at least one visual element and the body of a patient.

Paragraph 7: The device of paragraph 4, wherein the applicator comprises a casing having a lower side of the casing, wherein the magnetic field generating device is positioned between the positioning plate and the lower side of the casing.

Paragraph 8: The device of paragraph 4, wherein the applicator comprises a casing having a lower side of the casing, wherein the magnetic field generating device is positioned between the at least one visual element and the lower side of the casing.

Paragraph 9: The device of paragraph 4, wherein the applicator comprises one visual element.

Paragraph 10: The device of paragraph 9, wherein the one visual element is a central visual element.

Paragraph 11: The device of paragraph 9, wherein the one visual element is a third visual element.

Paragraph 12: The device of paragraph 9, wherein the one visual element is a central visual element.

Paragraph 13: The device of paragraph 9, wherein the one visual element is a triple dot mark Paragraph 14: The device of paragraph 9, wherein the one visual element is a double circle mark.

Paragraph 15: The device of paragraph 9, wherein the one visual element is a short line.

Paragraph 16: A device of at least one of paragraph 9 to 15, wherein the applicator comprises a casing having a lower side of the casing, wherein the magnetic field generating device is positioned between the one visual element and the lower side of the casing.

Paragraph 17: A device for providing a time-varying magnetic field to the left dorsolateral prefrontal cortex in order to temporarily reduce the food cravings.

Paragraph 18: A method of positioning of the applicator to reduce food cravings.

What is claimed is:

1. A device for generating a time-varying magnetic field, the device comprising:
  a positioning arm;
  a main body comprising:
    an energy source;
    an energy storage device configured to be charged by the energy source; and
    a switching device configured to be switched to discharge energy from the energy storage device to a magnetic field generating device to generate an impulse of the time-varying magnetic field;
    a connecting tube configured to connect an applicator to the main body; and
    the applicator, the applicator comprising:
    the magnetic field generating device;
    a rear side proximate to the connecting tube and a front side less proximate to the connecting tube than the rear side;
    a left side and a right side, wherein the right side and the left side are both adjacent to the front side and the rear side, and wherein the right side is opposite to the left side;
    a lower side configured to be positioned to a patient;
    an upper side configured to be positioned less proximate to the patient than the lower side, wherein the upper side comprises:
    a left visual element proximate to the left side and less proximate to the right side, and wherein the left visual element is proximate to the front side;
    a right visual element proximate to the right side and less proximate to the left side, and wherein the right visual element is less proximate to the front side than the left visual element; and a center visual element proximate to the front side and less proximate to the rear side, wherein the applicator is configured to be positioned to the patient such that:
    the left visual element is aligned with a first anatomical structure and the center visual element is aligned towards a second anatomical structure on the patient's right side, or
    the right visual element is aligned with the first anatomical structure and the center visual element is aligned towards the second anatomical structure on the patient's left side,
    wherein the first anatomical structure is different from the second anatomical structure.

2. The device of claim 1, wherein the center visual element comprises a first line in a direction from the rear side of the applicator to the front side of the applicator, and
  wherein the left visual element and the right visual element are positioned distant from the center visual element.

3. The device of claim 2, wherein the left visual element comprises a second line positioned in a direction perpendicular to the first line, and wherein the right visual element comprises a third line positioned in a direction perpendicular to the first line.

4. The device of claim 1, wherein the applicator further comprises:
  a handle proximate to the front side and less proximate to the connecting tube,
    wherein the handle is positioned over the left side and the right side, and
  an operating member configured to adjust a magnetic flux density of the time-varying magnetic field,
    wherein the operating member is positioned proximate to the connecting tube and less proximate to the front side.

5. The device of claim 1, wherein the applicator further comprises an operating member configured to generate a single impulse of the time-varying magnetic field.

6. The device of claim 5, wherein the applicator is configured to be positioned such that:
  the center visual element is aligned with the patient's right ear and the left visual element is aligned with the patient's nose, or
  the center visual element is aligned with the patient's left ear and the right visual element is aligned with the patient's nose.

7. The device of claim 5, wherein the applicator is configured to be connected to the positioning arm configured to position the applicator proximate the patient,
  wherein the positioning arm comprises a parallelogram mechanism comprising a first link, a second link, a first frame and a second frame,
  wherein the first link is connected to the first frame and the second frame,
  wherein the second link is connected to the first frame and the second frame, and
  wherein the parallelogram mechanism is configured to maintain the first link in a parallel position relative to the second link.

8. A device for generating a time-varying magnetic field, the device comprising:
  a main body comprising:
    an energy source;
    an energy storage device configured to be charged by the energy source; and a switching device configured to be switched to discharge energy from the energy storage device to a magnetic field generating device to generate an impulse of the time-varying magnetic field;

a connecting tube configured to connect an applicator to the main body; and the applicator, the applicator comprising:

a rear side proximate to the connecting tube and a front side less proximate to the connecting tube than the rear side;

the magnetic field generating device positioned less proximate to the rear side than to the front side;

an upper side configured to be positioned less proximate to a patient than a lower side, and a positioning plate on the upper side, wherein the positioning plate comprises:

a center visual element oriented in a direction from the rear side of the applicator to the front side of the applicator such that the center visual element is configured to visually divide the positioning plate into a left portion and a right portion, wherein the left portion and the right portion are both positioned adjacent to the front side and the rear side;

a first marker oriented to divide the center visual element in a direction perpendicular to the center visual element, and the first marker is positioned on the left portion and the right portion, the first marker comprising:

a left visual element positioned on the left portion and configured to be aligned with a nose of the patient, a first visual element positioned on the right portion and opposite to the left visual element, the first visual element configured to be aligned with a crown of the patient's head.

9. The device of claim 8, wherein the applicator further comprises:

a handle proximate to the front side and less proximate to the connecting tube, and an operating member configured to adjust a magnetic flux density of the time-varying magnetic field or generate a single impulse of the time-varying magnetic field, wherein the operating member is proximate to the connecting tube and less proximate to the front side.

10. The device of claim 8, wherein the applicator further comprises a visual element positioned to align with a center of the magnetic field generating device.

11. The device of claim 8, wherein the applicator further comprises an inlet proximate to the rear side and less proximate to the front side, and an outlet proximate to the front side and less proximate to the rear side, wherein the upper side further comprises a second marker oriented upside-down with respect to the first marker.

12. The device of claim 8, wherein the upper side further comprises:

a second marker oriented to divide the center visual element in a direction perpendicular to the center visual element, wherein the second marker is positioned on the left portion and the right portion, and wherein the second marker comprises:

a right visual element positioned on the right portion and configured to be aligned with the nose of the patient, and a second visual element positioned on the left portion and opposite to the right visual element, wherein the second visual element is configured to be aligned with the crown of the patient's head.

13. The device of claim 12, further comprising a positioning arm coupled to the applicator via a connection on the rear side, wherein the front side comprises a handle configured to be held by an operator, and wherein the first visual element and the second visual element are positioned between the connection and the front side.

14. The device of claim 12, further comprising a positioning pillow configured to maintain the patient's head in a static position, wherein the positioning pillow comprises a pillow visual element configured to be aligned with either the first visual element or the second visual element to position the applicator to a position to determine a motor threshold value of a magnetic flux density.

15. A device for generating a time-varying magnetic field, the device comprising:

a main body comprising:

an energy source;

an energy storage device configured to be charged by the energy source; and a switching device configured to be switched to discharge energy from the energy storage device to a magnetic field generating device to generate an impulse of the time-varying magnetic field;

a connecting tube; and an applicator comprising:

a rear side proximate to the connecting tube and a front side less proximate to the connecting tube than the rear side;

a left side and a right side, wherein the right side and the left side are both adjacent to the front side and the rear side, and wherein the right side is opposite to the left side;

the magnetic field generating device;

an outlet proximate to the front side and less proximate to the connecting tube;

an inlet proximate to the rear side and less proximate to the front side, wherein the inlet is between the connecting tube and the outlet; and a plurality of visual elements comprising:

a center visual element positioned proximate to the front side, wherein the center visual element is configured to be aligned with a second anatomical structure of a patient, and wherein the second anatomical structure is a left ear or a right ear of the patient;

a right visual element positioned on the right side of the applicator, wherein the right visual element is configured to be aligned with a first anatomical structure of the patient; and a left visual element positioned on the left side of the applicator, wherein the left visual element is configured to be aligned with the first anatomical structure of the patient.

16. The device of claim 15, further comprising a positioning arm configured to maintain the applicator proximate to the patient, wherein the positioning arm comprises a parallelogram mechanism and a resilient member configured to compensate a weight of the applicator.

17. The device of claim 16, wherein the parallelogram mechanism comprises the resilient member, wherein the positioning arm includes a lock configured to be moved between a first position and a second position, wherein the first position is configured to disable a movement of the resilient member such that the movement of the parallelogram mechanism is disabled, and wherein the second position is configured to enable a movement of the resilient member such that the parallelogram mechanism is free to move.

18. The device of claim 17, wherein the lock comprises a locking member and a pulling member, wherein the pulling member is configured to be moveable between a first position along the locking member and a second position along the locking member, wherein a lower end of the pulling member is configured to be positioned proximate to an upper side of the locking member in the first position to enable a movement of the positioning arm, and wherein the lower end of the pulling member is configured to be positioned distant from the upper side of the locking member in the second position to disable the movement of the positioning arm.

19. The device of claim 18, wherein the locking member comprises:

the upper side;

a lower side; and a protrusion between the upper side and the lower side.

20. The device of claim 16, wherein the positioning arm comprises a first end configured to be connected to the main body, and a second end configured to be coupled to the applicator, wherein the second end is less proximate to the main body than the first end, wherein the second end comprises:

a locking mechanism configured to connect the applicator to the positioning arm; and a gap, wherein the applicator further comprises a latching member proximate to the rear side, wherein the latching member is configured to fit in the gap to connect the applicator to the positioning arm.

21. The device of claim 15, wherein the applicator comprises a handle proximate to the front side and less proximate to the rear side, wherein the handle is coupled to the left side and the right side.

22. The device of claim 21, wherein the handle is configured to be held by a left hand of an operator such that the applicator is positioned proximate to the patient in a first position, wherein in the first position the center visual element is aligned with the left ear of the patient and the right visual element is aligned with a nose of the patient, and wherein the handle is configured to be held by a right hand of the operator such that the applicator is configured to be positioned proximate to the patient in a second position, and wherein in the second position the center visual element is aligned with the right ear of the patient and the left visual element is aligned with the nose of the patient.

23. A method for applying a time-varying magnetic field to a patient by a device comprising a main body, a connecting tube, and an applicator, the method comprising:

charging an energy storage device by an energy source;

switching a switching device to discharge the energy storage device to a magnetic field generating device to generate the time-varying magnetic field;

positioning the applicator proximate to the patient, wherein the applicator comprises:

a rear side proximate to the connecting tube and a front side less proximate to the connecting tube than the rear side, a left side and a right side, wherein the right side and the left side are both adjacent to the front side and the rear side, and wherein the right side is opposite to the left side, a handle positioned less proximate to the rear side than to the front side and wherein the handle is coupled to the left side and the right side, and an upper side facing away from the patient, wherein the upper side comprises a left visual element, a right visual element, and a center visual element;

positioning the applicator to a position to determine a motor threshold value of a magnetic flux density, wherein the positioning comprises:

aligning the left visual element with a first anatomical structure, or aligning the right visual element with the first anatomical structure; and aligning the center visual element with a second anatomical structure of the patient, wherein the first anatomical structure is different from the second anatomical structure;

applying at least one impulse of the time-varying magnetic field to the patient;

increasing the magnetic flux density of the time-varying magnetic field;

determining the motor threshold value of the magnetic flux density;

positioning the applicator toward a nose of the patient;

generating the time-varying magnetic field based on a protocol; and applying the time-varying magnetic field to a target location in the protocol.

24. The method of claim 23, further comprising aligning a first visual element or a second visual element with the patient's crown, wherein:

the first visual element is positioned on the right side of the applicator and opposite to the left visual element, or the second visual element is positioned on the left side of the applicator and opposite to the right visual element.

25. The method of claim 23, further comprising positioning a head of the patient on a positioning pillow to maintain the patient's head in a static position.

26. The method of claim 25, further comprising maintaining the applicator proximate to the patient's head by a belt.

27. The method of claim 25, wherein the positioning pillow comprises a pillow visual element, the method further comprising aligning the first visual element or the second visual element with the pillow visual element.

28. The method of claim 23, further comprising:

determining, by a control unit, a first value of the magnetic flux density based on the motor threshold value of the magnetic flux density and a scaling factor;

assembling a plurality of impulses of the time-varying magnetic field into a trapezoidal envelope comprising:

a first plurality of impulses of an increasing magnetic flux density up to the first value of the magnetic flux density, wherein the first plurality of impulses is generated for a first time period, and wherein the first plurality of impulses comprises a first number of impulses, a second plurality of impulses equal to the first value of the magnetic flux density, wherein the second plurality of impulses is generated for a second time period, and wherein the second plurality of impulses comprises a second number of impulses, and a third plurality of impulses of a decreasing magnetic flux density from the first value of the magnetic flux density, wherein the third plurality of impulses is generated for a third time period, and wherein the third plurality of impulses comprises a third number of impulses, calculating by the control unit, an increment based on the first value of the magnetic flux density and the first number of impulses;

calculating by the control unit, a decrement based on the first value of the magnetic flux density and the third number of impulses;

generating the first plurality of impulses, wherein the magnetic flux density of the first plurality of impulses increases by the increment up to the first value of the magnetic flux density;

generating the second plurality of impulses with magnetic flux density equal to the first value of the magnetic flux density, and generating the third plurality of impulses, wherein the magnetic flux density of the third plurality of impulses decreases by the decrement from the first value of the magnetic flux density.

29. The method of claim 23, further comprising:

selecting the protocol via a human machine interface comprising a plurality of icons for sending a treatment instruction to a control unit to adjust treatment parameters; and displaying a positioning instruction for positioning the applicator to a position of the applicator to determine the motor threshold value of the magnetic flux density.

30. The method of claim 23, further comprising shifting the applicator in a direction of:

the left visual element when the left visual element is aligned with the first anatomical structure, or the right visual element when the right visual element is aligned with the first anatomical structure, and applying the time-varying magnetic field to a dorsolateral prefrontal cortex and reducing food craving.

*  *  *  *  *